US007741091B2

(12) United States Patent
DeAngelis et al.

(10) Patent No.: US 7,741,091 B2
(45) Date of Patent: *Jun. 22, 2010

(54) METHODS OF PRODUCING HYALURONIC ACID AND CHIMERIC AND HYBRID GLYCOSAMINOGLYCAN POLYMERS

(75) Inventors: Paul L. DeAngelis, Edmond, OK (US); Wei Jing, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 499 days.

This patent is subject to a terminal disclaimer.

(21) Appl. No.: 11/698,311

(22) Filed: Jan. 25, 2007

(65) Prior Publication Data
US 2007/0117188 A1 May 24, 2007

Related U.S. Application Data

(63) Continuation of application No. 10/195,908, filed on Jul. 15, 2002, now abandoned, and a continuation-in-part of application No. 10/142,143, filed on May 8, 2002, now Pat. No. 7,307,159, and a continuation-in-part of application No. 09/842,484, filed on Apr. 25, 2001, now abandoned, and a continuation-in-part of application No. 09/437,277, filed on Nov. 10, 1999, now Pat. No. 6,444,447, and a continuation-in-part of application No. 09/283,402, filed on Apr. 1, 1999, now abandoned.

(60) Provisional application No. 60/305,263, filed on Jul. 13, 2001, provisional application No. 60/107,929, filed on Nov. 11, 1998, provisional application No. 60/080,414, filed on Apr. 2, 1998, provisional application No. 60/199,538, filed on Apr. 25, 2000, provisional application No. 60/289,554, filed on May 8, 2001, provisional application No. 60/350,642, filed on Jan. 22, 2002, provisional application No. 60/345,497, filed on Nov. 9, 2001, provisional application No. 60/391,787, filed on Jun. 20, 2002.

(51) Int. Cl.
*C12N 9/10* (2006.01)
*C12N 1/20* (2006.01)
(52) U.S. Cl. .................. 435/193; 435/85; 435/183; 435/252.3; 435/320.1; 536/23.2
(58) Field of Classification Search ............ None
See application file for complete search history.

(56) References Cited

U.S. PATENT DOCUMENTS

| | | | |
|---|---|---|---|
| 4,224,179 A | 9/1980 | Schneider | |
| 4,235,871 A | 11/1980 | Papahadjopoulos et al. | |
| 4,511,478 A | 4/1985 | Nowinski et al. | |
| 4,517,295 A | 5/1985 | Bracke et al. | |
| 4,585,754 A | 4/1986 | Meisner et al. | |
| 4,615,697 A | 10/1986 | Robinson | |
| 4,708,861 A | 11/1987 | Popescu et al. | |
| 4,780,414 A | 10/1988 | Nimrod et al. | |
| 4,782,046 A | 11/1988 | Brown et al. | |
| 4,784,990 A | 11/1988 | Nimrod et al. | |
| 4,801,539 A | 1/1989 | Akasaka et al. | |
| 4,822,867 A | 4/1989 | Erhan | |
| 4,983,392 A | 1/1991 | Robinson | |
| 4,990,601 A | 2/1991 | Skjak-Braek et al. | |
| 5,008,253 A | 4/1991 | Casu et al. | |
| 5,015,577 A | 5/1991 | Weigel et al. | |
| 5,023,175 A | 6/1991 | Hosoya et al. | |
| 5,071,751 A | 12/1991 | Morita et al. | |
| 5,171,689 A | 12/1992 | Kawaguri et al. | |
| 5,217,743 A | 6/1993 | Farah | |
| 5,314,876 A | 5/1994 | Lormeau et al. | |
| 5,337,747 A | 8/1994 | Neftel | |
| 5,384,398 A | 1/1995 | Lormeau et al. | |
| 5,472,704 A | 12/1995 | Santus et al. | |
| 5,473,034 A | 12/1995 | Yasui et al. | |
| 5,510,418 A | 4/1996 | Rhee et al. | |
| 5,607,694 A | 3/1997 | Marx | |
| 5,610,241 A | 3/1997 | Lee et al. | |
| 5,622,850 A | 4/1997 | Sloma et al. | |
| 5,631,019 A | 5/1997 | Marx | |
| 5,651,982 A | 7/1997 | Marx | |
| 5,876,433 A | 3/1999 | Lunn | |
| 5,948,900 A | 9/1999 | Yother et al. | |

(Continued)

FOREIGN PATENT DOCUMENTS

EP 0195303 11/1989

(Continued)

OTHER PUBLICATIONS

"The Combinations of Haemoglobin With Oxygen and With Carbon Monoxide.", Hill, J. Biochem., 7:471-480 (1913).
"Die Kinetik Der Invertinwirkung", Michaelis and Menten, Biochem. Z., 49: 333-338 (1913) (No translation available).
"The Role of the Mucoid Polysaccharide (Hyaluronic Acid) in the Virulence of Group A Hemolytic *Streptococci*", Kass et al., J. Of Exp. Med., 79:319-330 (1944).
"The Production of Capsules, Hyaluronic Acid and Hyaluronidase by Group A and Group C *Streptocooci*", MacLennan, J. Gen. Microbiol., 14:134-142 (1956).
"The Isolation and Characterization of a Hyaluronidase Produced by a Capsulated Strain of Group C *Streptococcus*", MacLennan, J. Gen. Microbiol., 14:143-152 (1956).

(Continued)

*Primary Examiner*—Christian L Fronda
(74) *Attorney, Agent, or Firm*—Dunlap Codding, P.C.

(57) ABSTRACT

The present invention relates to methodology for polymer grafting by a polysaccharide synthase and, more particularly, polymer grafting using the hyaluronate or chondroitin or heparin/heparosan synthases from *Pasteurella multocida*, in order to create a variety of glycosaminoglycan oligosaccharides having a natural or chimeric or hybrid sugar structure.

10 Claims, 35 Drawing Sheets

U.S. PATENT DOCUMENTS

| | | | |
|---|---|---|---|
| 5,958,899 | A | 9/1999 | Zoppetti et al. |
| 6,120,536 | A | 9/2000 | Ding et al. |
| 6,156,373 | A | 12/2000 | Zhong et al. |
| 6,162,797 | A | 12/2000 | Zoppetti et al. |
| RE37,336 | E | 8/2001 | Weigel et al. |
| 6,423,514 | B1 | 7/2002 | Briskin |
| 6,444,447 | B1 * | 9/2002 | DeAngelis ............... 435/97 |
| 7,223,571 | B2 * | 5/2007 | DeAngelis et al. ......... 435/97 |
| 2003/0100534 | A1 | 5/2003 | Zoppetti et al. |

FOREIGN PATENT DOCUMENTS

| | | |
|---|---|---|
| EP | 0144019 | 6/1990 |
| EP | 0266578 | 7/1993 |
| EP | 0244757 | 11/1994 |
| EP | 00300035 | 5/1995 |
| EP | 0036776 | 5/1998 |
| EP | 01304338 | 4/2003 |
| GB | 2249315 | 5/1992 |
| JP | 61-257169 | 11/1986 |
| JP | 62032893 | 2/1987 |
| JP | 63094988 | 4/1988 |
| JP | 4-80202 | 3/1992 |
| JP | 4-124854 | 4/1992 |
| JP | 4-134854 | 5/1992 |
| JP | 4-158796 | 6/1992 |
| JP | 8-38336 | 9/1997 |
| WO | 91/03559 | 3/1991 |
| WO | 94/00463 | 1/1994 |
| WO | 95/24497 | 9/1995 |
| WO | 95/33067 | 12/1995 |
| WO | 97/20061 | 6/1997 |
| WO | 00/27437 | 5/2000 |
| WO | 01/02597 | 1/2001 |
| WO | PCT/US01/13395 | 11/2001 |
| WO | PCT/JP02/07859 | 2/2003 |

OTHER PUBLICATIONS

"The Biosynthesis of Hyaluronic Acid by Group A *Streptococcus*", Markovitz et al., J. Biol. Chem., 234 (9):2343-2350 (1959).

"The Biosynthesis of Hyaluronic Acid by *Streptococcus*," Stoolmiller, et al., Journal of Biological Chemistry, vol. 244, No. 2, pp. 236-246 (1969).

"Cleavage of Structural Proteins During the Assembly of the Head of Bacteriophage T4", Laemmli, Nature, 227:680-685 (1970).

"The Isolation and Characterization of Hyaluronic Acid From *Pasteurella multocida*", Cifonelli, et al., Carbohydrate Research, 14, 272-276, (1970).

"A Rapid and Sensitive Method for the Quantitation of Microgram Quantities of Protein Utilizing the Principle of Protein-Dye Binding", Bradford, Analytical Biochemistry, 72:248-254 (1976).

"Genetic Mapping of the K1 and K4 Antigens (L) of *Escherichia coli*. Non-Allelism of K(L) Antigens With K Antigens of O8:K27(A), O8:K8 (L) and O9:K57 (B)", Orskov et al., Acta Pathol Microbiol Scand B, 84:125-131 (1976).

"Synthesis and Assembly of the Membrane Proteins in *E. coli*", Ito et al., Cell, 11:551-559 (1977).

"Electrophoretic Transfer of Proteins From Polyacrylamide Gels to Nitrocellulose Sheets: Procedure and Some Applications", Biochemistry, 76: 4350-4354 (1979).

"Biosynthesis of Hyaluronic Acid by *Streptococcus*", Sugahara et al., J. Biol. Chem., 254:6252-6261 (1979).

"Modern Genetics", Ayala, et al., Benjamin/Cummings Publishing Col., Menlo Park CA, p. 45 (1980).

"Hyaluronidase Production by Type B *Pasteurella multocida* From Cases of *Hemorrhagic septicemia*", Carter, et al., Journal of Clinical Microbiology, p. 94-96, (1980).

"Hyaluronate Capsule Prevents Attachment of Group A *Streptococci* to Mouse Peritoneal Macrophages", Whitnack et al., Infection and Immunity, 31(3):985-991 (1981).

"Strains of *Escherichia coli* Carrying the Structural Gene for Histidyl-tRNA Synthetase on a High Copy-Number Plasmid", Eisenbeis, et al., Mol. Gen. Genet. 183:115-122 (1981).

"The Structure of the Capsular Polysaccharide (K5 Antigen) of Urinary-Tract-Infective *Escherichia coli* 010:K5:H4", Vann et al., Biochem J. 116:359-364 (1981).

"Synthesis of Hyaluronate in Differentiated Teratocarcinoma Cells," Prehm, et al., J. Biochem, vol. 211, pp. 181-189 (1983).

"*Streptococcal* Hyaluronic Acid: Proposed Mechanisms of Degradation and Loss of Synthesis During Stationary Phase", Van de Rijn, J. Bacteriol., 156(3):1059-1065 (1983).

"Differences in the Effects of pH on the Hydrolytic and Transgalactosylic Reactions of Beta-Galactosidase (*Escherichia coli*)", Huber et al., Can. J. Biochem. Cell Biol., 61:198-206 (1983).

"Hyaluronate is Synthesized at Plasma Membranes", Prehm, Biochem. J., 220:597-600 (1984).

"Subcellular Locations of Hyaluronate Synthase in Oligodendroglioma Cells", Philipson et al., J. Biol. Chem., 259(8):5017-5023 (1984).

"Binding and Reactivity at the 'Glucose' Site of Galactosyl-Beta-Galactosidase (*Escherichia coli*)", Huber et al., Arch Biochem Biophys., 234: 151-160 (1984).

"Heparin, Its Fractions, Fragments and Derivatives. Some Newer Perspectives", Fareed, Seminars in Thrombosis and Hemostasis. 11(1):1-9 (1985).

"Solubilization of Hyaluronic Acid Synthetic Activity From *Streptococci* and its Activation With Phospholipids", Triscott et al., J. Biol. Chem., 261(13):6004-6009 (1986).

"Isolation of Streptococcal Hyaluronate Synthase", Prehm et al., Biochem. J., 235:887-889 (1986).

"Effect of Replacing Uridine 33 in Yeast tRNAPhe on the Reaction With Ribosomes", Dix et al., J. Biol. Chem., 261(22):10112-8 (1986).

"Molecular Cloning and Analysis of Genes for Production of K5, K7, K12, and K92 Capsular Polysaccharides in *Escherichia coli*", Roberts et al., J. Bacteriology. 168(3):1228-1233 (1986).

"Isolation, Structure and Expression of Mammalian Genes for Histidyl-tRNA Synthetase," Tsui, et al., Nucleic Acids Research, vol. 15, No. 8, pp. 3349-3367, (1987).

"Role of Cysteine in Glutathione Synthase From *Escherichia coli* B", Kato et al., J. Biol. Chem., 263(24):11646-11651 (1988).

"Structure and Serological Characteristics of the Capsular K4 Antigen of *Escherichia coli* O5:K4:H4, A Fructose-Containing Polysaccharide With a Chondroitin Backbone", Rodriguez et al., Eur. J. Biochem., 177:117-124 (1988).

"The Carboxy-Terminal Domain of the LexA Repressor Oligomerises Essentially as the Entire Protein", Schnarr et al., FEBS Lett., 234:56-60 (1988).

"Common Organization of Gene Clusters for Production of Different Capsular Polysaccharides (K Antigens) in *Escherichia coli*", Roberts, J. Bacteriology. 170(3):1305-1310 (1988).

"The Biology of Hyaluronan", Evered and Whelan Eds., CIBA Foundation Symposium 143 (1989).

"A Cryptic Fimbrial Gene in *Serratia marcescens*", Moriya et al., J. Bacteriol., 171(12): 6629-36 (1989).

"Monoclonal Antibodies Specific for K88ab, K88ac and K88ad Antigens of *Escherichia coli*", Li et al., Wei Sheng Wu Xue Bao, 29:348-353 (1989). (Abstract only).

"Kinetic Characterization of the Unisite Catalytic Pathway of Seven Beta-Subunit Mutant F1-ATPases From *Escherichia coli*", al-Shawi et al., J. Biol. Chem., 264(26): 15376-83 (1989).

"The Role of Bacterial Polysaccharide Capsules as Virulence Factors", Moxon et al., Current Topics in Microbiology and Immunology, 150:65-85 (1990).

"Slow-Binding Inhibition of the *Escherichia coli* Pyruvate Dehydrogenase Multienzyme Complex by Acetylphosphinate", Schonbrunn-Hanebeck et al., Biochemistry, 29(20): 4880-5 (1990).

"Molecular Cloning and Expression of the Genes Encoding the *Escherichia coli* K4 Capsular Polysaccharide, A Fructose-Substituted Chondroitin", Drake et al., FEMS Microbiol. Lett., 54(1-3):227-30 (1990).

"Expression of the *Escherichia coli* K5 Capsular Antigen: Immunoelectron Microscopic and Biochemical Studies with Recombinant *E. coli*", Kroncke et al., J. Bacteriology. 172(2):1085-1091 (1990).

"Molecular analysis of the *Escherichia coli* K5 kps locus: identification and characterization of an inner-membrane capsular polysaccharide transport system", Smith et al., Molecular Microbiology. 4(11):1863-1869 (1990).

"Shuttle Vectors Containing a Multiple Cloning Site and a Lacza Gena for Conjugal Transfer of DNA From *Escherichia coli* to Gram-Positive Bacteria," Trieu-Cout, et al., Gene, vol. 102, pp. 99-104, (1991).

"Hyaluronic Acid Capsule is a Virulence Factor for Mucoid Group A *Streptococci*", Wessels et al., Microbiology, 88:8317-8321 (1991).

"Electron Microscopic Study of Coexpression of Adhesive Protein Capsules and Polysaccharide Capsules in *Escherichia coli*", Kronke et al., Infect. Immunity, 58:2710-4 (1991).

"Transport and Utilization of Ferrioxamine-E-Bound Iron in *Erwinia herbicola* (*Pantoea agglomerans*)", Matzanke et al., Biol. Met., 181-185 (1991).

"Modulation of the Tight Binding of Carboxyarabinitol 1,5-Biphosphate to the Large Subunit of Ribulose 1,5-Bisphosphate Carboxylase/Oxygenase", Smrcka et al., Arch. Biochem. Biophys., 286: 14-9 (1991).

"Biosynthesis of heparin. Use of *Escherichia coli* K5 capsular polysaccharide as a model substrate in enzymic polymer-modification reactions", Kusche et al., Biochem J. 275(pt1):151-8 (1991).

"Experimental and Clinical Pharmacology of Glycosaminoglycans (GAGs)". Soldani et al., Drugs Exptl. Clin. Res. XVII(1):81-85 (1991).

"Analysis of the *Streptococcal* Hyaluronic Acid Synthase Complex Using the Photoaffinity Probe 5-Azido-Udp-Glucuronic Acid," Van de Rijn, et al., J. Biol., Chem., vol. 267, No. 34, pp. 24302-24306, (1992).

"Molecular Characterization of a Locus Required for Hyaluronic Acid Capsule Production in Group A *Streptococci*," Dougherty, et al., J. Exp. Med., vol. 175, pp. 1291-1299, (1992).

"Hyaluronan," Laurent, et al., FASEB Journal, vol. 6, pp. 2397-2404, (1992).

"Role of Cysteins 640, 656, and 661 in Steroid Binding to Rat Glucocorticoid Receptors", Chakraborti et al., J. Biol. Chem., 267(16):11366-11373 (1992).

"Slow-Onset Inhibition of Ribosomal Peptidyltransferase by Lincomycin", Kallia-Raftopoulos et al., Arch. Biochem. Biophys., 298: 332-339 (1992).

"Enhanced Catalysis by Active-Site Mutagenesis at Aspartic Acid 153 in *Escherichia coli* Alkaline Phosphatase", Matlin et al., Biochemistry, 31(35): 8196-8200 (1992).

"A Study of Vitamin Inhibition on the Mutagenicity of the Antineoplastic Drugs", Zhao and Huang, Zhonghua Yu Fang Yi Xue Za Zhi, 26:291-293 (1992). (Abstract only).

"Biosynthesis of heparin. The D-glucuronosyl- and N-acetyl-D-glucosaminyltransferase reactions and their relation to polymer modification", Lidholt et al., Biochem J. 287(pt 1):21-9 (1992).

"Hyaluronic Acid and a (1-4)-B-D-Xylan, Extracellular Polysaccharides of *Pasteurella multocida* (Carter Type A) Strain 880", Rosner, et al., Carbohydrate Research, 223, 329-333 (1992).

"Localization of Hyaluronan in Mouse Embryos During Implantation, Gastrulation and Organogenesis", Fenderson et al., Differentiation, 54:85-98 (1993).

"Hyaluronan-Binding Proteins in Development, Tissue Homeostasis, and Disease", Knudson et al., FASEB, 7:1233-1241 (1993).

"Molecular Cloning, Identification, and Sequence of the Hyaluronan Synthase Gene From Group A *Streptococcus pyogenes*", DeAngelis et al., J. Biol. Chem., 268(26):19181-19184 (1993).

"Isolation of a *Streptococcus pyogenes* Gene Locus That Directs Hyaluronan Biosynthesis in Acapsular Mutants and in Heterologous Bacteria," DeAngelis, et al., J. Biol. Chem., vol. 268, No. 20, pp. 14568-14571, (1993).

"Hyaluronate Synthase: Cloning and Sequencing of the Gene From *Streptococcus* Sp.," Lansing, et al., J. Biochem., vol. 289, pp. 179-184, (1993).

"Molecular Characterization of HASB From an Operon Required for Hyaluronic Acid Synthesis in Group A *Streptococci*," Dougherty, et al., J. Biol. Chem., vol. 268, No. 10, pp. 7118-7124, (1993).

"Preliminary Study of Test Methods to Assess the Virucidal Activity of Skin Disinfectants Using Poliovirus and Bacteriophages", Davies et al., Journal of Hospital Infection, 25(2): 125-131 (1993).

"The *Escherichia coli* serA-Linked Capsule Locus and its Flanking Sequences Are Polymorphic, Genetic Evidence for the Existence of More Than Two Groups of Capsule Gene Clusters", Drake et al., J. Gen. Microbiol., 139 (Pt. 8): 1707-1714 (1993).

"Reaction of Modified and Unmodified tRNA (Tyr) Substrates With Tyrosyl-tRNA Synthetase (*Bacillus stearothermophilus*)", Avis et al., Biochemistry, 32(20): 5312-5320 (1993).

"Effect of pH on Solubility and Ionic State of Lipopolysaccharide Obtained From the Deep Rough Mutant of *Escherichia coli*", Din et al., Biochemistry, 32(17): 4579-4586 (1993).

"Synthesis of the K5 (group II) capsular polysaccharide in transport-deficient recombinant *Escherichia coli*", Bronner et al., FEMS Microbiology Letters 113:273-284 (1993).

"Biosynthesis of Heparin/Heparan Sulfate", Lind et al., The Journal of Biological Chemistry. 268(28):20705-20708 (1993).

"Capsular hyaluronic acid in *Pasteurella multocida* type A and its counterpart in type D", Pandit et al., Research in Veterinary Science. 54:20-24 (1993).

"Effects on Virulence of Mutations in a Locus Essential for Hyaluronic Acid Capsule Expression in Group A *Streptococci*", Wessels et al., Infection and Immunity, 62(2):433-441 (1994).

"A Hyaluronidase Activity of the Sperm Plasma Membrane Protein Ph-20 Enables Sperm to Penetrate the Cumulus Cell Layer Surrounding the Egg", Lin et al., The Journal of Cell Biology, 125(5): 1157-1163 (1994).

"Dynamics of Lactose Permease of *Escherichia coli* Determined by Site-Directed Fluorescense Labeling", Jung et al., Biochemistry, 33:3980-3985 (1994).

"Cysteine 148 in the Lactose Permease of *Escherichia coli* is a Component of a Substrate Binding Site", Wu et al., Biochemistry, 33:12166-12171 (1994).

"Molecular Characterization of HASA From an Operon Required for Hyaluronic Acid Synthesis in Group A *Streptococci*," Dougherty, et al., J. Biol. Chem., vol. 269, No. 1, pp. 169-175, (1994).

"The *Streptococcus pyogenes* Hyaluronan Sytnhase: Sequence Comparison and Conservation Among Various Group A Strains," DeAngelis, et al., Biochem. and Biophy. Res. Comm., vol. 199, No. 1, pp. 1-10, (1994).

"Molecular Fingerprinting of *Pasteurella multocida* Associated With Progressive Atrophic Rhinitis in Swine Herds". Gardner et al. Database Medline on Diaolog, US Nat'l. Library of Medicine (Bethesda, MD, USA) No. 95161494, Abstract, J. Vet. Diagn. Invest. Oct. 1994. vol. 6, No. 4 pp. 442-447, see entire abstract.

"Amino Acid Residues of the Kringle-4 and Kringle-5 Domains of Human Plasminogen That Stabilize Their Interactions With Omega-Amino Acid Ligands", McCance et al., J. Biol. Chem., 269(51):32405-32410 (1994).

"Heparin-like compounds prepared by chemical modification of capsular polysaccharide from *E. coli*", Casu et al., Elsevier Science. 263:271-284 (1994).

"Substrate specificities of glycosyltransferases involved in formation of heparin precursor and *E. coli* K5 capsular polysaccharides", Lidholt et al., Carbohydrate Research. 255:87-101 (1994).

"Presumptive Identification of *Pasteurella multocida* serogroups A, D and F by capsule depolymerisation with mucopolysaccharidases", Rimler, Veterinary Record.134:191-192 (1994).

"Hyaluronidase and Chondroitinase Activity of *Pasteurella multocida* Serotype B:2 Involved in *Haemorrhagic septicaemia*", Rimler, et al., Veterinary Record 134, 67-68 (1994).

The Elucidation of Novel Capsular Genotypes of *Haemophilus influenzae* Type B With the Polymerase Chain Reaction. Leaves et al. J. Medical Microbiology. 1995, vol. 43, pp. 120-124, entire document.

"Kinetic Mechanism of Kinesin Motor Domain", Ma and Taylor, Biochemistry, 34(40): 13233-13241 (1995).

"Cloning of the putative tumor suppressor gene for hereditary multiple exostoses (EXT1)", Ahn et al., Nat. Genet. 11(2):137-43 (1995).

"Region 2 of the *Escherichia coli* K5 capsule gene cluster encoding proteins for the biosynthesis of the K5 polysaccharide", Petit et al., Molecular Microbiology. 17(4):611-620 (1995).

"Structural and functional properties of heparin analogues obtained by chemical sulphation of *Escherichia coli* K5 capsular polysaccharide", Razi et al., Biochem J. 309 (pt2):465-72 (1995).

"Influence of chondroitinase on direct hemagglutination titers and phagocytosis of *Pasteurella multocida* serogroups A, D and F", Rimler et al., Veterinary Microbiology. 47:287-294 (1995).

"Homologs of the Xenopus Developmental Gene DG42 Are Present in Zebrafish and Mouse and Are Involved in the Synthesis of Nod-Like Chitin Oligosaccharides During Early Embryogenesis", Semino et al., Proc. Natl Acad. Sci. USA, 93:4548-4553 (1996).

"Enzymological Characterization of the *Pasteurella multocida* Hyaluronic Acid Synthase", DeAngelis, Biochemistry, 35 (30): 9768-9771 (1996).

"Construction and Characterization of a Potential Live Oral Carrier-Based Vaccine Against *Vibrio chlolerae*". Favre et al. Infection and Immunity. Sep. 1996. vol. 64, No. 9 pagres 3565-3570, entire document.

"Functional Cloning of the cDNA for a Human Hyaluronan Synthase", Shyjan et al., J. Biol. Chem., 271(38):23395-23399 (1996).

"Coating the Surface: A Model for Expression of Capsular Polysialic Acid in *Escherichia coli* K1", Bliss et al., Molecular Microbiology, 21(2):221-231 (1996).

"Molecular Cloning and Characterization of a Putative Mouse Hyaluronan Synthase", Spicer et al., J. Biol. Chem., 271(38):23400-23406 (1996).

"Expression Cloning and Molecular Characterization of HAS Protein, a Eukaryotic Hyaluronan Synthase", Itano et al., J. Biol. Chem., 271(17):9875-9878 (1996).

"Molecular Identification of a Putative Human Hyaluronan Synthase", Wantanabe et al., J. Biol. Chem., 271(38):22945-22948 (1996).

"Molecular Cloning of a Human Hyaluronan Synthase", Itano et al., Biochemical and Biophysical Research Communications, 222:816-820 (1996).

"Production and Purification of an Extracellularly Produced K4 Polysachharide From *Escherichia coli*", Manzoni et al., Biotechnol. Lett., 18(4): 383-386 (1996).

"A Novel Family of Phospholipase D Homologues That Includes Phospholipid Synthases and Putative Endonucleases: Identification of Duplicated Repeats and Potential Active Site Residues", Ponting and Kerr, Protein Science, 914-922 (May 1996).

"Biosynthesis of Dermatan Sulphate. Defructosylated *Escherichia coli* K4 Capsular Polysaccharide as a Substrate for the D-Glucuronyl C-5 Epimerase, and an Indication of a Two-Base Reaction Mechanism", Hannesson et al., Biochem. J., 313(Pt. 2): 589-596 (1996).

"The EXT2 multiple exostoses gene defines a family of putative tumor suppressor genes", Stickens et al., Nat. Genet. 14(1):25-32 (1996).

"Capsular Hyaluronic Acid-Mediated Adhesion of *Pasteurella multocida* to Turkey Air Sac Macrophages", Pruimboom, et al., Avian Diseases 40:887-893, (1996).

"Hyaluronan Synthases", Weigel et al., J. Biol. Chem., 272 (22): 13997-14000 (1997).

"Identification of Sulfhydryl-Modified Cysteine Residues in the Ligand Binding Pocket of Retinoic Acid Receptor β", Wolfgang et al., J. Biol. Chem., 272(2):746-753 (1997).

"Hyaluronan in Morphogenesis", B.P. Toole, Journal of Internal Medicine, 242:35-40 (1997).

"Hyaluronan Synthase of *Chlorella* Virus PBCV-1", DeAngelis et al, Science, 278:1800-1803 (1997).

"Molecular Cloning, Expression, and Characterization of the Authentic Hyaluronan Synthase From Group C *Streptococcus equisimilis*", Kumari and Weigel, J. Biol. Chem., 272(51):32539-32546 (1997).

"Site-Directed Spin Labeling of Transmembrane Domain VII and the 4B1 Antibody Epitope in the Lactose Permease of *Escherichia coli*", Voss et al., Biochemistry, 36:15055-15061 (1997).

"Reactive Cysteines of the Yeast Plasma-Membrane H -ATPase (PMA1)", Petrov et al., J. Biol. Chem., 272(3):1688-1693 (1997).

"Biosynthesis of the *Escherichia coli* K4 Capsule Polysaccharide: A Parallel System for Studies of Glycosyltransferases in Chondroitin Formation", Lidholt et al., J. Biol. Chem., 272(5):2682-2687 (1997).

"Kinetic Mechanism of Monomeric Non-Claret Disjunctional Protein (Ncd) ATPase", Pechatnikova et al., J. Biol. Chem., 272(49): 30735-30740 (1997).

"A Two-Site Mechanism for ATP Hydrolysis by the Asymmetric Rep Dimer P2S as Revealed by Site-Specific Inhibition With ADP-A1F4", Wong and Lohman, Biochemistry, 36(11): 3115-3125 (1997).

"The Structure of the Human Multiple Exostoses 2 Gene and Characterization of Homologs in Mouse and Caenorhabditis elegans", Clines et al., Cold Spring Harbor Laboratory Press. 7:359-367 (1997).

"Identification and Localization of the Gene for EXTL, a Third Member of the Multiple Exostoses Gene Family", Wise et al., Cold Spring Harbor Laboratory Press. 7:10-16 (1997).

"Identification and Molecular Cloning of a Unique Hyaluronan Synthase From *Pasteurella multocida*", DeAngelis et al., J. Biol. Chem., 273(14): 8454-8458 (1998).

The Capsule Biosynthetic Locus of *Pasteurella multocida* A:1. Chung, et al. FEMS Microbiol. Lett. Sep. 15, 1998, vol. 166, No. 2, pp. 289-296, entire document.

"Cys-Scanning Mutagenesis: A Novel Approach to Structure-Function Relationships in Polytopic Membrane Proteins", Frillingos et al., FASEB, 12:1281-1299 (Oct. 1998).

"Characterization and Molecular Evolution of a Vertebrate Hyaluronan Synthase Gene Family", Spicer et al., J. Biol. Chem., 273(4):1923-1932 (1998).

"Eukaryotic Hyaluronan Synthases", Spicer and McDonald, Glycoforum, Sep. 15, 1998.

"The Active *Streptococcal hyaluronan* Synthases (HASs) Contain a Single HAS Monomer and Multiple Cardiolipin Molecules", Tlapak-Simmons et al., J. Biol. Chem., 273(40):26100-26109 (1998).

"Role of Fimbriae-Mediated Adherence for Neutrophil Migration Across *Escherichia coli*-Infected Epithelial Cell Layers", Godaly et al., Molecular Microbiology, 30(4): 725-735 (1998).

"Complete Kinetic Mechanism of Elongation Factor Tu-Dependent Binding of Aminoacyl-tRNA to the A Site of the *E. Coli* Ribosome", Pape et al., EMBO J., 17(24): 7490-7497 (1998).

Wyatt Technology Corporation: Heparin Characterization. 4/5; www.tigc.org.

Griffiths, G., et al.: Characterization of the Glycosyltransferase Enzyme from the *Escherichia coli* K5 Capsule Gene Cluster and Identification and Charaterization of the Glucuronyl Active Site. The Journal of Biological Chemistry, 273(19):11752-11757 (1998).

"Expression and functional analysis of mouse EXT1, a homolog exostoses type 1 gene", Lin et al., Biochem Biophys Res Commun.; 248(3):738-43 (1998).

"The Putative Tumor Suppressors EXT1 and EXT2 Are Glycosyltransferases Required for the Biosynthesis of Heparan Sulfate", Lind et al., The Journal of Biological Chemistry, 273(41):26265-26268 (1998).

"The putative tumor suppressor EXT1 alters the expression of cell-surface *Heparan sulfate*", McCormick et al., Nat. Genet. 19(2):158-61 (1998).

"The localization of KpsC, S and T, and KfiA, C and D Proteins Involved in the biosynthesis of the *Escherichia coli* K5 capsular polysaccharide: evidence for a membrane-bound complex", Rigg et al., Microbiology 144, 2905-2914 (1998).

"Identification of a Third EXT-like Gene (EXTL3) Belonging to the EXT Gene Family", Van Hul et al., Genomics. 47(2):230-7 (1998).

"Transposon Tn916 Insertional Mutagenesis of *Pasteurella multocida* and Direct Sequencing of Disruption Site", Paul L. DeAngelis, Microbial Pathogenesis, 24: 203-209 (1998).

"Hyaluronan Synthase Expression in Bovine Eyes", Usui et al., Investigative Ophythamology & Visual Science, 40(3):563-567 (Mar. 1999).

"Three Isoforms of Mammalian Hyaluronan Synthases Have Distinct Enzymatic Properties", Itano et al., J. Biol. Chem., 274(35):25085-25092 (1999).

"Hyaluronan Synthases: Fascinating Glycosyltransferases From Vertebrates, Bacterial Pathogens and Algal Viruses", P.L. DeAngelis, CMLS, 56:670-682 (1999).

"Membrane Protein Folding and Stability: Physical Principles", White and Wimley, Annu. Rev. Biophys. Biomol. Struc., 28:319-365 (1999).

"Location of Helix III in the Lactose Permease of *Escherichia coli* As Determined by Site-Directed Thiol Cross-Linking", Wang and Kaback, Biochemistry, 38:16777-16782 (1999).

"Kinetic Characterization of the Recombinant Hyaluronan Synthases From *Streptococcus pyogenes* and *Streptococcus equisimilis*", Tlapak-Simmons, J. Biol. Chem., 274(7):4246-4253 (1999).

"Purification and Lipid Dependence of the Recombinant Hyaluronan Synthases From *Streptococcus pyogenes* and *Streptococcus equisimilis*", Tlapak-Simmons, J. Biol. Chem., 274(7):4239-4245 (1999).

"Structure/Function Studies of Glycoslytransferases", Breton and Imberty, Current Opinion in Structural Biology, 9:563-571 (1999).

"Transfer RNA Identity Contributes to Transition State Stabilization During Aminoacyl-tRNA Synthesis", Ibba et al., Nucleic Acids Research, 27(18):3631-3637 (1999).

"Contractile Function and Myoplasmic Free Ca2+ (Cam) in Coronary and Mesenteric Arteries of *Endotoxemic guinea* Pigs", Jones et al., Shock, 11: 64-71 (1999).

"Biosynthesis of the *Escherichia coli* K5 Polysaccharide, a Representative of Group II Polysaccharides: Polymerization In Vitro and Characterization of the Product", Finke et al., Journal of Bacteriology. 4088-4094 (1999).

"The Tumor Suppressor EXT-like Gene EXTL2 Encodes an 1, 4-N-Acetylhexosaminyltransferase That Transfers N-Acetylgalactosamine and N-Acetylglucosamine to the Common Glycosaminoglycan-Protein Linkage Region", Kitigawa et al., The Journal of Biological Chemistry. 273(20):13933-13937 (1999).

"Production and Chemical Processing of Low Molecular Weight Heparins", Linhardt et al., Thieme Medical Publishers, Inc. 25(3):5-16 (1999).

"New insights on the specificity of heparin and haparan sulfate lyases from *Flavobacterium heparinum* revealed by the use of synthetic derivatives of K5 polysaccharide from *E. coli* and 2-O-desulfated heparin", Nader et al., Glycoconj J. 16(6):265-70 (1999).

"A director interaction between EXT proteins and glycosyltransferases is defective in hereditary multple exostoses", Simmons et al., Hum. Mol. Genet. ; 8(12):2155-64 (1999).

"Identification of mutations in the human EXT1 and EXT2 genes", Song et al., Chin J. Med. Genet., 16(4):208-10 (1999).

"New Frontiers in Medical Sciences: Redefining Hyaluronan", Abatangelo and Weigel Eds., (2000).

"In Vitro Synthesis of Hyaluronan by a Single Protein Derived From Mouse HAS1 Gene and Characterization of Amino Acid Residues Essential for the Activity", Yoshida et al., J. Biol. Chem., 275(1):497-506 (2000).

"Regulation of Plasminogen Activator Inhibitor-1 and Urokinase by Hyaluronan Fragments in Mouse Macrophages", Horton et al., Am. J. Physiol. Lung Cell Mol. Physiol., 279:L707-L715 (2000).

Identification and Molecular Cloning of a Chondroitin Synthase From *Pasteurella multocida* Type F, Paul DeAngelis, et al., Journal of Biological Chemistry, vol. 275, No. 31, pp. 24124-24129, Apr. 2000.

"Kinetic Studies on the Interaction Between a Ribosomal Complex Active in Peptide Bond Formation and the Macrolide Antibiotics Tylosin and Erythromycin", Dinos et al., Biochemistry, 39(38): 11621-11628 (2000).

"Structure-Function Relationships in Novel Peptide Dodecamers With Broad-Spectrum Bactericidal and Endotoxin-Neutralizing Activities", Mayo et al., Biochemical Journal, 349(3): 717-728 (2000).

"*Pasteurella multocida* capsule: composition, function and genetics", Boyce et al., Journal of Biotechnology 83:153-160 (2000).

"Biosynthesis of heparin/heparan sulfate: kinetic studies of the glucuronyl C5-epimerase with N-sulfated derivatives of the *Escherichia coli* K5 capsular polysaccharide as substrates", Hagner-McWhirter et al., Glycobiology. 10(2):159-71 (2000).

"Identification That KfiA, a Protein Essential for the Biosynthesis of the *Escherichia coli* K5 Capsular Polysaccharide, Is a UDP-GlcNAc Glycosyltransferase", Hodson et al., The Journal of Biological Chemistry, 275(35):27311-27315 (2000).

"EXT 1 Gene Mutation Induces Chondrocyte Cytoskeletal Abnormalities and Defective Collagen Expression in the Exostoses", Legeai-Mallet et al., J Bone Miner Res. 15(8):1489-500 (2000).

"Disruption of gastrulation and heparan sulfate biosynthesis in EXT1-Deficient Mice", Lin et al., Dev. Biol. 224(2):299-311 (2000).

"The putative tumor suppressors EXT1 and EXT2 form a stable complex that accumulates in the Golgi apparatus and catalyzes the synthesis of heparan sulfate", McCormick et al., PNAS, 97(2):668-673 (2000).

"Heparan/Chondroitin Sulfate Biosynthesis", Pedersen et al., The Journal of Biological Chemistry, 275(44):34580-34585 (2000).

"Heparin and heparan sulfate: biosynthesis, structure and function", Sasisekharan et al., Elsevier Science, Ltd. 1367-5931:626-631 (2000).

"The EXT1/EXT2 tumor suppressors: catalytic activities and role in heparan sulfate biosynthesis", Senay et al., EMBO Reports 1(3):282-286 (2000).

"Structural Analysis of Glycosaminoglycans in *Drosophila* and *Caenorhabditis elegans* and Demonstrations That tout-velu, a *Drosophila* Gene Related to EXT Tumor Suppressors, Affects Heparan Sulfate in Vivo", Toyoda et al., The Journal of Biological Chemistry, 275( 4):2269-2275 (2000).

"Location of the Glucuronosyltransferase Domain in the Heparan Sulfate Copolymerase EXT1 by Analysis of Chinese Hamster Ovary Cell Mutants", Wei et al., The Journal of Biological Chemistry, 275(36):27733-27740 (2000).

"Complete Cysteine-Scanning Mutagenesis and Site Directed Chemical Modification of the Tn10-Encoded Metal-Tetracycline/H Antiporter", Tamura et al., J. Biol. Chem., 276(23):20330-20339 (2001).

"Identification and Disruption of Two Discrete Loci Encoding Hyaluronic Acid Capsule Biosynthesis Genes hasA, hasB, and hasC in *Streptococcus uberis*", Ward et al., Infection and Immunity, 69(1):392-399 (2001).

"Topological Organization of the Hyaluronan Synthase From *Streptococcus pyogenes*", Heldermon et al., J. Biol. Chem., 276(3):2037-2046 (2001).

"Site-Directed Mutation of Conserved Cysteine Residues Does Not Inactivate the *Streptococcus pyogenes* Hyaluronan Synthase", Heldermon et al., Glycobiology, 11(12):1017-1024 (2001).

"Molecular Cloning of Rabbit Hyaluronic Acid Synthases and Their Expression Patterns in Synovial Membrane and Articular Cartilage", Ohno et al., Biochimica et Biophysics Acta, 1520 (71-78) (2001).

Molecular Cloning and Expression of a Human Chondroitin Synthase, Hiroshi Kitagawa, et al., Journal of Biological Chemistry, vol. 276, No. 42, pp. 38721-38726, Aug. 2001.

Utility of Molecularly Dissected Synthases for Chemoenzymatic Synthesis of *Glycosaminoglycan oligosaccharides*, Paul DeAngelis, Glycobiology, vol. 11, No. 10, pp. 934, Oct. 2001.

"Ring Opening Is Not Rate-Limiting in the GTP Cyclohydrolase I Reaction", Bacher et al., J. Biol. Chem., 276(4): 2622-2626 (2001).

"Subunit Communication in Tetrameric Class 2 Human Liver *Aldehyde dehydrogenase* as the Basis for Half-Of-The-Site Reactivity and the Dominance of the Oriental Subunit in a Heterotetramer", Weiner et al., Chemico-Biological Interactions, 130-132(1-3):47-56 (2001).

Bio Tie Therapies; BioHeparin—Prospectus; Jun. 2001. (Finland).

"Etiological Point Mutations in the Hereditary Multiple Exostoses Gene EXT1: A Functional Analysis of Heparan Sulfate Polymerase Activity", Cheung et al., Am. J. Hum. Genet. 69:55-66, (2001).

"The link between heparan sulfate and hereditary bone disease: finding a function for the EXT family of putative tumor suppressor proteins", Duncan et al., The Journal of Clinical Investigation, 108(4):511-516 (2001).

"Human tumor suppressor EXT gene family members EXTL1 and EXTL3 encode alpha 1,4-N-acetylglucosaminyltransferases that likely are involved in heparan sulfate/heparin biosynthesis", Kim et al., Proc. Natl. Acad. Sci. U.S.A. 1998(13):7176-81 (2001).

"rib-2, a *Caenorhabditis elegans* Homolog of the Human Tumor Suppressor EXT Genes Encodes a Novel 1,4-N-Acetylglucosaminyltransferase Involved in the Biosynthetic Initiation and Elongation of Heparan Sulfate", Kitigawa et al., The Journal of Biological Chemistry, 276(7):4834-4838 (2001).

"Fibroblast Growth Factor-2 Antagonist Activity and Angiostatic Capacity of Sulfated *Escherichia coli* K5 Polysaccharide Derivatives", Leali et al., The Journal of Biological Chemistry, 276(41):37900-37908 (2001).

"Complete genomic sequence of *Pasteurella multocida*, Pm70", May et al., Proc. Natl. Acad. Sci. 98(6):3460-3465 (2001).

"Toward a Biotechnological Heparin through Combined Chemical and Enzymatic Modification of the *Escherichia coli* K5 Polysaccharide". Naggi et al., Seminars in Thrombosis and Hemostasis, 27(5):437-443 (2001).

"Genetic organization of *Pasteurella multocida* cap loci and development of a multiplex capsular typing system", Townsend et al., J. Clin. Microbiol. 39(3):924-929 (2001).

"Anticoagulation: The Present and Future" Van Aken et al., Clin. Appl. Thrombosis/Hemostasis, 7(3):195-204, (2001).

"The *Streptococcal hyaluronan* Synthases Are Inhibited by Sulfhydryl-Modifying Reagents, But Conserved Cysteine Residues Are Not Essential for Enzyme Function", Kumari et al., J. Biol. Chem., 277(16):13943-13952 (2002).

Biosynthesis of Chondroitin/Dermatan Sulfate, Jeremiah Silbert, et al., IUBMB Life, vol. 54, pp. 177-186, Oct. 2002.

Functional Characteristics and Catalytic Mechanisms of the Bacterial Hyaluronan Synthases, Paul Weigel, IUBMB Life, vol. 54, pp. 201-211, Oct. 2002.

Keratan Sulfate Biosynthesis, James Funderburgh, IUBMB Life, vol. 54, pp. 187-194, 2002.

Mammalian Hyaluronan Synthases, Naoki Itano, et al., IUBMB Life, vol. 54, pp. 195-199, 2002.

"Identification of the capsular polysaccharides of Type D and F *Pasteurella multocida* as unmodified heparin and chondroitin, respectively", DeAngelis et al., Carbohydrate Research 337:1547-1552 (2002).

"Identification and Molecular Cloning of a Heparosan Synthase from *Pasteurella multocida* Type D", DeAngelis et al., The Journal of Biological Chemistry. 277(9):7209-7213 (2002).

"Identification of the *Xenopus laevis* cDNA for EXT1: A Phylogenetic Perspective", Hill et al., DNA Sequence, 13 (2):85-92 (2002).

"cDNA cloning and distribution of XEXT1, the *Xenopus homologue* of EXT1", Katada et al., Dev Genese Evol. 212:248-250 (2002).

"Demonstration of a Novel Gene DEXT3 of *Drosophila melanogaster* as the Essential N-Acetylglucosamine Transferase in the Heparan Sulfate Biosynthesis", Kim et al., The Journal of Biological Chemistry, 277(16):13659-13665 (2002).

"Inhibition of B16-BL6 melanoma lung colonies by semisynthetic sulfaminoheparosan sulfates from *E. Coli* K5 polysaccharide", Poggi et al., Semin Thromb Hemost. 28(4):383-92 (2002).

"Heparin and Heparan Sulfate Biosynthesis", Sugahara et al., Life, 54:163-175 (2002).

"Hereditary multiple exostoses and heparan sulfate polymerization", Zak et al., Biochimica et Biophysica Acta 1573:346-355 (2002).

Molecular Cloning and Expression of Human Chondroitin N-Acetylgalactosaminyltransferase, Toru Uyama, et al. Journal of Biological Chemistry, vol. 277, No. 11, pp. 8841-8846, Jan. 2002.

Molecular Cloning and Characterization of Chondroitin Polymerase From *Escherichia coli* Strain K4, Toshio Ninomiya, et al., Journal of Biological Chemistry, vol. 277, No. 24, pp. 21567-21575, Apr. 2002.

Molecular Cloning and Characterization of a Novel Chondroitin Sulfate Glucuronyltransferase That Transfers Glucuronic Acid to N-Acetylgalactosamine, Masanori Gotoh, et al., Journal of Biological Chemistry, vol. 277, No. 41, pp. 38179-38188, Jul. 2002.

Structure Function Analysis of *Pasteurella glycosaminoglycan* Synthesis, Wei Jing, et al., Glycobiology, vol. 12, No. 10, pp. 705, Oct. 2002.

"Detection of Submicrogram Quantities of Glycosaminoglycans on Agarose Gels by Sequential Staining With Toluidine Blue and Stains-All", Volpi and Maccari, Electrophoresis, 23(24):4060-4066 (2002).

"Structural/Functional Characterization of the Alpha 2-Plasmin Inhibitor C-Terminal Peptide", Frank et al., Biochemistry, 42:1078-1085 (2003).

"Trp-999 of Beta-Galactosidase (*Escherichia coli*) is a Key Residue for Binding, Catalysis, and Synthesis of Allolactose, The Natural LAC Operon Inducer", Huber et al., Biochemistry, 42(6): 1796-1803 (2003).

"Separation of Capsular Polysaccharide K4 and Defructosylated K4 Derived Disaccharides by High-Performance Capillary Electrophoresis and High-Performance Liquid Chromatography", Volpi, Electrophoresis, 24(6): 1063-1068 (2003).

"Milligram-Scale Preparation and Purification of Oligosaccharides of Defined Length Possessing the Structure of Chondroitin From Defructosylated Capsular Polysaccharide K4", Volpi, Glycobiology, 13(9):635-640 (2003).

"Broad spectrum inhibition of HIV-1 infection by sulfated K5 *Escherichia coli* polysaccharide derivatives", Vicenzi et al., AIDS. 17(2):177-81 (2003).

* cited by examiner

Figure 9

| Mutants | Enzyme Specific Activity | | |
|---|---|---|---|
| | HAS | GlcNAc-Tase | GlcUA-Tase |
| D477N | 4.7 % | 198.8 % | 2 % |
| D477K | 0.15 % | 71.3 % | 1.8 % |
| D477E | 7.1 % | 51.8 % | 4.7 % |
| D196N | 0.1 % | 0 | 73.9 % |
| D196K | 0.01 % | 3.4 % | 98 % |
| D196E | 0.26 % | 6.75 % | 60 % |

```
1                                                          972
|──────────────────────────────────────────────────────────|  pmHAS 1                                      703
|──────────────────────────────────────|  pmHAS^(1-703)

[Domain A1]         [Domain A2]
       *                   *
    D247/249            D527/529
```

B

```
A1  SIIVTTFNRPAILSITLACLVNQKTHYPFEVIVTD
A2  SIYIPAYNCANYIQRCVDSALNQ-TTVDLEVCICN

A1  DGSQEDLSPIIRQYENKLDIRYVRQKDNGFQASAAR
A2  DGSTDNTLEVINKLYGNNPRVRIMSKPNGGIASAS-
          *
       D247/249

A1  NMGLRLAKYDFIGLLDCDMAPNPLWVHSYVAELLED
A2  NAAVSFAKGYYIGQLDSDDYLEPDAVELCLKEFLKD
          *
       D527/529
```

Figure 15

```
        1                                                                    50
pmCS    MNTLSQAIKA YNSNDYELAL KLFEKSAETY GRKIVEFQII KCKEKLSTNS
pmHAS   ---------- ------Q--- --------I- ---------T --------AHP 51                                                                  100
pmCS    YVS------- EDKKNSVCDS SLDIATQLLL SNVKKLTLSE SEKNSLKNKW
pmHAS   S-NSAHLSVN KEE-VN---- P--------- ------V--D ----T-----

101                                                                 150
pmCS    KSITGKKSEN AEIRKVELVP KDFPKDLVLA PLPDHVNDFT WYKNRKKSLG
pmHAS   -LL-E----- --V-A-A--- ---------- ---------- ---K---R--

151                                                                 200
pmCS    IKPVNKNIGL SIIIPTFNRS RILDITLACL VNQKTNYPFE VVVADDGSKE
pmHAS   ---EKQHV-- ---VT----P A--S------ ------H--- -I-T----Q-

201                                                                 250
pmCS    NLLTIVQKYE QKLDIKYVRQ KDYGYQLCAV RNLGLRTAKY DFVSILDCDM
pmHAS   D-SP-IRQ-- N----R---- --N-F-AS-A --M---L--- --IGL-----

251                                                                 300
pmCS    APQQLWVHSY LTELLEDNDI VLIGPRKYVD THNITAEQFL NDPYLIESLP
pmHAS   --NP------ VA-----D-L TI------I- -QH-DPKD-- -NAS-L----

301                                                                 350
pmCS    ETATNNNPSI TSKGNISLDW RLEHFKKTDN LRLCDSPFRY FVAGNVAFSK
pmHAS   -VK---SVAA KGE-TV---- ---Q-E--E- ---S-----F -A------A-

351                                                                 400
pmCS    EWLNKVGNFD EEFNHWGGED VEFGYRLFAK GCFFRVIDGG MAIHQEPPGK
pmHAS   K----S-F-- ---------- --------R- -S--KT---I --Y-------

401                                                                 450
pmCS    ENETEREAGK SITLKIVKEK VPYIYRKLLP IEDSHIHRIP LVSIYIPAYN
pmHAS   ----D----- N---D-MR-- ---------- ------N-V- ----------

451                                                                 500
pmCS    CANYIQRCVD SALNQTVVDL EVCICNDGST DNTLEVINKL YGNNPRVRIM
pmHAS   ---------- ---------- ---------- ---------- ----------

501                                                                 550
pmCS    SKPNGGIASA SNAAVSFAKG YYIGQLDSDD YLEPDAVELC LKEFLKDKTL
pmHAS   ---------- ---------- ---------- ---------- ----------

551                                                                 600
pmCS    ACVYTTNRNV NPDGSLIANG YNWPEFSREK LTTAMIAHHF RMFTIRAWHL
pmHAS   ---------- ---------- ---------- ---------- ----------

601                                                                 650
pmCS    TDGFNENIEN AVDYDMFLKL SEVGKFKHLN KICYNRVLHG DNTSIKKLGI
pmHAS   ------K--- ---------- ---------- ---------- ----------

651                                                                 700
pmCS    QKKNHFVVVN QSLNRQGINY YNYDKFDDLD ESRKYIFNKT AEYQEEMDML
pmHAS   ---------- --------T- ----E----- ---------- ------I-I-

701                                                                 750
pmCS    KDLKLIQNKD AKIAVSIFYP NTLNGLVKKL NNITEYNKNI FVIILHVDKN
pmHAS   --I-I----- ---------- ---------- ---------- ---V------

751                                                                 800
pmCS    HLTPDIKKEI LAFYHKHQVN ILLNNDISYY TSNRLIKTEA HLSNINKLSQ
pmHAS   ---------- ---------- ---------- ---------- ----------

801                                                                 850
pmCS    LNLNCEYIIF DNHDSLFVKN DSYAYMKKYD VGMNFSALTH DWIEKINAHP
pmHAS   ---------- ---------- ---------- ---------- ----------

851                                                                 900
pmCS    PFKKLIKTYF NDNDLRSMNV KGASQGMFMK YALPHELLTI IKEVITSCQS
pmHAS   ---------- -----K---- ---------T ---A------ ----------

901                                                                 950
pmCS    IDSVPEYNTE DIWFQFALLI LEKKTGHVFN KTSTLTYMPW ERKLQWTNEQ
pmHAS   ---------- ---------- ---------- ---------- ----------

951              972
pmCS    IQSAKKGENI PVNKFIINSI TL
pmHAS   -E---R---- ---------- --
```

Figure 19

```
HS1   APPLVSIIMTSHNTEKFIEASINSLLLQTYNNLEVIVVDDYSTDKTFQIA
KfiC  GKDLVSIIMSVFNSEDTIAYSLHSLLNQTYENIEILVCDDCSSDKSLEII      140
con   ...LVSIIM*..N*E..I...S..SLL.QTY#N.E!.V.DD.S*DK*.#I.

141
HS1   SRIANSTSKVKTFRLNSNLGTYFAKNTGILKSKGDIIFFQDSDDVCHHER
KfiC  KSIAYSSSRVKVYSSRKNQGPYNIRNELIKKAHGNFITFQDADDLSHPER      190
con   ..IA.S*S*VK.%....N.G.Y...N..I.K..G#.I.FQD.DD..H.ER 191
HS1   IERCVNALLSNKDNIAVRCAYSRINLETQNIIKVNDNKYKLGLITLGVYR
KfiC  IQRQVEVLRNNKAVICM.ANWIRVASNGKIQFFYDDKATRMSVVSSMIKK      240
con   I#R.V#.L..NK..I......R!.....#D...*$..!*..!.*

441
HS2   YITCDDDIRYPADYINTMIKKINKYND.KAAIGLHGVIFPSRVNKYFSSD
KfiA  IVLTDDDIIYPPDYVEKMLNFYNSFAIFNCIVGIHGCIYIDAFDGD.QSK      490
con   .!..DDDI.YP.DY!#.M....N.%......IG.HG.I%......S.

491
HS2   RIVYNFQKTFRKDTAVNILGTGTVAFRVSIFNKFSLSDEEHPGMVDIYFS
KfiA  RKVFSFTQGLLRPRVVNQLGTGTVFLKADQLPSLKYMDGSQR.FVDVRFS      540
con   R.V%.F.....*...VN.LGTGTV..*.......D......VD!.FS
```

Figure 21
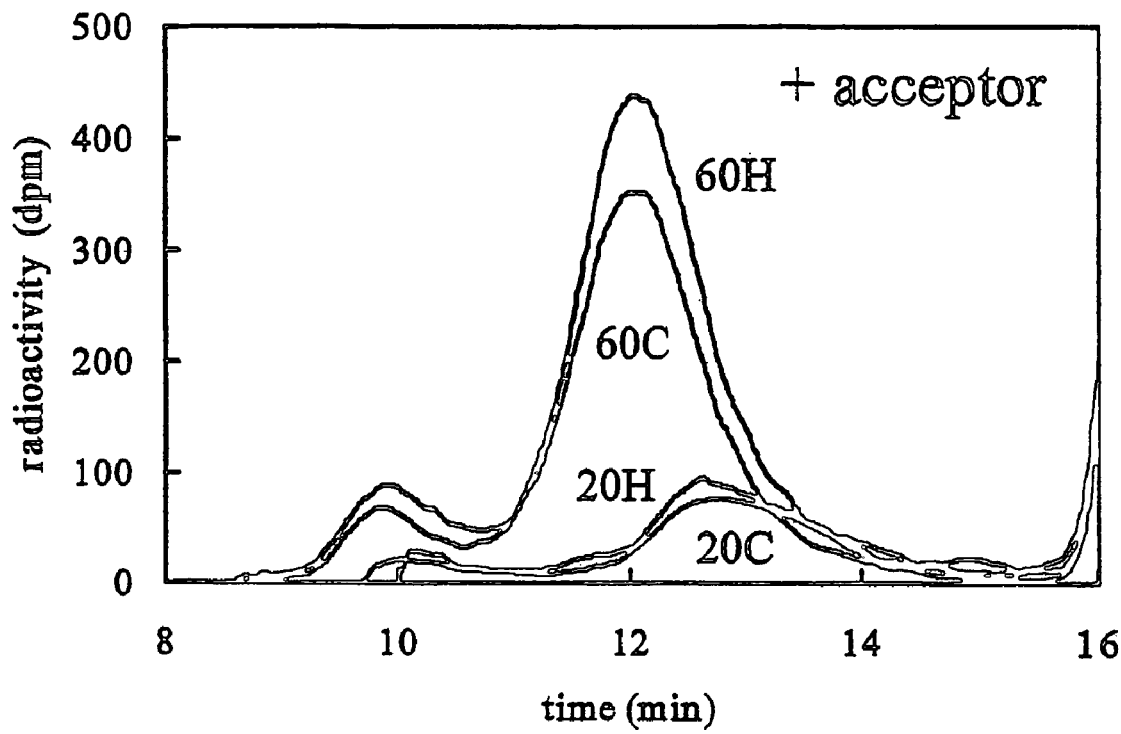
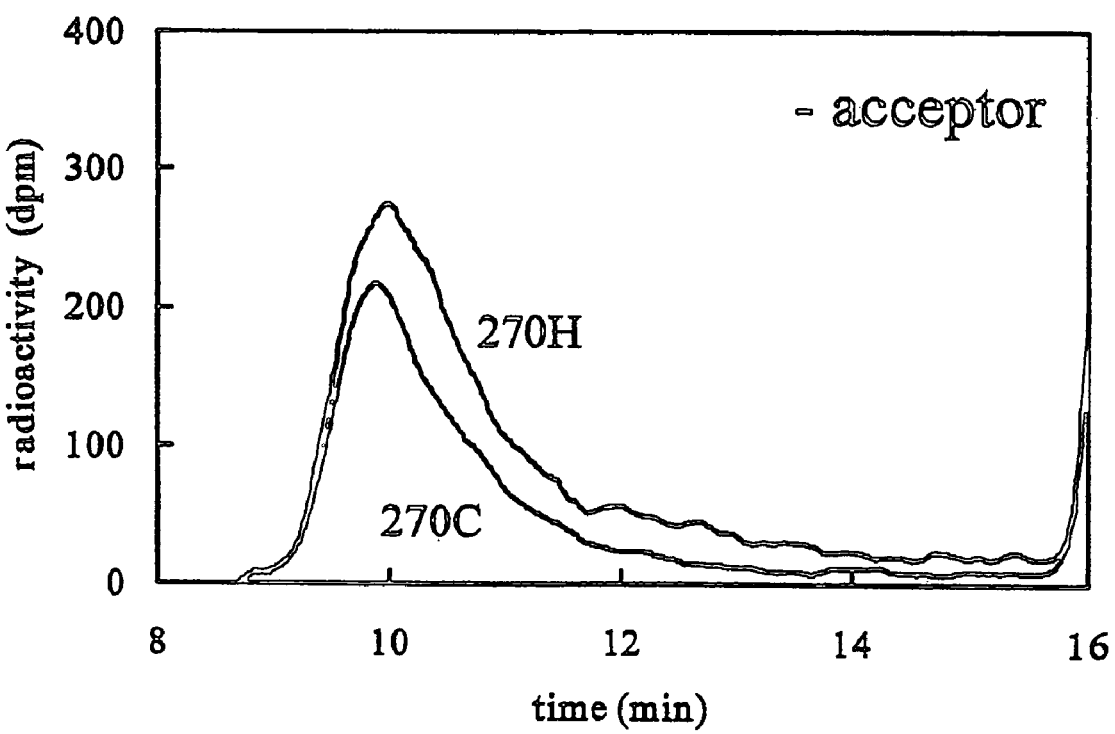

FIG. 22B

```
                1        10        20        30        40        50        60        70
                |---------+---------+---------+---------+---------+---------+---------|
       pmHS                         MSLFKRATELFKSGNYKDALTLYENIAKIYG----SESLVKYNIDI
       pglA     MKRKKEMTQKQMTKNPPQHEKENELNTFQMKIDSLKTTLNKDIISQQTLLAKQDSKHPLSASLENEMKLL
       DcbF                         MSLFKRATELFKSGNYKDALTLYENIAKIYG----SESLVKYNIDI
   Consensus    .............6slFkratelfKsgnyKDaltlyeniAKiyg....SeSLvkyNidi 71       80        90       100       110       120       130       140
                |---------+---------+---------+---------+---------+---------+---------|
       pmHS     CKK-NITQSKSNKIEEDNISGENKF----SVSIKDLYNEISNSELGITKERLGAPPLVSIIMTSHNNTEK
       pglA     LKQLQLVLQEFEKIYTYNQRLEAKLEKDKQTTSITDLYNEVAKSDLGLVKETNSVNPLVSIIMTSHNNTAQ
       DcbF     CKK-NITQSKSNKIEEDNISGENEF----SVSIKDLYNEISNSELGITKERLGAPPLVSIIMTSHNNTEK
   Consensus    cKk.0itqsksNKIeedNisgEnkf.....svSIkDLYNEI snSOLGitKErlgapPLVSIIMTSHNNTek 141      150       160       170       180       190       200       210
                |---------+---------+---------+---------+---------+---------+---------|
       pmHS     FIERSINSLLLQTYNNLEVIVVDDYSTDKTFQIASRIANSTSKVKTFRLNSNLGTYFAKNTGILKSKGDI
       pglA     FIERSINSLLLQTYKNIEIIIVDDDSSDNTFEIASRIANTTSKVRVFRLNSNLGTYFAKNTGILKSKGDI
       DcbF     FIERSINSLLLQTYNNLEVIVVDDYSTDKTFQIASRIANSTSKVKTFRLNSNLGTYFAKNTGILKSKGDI
   Consensus    FIERSINSLLLQTYnNlEiIIiVDDySt.DkTF@IASRIANsTSKVktFRLNSNLGTYFAKNTGILKSKGDI 211      220       230       240       250       260       270       280
                |---------+---------+---------+---------+---------+---------+---------|
       pmHS     IFFQDSDDVCHHERIERCVNALLSNKDNIAVRCAYSRINLETQNIIKVNDNKYKLGLITLGVYRKVFNEI
       pglA     IFFQDSDDVCHHERIERCVNILLANKETIAVRCAYSRLAPETQHIIKVNNMDYRLGFITLGNHRKVFQEI
       DcbF     IFFQDSDDVCHHERIERCVNALLSNKDNIAVRCAYSRINLETQNIIKVNDNKYKLGLITLGVYRKVFNEI
   Consensus    IFFQDSDDVCHHERIERCVNaLLsNK@nIAVRCAYSRinlETQnIIKVN@nkYkLGLITLGvyRKVFQEI 281      290       300       310       320       330       340       350
                |---------+---------+---------+---------+---------+---------+---------|
       pmHS     GFFNCTTKASDDEFYHRIIKYYGKNRINNLFLPLYYNTHREDSLFSDMVENVDENNIKQKTSDARQNYLH
       pglA     GFFNCTTKGSDDEFFHRIAKYYGKEKIKNLLLPLYYNTHREMSLFTDNVEKIDNHNIIQKNSDTRQHYAT
       DcbF     GFFNCTTKASDDEFYHRIIKYYGKNRINNLFLPLYYNTHREDSLFSDMVENVDENNIKQKTSDARQNYLH
   Consensus    GFFNCTTKaSDDEFZHRIiKYYGK0rInNlflPLYYNTHREOSLFsDNVEM IO@nNIkQKtSDaRQnYlh 351      360       370       380       390       400       410       420
                |---------+---------+---------+---------+---------+---------+---------|
       pmHS     EFQKIHNERKLNELKEIFSFPRIHDALPISKENSKLSNPKIPVYINICSIPSRIKQLQYTIGVLKNQCDH
       pglA     LFQAMHNETASHDFKNLFQFPRIYDALPVPQENSKLSNPKIPVYINICSIPSRIAQLRRIIGILKNQCDH
       DcbF     EFQKIHNERKFNELKEIFSFPRIHDALPISKENSKLSNPKIPVYINICSIPSRIKQLQYTIGVLKNQCDH
   Consensus    eFQkiHNErk.n@lK@ifsFPRIhDALP!skENSKLSNPKIPVYINICSIPSRIkQLqytIGILKNQCDH 421      430       440       450       460       470       480       490
                |---------+---------+---------+---------+---------+---------+---------|
       pmHS     FHIYLDGYPEVPDFIKKLGMKATVINCQMKNESIRDNGKFILLEKLIKENKDGYYITCDDDIRYPADYTN
       pglA     FHIYLDGYVEIPDFIKNLGNKATVVHCKDKDNSIRDNGKFILLEELIEKNQDGYYITCDDDIIYPSDYIN
       DcbF     FHIYLDGYPEVPDFIKKLGNKATVINCQMKNESIRDNGKFILLEKLIKENKDGYYITCDDDIRYPADYIN
   Consensus    FHIYLDGYpEIPDFIKkLGNKATVInCq@K@@SIRDNGKFILLEkLIkeNkDGYYITCDDDIrYPaDYiN 491      500       510       520       530       540       550       560
                |---------+---------+---------+---------+---------+---------+---------|
       pmHS     TMIKKINKYNDKAAIGLHGVIFPSRVNKYFSSDRIVYNFQKPLENDTAVNILGTGTVAFRVSIFNKFSLS
       pglA     TMIKKLNEYDDKAVIGLHGILFPSRHTKYFSADRLVYSFYKPLEKDKAVMVLGTGTVSFRVSLFNQFSLS
       DcbF     TMIKKINKYNDKAAIGLHGVIFPSRVNKYFSSDRIVYNFQKTFRK
   Consensus    TMIKKi.NkYODKRaIGLHG!iFPSRvnKYFSsDRiVYnFq@Xplekd.avn.lgtgtv.frvs.fn.fsls 561      570       580       590       600       610       620       630
                |---------+---------+---------+---------+---------+---------+---------|
       pmHS     DFEHPGMVDIYFSILCKKNNILQVCISRPSNWLTEDNKNTETLFHEFQNRDEIQSKLIISNNPHGYSSIY
       pglA     DFTHSGMADIYFSLLCKKNNILQICISRPANWLTEDNRDSETLYHQYRDNDEQQTQLIHENGPHGYSSIY
       DcbF
   Consensus    df.h.gm.diyfs.lckknnilq.cisrp.nwltedn...etl.h.....de.q..li..n.pwgyssiy 631      640       651
                |---------+---------+|
       pmHS     PLLNNNANYSELIPCLSFYNE
       pglA     PLVKNHPKFTDLIPCLPFYFL
       DcbF
   Consensus    pl..n........lipcl.fy..
```

FIG. 22C

```
Multalin version 5.4.1
Copyright I.N.R.A. France 1989, 1991, 1994, 1996
Published research using this software should cite.
Multiple sequence alignment with hierarchical clustering
F. CORPET, 1988, Nucl. Acids Res., 16 (22), 10881-10890
Symbol comparison table: blosum62
Gap weight: 12
Gap length weight: 2
Consensus levels: high=90% low=50%
Consensus symbols:
 ! is anyone of IV
 $ is anyone of LM
 %. is anyone of FY
 # is anyone of NDQEBZ MSF:      651       Check:    0          ..
Name: A                 Len:  651  Check:  612   Weight:  0.58
Name: B                 Len:  651  Check:  249   Weight:  0.58
Name: pglA              Len:  651  Check: 7677   Weight:  1.08
Name: DcbF              Len:  651  Check: 7537   Weight:  1.76
Name: Consensus         Len:  651  Check: 5816   Weight:  0.00

//
```

```
                    1                                                                    50
         A2         ..........  ..........  ....MSLFKR  ATELFKSGNY  KDALTLYENI
        B10         ..........  ..........  ....MSLFKR  ATELFKSGNY  KDALTLYENI
       pglA         MKRKKEMTQK  QMTKNPPQHE  KENELNTFQN  KIDSLKTTLN  KDIISQQTLL
       DcbF         ..........  ..........  ....MSLFKR  ATELFKSGNY  KDALTLYENI
      sensus        ..........  ..........  ....$slFkr  at#lfKsgny  KDaltlyeni 51                                                                  100
         A2         AKIYG....S  ESLVKYNIDI  CKK.NITQSK  SNKIEEDNIS  GENKF.....
        B10         AKIYG....S  ESLVKYNIDI  CKK.NITQSK  SNKIEEDNIS  GENKF.....
       pglA         AKQDSKHPLS  ASLENENKLL  LKQLQLVLQE  FEKIYTYNQA  LEAKLEKDKQ
       DcbF         AKIYG....S  ESLVKYNIDI  CKK.NITQSK  SNKIEEDNIS  GENKF.....
    Consensus       AKiyg....S  eSLvkyNidi  cKk.#itqsk  s#KIeedNis  gEnkf.....

101                                                                 150
         A2         SVSIKDLYNE  ISNSELGITK  ERLGAPPLVS  IIMTSHNTEK  FIEASINSLL
        B10         SVSIKDLYNE  ISNSELGITK  ERLGAPPLVS  IIMTSHNTEK  FIEASINSLL
       pglA         TTSITDLYNE  VAKSDLGLVK  ETNSVNPLVS  IIMTSHNTAQ  FIEASINSLL
       DcbF         SVSIKDLYNE  ISNSELGITK  ERLGAPPLVS  IIMTSHNTEK  FIEASINSLL
    Consensus       svSIkDLYNE  !snS#LGitK  ErlgapPLVS  IIMTSHNTek  FIEASINSLL 151                                                                 200
         A2         LQTYNNLEVI  VVDDYSTDKT  FQIASRIANS  TSKVKTFRLN  SNLGTYFAKN
        B10         LQTYNNLEVI  VVDDYSTDKT  FQIASRIANS  TSKVKTFRLN  SNLGTYFAKN
       pglA         LQTYKNIEII  IVDDDSSDNT  FEIASRIANT  TSKVRVFRLN  SNLGTYFAKN
       DcbF         LQTYNNLEVI  VVDDYSTDKT  FQIASRIANS  TSKVKTFRLN  SNLGTYFAKN
    Consensus       LQTYnNlE!I  !VDDyStDkT  F#IASRIANs  TSKVktFRLN  SNLGTYFAKN
```

FIG. 22C cont'd.

```
             201                                                              250
       A2    TGILKSKGDI  IFFQDSDDVC  HHERIERCVN  ALLSNKDNIA  VRCAYSRINL
      B10    TGILKSKGDI  IFFQDSDDVC  HHERIERCVN  ALLSNKDNIA  VRCAYSRINL
      pglA   TGILKSKGDI  IFFQDSDDVC  HHERIERCVN  ILLANKETIA  VRCAYSRLAP
      DcbF   TGILKSKGDI  IFFQDSDDVC  HHERIERCVN  ALLSNKDNIA  VRCAYSRINL
 Consensus   TGILKSKGDI  IFFQDSDDVC  HHERIERCVN  aLLsNK#nIA  VRCAYSRinl 251                                                              300
       A2    ETQNIIKVND  NKYKLGLITL  GVYRKVFNEI  GFFNCTTKAS  DDEFYHRIIK
      B10    ETQNIIKVND  NKYKLGLITL  GVYRKVFNEI  GFFNCTTKAS  DDEFYHRIIK
      pglA   ETQHIIKVNN  MDYRLGFITL  GMHRKVFQEI  GFFNCTTKGS  DDEFFHRIAK
      DcbF   ETQNIIKVND  NKYKLGLITL  GVYRKVFNEI  GFFNCTTKAS  DDEFYHRIIK
 Consensus   ETQnIIKVN#  nkYkLGlITL  GvyRKVF#EI  GFFNCTTKaS  DDEF%HRIiK 301                                                              350
       A2    YYGKNRINNL  FLPLYYNTMR  EDSLFSDMVE  WVDENNIKQK  TSDARQNYLH
      B10    YYGKNRINNL  FLPLYYNTMR  EDSLFSDMVE  WVDENNIKQK  TSDARQNYLH
      pglA   YYGKEKIKNL  LLPLYYNTMR  ENSLFTDMVE  WIDNHNIIQK  MSDTRQHYAT
      DcbF   YYGKNRINNL  FLPLYYNTMR  EDSLFSDMVE  WVDENNIKQK  TSDARQNYLH
 Consensus   YYGK#rInNL  fLPLYYNTMR  E#SLFsDMVE  W!D#nNIkQK  tSDaRQnYlh 351                                                              400
       A2    EFQKIHNERK  LNELKEIFSF  PRIHDALPIS  KEMSKLSNPK  IPVYINICSI
      B10    EFQKIHNERK  LNELKEIFSF  PRIHDALPIS  KEMSKLSNPK  IPVYINICSI
      pglA   LFQAMHNETA  SHDFKNLFQF  PRIYDALPVP  QEMSKLSNPK  IPVYINICSI
      DcbF   EFQKIHNERK  FNELKEIFSF  PRIHDALPIS  KEMSKLSNPK  IPVYINICSI
 Consensus   eFQkiHNErk  .n#lK#iFsF  PRIhDALP!s  kEMSKLSNPK  IPVYINICSI 401                                                              450
       A2    PSRIKQLQYT  IGVLKNQCDH  FHIYLDGYPE  VPDFIKKLGN  KATVINCQNK
      B10    PSRIKQLQYT  IGVLKNQCDH  FHIYLDGYPE  VPDFIKKLGN  KATVINCQNK
      pglA   PSRIAQLRRI  IGILKNQCDH  FHIYLDGYVE  IPDFIKNLGN  KATVVHCKDK
      DcbF   PSRIKQLQYT  IGVLKNQCDH  FHIYLDGYPE  VPDFIKKLGN  KATVINCQNK
 Consensus   PSRIkQLqyt  IG!LKNQCDH  FHIYLDGYpE  !PDFIKkLGN  KATV!nCq#K 451                                                              500
       A2    NESIRDNGKF  ILLEKLIKEN  KDGYYITCDD  DIRYPADYTN  TMIKKINKYN
      B10    NESIRDNGKF  ILLEKLIKEN  KDGYYITCDD  DIRYPADYIN  TMIKKINKYN
      pglA   DNSIRDNGKF  ILLEELIEKN  QDGYYITCDD  DIIYPSDYIN  TMIKKLNEYD
      DcbF   NESIRDNGKF  ILLEKLIKEN  KDGYYITCDD  DIRYPADYIN  TMIKKINKYN
 Consensus   ##SIRDNGKF  ILLEkLIkeN  kDGYYITCDD  DIrYPaDYiN  TMIKKiNkY#

501                                                              550
       A2    DKAAIGLHGV  IFPSRVNKYF  SSDRIVYNFQ  KPLENDTAVN  ILGTGTVAFR
      B10    DKAAIGLHGV  IFPSRVNKYF  SSDRIVYNFQ  KPLENDTAVN  ILGTGTVAFR
      pglA   DKAVIGLHGI  LFPSRMTKYF  SADRLVYSFY  KPLEKDKAVN  VLGTGTVSFR
      DcbF   DKAAIGLHGV  IFPSRVNKYF  SSDRIVYNFQ  KTFRK.....  ..........
 Consensus   DKAaIGLHG!  iFPSRvnKYF  SsDRiVYnFq  Kplekd.avn  .lgtgtv.fr 551                                                              600
       A2    VSIFNKFSLS  DFEHPGMVDI  YFSILCKKNN  ILQVCISRPS  NWLTEDNKNT
      B10    VSIFNKFSLS  DFEHPGMVDI  YFSILCKKNN  ILQVCISRPS  NWLTEDNKNT
      pglA   VSLFNQFSLS  DFTHSGMADI  YFSLLCKKNN  ILQICISRPA  NWLTEDNRDS
      DcbF   ..........  ..........  ..........  ..........  ..........
 Consensus   vs.fn.fsls  df.h.gm.di  yfs.lckknn  ilq.cisrp.  nwltedn...
```

FIG. 22C cont'd.

```
            601                                                      650
       A2   ETLFHEFQNR  DEIQSKLIIS  NNPWGYSSIY  PLLNNNANYS  ELIPCLSFYN
      B10   ETLFHEFQNR  DEIQSKLIIS  NNPWGYSSIY  PLLNNNANYS  ELIPCLSFYN
      pglA  ETLYHQYRDN  DEQQTQLIME  NGPWGYSSIY  PLVKNHPKFT  DLIPCLPFYF
      DcbF  ..........  ..........  ..........  ..........  ..........
Consensus   etl.h.....  de.q..li..  n.pwgyssiy  pl..n.....  .lipcl.fy.

651
       A2   E
      B10   E
      pglA  L
      DcbF  .
Consensus   .
```

FIG. 22D

```
Multalin version 5.4.1
Copyright I.N.R.A. France 1989, 1991, 1994, 1996
Published research using this software should cite
Multiple sequence alignment with hierarchical clustering
F. CORPET, 1988, Nucl. Acids Res., 16 (22), 10881-10890
Symbol comparison table: blosum62
Gap weight: 12
Gap length weight: 2
Consensus levels: high=90% low=50%
Consensus symbols:
 ! is anyone of IV
 $ is anyone of LM
 % is anyone of FY
 # is anyone of NDQEBZ MSF:     651      Check:    0      ..
Name: pmHS            Len:   651  Check:  612  Weight:  0.75
Name: pglA            Len:   651  Check: 7677  Weight:  0.75
Name: DcbF            Len:   651  Check: 7537  Weight:  1.49
Name: Consensus       Len:   651  Check: 5816  Weight:  0.00

//
```

```
                   1                                                                       50
         pmHS      ..........  ..........  ....MSLFKR  ATELFKSGNY  KDALTLYENI
         pglA      MKRKKEMTQK  QMTKNPPQHE  KENELNTFQN  KIDSLKTTLN  KDIISQQTLL
         DcbF      ..........  ..........  ....MSLFKR  ATELFKSGNY  KDALTLYENI
    Consensus      ..........  ..........  ....$slFkr  at#lfKsgny  KDaltlyeni 51                                                                     100
         pmHS      AKIYG....S  ESLVKYNIDI  CKK.NITQSK  SNKIEEDNIS  GENKF.....
         pglA      AKQDSKHPLS  ASLENENKLL  LKQLQLVLQE  FEKIYTYNQA  LEAKLEKDKQ
         DcbF      AKIYG....S  ESLVKYNIDI  CKK.NITQSK  SNKIEEDNIS  GENEF.....
    Consensus      AKiyg....S  eSLvkyNidi  cKk.#itqsk  s#KIeedNis  gEnkf.....

101                                                                    150
         pmHS      SVSIKDLYNE  ISNSELGITK  ERLGAPPLVS  IIMTSHNTEK  FIEASINSLL
         pglA      TTSITDLYNE  VAKSDLGLVK  ETNSVNPLVS  IIMTSHNTAQ  FIEASINSLL
         DcbF      SVSIKDLYNE  ISNSELGITK  ERLGAPPLVS  IIMTSHNTEK  FIEASINSLL
    Consensus      svSIkDLYNE  !snS#LGitK  ErlgapPLVS  IIMTSHNTek  FIEASINSLL 151                                                                    200
         pmHS      LQTYNNLEVI  VVDDYSTDKT  FQIASRIANS  TSKVKTFRLN  SNLGTYFAKN
         pglA      LQTYKNIEII  IVDDDSSDNT  FEIASRIANT  TSKVRVFRLN  SNLGTYFAKN
         DcbF      LQTYNNLEVI  VVDDYSTDKT  FQIASRIANS  TSKVKTFRLN  SNLGTYFAKN
    Consensus      LQTYnNlE!I  !VDDyStDkT  F#IASRIANs  TSKVktFRLN  SNLGTYFAKN 201                                                                    250
         pmHS      TGILKSKGDI  IFFQDSDDVC  HHERIERCVN  ALLSNKDNIA  VRCAYSRINL
         pglA      TGILKSKGDI  IFFQDSDDVC  HHERIERCVN  ILLANKETIA  VRCAYSRLAP
         DcbF      TGILKSKGDI  IFFQDSDDVC  HHERIERCVN  ALLSNKDNIA  VRCAYSRINL
    Consensus      TGILKSKGDI  IFFQDSDDVC  HHERIERCVN  aLLsNK#nIA  VRCAYSRinl 251                                                                    300
         pmHS      ETQNIIKVND  NKYKLGLITL  GVYRKVFNEI  GFFNCTTKAS  DDEFYHRIIK
         pglA      ETQHIIKVNN  MDYRLGFITL  GMHRKVFQEI  GFFNCTTKGS  DDEFFHRIAK
         DcbF      ETQNIIKVND  NKYKLGLITL  GVYRKVFNEI  GFFNCTTKAS  DDEFYHRIIK
    Consensus      ETQnIIKVN#  nkYkLGlITL  GvyRKVF#EI  GFFNCTTKaS  DDEF%HRIiK
```

FIG. 22D cont'd.

```
              301                                                      350
       pmHS   YYGKNRINNL FLPLYYNTMR EDSLFSDMVE WVDENNIKQK TSDARQNYLH
       pglA   YYGKEKIKNL LLPLYYNTMR ENSLFTDMVE WIDNHNIIQK MSDTRQHYAT
       DcbF   YYGKNRINNL FLPLYYNTMR EDSLFSDMVE WVDENNIKQK TSDARQNYLH
  Consensus   YYGK#rInNL fLPLYYNTMR E#SLFsDMVE W!D#nNIkQK tSDaRQnYlh 351                                                      400
       pmHS   EFQKIHNERK LNELKEIFSF PRIHDALPIS KEMSKLSNPK IPVYINICSI
       pglA   LFQAMHNETA SHDFKNLFQF PRIYDALPVP QEMSKLSNPK IPVYINICSI
       DcbF   EFQKIHNERK FNELKEIFSF PRIHDALPIS KEMSKLSNPK IPVYINICSI
  Consensus   eFQkiHNErk .n#lK#iFsF PRIhDALP!s kEMSKLSNPK IPVYINICSI 401                                                      450
       pmHS   PSRIKQLQYT IGVLKNQCDH FHIYLDGYPE VPDFIKKLGN KATVINCQNK
       pglA   PSRIAQLRRI IGILKNQCDH FHIYLDGYVE IPDFIKNLGN KATVVHCKDK
       DcbF   PSRIKQLQYT IGVLKNQCDH FHIYLDGYPE VPDFIKKLGN KATVINCQNK
  Consensus   PSRIkQLqyt IG!LKNQCDH FHIYLDGYpE !PDFIKkLGN KATV!nCq#K 451                                                      500
       pmHS   NESIRDNGKF ILLEKLIKEN KDGYYITCDD DIRYPADYTN TMIKKINKYN
       pglA   DNSIRDNGKF ILLEELIEKN QDGYYITCDD DIIYPSDYIN TMIKKLNEYD
       DcbF   NESIRDNGKF ILLEKLIKEN KDGYYITCDD DIRYPADYIN TMIKKINKYN
  Consensus   ##SIRDNGKF ILLEkLIkeN kDGYYITCDD DIrYPaDYiN TMIKKiNkY#

501                                                      550
       pmHS   DKAAIGLHGV IFPSRVNKYF SSDRIVYNFQ KPLENDTAVN ILGTGTVAFR
       pglA   DKAVIGLHGI LFPSRMTKYF SADRLVYSFY KPLEKDKAVN VLGTGTVSFR
       DcbF   DKAAIGLHGV IFPSRVNKYF SSDRIVYNFQ KTFRK..... ..........
  Consensus   DKAaIGLHG! iFPSRvnKYF SsDRiVYnFq Kplekd.avn .lgtgtv.fr 551                                                      600
       pmHS   VSIFNKFSLS DFEHPGMVDI YFSILCKKNN ILQVCISRPS NWLTEDNKNT
       pglA   VSLFNQFSLS DFTHSGMADI YFSLLCKKNN ILQICISRPA NWLTEDNRDS
       DcbF   .......... .......... .......... .......... ..........
  Consensus   vs.fn.fsls df.h.gm.di yfs.lckknn ilq.cisrp. nwltedn...

601                                                      650
       pmHS   ETLFHEFQNR DEIQSKLIIS NNPWGYSSIY PLLNNNANYS ELIPCLSFYN
       pglA   ETLYHQYRDN DEQQTQLIME NGPWGYSSIY PLVKNHPKFT DLIPCLPFYF
       DcbF   .......... .......... .......... .......... ..........
  Consensus   etl.h..... de.q..li.. n.pwgyssiy pl..n..... .lipcl.fy.

651
       pmHS   E
       pglA   L
       DcbF   .
  Consensus   .
```

Figure 23

| enzyme | activity |
|---|---|
| pmHAS 1-703 | HAS |
| pmCS 1-704 | CS |
| pm-EG | GlcUA-Tase |
| pm-FH | CS |
| pm-IK | GlcUA-Tase |
| pm-JL | HAS |

Figure 24

```
             211        220         230         240         250
             |----------+-----------+-----------+-----------+-
    PnHAS    NKLDIRYVRQKDNGFQASAARNNGLRLAKYDFIGLLDCDM
    PnCS     QKLDIKYVRQKDYGYQLCAVRNLGLRTAKYDFVSILDCDM
    Turkey   EKLDIKYVRQKDYGYQLCAVRNLGLRTAKYDFVSILDCDM
    Goose        VDIKYVRQKDYGYQLCAVRNLGLRTAKYDFVSILDC
    Sea-lion       KYVRQKDYGYQLCAVRNLGLRTAKYDFVSILDC
    Consensus  ...dikYVRQKDyGXQlcAvRN$GLRtAKYDF!siLDC...
                              □       ═                ─
              mutant 1        ☆
              mutant 2              ☆
              mutant 3               ☆
              mutant 4        ☆     ☆
              mutant 5        ☆      ☆
              mutant 6              ☆☆
              mutant 7        ☆     ☆☆
              mutant 8
              mutant 9                               ☆☆☆
```

Figure 26

| enzyme | activity | | |
|---|---|---|---|
| | HAS | CS | GlcUA-Tase |
| pm-BD | - | + | |
| pm-AC | + | - | |
| pm-FH | - | + | + |
| pm-EG | - | - | + |
| Pm-JL | + | - | + |
| pm-IK | - | - | + |
| pmCHC | + | + | + |
| pmHCH | not expressed | | |

METHODS OF PRODUCING HYALURONIC ACID AND CHIMERIC AND HYBRID GLYCOSAMINOGLYCAN POLYMERS

CROSS-REFERENCE TO RELATED APPLICATIONS

This application is a continuation of U.S. Ser. No. 10/195,908, filed Jul. 15, 2002, now abandoned; which claims benefit under 35 U.S.C. 119(e) of U.S. Ser. No. 60/305,263, filed Jul. 13, 2001.

Said application U.S. Ser. No. 10/195,908 is also a continuation-in-part of U.S. Ser. No. 09/437,277, filed Nov. 10, 1999, now U.S. Pat. No. 6,444,447, issued Sep. 3, 2002; which claims benefit under 35 U.S.C. 119(e) of U.S. Ser. No. 60/107,929, filed Nov. 11, 1998.

Said application U.S. Ser. No. 10/195,908 is also a continuation-in-part of U.S. Ser. No. 09/283,402, filed Apr. 1, 1999, now abandoned; which claims benefit under 35 U.S.C. 119(e) of U.S. Ser. No. 60/080,414, filed Apr. 2, 1998.

Said application U.S. Ser. No. 10/195,908 is also a continuation-in-part of U.S. Ser. No. 09/842,484, filed Apr. 25, 2001, now abandoned; which claims benefit under 35 U.S.C. 119(e) of U.S. Ser. No. 60/199,538, filed Apr. 25, 2000.

Said application U.S. Ser. No. 10/195,908 is also a continuation-in-part of U.S. Ser. No. 10/142,143, filed May 8, 2002; now U.S. Pat. No. 7,307,159 which claims benefit under 35 U.S.C. 119(e) of U.S. Ser. No. 60/289,554, filed May 8, 2001

Said application U.S. Ser. No. 10/195,908 also claims benefit under 35 U.S.C. 119(e) of U.S. Ser. No. 60/350,642, filed Jan. 22, 2002; U.S. Ser. No. 60/345,497, filed Nov. 9, 2001; and U.S. Ser. No. 60/391,787, filed Jun. 20, 2002.

The contents of each of the above-referenced patents and patent applications are hereby expressly incorporated herein by reference in their entirety.

STATEMENT REGARDING FEDERALLY SPONSORED RESEARCH OR DEVELOPMENT

This application was supported in part by a grant from the National Science Foundation (grant number 9876193). The United States Government may have rights in and to this application by virtue of this funding.

BACKGROUND OF THE INVENTION

1. Field of the Invention

The present invention relates to methodology for the production of polymers, such as oligosaccharides, by a glycosaminoglycan synthase and, more particularly, polymer production utilizing glycosaminoglycan synthases from *Pasteurella multocida*.

Various oligosaccharides (small sugar chains) show potential as non-toxic therapeutic agents to modulate blood coagulation, cancer metastasis, or cell growth. Complex sugars cause biological effects by binding to target proteins including enzymes and receptors. Methodologies to synthesize many compounds, however, and to test for potency and selectivity are limiting steps in drug discovery. As such, the presently claimed and disclosed invention also relates to a chemoenzymatic synthesis methodology to create both pure, chimeric, and hybrid polymers, such as oligosaccharides, composed of hyaluronan, chondroitin, keratan, dermatan, heparin units, and combinations thereof (e.g., "chimeric or hybrid" polymers). A library of distinct oligosaccharides is used in parallel using a microarray format or a microtiter plate, for example. Target proteins implicated in diseases are thereafter tested for their ability to bind to microarrays or microtiter plates and thus have potential as therapeutic agents.

2. Description of the Related Art

Polysaccharides are large carbohydrate molecules comprising from about 25 sugar units to thousands of sugar units. Oligosaccharides are smaller carbohydrate molecules comprising less than about 25 sugar units. Animals, plants, fungi and bacteria produce an enormous variety of polysaccharide structures that are involved in numerous important biological functions such as structural elements, energy storage, and cellular interaction mediation. Often, the polysaccharide's biological function is due to the interaction of the polysaccharide with proteins such as receptors and growth factors. The glycosaminoglycan class of polysaccharides and oligosaccharides, which includes heparin, chondroitin, dermatan, keratan, and hyaluronic acid, plays major roles in determining cellular behavior (e.g., migration, adhesion) as well as the rate of cell proliferation in mammals. These polysaccharides and oligosaccharides are, therefore, essential for the correct formation and maintenance of the organs of the human body.

Several species of pathogenic bacteria and fungi also take advantage of the polysaccharide's role in cellular communication. These pathogenic microbes form polysaccharide surface coatings or capsules that are identical or chemically similar to host molecules. For instance, Group A & C *Streptococcus* and Type A *Pasteurella multocida* produce authentic hyaluronic acid capsules, and other *Pasteurella multocida* (Type F and D) and pathogenic *Escherichia coli* (K4 and K5) are known to make capsules composed of polymers very similar to chondroitin and heparin. The pathogenic microbes form the polysaccharide surface coatings or capsules because such a coating is nonimmunogenic and protects the bacteria from host defenses, thereby providing the equivalent of molecular camouflage.

Enzymes alternatively called synthases, synthetases, or transferases, catalyze the polymerization of polysaccharides found in living organisms. Many of the known enzymes also polymerize activated sugar nucleotides. The most prevalent sugar donors contain UDP, but ADP, GDP, and CMP are also used depending on (1) the particular sugar to be transferred and (2) the organism. Many types of polysaccharides are found at, or outside of, the cell surface. Accordingly, most of the synthase activity is typically associated with either the plasma membrane on the cell periphery or the Golgi apparatus membranes that are involved in secretion. In general, these membrane-bound synthase proteins are difficult to manipulate by typical procedures, and only a few enzymes have been identified after biochemical purification.

A larger number of synthases have been cloned and sequenced at the nucleotide level using "reverse genetic" approaches in which the gene or the complementary DNA (cDNA) was obtained before the protein was characterized. Despite this sequence information, the molecular details concerning the three-dimensional native structures, the active sites, and the mechanisms of catalytic action of the polysaccharide synthases, in general, are very limited or absent. For example, the catalytic mechanism for glycogen synthesis is not yet known in detail even though the enzyme was discovered decades ago. In another example, it is still a matter of debate whether most of the enzymes that produce heteropolysaccharides utilize one UDP-sugar binding site to transfer both precursors, or alternatively, if there exists two dedicated regions for each substrate.

A wide variety of polysaccharides are commercially harvested from many sources, such as xanthan from bacteria, carrageenans from seaweed, and gums from trees. This substantial industry supplies thousands of tons of these raw materials for a multitude of consumer products ranging from ice cream desserts to skin cream cosmetics. Vertebrate tissues and pathogenic bacteria are the sources of more exotic polysaccharides utilized in the medical field—e.g., as surgical aids, vaccines, and anticoagulants. For example, two glycosaminoglycan polysaccharides, heparin from pig intestinal mucosa and hyaluronic acid from rooster combs, are employed in several applications including clot prevention and eye surgery, respectively. Polysaccharides extracted from bacterial capsules (e.g., various *Streptococcus pneumoniae* strains) are utilized to vaccinate both children and adults against disease with varying levels of success. However, for the most part, one must use the existing structures found in the raw materials as obtained from nature. In many of the older industrial processes, chemical modification (e.g., hydrolysis, sulfation, and deacetylation) is used to alter the structure and properties of the native polysaccharide. However, the synthetic control and the reproducibility of large-scale reactions are not always successful. Additionally, such polysaccharides are only available having a large molecular weight distribution, and oligosaccharides of the same repeat units are not available.

Some of the current methods for designing and constructing carbohydrate polymers in vitro utilize: (i) difficult, multistep sugar chemistry, or (ii) reactions driven by transferase enzymes involved in biosynthesis, or (iii) reactions harnessing carbohydrate degrading enzymes catalyzing transglycosylation or hydrolysis. The latter two methods are often restricted by the specificity and the properties of the available naturally occurring enzymes. Many of these enzymes are neither particularly abundant nor stable but are almost always expensive. Overall, the procedures currently employed yield polymers containing between 2 and about 12 sugars. Unfortunately, many of the physical and biological properties of polysaccharides do not become apparent until the polymer contains 25, 100, or even thousands of monomers.

As stated above, polysaccharides are the most abundant biomaterials on earth, yet many of the molecular details of their biosynthesis and function are not clear. Hyaluronic acid or "HA" is a linear polysaccharide of the glycosaminoglycan class and is composed of up to thousands of $\beta(1,4)$GlcUA-$\beta$(1,3)GlcNAc repeats. In vertebrates, HA is a major structural element of the extracellular matrix and plays roles in adhesion and recognition. HA has a high negative charge density and numerous hydroxyl groups, therefore, the molecule assumes an extended and hydrated conformation in solution. The viscoelastic properties of cartilage and synovial fluid are, in part, the result of the physical properties of the HA polysaccharide. HA also interacts with proteins such as CD44, RHAMM, and fibrinogen thereby influencing many natural processes such as angiogenesis, cancer, cell motility, wound healing, and cell adhesion.

There are numerous medical applications of HA. For example, HA has been widely used as a viscoelastic replacement for the vitreous humor of the eye in ophthalmic surgery during implantation of intraocular lenses in cataract patients. HA injection directly into joints is also used to alleviate pain associated with arthritis. Chemically cross-linked gels and films are also utilized to prevent deleterious adhesions after abdominal surgery. Other researchers using other methods have demonstrated that adsorbed HA coatings also improve the biocompatibility of medical devices such as catheters and sensors by reducing fouling and tissue abrasion.

HA is also made by certain microbes that cause disease in humans and animals. Some bacterial pathogens, namely Gram-negative *Pasteurella multocida* Type A and Gram-positive *Streptococcus* Group A and C, produce an extracellular HA capsule which protects the microbes from host defenses such as phagocytosis. Mutant bacteria that do not produce HA capsules are $10^2$- and $10^3$-fold less virulent in comparison to the encapsulated strains. Furthermore, the *Paramecium bursaria Chlorella* virus (PBCV-1) directs the algal host cells to produce a HA surface coating early in infection.

The various HA synthases ("HAS"), the enzymes that polymerize HA, utilize UlP-GlcUA and UDP-GlcNAc sugar nucleotide precursors in the presence of a divalent Mn, Mg, or Co ion to polymerize long chains of HA. The HA chains can be quite large ($n=10^2$ to $10^4$). In particular, the HASs are membrane proteins localized to the lipid bilayer at the cell surface. During HA biosynthesis, the HA polymer is transported across the bilayer into the extracellular space. In all HASs, a single species of polypeptide catalyzes the transfer of two distinct sugars. In contrast, the vast majority of other known glycosyltransferases transfer only one monosaccharide.

HasA (or spHAS) from Group A *Streptococcus pyogenes* was the first HA synthase to be described at the molecular level. The various vertebrate homologs (*Xenopus* DG42 or XlHAS1; murine and human HAS1, HAS2, and HAS3) and the viral enzyme, A98R, are quite similar at the amino acid level to certain regions of the HasA polypeptide chain (~30% identity overall) and were discovered only after the sequence of spHAS was disclosed in 1994. At least 7 short motifs (5-9 residues) interspersed throughout these Class I enzymes are identical or quite conserved. The evolutionary relationship among these HA synthases from such dissimilar sources is not clear at present. The enzymes are predicted to have a similar overall topology in the bilayer: membrane-associated regions at the amino and the carboxyl termini flank a large cytoplasmic central domain (~200 amino acids). The amino terminal region appears to contain two transmembrane segments, while the carboxyl terminal region appears to contain three to five membrane-associated or transmembrane segments, depending on the species. Very little of these HAS polypeptide chains are expected to be exposed to the outside of the cell.

With respect to the reaction pathway utilized by this group of enzymes, mixed findings have been reported from indirect experiments. The Group A *streptococcal* enzyme was reported to add sugars to the nonreducing terminus of the growing chain as determined by selective labeling and degradation studies. Using a similar approach, however, two laboratories working with the enzyme preparations from mammalian cells concluded that the new sugars were added to the reducing end of the nascent chain. In comparing these various studies, the analysis of the enzymatically-released sugars from the *streptococcal* system added more rigorous support for their interpretation. In another type of experiment, HA made in mammalian cells was reported to have a covalently attached UDP group as measured by an incorporation of low amounts of radioactivity derived from $^{32}$P-labeled UDP-sugar into an anionic polymer. This data implied that the last sugar was transferred to the reducing end of the polymer. Thus, it remains unclear if these rather similar HAS polypeptides from vertebrates and streptococci actually utilize different reaction pathways.

On the other hand, the Class II HAS, pmHAS, has many useful catalytic properties including the ability to elongate exogenous acceptors at the non-reducing end with HA chains.

The homologous chondroitin synthase, pmCS, also is useful, but it adds chondroitin chains to the acceptor's non-reducing terminus.

To facilitate the development of biotechnological medical improvements, the present invention provides a method for the production of polysaccharides or oligosaccharides of HA, chondroitin, and chimeric or hybrid molecules incorporating both HA and chondroitin.

The present invention also encompasses the use of modified synthases that are controllable single-action catalysts that allow step-wise synthesis of polymers. An advantage of these mutant enzymes is that during synthesis of oligosaccharides, the intermediates do not need to be purified at every step, and each individual step can be driven to completion.

The present invention also encompasses the methodology of polysaccharide or oligosaccharide polymer grafting, i.e., HA or chondroitin, using either a hyaluronan synthase (pmHAS) or a chondroitin synthase (pmCS) or a heparin synthase (pmHS, PgIA) from various types of *P. multocida*. Modified versions of the pmHAS or pmCS or pmHS, or PgIA enzymes (whether genetically or chemically modified) can also be utilized to graft on polysaccharides of various size and composition. Such grafting methodologies have uses, but are not limited thereto, for the production of sugar libraries (both natural and chimeric or hybrid), protein-testing or cell-testing in microarray or microtiter plate formats.

SUMMARY OF THE INVENTION

A unique HA synthase, pmHAS, from the fowl cholera pathogen, Type A *P. multocida*, has been identified and cloned and is disclosed and claimed in co-pending U.S. Ser. No. 09/283,402, filed Apr. 1, 1999, and entitled "DNA Encoding Hyaluronan Synthase From *Pasteurella Multocida* and Methods," the contents of which are hereby expressly incorporated herein in their entirety. Expression of this single, 972-residue protein allows *Escherichia coli* host cells to produce HA capsules in vivo; normally *E. coli* does not make HA. Extracts of recombinant *E. coli*, when supplied with the appropriate UDP-sugars, make HA in vitro. Thus, the pmHAS is an authentic HA synthase.

A unique chondroitin synthase, pmCS, from Type F *P. multocida*, has been identified and cloned and is disclosed and claimed in co-pending U.S. Ser. No. 09/842,484, filed Apr. 25, 2002, and entitled "Chondroitin Synthase Gene and Methods of Making and Using Same", the contents of which are hereby expressly incorporated herein in their entirety. Expression of the catalytically active portion (residues 1-704) of this single, 965-residue protein allows *E. coli* host cells to produce an enzyme that will polymerize chondroitin chains. Laboratory strains of *E. coli* normally do not make chondroitin. Extracts of recombinant *E. coli*, when supplied with the appropriate UDP-sugars, make chondroitin in vitro. Thus, the pmCS is an authentic chondroitin synthase.

Two unique heparin synthases, PgIA and pmHS, from Type A, D, and F *P. multocida* and Type D *P. multocida*, respectively, have been identified and cloned and are disclosed and claimed in co-pending U.S. Ser. No. 10/142,143, filed May 8, 2002, and entitled "Heparin/Heparosan Synthase from *P. multocida* and Methods of Making and Using Same", the contents of which are hereby expressly incorporated herein in their entirety. Expression of these single 652-residue and 617-residue, respectively, proteins allows *E. coli* host cells to produce enzymes that polymerize heparosan chains. Laboratory strains of *E. coli* normally do not make heparin. Extracts of recombinant *E. coli*, when supplied with the appropriate UDP-sugars, make heparin in vitro. Thus, the PgIA and the pmHS are authentic heparin synthases.

It has also been determined that the recombinant pmHAS, pmHS, PgIA, and pmCS synthases add sugars to the nonreducing end of a growing polymer chain. The correct monosaccharides are added sequentially in a stepwise fashion to the nascent chain or a suitable exogenous HA or chondroitin oligosaccharide acceptor molecule. The pmHAS sequence, however, is significantly different from the other known HA synthases. There appears to be only two short potential sequence motifs ([D/N]DGS[S/T]; DSD[D/T]Y) in common between pmHAS and the Group A HAS-spHAS. Instead, a portion of the central region of the pmHAS is more homologous to the amino termini of other bacterial glycosyltransferases that produce different capsular polysaccharides or lipopolysaccharides. Furthermore, pmHAS is about twice as long as any other HAS enzyme.

When the pmHAS is given long elongation reaction times, HA polymers of at least 400 sugars long are formed. Unlike the Class I HA synthases, recombinant versions of pmHAS and pmCS produced in certain foreign hosts also have the ability to extend exogenously supplied HA or chondroitin oligosaccharides with long HA and chondroitin polymers in vitro, respectively. The recombinant pmHS and PgIA enzymes produced in a foreign host have the ability to extend HA, chondroitin, or heparin oligosaccharides with long heparosan chains in vitro. See e.g., U.S. Provisional Application No. 60/350,642 filed Jan. 22, 2002, the contents of which are expressly incorporated herein by reference in their entirety. If recombinant versions of pmHAS or pmCS or pmHS or PgIA are supplied with functional acceptor oligosaccharides, total HA, chondroitin and heparin biosynthesis is increased up to 50-fold over reactions without the exogenous oligosaccharide. The native versions of the pmHAS, pmCS, pmHS, and PgIA enzymes isolated from *P. multocida* do not perform such elongation reactions with exogenous acceptor (or perform with very low efficiency) due to the presence of a nascent HA, chondroitin, or heparin chain in the natural host. The nature of the polymer retention mechanism of the pmHAS, pmCS, pmHS, and PgIA polypeptide might be the causative factor for this activity: i.e. a HA- or chondroitin- or heparin-binding site may exist that holds onto the HA or chondroitin or heparin chain during polymerization. Small HA or chondroitin or heparin oligosaccharides supplied by the hand of man are also capable of occupying this site of the recombinant enzyme and thereafter be extended into longer polysaccharide chains.

Most membrane proteins are relatively difficult to study due to their insolubility in aqueous solution, and the native HASs, CSs, HSs, and PgIAs are no exception. The HAS enzyme from Group A and C *Streptococcus* bacteria has been detergent-solubilized and purified in an active state in small quantities. Once isolated in a relatively pure state, the *streptococcal* enzyme has very limited stability. A soluble recombinant form of the HAS enzyme from *P. multocida* called pmHAS$^{1-703}$ comprises residues 1-703 of the 972 residues of the native pmHAS enzyme. pmHAS$^{1-703}$ can be mass-produced in *E. coli* and purified by chromatography. The pmHAS$^{1-703}$ enzyme retains the ability of the parent enzyme to add onto either a long HA polymer, a short HA primer, a long chondroitin polymer, a short chondroitin primer, a short chondroitin polymer, as well as other exogenous acceptors. The chondroitin chain may also be sulfated. Furthermore, the purified pmHAS$^{1-703}$ enzyme is stable in an optimized buffer for days on ice and for hours at normal reaction temperatures. One formulation of the optimal buffer consists of 1M ethylene glycol, 0.1-0.2 M ammonium sulfate, 50 mM Tris, pH 7.2, and protease inhibitors which also allow the stability and specificity at typical reaction conditions for sugar transfer. For the reaction UDP-sugars and divalent manganese (10-20 mM) are added. pmHAS$^{1-703}$ will also add a HA polymer onto plastic beads with an immobilized short HA primer or any other substrate capable of having an acceptor molecule or acceptor group thereon.

pmCS, pmHAS, pnHS, and PgIA possess two separate glycosyltransferase sites. Protein truncation studies demonstrated that residues 1-117 of pmHAS can be deleted without affecting catalytic activity; similar truncation of the homologous pmCS, pmHS, and PgIA enzymes may also be preferred. The carboxyl-terminal boundary of the GlcUA-transferase of pmHAS resides within residues 686-703 and within residues 686-704 of pmCS. These sites each contain a DGS and DXD motif; all aspartate residues of these motifs are essential for HA synthase activity. D196, D247 and D249 mutants possessed only GlcUA-transferase activity while D477, D527 and D529 mutants possessed only GlcNAc-transferase activity. These results further confirm our previous assignment of the active sites within the synthase polypeptide. The WGGED sequence motif appears to be involved in GlcNAc-transferase activity because E396 mutants and D370 mutants possessed only GlcUA-transferase activity. The highly homologous (90% identical) pmCS can also be mutated in the same fashion. For example, mutating the homologous DXD motif in the GlcUA site of pmCS results in an enzyme with only GalNAc-transferase activity.

Type F P. multocida synthesizes an unsulfated chondroitin (β3N-acetylgalactosamine [GalNAc]-β4GlcUA) capsule. Domain swapping between pmHAS and the homologous chondroitin synthase, pmCS, has been performed. A chimeric or hybrid enzyme consisting of residues 1427 of pmHAS and residues 421-704 of pmCS was an active HA synthase. On the other hand, the converse chimeric or hybrid enzyme consisting of residues 1-420 of pmCS and residues 428-703 of pmHAS was an active chondroitin synthase. Overall, these findings support the model of two independent transferase sites within a single polypeptide as well as further delineate the site boundaries of both enzymes. The hexosamine-transferase site resides in the N-terminal domain while the GlcUA-transferase site resides in the COOH-terminal domain of these GAG synthases.

The present invention encompasses methods of producing a variety of unique biocompatible molecules and coatings based on polysaccharides. Polysaccharides, especially those of the glycosaminoglycan class, serve numerous roles in the body as structural elements and signaling molecules. By grafting or making hybrid molecules composed of more than one polymer backbone, it is possible to meld distinct physical and biological properties into a single molecule without resorting to unnatural chemical reactions or residues. The present invention also incorporates the propensity of certain recombinant enzymes, when prepared in a virgin state, to utilize various acceptor molecules as the seed for further polymer growth: naturally occurring forms of the enzyme or existing living wild-type host organisms do not display this ability. Thus, the present invention results in (a) the production of hybrid oligosaccharides or polysaccharides and (b) the formation of polysaccharide coatings. Such hybrid polymers can serve as "molecular glue"—i.e., when two cell types or other biomaterials interact with each half of a hybrid molecule, then each of the two phases are bridged.

Such polysaccharide coatings are useful for integrating a foreign object within a surrounding tissue matrix. For example, a prosthetic device is more firmly attached to the body when the device is coated with a naturally adhesive polysaccharide. Additionally, the device's artificial components could be masked by the biocompatible coating to reduce immunoreactivity or inflammation. Another aspect of the present invention is the coating or grafting of GAGs onto various drug delivery matrices or bioadhesives or suitable medicaments to improve and/or alter delivery, half-life, persistence, targeting and/or toxicity.

Recombinant pmHAS, pmCS, pmHS, and PgIA elongate exogenous functional oligosaccharide acceptors to form long or short polymers in vitro; thus far no other Class I HA synthase has displayed this capability. The directionality of synthesis was established definitively by testing the ability of pmHAS and pmCS and pmHS and PgIA to elongate defined oligosaccharide derivatives. The non-reducing end sugar addition allows the reducing end to be modified for other purposes; the addition of GAG chains to small molecules, polymers, or surfaces is thus readily performed. Analysis of the initial stages of synthesis demonstrated that pmHAS and pmCS and pmHS and PgIA added single monosaccharide units sequentially. Apparently the fidelity of the individual sugar transfer reactions is sufficient to generate the authentic repeating structure of HA or chondroitin or heparin. Therefore, simultaneous addition of disaccharide block units is not required as hypothesized in some recent models of polysaccharide biosynthesis. pmHAS and pmCS and pmHS and PgIA appear distinct from most other known HA and chondroitin and heparin synthases based on differences in sequence, topology in the membrane, and/or putative reaction mechanism.

As mentioned previously, pmHAS, the 972-residue membrane-associated hyaluronan synthase, catalyzes the transfer of both GlcNAc and GlcUA to form an HA polymer. In order to define the catalytic and membrane-associated domains, pmHAS and pmCS mutants have been analyzed. pmHAS$^{1-703}$ is a soluble, active HA synthase suggesting that the carboxyl-terminus is involved in membrane association of the native enzyme. pmHAS$^{1-650}$ is inactive as a HA synthase, but retains GlcNAc-transferase activity. Within the pmHAS sequence, there is a duplicated domain containing a short motif, DGS or Asp-Gly-Ser, that is conserved among many glycosyltransferases. Changing this aspartate in either domain to asparagine, glutamate, or lysine reduced the HA synthase activity to low levels. The mutants substituted at residue 196 possessed GlcUA-transferase activity while those substituted at residue 477 possessed GlcNAc-transferase activity. The Michaelis constants of the functional transferase activity of the various mutants, a measure of the apparent affinity of the enzymes for the precursors, were similar to wild-type values. Furthermore, mixing D196N and D477K mutant proteins in the same reaction allowed HA polymerization at levels similar to the wild-type enzyme. These results provide the first direct evidence that the synthase polypeptide utilizes two separate glycosyltransferase sites. Likewise, pmCS mutants were made and tested having the same functionality and sequence similarity to the mutants created for pmHAS.

Pasteurella multocida Type F, the minor fowl cholera pathogen, produces an extracellular polysaccharide capsule that is a putative virulence factor. As outlined in U.S. Ser. No. 09/842,484, filed Apr. 25, 2002, and entitled "Chondroitin Synthase Gene and Methods of Making and Using Same", the contents of which are hereby expressly incorporated herein in their entirety, the capsule of Pasteurella multocida Type F was removed by treating microbes with chondroitin AC lyase. It was found by acid hydrolysis that the polysaccharide contained galactosamine and glucuronic acid. A Type F polysaccharide synthase was molecularly cloned and its enzymatic activity was characterized. The 965-residue enzyme, called pmCS, is 90% identical at the nucleotide and the amino acid level to the hyaluronan synthase, pmHAS, from *P. multocida* Type A. A recombinant *Escherichia coli*-derived, truncated, soluble version of pmCS (residues 1-704) was shown to catalyze the repetitive addition of sugars from UDP-GalNAc and UDP-GlcUA to chondroitin oligosaccharide acceptors in vitro. Other structurally related sugar nucleotide precursors did not substitute in the elongation reaction. Polymer molecules composed of ~$10^3$ sugar residues were produced as measured by gel filtration chromatography. The polysaccharide synthesized in vitro was sensitive to the action of chondroitin AC lyase but resistant to the action of hyaluronan lyase. This was the first report identifying a glycosyltransferase that forms a polysaccharide composed of chondroitin disaccharide repeats, $[\beta(1,4)GlcUA-\beta(1,3)GalNAc]_n$. In analogy to known hyaluronan synthases, a single polypeptide species, pmCS, possesses both transferase activities. The heparin synthases, pmHS and PgIA, from *P. multocida*, also are single polypeptide specie that possesses both transferase activities to catalyze heparin/heparosan.

A major impetus for synthesizing HA and chondroitin and HA/chondroitin chimeric or hybrid oligosaccharides composed of 10 to 14 sugars according to the methodologies of the presently disclosed and claimed invention was triggered by reports demonstrating that these types of sugars have astounding effects on cellular behavior including the inhibition of cancer cell growth and metastasis (migration from the initial tumor). Dr. Bryan Toole of Tufts University has initially characterized the anticancer effects of HA sugars. See e.g. U.S. Pat. No. 5,902,795, the contents of which are hereby expressly incorporated herein in their entirety by reference. Unfortunately, Dr. Toole utilized primitive methods to prepare tiny amounts of the active sugars; therefore the animal studies conducted by Dr. Toole are limited by the quantity of oligosaccharide available by traditional means. The presently disclosed and claimed invention provides for the synthesis of oligosaccharide sugars that have been given the name "NanoHA." The term nanoHA signifies the very small molecular size of these oligosaccharides as well the precise step-wise control of synthesis.

Metastasis, the escape of cancer cells throughout the body, is one of the biggest fears of both the ailing patient and the physician, and this area is a well studied application with respect to HA involvement. nanoHA will serve as a supplemental treatment to inhibit cancer growth and metastasis in conjunction with existing cancertherapies. Large and economically available quantities of pure and exact molecular weight oligosaccharides of HA, chondroitin, heparin and HA/chondroitin/heparin chimeric or hybrid oligosaccharides have never been available.

HA oligosaccharide treatment of cancer cell lines in culture reduces their rate of proliferation. HA oligosaccharides are also very promising in an in vivo assay for tumor growth and metastasis. In the reported assay, mice were injected with an invasive and virulent tumor cell line, and the progression of disease (e.g., general health, number of tumors, size of tumors) was monitored at a 10 day timepoint. Treatment with HA oligosaccharides greatly reduced the number and the size of tumors. Untreated animals required euthanasia within 2-4 weeks because of tremendous tumor growth. Various cancer cell lines, including melanoma, glioma, carcinomas from lung, breast and ovary, are susceptible to the therapeutic action of HA oligosaccharides.

A very desirable attribute of HA-oligosaccharides for therapeutics is that these sugar molecules are natural by-products that occur in small amounts in the healthy human body during the degradation of HA polymer; no untoward innate toxicity, antigenicity, or allergenic concerns are obvious. The major current problem facing the development of the HA-based sugar therapeutics is that only very small amounts can be prepared by the currently known and used technologies.

The most promising initial target oligosaccharides for inhibition of cancer metastasis are HA chains composed of 10 to 14 sugars. The two current competing state-of-the-art techniques for creating the desired HA-oligosaccharides are extremely limited and will not allow the medical potential of the sugars to be achieved. Small HA molecules are presently made either by: (1) partially depolymerizing costly large polymers with degradative enzymes or with chemical means (e.g., heat, acid, sonification), or (2) highly demanding organic chemistry-based carbohydrate synthesis. The former method is difficult to control, inefficient, costly, and is in a relatively stagnant development stage. For example, the enzyme wants to degrade the polymer to the 4 sugar end stage product, but this sugar is inactive for cancer treatment. The use of acid hydrolysis also removes a fraction of the acetyl groups from the GlcNAc groups thereby introducing a positive charge into an otherwise anionic molecule. The latter method, chemical synthesis, involves steps with low to moderate repetitive yield and has never been reported for a HA-oligosaccharide longer than 6 sugars in length. Also racemization (e.g., production of the wrong isomer) during chemical synthesis creates inactive or harmful molecules; the inclusion of the wrong isomer in a therapeutic preparation in the past has had tragic consequences as evidenced by the birth defects spawned by the drug Thalidomide. As sugars contain many similar reactive hydroxyl groups, in order to affect proper coupling between two sugars in a chemical synthesis, most hydroxyl groups must be blocked or protected. At the conclusion of the reaction, all of the protecting groups must be removed, but this process is not perfect; as a result, a fraction of the product molecules retain these unnatural moieties. The issues of racemization and side-products from chemical synthesis are not problems for the high-fidelity enzyme catalysts of the presently claimed and disclosed invention.

The partial depolymerization method only yields fragments of the original HA polymer and is essentially useless for creating novel sugars beyond simple derivatizations (e.g., esterifying some fraction of GlcUA residues in an indiscriminate fashion). Chemical synthesis may suffice in theory to make novel sugars, but the strategy needs to be customized for adding a new sugar, plus the problems with side-reactions/isomerization and the ultimate oligosaccharide size still pose the same trouble as described earlier. Another distinct method using the degradative enzymes to generate small molecules by "running in reverse" on mixtures of two polymers (e.g. HA and chondroitin) has some potential for novel GAG oligosaccharide synthesis. However, this technology can make only a very limited scope of products with a block pattern (no single or specifically spaced substitutions possible) using slow reactions that cannot easily be customized or controlled. No other technology is as versatile as the presently claimed and disclosed biocatalytic system with respect to flexibility of final oligosaccharide structure in the 3 to 25 sugar size range. Novel, "designer" molecules can be prepared with minimal re-tooling by use of the appropriate hyaluronic acid or chondroitin or heparin enzyme catalysts and substrates.

BRIEF DESCRIPTION OF THE SEVERAL VIEWS OF THE DRAWINGS

FIG. 9 is a tabular representation showing enzyme activity of the pmHAS-D mutants.

FIG. 10A is a Western Blot showing the hybridization of the pmCS gene with the KfoC gene.

FIG. 12 is a pictorial representation of domains A1 and A2 of pmHAS. (A) The approximate relative positions of domain A1 and A2 in pmHAS and pmHAS$^{1-703}$. (B) Partial alignment of the amino acid sequences of the two domains (residue 161-267 and 443-547). The aspartate residues mutated in our studies were marked with *. Identical residues are in bold.

FIG. 15 is a sequence alignment of pmCS and pmHAS. The two *Pasteurella* GAG synthases are highly homologous. Identical residues are denoted with the hyphen. The numbering scheme corresponds to the slightly longer pmHAS sequence. The putative A1 (residues 161-267) and A2 (residues 443-547) domains correspond to regions important for hexosamine transferase or for glucuronic acid transferase activity, respectively (33). Most sequence differences are found in the amino-terminal half of the polypeptides.

FIG. 21 Gel Filtration Analysis of Radiolabeled Polymer Synthesized in vitro. The crude membranes containing pmHS (0.7 mg total protein) were incubated with UDP-[$^{14}$C]GlcUA and UDP-[$^{3}$H]GlcNAc (each 500 □M, 0.4 □Ci) in a 200 □l reaction volume either in the presence (top panel) or absence (bottom panel) of acceptor polymer (1 µg uronic acid). After various reaction times (denoted on curves: 20, 60, or 270 min), portions of the samples (75%) were analyzed on the PolySep column (calibration elution times in minutes: void volume, 9.8; 580 kDa dextran, 12.3; 145 kDa dextran, 12.75, totally included volume, 16.7). The starting acceptor polymer eluted at 12.8 min. Large polymers composed of both radiolabeled sugars ($^{14}$C, C; $^{3}$H, H) in an equimolar ratio were synthesized by pmHS.

FIG. 23 depicts chimeric constructs of pm-EG, pm-FH, pm-IK, and pm-JL. PCR-overlap-extension was performed. Pm-EG contains residues 1-265 from pmHAS and residues 259-704 from pmCS and is a GlcUA-Tase. Pm-FH contains residues 1-258 from pmCS and residues 266-703 from pmHAS and is an active chondrotin synthase. Pm-IK contains residues 1-221 from pmHAS and residues 215-704 from pmCS and is a Glc-UA-Tase. Pm-JL contains residues 1-214 from pmCS and residues 222-703 from pmHAS and is an active HA synthase. The switch of Gal-NAc-transferring activity into GlcNAc-transferring activity indicated that 222-265 of pmHAS and possibly the corresponding residues 215-258 of pmCS play critical role in the selectivity between binding and/or transferring of GalNAc and GlcNAc substrate.

FIG. 24 depicts a comparison of partial primary sequences of pmHAS and different pmCSs. Primary sequences of presumably chondroitin synthases from different Type F *Pasteruella multocida* were obtained by directly sequencing the products of colony-lysis PCR. The MULTALIN alignment indicates that most of the differences between pmHAS and pmCS are conserved among these independent strains. Residues that were substituted in site-mutagenesis studies were underlined. The mutant polypeptides contain a single or combination of different mutations, indicated by star(s). None of these mutations changes the specificity of the original enzymes.

FIG. 26 depicts a summary of enzyme activities of chimeric proteins. The enzymes are drawn as bars. Black bars represent pmCS. White bars represent pmHAS. +, active; –, inactive. PmCHC represents pmCS$^{1-214}$-HAS$^{222-265}$-CS$^{258-704}$. The roles of the two domains are confirmed and we have localized a 44-residue region critical for distinguishing C4 epimers of the hexosamine precursor.

DETAILED DESCRIPTION OF THE INVENTION

Figure 1:
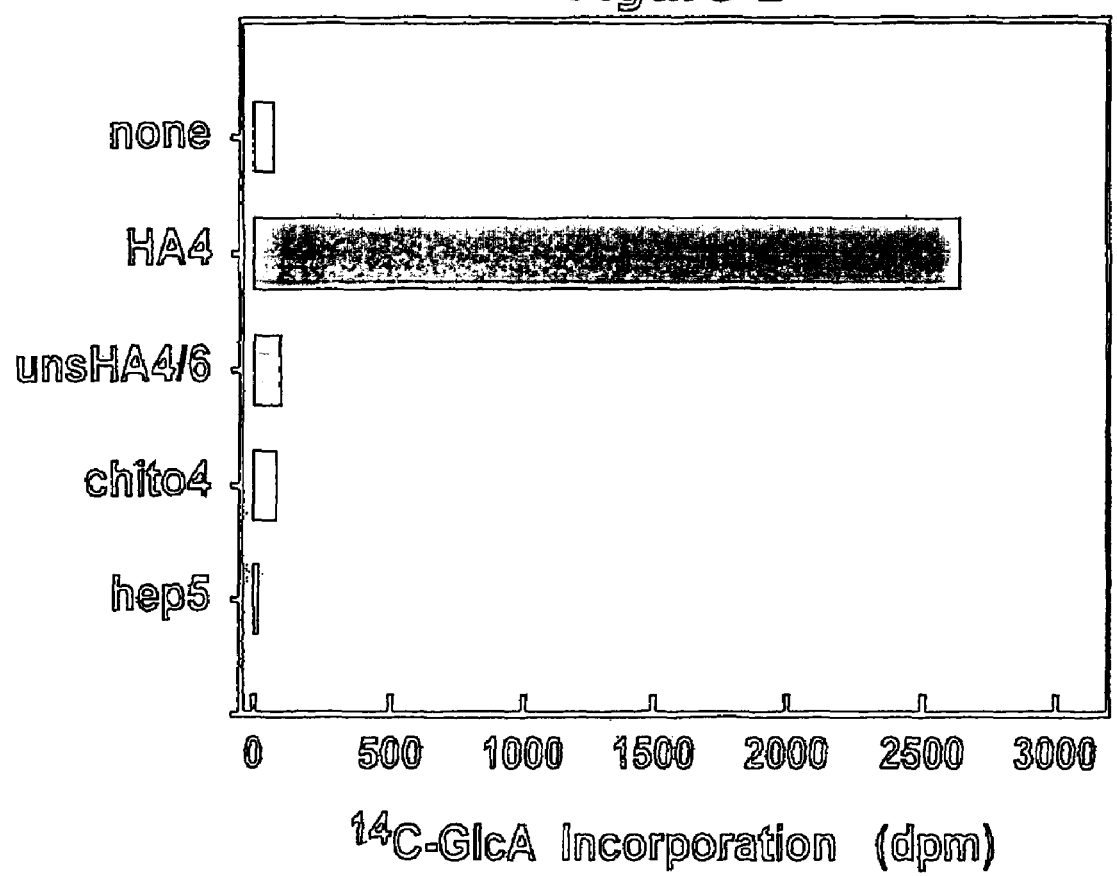
FIG. 1 is a graphical representation showing that an HA tetramer stimulates pmHAS polymerization.

Before explaining at least one embodiment of the invention in detail, it is to be understood that the invention is not limited in its application to the details of construction and the arrangements of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

Glycosaminoglycans ("GAGs") are linear polysaccharides composed of repeating disaccharide units containing a derivative of an amino sugar (either glucosamine or galactosamine). Hyaluronan [HA], chondroitin, and heparan sulfate/heparin contain a uronic acid as the other component of the disaccharide repeat while keratan contains a galactose. The GAGs are summarized in Table I.

TABLE I

| Polymer | Disaccharide Repeat | Post-Polymerization Modifications | |
|---|---|---|---|
| | | Vertebrates | Bacteria |
| Hyaluronan | β3GlcNAc β4GlcUA | none | none |
| Chondroitin | β3GalNAc β4GlcUA | O-sulfated/ epimerized | none |
| Heparin/heparan | α4GlcNAc β4GlcUA | O,N-sulfated/ epimerized | none |
| Keratan | β4GlcNAc β3Gal | O-sulfated | not reported |

Vertebrates may contain all four types of GAGs, but the polysaccharide chain is often further modified after sugar polymerization. One or more modifications including O-sulfation of certain hydroxyls, deacetylation and subsequent N-sulfation, or epimerization of glucuronic acid to iduronic acid are found in most GAGs except HA. An amazing variety of distinct structures have been reported for chondroitin sulfate and heparan sulfate/heparin even within a single polymer chain. A few clever pathogenic microbes also produce unmodified GAG chains; the bacteria use extracellular polysaccharide coatings as molecular camouflage to avoid host defenses. The chondroitin and heparan sulfate/heparin chains in vertebrates are initially synthesized by elongation of a xylose-containing linkage tetrasaccharide attached to a variety of proteins. Keratan is either O-linked or N-linked to certain proteins depending on the particular molecule. HA and all of the known bacterial GAGs are not part of the classification of proteins known as glycoproteins. All GAGs except HA are found covalently linked to a core protein, and such combination is referred to as a proteoglycan. Glycoproteins are usually much smaller than proteoglycans and only contain from 1-60% carbohydrate by weight in the form of numerous relatively short, branched oligosaccharide chains, whereas a proteoglycan can contain as much as 95% carbohydrate by weight. The core protein in a proteoglycan is also usually a glycoprotein, therefore usually contains other oligosaccharide chains besides the GAGs.

GAGs and their derivatives are currently used in the medical field as ophthalmic and viscoelastic supplements, adhesion surgical aids to prevent post-operative adhesions, catheter and device coatings, and anticoagulants. Other current or promising future applications include anti-cancer medications, tissue engineering matrices, immune and neural cell modulators, and drug targeting agents.

Complex carbohydrates, such as GAGs, are information rich molecules. A major purpose of the sugars that make up GAGs is to allow communication between cells and extracellular components of multicellular organisms. Typically, certain proteins bind to particular sugar chains in a very selective fashion. A protein may simply adhere to the sugar, but quite often the protein's intrinsic activity may be altered and/or the protein transmits a signal to the cell to modulate its behavior. For example, in the blood coagulation cascade, heparin binding to inhibitory proteins helps shuts down the clotting response. In another case, HA binds to cells via the CD44 receptor that stimulates the cells to migrate and to proliferate. Even though long GAG polymers (i.e., >$10^2$ Da) are found naturally in the body, typically the protein's binding site interacts with a stretch of 4 to 10 monosaccharides. Therefore, oligosaccharides can be used to either (a) substitute for the polymer or (b) to inhibit the polymer's action depending on the particular system.

HA polysaccharide plays structural roles in the eye, skin, and joint synovium. Large HA polymers (~$10^6$ Da) also stimulate cell motility and proliferation. On the other hand, shorter HA polymers (~$10^4$ Da) often have the opposite effect. HA-oligosaccharides composed of 10 to 14 sugars [$HA_{10-14}$] have promise for inhibition of cancer cell growth and metastasis. In an in vivo assay, mice injected with various invasive and virulent tumor cell lines (melanoma, glioma, carcinomas from lung, breast and ovary) develop a number of large tumors and die within weeks. Treatment with HA oligosaccharides greatly reduced the number and the size of tumors. Metastasis, the escape of cancer cells throughout the body, is one of the biggest fears of both the ailing patient and the physician. HA or HA-like oligosaccharides appear to serve as a supplemental treatment to inhibit cancer growth and metastasis.

The preliminary mode of action of the HA-oligosaccharide sugars is thought to be mediated by binding or interacting with one of several important HA-binding proteins (probably CD44 or RHAM) in the mammalian body. One proposed scenario for the anticancer action of HA-oligosaccharides is that multiple CD44 protein molecules in a cancer cell can bind simultaneously to a long HA polymer. This multivalent HA binding causes CD44 activation (perhaps mediated by dimerization or a receptor patching event) that triggers cancer cell activation and migration. However, if the cancer cell is flooded with small HA-oligosaccharides, then each CD44 molecule individually binds a different HA molecule in a monovalent manner such that no dimerization/patching event occurs. Thus no activation signal is transmitted to the cell. Currently, it is believed that the optimal HA-sugar size is 10 to 14 sugars. Although this size may be based more upon the size of HA currently available for testing rather than biological functionality—i.e. now that HA molecules and HA-like derivatives <10 sugars are available according to the methodologies of the present invention, the optimal HA size or oligosaccharide composition may be found to be different.

It has also been shown that treatment with certain anti-CD44 antibodies or CD44-antisense nucleic acid prevents the growth and metastasis of cancer cells in a fashion similar to HA-oligosaccharides; in comparison to the sugars, however, these protein-based and nucleic acid-based reagents are somewhat difficult to deliver in the body and/or may have long-term negative effects. A very desirable attribute of HA-oligosaccharides for therapeutics is that these sugar molecules are natural by-products that can occur in small amounts in the healthy human body during the degradation of HA polymer; no untoward innate toxicity, antigenicity, or allergenic concerns are obvious.

Other emerging areas for the potential therapeutic use of HA oligosaccharides are the stimulation of blood vessel formation and the stimulation of dendritic cell maturation. Enhancement of wound-healing and resupplying cardiac oxygenation may be additional applications that harness the ability of HA oligosaccharides to cause endothelial cells to form tubes and sprout new vessels. Dendritic cells possess adjuvant activity in stimulating specific CD4 and CD8 T cell responses. Therefore, dendritic cells are targets in vaccine development strategies for the prevention and treatment of infections, allograft reactions, allergic and autoimmune diseases, and cancer.

Heparin interacts with many proteins in the body, but two extremely interesting classes are coagulation cascade proteins and growth factors. Antithrombin III [ATIII] and certain other hemostasis proteins are 100,000-fold more potent inhibitors of blood clotting when complexed with heparin. Indeed, heparin is so potent it must be used in a hospital setting and requires careful monitoring in order to avoid hemorrhage. Newer, processed lower molecular weight forms of heparin are safer, but this material is still a complex mixture. It has been shown that a particular pentasaccharide (5 sugars long) found in heparin is responsible for the ATIII-anticoagulant effect. But since heparin is a very heterogeneous polymer, it is difficult to isolate the pentasaccharide (5 sugars long) in a pure state. The pentasaccharide can also be prepared in a conventional chemical synthesis involving ~50 to 60 steps. However, altering the synthesis or preparing an assortment of analogs in parallel is not always feasible—either chemically or financially.

Many growth factors, including VEGF (vascular endothelial growth factor), HBEGF (heparen-binding epidermal growth factor), and FGF (fibroblast growth factor), bind to cells by interacting simultaneously with the growth factor receptor and a cell-surface heparin proteoglycan; without the heparin moiety, the potency of the growth factor plummets. Cell proliferation is modulated in part by heparin; therefore, diseases such as cancer and atherosclerosis are potential targets. Abnormal or unwanted proliferation would be curtailed if the growth factor was prevented from stimulating target disease-state cells by interacting with a heparin-like oligosaccharide analog instead of a surface-bound receptor. Alternatively, in certain cases, the heparin oligosaccharides alone have been shown to have stimulatory effects.

Chondroitin is the most abundant GAG in the human body, but all of its specific biological roles are not yet clear. Phenomenon such as neural cell outgrowth appears to be modulated by chondroitin. Both stimulatory and inhibitory effects have been noted depending on the chondroitin form and the cell type. Therefore, chondroitin or similar molecules are of utility in re-wiring synaptic connections after degenerative diseases (e.g., Alzheimer's) or paralytic trauma. The epimerized form of chondroitin (GlcUA converted to the C5 isomer, iduronic acid or IdoUA), dermatan, selectively inhibits certain coagulation proteins such as heparin cofactor II. By modulating this protein in the coagulation pathway instead of ATIII, dermatan appears to allow for a larger safety margin than heparin treatment for reduction of thrombi or clots that provoke strokes and heart attacks.

Many details of GAG/protein interactions are not yet clear due to (a) the heterogeneity of GAGs (in part due to their biosynthesis pathway) and (b) the difficulty in analyzing long polysaccharides and membrane receptor proteins at the molecular level. Fortunately, many short oligosaccharides have biological activities that serve to assist research pursuits as well as to treat disease in the near future. Conventional chemical synthesis of short GAG oligosaccharides is possible, but the list of roadblocks includes: (i) difficult multi-step syntheses that employ toxic catalysts, (ii) very low yield or high failure rates with products longer than ~6 monosaccharides, (iii) imperfect control of stereoselectivity (e.g., wrong anomer) and regioselectivity (e.g., wrong attachment site), and (iv) the possibility for residual protection groups (non-carbohydrate moieties) in the final product.

Chemoenzymatic synthesis, however, employing catalytic glycosyltransferases with exquisite control and superb efficiency is currently being developed by several universities and companies. A major obstacle is the production of useful catalyst because the vast majority of glycosyltransferases are rare membrane proteins that are not particularly robust. In the copending applications referenced herein and in the presently claimed and disclosed invention, several practical catalysts from Pasteurella bacteria that allow for the synthesis of the three most important human GAGs (i.e., the three known acidic GAGs) are described and enabled (e.g., HA, chondroitin, and heparin).

All of the known HA, chondroitin and heparan sulfate/heparin glycosyltransferase enzymes that synthesize the alternating sugar repeat backbones in microbes and in vertebrates utilize UDP-sugar precursors and divalent metal cofactors (e.g., magnesium, cobalt and/or manganese ion) near neutral pH according to the overall reaction:

$$n\text{UDP-GlcUA} + n\text{UDP-HexNAc} \rightarrow 2n\text{UDP} + [\text{GlcUA-HexNAc}]_n$$

where HexNAc=GlcNAc or GalNAc. Depending on the specific GAG and the particular organism or tissue examined, the degree of polymerization, n, ranges from about 25 to about 10,000. If the GAG is polymerized by a single polypeptide, the enzyme is called a synthase or co-polymerase.

As outlined in copending and incorporated by reference in the "Cross-Reference" section of this application hereinabove, the present applicant(s) have discovered four new dual-action enzyme catalysts from distinct isolates of the Gram-negative bacterium Pasteurella multocida using various molecular biology strategies. P. multocida infects fowl, swine, and cattle as well as many wildlife species. The enzymes are: a HA synthase, or (pmHAS); a chondroitin synthase, or (pmCS); and two heparosan synthases, or (pmHS and PgIA). To date, no keratan synthase from any source has been identified or reported in the literature.

In copending U.S. Ser. No. 09/283,402, the molecular directionality of pmHAS synthesis was disclosed and claimed. pmHAS is unique in comparison to all other existing HA synthases of Streptococcus bacteria, humans and an algal virus. Specifically, recombinant pmHAS can elongate exogeneously-supplied short HA chains (e.g., 2-4 sugars) into longer HA chains (e.g., 3 to 150 sugars). The pmHAS synthase has been shown to add monosaccharides one at a time in a step-wise fashion to the growing chain. The pmHAS enzyme's exquisite sugar transfer specificity results in the repeating sugar backbone of the GAG chain. The pmCS enzyme, which is about 90% identical at the amino acid level to pmHAS, performs the same synthesis reactions but transfers GalNAc instead of GlcNAc. The pmCS enzyme was described and enabled in copending U.S. Ser. No. 09/842,484. The pmHS and PgIA enzymes are not very similar at the amino acid level to pmHAS, but perform the similar synthesis reactions; the composition of sugars is identical but the linkages differ because heparosan is Beta4GlcUA-alpha4GlcNAc. The pmHS and PgIA enzymes were described and enabled in copending U.S. Ser. No. 10/142,143.

The explanation for the step-wise addition of sugars to the GAG chain during biosynthesis was determined by analyzing mutants of the pmHAS enzyme. pmHAS possesses two independent catalytic sites in one polypeptide. Mutants were created that transferred only GlcUA, and distinct mutants were also created that transferred only GlcNAc. These mutants cannot polymerize HA chains individually, but if the two types of mutants are mixed together in the same reaction with an acceptor molecule, then polymerization was rescued. The chondroitin synthase, pmCS, has a similar sequence and similar two-domain structure. The heparosan synthases, pmHS and PgIA, also contain regions for the two active sites. Single action mutants have also been created for the chondroitin synthase, pmCS, and are described hereinafter in detail.

The Pasteurella GAG synthases are very specific glycosyltransferases with respect to the sugar transfer reaction; only the correct monosaccharide from the authentic UDP-sugar is added onto acceptors. The epimers or other closely structurally related precursor molecules (e.g., UDP-glucose) are not utilized. The GAG synthases do, however, utilize certain heterologous acceptor sugars. For example, pmHAS will elongate short chondroitin acceptors with long HA chains. pmHS will also add long heparosan chains onto HA acceptor oligosaccharides as well as heparin oligosaccharides (see hereinbelow). Therefore, the presently claimed and disclosed invention encompasses a wide range of hybrid or chimeric GAG oligosaccharides prepared utilizing these P. multocida GAG catalysts.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Hyaluronate Synthase ("HAS") coding sequence or Chondroitin Synthase ("CS") coding sequence or Heparin/Heparosan Synthase ("HS") coding sequence yet is isolated away from, or purified free from, unrelated genomic DNA, for example, total Pasteurella multocida. Included within the term "DNA segment", are DNA segments and smaller fragments of such segments, and also recombinant vectors, including, for example, plasmids, cosmids, phage, viruses, and the like.

Similarly, a DNA segment comprising an isolated or purified pmHAS or pmCS or pmHS or PgIA gene refers to a DNA segment including HAS or CS or HS coding sequences isolated substantially away from other naturally occurring genes or protein encoding sequences. In this respect, the term "gene" is used for simplicity to refer to a functional protein-, polypeptide- or peptide-encoding unit. As will be understood by those in the art, this functional term includes genomic sequences, cDNA sequences or combinations thereof. "Isolated substantially away from other coding sequences" means that the gene of interest, in this case pmHAS or pmCS or pmHS or PgIA forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

Due to certain advantages associated with the use of prokaryotic sources, one will likely realize the most advantages upon isolation of the HAS or CS or HS gene from the prokaryote P. multocida. One such advantage is that, typically, eukaryotic genes may require significant post-transcriptional modifications that can only be achieved in a eukaryotic host. This will tend to limit the applicability of any eukaryotic HAS or CS or HS gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library and (b) the ease of manipulation because the overall size of the coding region of a prokaryotic gene is significantly smaller due to the absence of introns. Furthermore, if the product of the pmHAS or pmCS or pmHS or PgIA gene (i.e., the enzyme) requires posttranslational modifications, these would best be achieved in a similar prokaryotic cellular environment (host) from which the gene was derived.

Preferably, DNA sequences in accordance with the present invention will further include genetic control regions which allow the expression of the sequence in a selected recombinant host. The genetic control region may be native to the cell from which the gene was isolated, or may be native to the recombinant host cell, or may be an exaggerous segment that is compatible with and recognized by the transcriptional machinery of the selected recbominant host cell. Of course, the nature of the control region employed will generally vary depending on the particular use (e.g., cloning host) envisioned. In particular embodiments, the invention concerns isolated DNA segments and recombinant vectors incorporating DNA sequences which encode a pmHAS or pmCS or pmHS or PgIA gene, that includes within its amino acid sequence an amino acid sequence in accordance with SEQ ID NO:2, 4, 6, 8, 9, or 70, respectively. Moreover, in other particular embodiments, the invention concerns isolated DNA segments and recombinant vectors incorporating DNA sequences which encode a gene that includes within its nucleic acid sequence an amino acid sequence encoding HAS or CS or HS pepetides or peptide fragment thereof, and in particular to a HAS or CS or HS peptide or peptide fragment thereof, corresponding to *Pasteurella multocida* HAS or CS or HS. For example, where the DNA segment or vector encodes a full length HAS or CS or HS protein, or is intended for use in expressing the HAS or CS or HS protein, preferred sequences are those which are essentially as set forth in SEQ ID NO:1, 3, 5, 7, 69, or 71, respectively.

Truncated pmHAS gene (such as, but not limited to, $pmHAS^{1-703}$, SEQ ID NO:71) also falls within the definition of preferred sequences as set forth above. For instance, at the carboxyl terminus, approximately 270-272 amino acids may be removed from the sequence and still have a functioning HAS. Those of ordinary skill in the art would appreciate that simple amino acid removal from either end of the pmHAS sequence can be accomplished. The truncated versions of the sequence (as disclosed hereinafter) simply have to be checked for HAS activity in order to determine if such a truncated sequence is still capable of producing HAS. The other GAG synthases disclosed and claimed herein are also amenable to truncation or alteration with preservation of activity and such truncated or alternated GAG synthases also fall within the scope of the present invention.

Nucleic acid segments having HAS or CS or HS activity may be isolated by the methods described herein. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability of prokaryotes to produce HA or a hyaluronic acid or chondroitin or heparin polymer in vitro or in vivo. In the above examples "X" refers to either SEQ ID NO: 1, 2, 3, 4, 5, 6, 7, 8, 9, 69, 70 or 71 or any additional sequences set forth herein, such as the truncated or mutated versions of $pmHAS^{1-703}$ that are contained generally in SEQ ID NOS:10-60.

The art is replete with examples of practitioner's ability to make structural changes to a nucleic acid segment (i.e. encoding conserved or semi-conserved amino acid substitutions) and still preserve its enzymatic or functional activity when expressed. See for special example of literature attesting to such: (1) Risler et al. "Amino Acid Substitutions in Structurally Related Proteins. A Pattern Recognition Approach." J. Mol. Biol. 204:1019-1029 (1988) [" . . . according to the observed exchangeability of amino acid side chains, only four groups could be delineated; (I) Ile and Val; (ii) Leu and Met, (iii) Lys, Arg, and Gin, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481-497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216-226 (1992) ["Analysis of the pattern of observed substitutions as a function of local environment shows that there are distinct patterns. . . . " Compatible changes can be made.]

These references and countless others, indicate that one of ordinary skill in the art, given a nucleic acid sequence or an amino acid, could make substitutions and changes to the nucleic acid sequence without changing its functionality (specific examples of such changes are given hereinafter and are generally set forth in SEQ ID NOS:10-60). Also, a substituted nucleic acid segment may be highly identical and retain its enzymatic activity with regard to its unadulterated parent, and yet still fail to hybridize thereto. Additionally, the present application discloses 4 enzymes and numerous mutants of these enzymes that still retain at least 50% of the enzymatic activity of the unmutated parent enzyme—i.e., ½ of the dual action transferase activity of the unadulterated parent. As such, variations of the sequences and enzymes that fall within the above-defined functional limitations have been disclosed and enabled. One of ordinary skill in the art, given the present specification, would be able to identify, isolate, create, and test DNA sequences and/or enzymes that produce natural or chimeric or hybrid GAG molecules. As such, the presently claimed and disclosed invention should not be regarded as being solely limited to the specific sequences disclosed herein.

The invention discloses nucleic acid segments encoding an enzymatically active HAS or CS or HS from *P. multocida*-pmHAS, pmCS, pmHS, and PgIA, respectively. One of ordinary skill in the art would appreciate that substitutions can be made to the pmHAS or pmCS or pmHS or PgIA nucleic acid segments listed in SEQ ID NO:1, 3, 5, 7, 69, and 71, respectively, without deviating outside the scope and claims of the present invention. Indeed, such changes have been made and are described hereinafter with respect to the mutants produced. Standardized and accepted functionally equivalent amino acid substitutions are presented in Table II.

TABLE II

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Another preferred embodiment of the present invention is a purified nucleic acid segment that encodes a protein in accordance with SEQ ID NO:1 or 3 or 5 or 7 or 71, respectively, further defined as a recombinant vector. As used herein, the term "recombinant vector" refers to a vector that has been modified to contain a nucleic acid segment that encodes an HAS or CS or HS protein, or fragment thereof. The recombinant vector may be further defined as an expression vector comprising a promoter operatively linked to said HAS- or CS- or HS-encoding nucleic acid segment.

A further preferred embodiment of the present invention is a host cell, made recombinant with a recombinant vector comprising an HAS or CS or HS gene. The preferred recombinant host cell may be a prokaryotic cell. In another embodiment, the recombinant host cell is an eukaryotic cell. As used herein, the term "engineered" or "recombinant" cell is intended to refer to a cell into which a recombinant gene, such as a gene encoding HAS or CS or HS, has been introduced mechanically or by the hand of man. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter associated or not naturally associated with the particular introduced gene.

In preferred embodiments, the HAS- or CS- or HS-encoding DNA segments further include DNA sequences, known in the art functionally as origins of replication or "replicons", which allow replication of contiguous sequences by the particular host. Such origins allow the preparation of extrachromosomally localized and replicating chimeric or hybrid segments or plasmids, to which HAS- or CS- or HS-encoding DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HAS- or CS- or HS-coding gene sequence together with an appropriate replication origin and under the control of selected control regions.

Thus, it will be appreciated by those of skill in the art that other means may be used to obtain the HAS or CS or HS gene or cDNA, in light of the present disclosure. For example, polymerase chain reaction or RT-PCR produced DNA fragments may be obtained which contain full complements of genes or cDNAs from a number of sources, including other strains of Pasteurella or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HAS or CS or HS.

Once the DNA has been isolated, it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both biotechnologically useful Gram-positive or Gram-negative bacteria (e.g. Bacillus, Lactococcus, or E. coli) are employed.

Vectors such as these, exemplified by the pSA3 vector of Dao and Ferretti or the pAT19 vector of Trieu-Cuot, et al., allow one to perform clonal colony selection in an easily manipulated host such as E. coli, followed by subsequent transfer back into a food grade Lactococcus or Bacillus strain for production of hyaluronan or chondroitin or heparin polymer. In another embodiment, the recombinant vector is employed to make the functional GAG synthase for in vitro use. These are benign and well studied organisms used in the production of certain foods and biotechnology products and are recognized as GRAS (generally recognized as safe) organisms. These are advantageous in that one can augment the Lactococcus or Bacillus strain's ability to synthesize HA or chondroitin or heparin through gene dosing (i.e., providing extra copies of the HAS or CS or HS gene by amplification) and/or inclusion of additional genes to increase the availability of HA or chondroitin or heparin precursors. The inherent ability of a bacterium to synthesize HA or chondroitin or heparin can also be augmented through the formation of extra copies, or amplification, of the plasmid that carries the HAS or CS or HS gene. This amplification can account for up to a 10-fold increase in plasmid copy number and, therefore, the HAS or CS or HS gene copy number.

Another procedure to further augment HAS or CS or HS gene copy number is the insertion of multiple copies of the gene into the plasmid. Another technique would include integrating at least one copy of the HAS or CS or HS gene into chromosomal DNA. This extra amplification would be especially feasible, since the bacterial HAS or CS or HS gene size is small. In some scenarios, the chromosomal DNA-ligated vector is employed to transfect the host that is selected for clonal screening purposes such as E. coli, through the use of a vector that is capable of expressing the inserted DNA in the chosen host.

In certain other embodiments, the invention concerns isolated DNA segments and recombinant vectors that include within their sequence a nucleic acid sequence essentially as set forth in SEQ ID NO:1,3,5,7,69, or 71. The term "essentially as set forth" in SEQ ID NO: 1,3,5,7,69, or 71 is used in the same sense as described above and means that the nucleic acid sequence substantially corresponds to a portion of SEQ ID NO: 1,3,5,7,69, or 71 and has relatively few codons which are not identical, or functionally equivalent, to the codons of SEQ ID NO: 1,3,5,7,69, or 71. The term "functionally equivalent codon" is used herein to refer to codons that encode the same amino acid, such as the six codons for arginine or serine, and also refers to codons that encode biologically equivalent amino acids, as set forth in Table II.

It will also be understood that amino acid and nucleic acid sequences may include additional residues, such as additional N- or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzyme activity is concerned. The addition of terminal sequences particularly applies to nucleic acid sequences which may, for example, include various non-coding sequences flanking either of the 5' or 3' portions of the coding region or may include various internal sequences, which are known to occur within genes. Furthermore, residues may be removed from the N- or C-terminal amino acids and yet still be essentially as set forth in one of the sequences disclosed herein, so long as the sequence meets the criteria set forth above, as well.

Allowing for the degeneracy of the genetic code as well as conserved and semi-conserved substitutions, sequences which have between about 40% and about 99%; or more preferably, between about 80% and about 90%; or even more preferably, between about 90% and about 99% identity to the nucleotides of SEQ ID NO:1, 3, 5, 7, 69 or 71 will be sequences which are "essentially as set forth" in SEQ ID NO:1, 3, 5, 7, 69 or 71. Sequences which are essentially the same as those set forth in SEQ ID NO:1, 3, 5, 7, 69 or 71 may also be functionally defined as sequences which are capable of hybridizing to a nucleic acid segment containing the complement of SEQ ID NO:1, 3, 5, 7, 69 or 71 under "standard stringent hybridization conditions," "moderately stringent hybridization conditions," "less stringent hybridization conditions," or "low stringency hybridization conditions." Suitable "standard" or "less stringent" hybridization conditions will be well known to those of skill in the art and are clearly set forth hereinbelow. In a preferred embodiment, standard stringent hybridization conditions or less stringent hybridization conditions are utilized.

The terms "standard stringent hybridization conditions," "moderately stringent conditions," and "less stringent hybridization conditions" or "low stringency hybridization conditions" are used herein, describe those conditions under which substantially complementary nucleic acid segments will form standard Watson-Crick base-pairing and thus "hybridize" to one another. A number of factors are known that determine the specificity of binding or hybridization, such as pH; temperature; salt concentration; the presence of agents, such as formamide and dimethyl sulfoxide; the length of the segments that are hybridizing; and the like. There are various protocols for standard hybridization experiments. Depending on the relative similarity of the target DNA and the probe or query DNA, then the hybridization is performed under stringent, moderate, or under low or less stringent conditions.

The hybridizing portion of the hybridizing nucleic acids is typically at least about 14 nucleotides in length, and preferably between about 14 and about 100 nucleotides in length. The hybridizing portion of the hybridizing nucleic acid is at least about 60%, e.g., at least about 80% or at least about 90%, identical to a portion or all of a nucleic acid sequence encoding a HAS or chondroitin or heparin synthase or its complement, such as SEQ ID NO:1,3,5,7,69, or 71 or the complement thereof. Hybridization of the oligonucleotide probe to a nucleic acid sample typically is performed under standard or stringent hybridization conditions. Nucleic acid duplex or hybrid stability is expressed as the melting temperature or $T_m$, which is the temperature at which a probe nucleic acid sequence dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC, SSPE, or HPB). Then, assuming that 1% mismatching results in a 1° C. decrease in the $T_m$, the temperature of the final wash in the hybridization reaction is reduced accordingly (for example, if sequences having >95% identity with the probe are sought, the final wash temperature is decreased by about 5° C.). In practice, the change in $T_m$ can be between about 0.5° C. and about 1.5° C. per 1% mismatch. Examples of standard stringent hybridization conditions include hybridizing at about 68° C. in 5×SSC/5× Denhardt's solution/1.0% SDS, followed with washing in 0.2×SSC/0.1% SDS at room temperature or hybridizing in 1.8×HPB at about 30° C. to about 45° C. followed with washing a 0.2-0.5×HPB at about 45° C. Moderately stringent conditions include hybridizing as described above in 5×SSC/5× Denhardt's solution 1% SDS washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, (Cold Spring Harbor Press, N.Y.); and Ausubel et al. (eds.), 1995, Current Protocols in Molecular Biology, (John Wiley & Sons, N.Y.). Several examples of low stringency protocols include: (A) hybridizing in 5×SSC, 5× Denhardts reagent, 30% formamide at about 30° C. for about 20 hours followed by washing twice in 2×SSC, 0.1% SDS at about 30° C. for about 15 min followed by 0.5×SSC, 0.1% SDS at about 30° C. for about 30 min (FEMS Microbiology Letters, 2000, vol. 193, p. 99-103); (B) hybridizing in 5×SSC at about 45° C. overnight followed by washing with 2×SSC, then by 0.7×SSC at about 55° C. (J. Viological Methods, 1990, vol. 30, p. 141-150); or (C) hybridizing in 1.8XHPB at about 30° C. to about 45° C.; followed by washing in 1×HPB at 23° C.

Naturally, the present invention also encompasses DNA segments which are complementary, or essentially complementary, to the sequences set forth in SEQ ID NO:1 or 3 or 5 or 7 or 69 or 71. Nucleic acid sequences which are "complementary" are those which are capable of base-pairing according to the standard Watson-Crick complementarity rules. For example, the sequence 5'-ATAGCG-3' is complementary to the sequence 5'-CGCTAT-3" because when the two sequences are aligned, each "T" is able to base-pair with an "A", which each "G" is able to base pair with a "C". As used herein, the term "complementary sequences" means nucleic acid sequences which are substantially complementary, as may be assessed by the nucleotide comparison set forth above, or as defined as being capable of hybridizing to the nucleic acid segment of SEQ ID NO:1,3,5,7, or 69, or 71 under standard stringent, moderately stringent, or less stringent hybridizing conditions.

The nucleic acid segments of the present invention, regardless of the length of the coding sequence itself, may be combined with other DNA sequences, such as promoters, polyadenylation signals, additional restriction enzyme sites, multiple cloning sites, epitope tags, polyhistidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular amino acid and nucleic acid sequences of SEQ ID NO:1, 2, 3, 4, 5, 6, 7, 8, 9, 69, 70, or 71. Recombinant vectors and isolated DNA segments may therefore variously include the HAS or CS or HS coding regions themselves, coding regions bearing selected alterations or modifications in the basic coding region, or they may encode larger polypeptides which nevertheless include HAS or CS or HS coding regions or may encode biologically functional equivalent proteins or peptides which have variant amino acid sequences.

The DNA segments of the present invention encompass DNA segments encoding biologically functional equivalent HAS or CS or HS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HAS or CS or HS protein or to test HAS or CS or HS mutants in order to examine HAS or CS or HS activity at the molecular level or to produce HAS or CS or HS mutants having changed or novel enzymatic activity and/or sugar substrate specificity.

Traditionally, chemical or physical treatments of polysaccharides were required to join two dissimilar materials. For example, a reactive nucleophile group of one polymer or surface was exposed to an activated acceptor group of the other material. Two main problems exist with this approach, however. First, the control of the chemical reaction cannot be refined, and differences in temperature and level of activation often result in a distribution of several final products that vary from lot to lot preparation. For instance, several chains may be cross-linked in a few random, ill-defined areas, and the resulting sample is not homogenous. Second, the use of chemical reactions to join molecules often leaves an unnatural or nonbiological residue at the junction of biomaterials. For example, the use of an amine and an activated carboxyl group would result in an amide linkage. This inappropriate residue buried in a carbohydrate may pose problems with biological systems such as the subsequent production of degradation products which accumulate to toxic levels or the triggering of an immune response.

Use of pmHAS for Polymer Grafting and Oligosaccharide Production.

Most polysaccharide polymers must be of a certain length before their physical or biological properties become apparent. Often the polysaccharide must comprise at least 20-100 sugar units. Certain enzymes that react with exogenous polymers have been previously available, but typically add only one sugar unit. The unique enzymes described in the present invention, (e.g. pmHAS, pmCS, pmHS, and PgIA) form polymers of at least 100-400 sugar units in length. Thus, one embodiment of the presently claimed and disclosed invention, results in long, defined linear polymers composed of only natural glycosidic linkages.

The four known glycosaminoglycan synthesizing enzymes from *Pasteurella multocida* bacteria normally make polymers similar to or identical to vertebrate polymers. These bacteria employ the polysaccharide, either HA (Type A bacteria), chondroitin (Type F bacteria), or heparosan (unsulfated, unepimerized heparin—Type D bacteria) as an extracellular coating to serve as molecular camouflage. Native enzymes normally make polymer chains of a single type of sugar repeat. If a recombinant HAS or CS or HS enzyme is employed, however, the enzyme can be forced to work on an exogenous functional acceptor molecule. For instance, the recombinant enzyme may be incubated with a polymer acceptor, and the recombinant enzyme will then elongate the acceptor with UDP-sugar precursors. The known native enzymes do not perform this reaction since they already contain a growing polymer chain that was formed in the living cell; enzyme preparations from native cells retain the polymer following isolation.

pmHAS (SEQ ID NO:2), a 972 amino acid residue protein from *Pasteurella multocida*, is made in a functional state in recombinant *Escherichia coli*. The pmHAS gene is given in SEQ ID NO:1. Other functional derivatives of pmHAS, for example an enzyme called $pmHAS^{1-703}$ (SEQ ID NO:9) and the $pmHAS^{1-703}$ gene (SEQ ID NO:71), have been produced which are soluble. The soluble form can be prepared in larger quantities and in a purer state than the naturally occurring full-length enzyme. The preferred *E. coli* strains do not have an UDP-Glc dehydrogenase and therefore the recombinant enzyme does not make HA chain in the foreign host. Therefore, the enzyme is in a "virgin" state since the empty acceptor site can be occupied with foreign polymers. For example, the recombinant enzyme may be incubated in a mixture comprising from about 10 to about 50 mM Tris pH 7.2, from about 20 mM $MnCl_2$, from about 0.1 to about 15 mM UDP-GlcUA, from about 0.1 to about 15 mM UDP-GlcNAc, and a suitable acceptor at about 30° C. for from about 1 to about 180 minutes. Suitable acceptors can be any functional acceptor, such as a glycosaminoglycan acceptor or sugar acceptor, for example, but not by limitation, short HA chains (two or more sugar units such as $HA_4$) or short chondroitin sulfate chains (5 sugar units) or long chondroitin sulfate chains (~$10^2$ sugar units) or short or long heparosan chains. In the case of the latter acceptors, pmHAS (or its derivatives), then elongates the foreign acceptors (i.e. long or short chondroitin or heparosan oligosaccharides) at their nonreducing termini with authentic HA chains. The length of the HA chain added onto the acceptor is controlled by altering the concentration of UDP-sugars and/or the reaction time. Immobilized acceptors, such as beads or other solid objects with bound acceptor oligosaccharides, can also be extended by the pmHAS enzyme using UDP-sugars. In this manner, the pmHAS enzyme (or its derivatives) can be used to attach polysaccharide chains to any suitable acceptor molecule.

Type A *P. multocida* produces HA capsule [GlcUA-GlcNAc repeats] and possesses the pmHAS enzyme. On the other hand, Type F *P. multocida* produces a chondroitin or chondroitin-like polymer capsule [GlcUA-GalNAc repeats]. The DNA encoding an open reading frame (GenBank accession #AF195517) that is 90% identical to pmHAS at the protein level has been cloned; this enzyme is called PmCS, the *P. multocida* chondroitin synthase. The amino acid sequence of pmCS is set forth in Seq ID NO:4 and the pmCS gene sequence is set forth in SEQ ID NO:3. As the PmCS enzyme's sequence is so similar to pmHAS, one of ordinary skill in the art, given the present specification, is able to manipulate the pmCS in the same manner as that for pmHAS and any manipulation that is successful with regard to the pmHAS would be performable with the pmCS, with the exception that chondroitin chains would be grafted instead of HA. Either HA or chondroitin or heparin chains can serve as acceptors for pmCS as both acceptors serve well for pmHAS.

Such hybrid polysaccharide materials composed of HA, chondroitin and heparin cannot be formed by any other existing process without (1) leaving unnatural residues and/or (2) producing undesirable crosslinking reactions. The chimeric or hybrid polysaccharide materials can serve as biocompatible molecular glue for cell/cell interactions in artificial tissues or organs and the HA/chondroitin/heparin hybrid mimics natural proteoglycans that normally contain an additional protein intermediate between polymer chains. The present invention, therefore, obviates the requirement for a protein intermediary. A recombinant HA/chondroitin/heparin chimeric or hybrid polysaccharide, devoid of such an intermediary protein, is desirous since molecules from animal sources are potentially immunogenic—the chimeric or hybrid polysaccharide, however, would not appear as "foreign" to the host, thus no immune response is generated. Also, the recombinant polymers can be made free of adventitious agents (e.g., prions, viruses etc.)

An intrinsic and essential feature of polysaccharide synthesis is the repetitive addition of sugar monomer units to the growing polymer. The glycosyltransferase remains. in association with the nascent chain. This feature is particularly relevant for HA biosynthesis as the HA polysaccharide product, in all known cases, is transported out of the cell; if the polymer was released, then the HAS would not have another chance to elongate that particular molecule. Three possible mechanisms for maintaining the growing polymer chain at the active site of the enzyme are immediately obvious. First, the enzyme possesses a carbohydrate polymer binding pocket or cleft. Second, the nascent chain is covalently attached to the enzyme during its synthesis. Third, the enzyme binds to the nucleotide base or the lipid moiety of the precursor while the nascent polymer chain is still covalently attached.

The HAS activity of the native pmHAS enzyme found in *P. multocida* membrane preparations is not stimulated by the addition of HA oligosaccharides; theoretically, the endogenous nascent HA chain initiated in vivo renders the exogenously supplied acceptor unnecessary. However, recombinant pmHAS produced in an *E. coli* strain that lacks the UDP-GlcUA precursor, and thus lacks a nascent HA chain, is able to bind and to elongate exogenous HA oligosaccharides. As mentioned above, there are three likely means for a nascent HA chain to be held at or near the active site. In the case of pmHAS, it appears that a HA-binding site exists near or at the sugar transferase catalytic site.

Defined oligosaccharides that vary in size and composition are used to discern the nature of the interaction between pmHAS and the sugar chain. For example, it appears that the putative HA-polymer binding pocket of pmHAS will bind and elongate at least an intact HA disaccharide with increased efficiency occurring when a trisaccharide is used (reduced tetramer or a synthetic trisaccharide). Oligosaccharide binding to pmHAS appears to be somewhat selective because the heparosan pentamer, which only differs in the glycosidic linkages from HA-derived oligosaccharides, does not serve as an acceptor. However, chondroitin [GlcUA-GalNAc repeat] does serve as an acceptor for pmHAS.

To date, no other HA synthase besides pmHAS has been shown to utilize an exogenous acceptor or primer sugar. In an early study of a cell-free HA synthesis system, preparations of native Group A *Streptococcal* HAS were neither inhibited nor stimulated by the addition of various HA oligosaccharides including the HA tetramer derived from testicular hyaluronidase digests. These membrane preparations were isolated from cultures that were producing copious amounts of HA polysaccharide. The cells were hyaluronidase-treated to facilitate handling. Therefore, it is quite likely that the native *streptococcal* enzyme was isolated with a small nascent HA chain attached to or bound to the protein much as suspected in the case of the native pmHAS. Theoretically, the existing nascent chain formed in vivo would block the entry and subsequent utilization of an exogenous acceptor by the isolated enzyme in vitro. With the advent of molecularly cloned HAS genes, it is possible to prepare virgin enzymes lacking a nascent HA chain if the proper host is utilized for expression. In these tests, recombinant yeast with spHAS did not use HA acceptors proving that the Class I enzyme intrinsically cannot elongate such acceptors.

Both heparin and chondroitin, in mammalian systems, are synthesized by the addition of sugar units to the nonreducing end of the polymer chain. In vivo, the glycosyltransferases initiate chain elongation on at least primer monosachharides [more preferably tetrasaccharides such as xylose-galactose-galactose-GlcUA] that are attached to serine residues of proteoglycan core molecules. In vitro, enzyme extracts transfer a single sugar to exogenously added heparin or chondroitin oligosaccharides; unfortunately, the subsequent sugar of the disaccharide unit is usually not added and processive elongation to longer polymers does not occur. Therefore it is likely that some component is altered or missing in the in vitro system. In the case of heparin biosynthesis, a single enzyme transfers both GlcUA and GlcNAc sugars to the glycosaminoglycan chain based on co-purification or expression studies.

Recent work with the *E. coli* K5 KfiA and KfiC enzymes, which polymerize heparosan, indicates that a pair of proteins can transfer both sugars to the nonreducing end of acceptor molecules in vitro. Processive elongation, however, was not demonstrated in these experiments; crude cell lysates transferred a single sugar to defined even- or odd-numbered oligosaccharides.

Recombinant pmHAS adds single monosaccharides in a sequential fashion to the nonreducing termini of the nascent HA chain. Elongation of HA polymers containing hundreds of sugars has been demonstrated in vitro. The simultaneous formation of the disaccharide repeat unit is not necessary for generating the alternating structure of the HA molecule. The intrinsic specificity and fidelity of each half-reaction (e.g. GlcUA added to a GlcNAc residue or vice versa) apparently is sufficient to synthesize authentic HA chains.

A great technical benefit resulting from the alternating disaccharide structure of HA is that the reaction can be dissected by controlling the availability of UDP-sugar nucleotides. By omitting or supplying precursors in a reaction mixture, the glycosyltransferase may be stopped and started at different stages of synthesis of the heteropolysaccharide. In contrast, there is no facile way to control in a step-wise fashion the glycosyltransferase enzymes that produce important homopolysaccharides such as chitin, cellulose, starch, and glycogen.

An alternative method for controlling polymerization has been accomplished by creating mutants that only add one sugar linkage onto a short HA oligosaccharide. For example, $pmHAS^{1-650}$ (SEQ. ID NO:10) can only add single GlcNAc sugars onto the non-reducing end (i.e., HA tetrasaccharide [GlcNAc-GlcUA-GlcNAc-GlcUA]) of an acceptor (i.e. forms the HA pentamer). On the other hand, a mutant has been created and called $pmHAS^{1-703}$-D477N (SEQ. ID NO:11) [pmHAS residues 1-703 with an asparagine substituted for the asparatate at position 477], that transfers only a single GlcNAc residue onto the non-reducing terminal GlcUa group of the short HA oligosaccharide. If extracts of two such single-action point mutants (e.g., D477N, SEQ ID NO:11 and D196N [i.e. pmHAS residues 1-703 with an asparagine substituted for the aspartate at position 196], SEQ ID NO:12) are mixed together with an acceptor in the presence of UDP-GlcNAc and UDP-GlcUA, then significant polymerization is achieved. It is also obvious that by carrying out the steps of GlcNAc or GlcUA transfer separately and sequentially, almost any HA chain length is possible. The same is also true with regard to PmCS either alone or in combination with pmHAS as well as pmHS or PgIA either alone or in combination with pmCS and pmHAS, individually or as a group.

As stated above, membrane preparations from recombinant *E coli* containing a pmHAS protein had HA synthase activity as judged by incorporation of radiolabel from UDP-[$^{14}$C]GlcUA into polymer when co-incubated with both UDP-GlcNAc and Mn ion. Due to the similarity at the amino acid level of pmHAS to several lipopolysaccharide transferases, it was hypothesized that HA oligosaccharides serve as acceptors for GlcUA and GlcNAc transfer. Addition of unlabeled even-numbered HA tetramer (from testicular hyaluronidase digests) to reaction mixtures with recombinant $pmHAS^{1-703}$ stimulates incorporation of radiolabel from UDP-[$^{14}$C]GlcUA into HA polymer by ~20- to 60-fold in comparison to reactions without oligosaccharides as shown in FIG. 1.

In FIG. 1, a series of reactions containing pmHAS$^{1-703}$ (30 µg total membrane protein) were incubated with UDP-[$^{14}$C] GlcUA (2×10$^4$ dpm, 120 µM) and UDP-GlcNAc (450 µM) in assay buffer (50 µl reaction vol) in the presence of no added sugar (none) or various oligosaccharides (HA4, 4 µg HA tetramer; unsHA4/6, 4 µg unsaturated HA "tetramer" and "hexamer"; chito4, 50 µg chitotetraose; hep5, 20 µg heparosan pentamer). After 1 hour, the reactions were analyzed by descending paper chromatography. Incorporation of radiolabel from UDP-[$^{14}$C]GlcUA into high molecular weight HA is shown. The intact tetramer (HA4) served as a functional acceptor. Reactions with heparosan and chitooligosaccharides, as well as GlcNAc and/or GlcUA (not shown), incorporated as much radiolabel as parallel reactions with no acceptor. The free monosaccharides GlcUA and GlcNAc, either singly or in combination at concentrations of up to 100 µM, do not serve as acceptors; likewise, the beta-methyl glycosides of these sugars do not stimulate HAS activity.

In the same manner, pmHAS$^{1-703}$ has been shown to add sugars onto a chondroitin pentamer acceptor. The pmHAS$^{1-703}$ and reagents were prepared in the same manner as shown in FIG. 1, except that a chondroitin pentamer was used as the acceptor molecule. The results of this experiment are shown in TABLE III.

TABLE III

| Sugar | Mass | Incorporation of $^{14}$C-GlcUA dpm |
| --- | --- | --- |
| None | not applicable | 60 |
| HA$_4$ | 5 µg | 2,390 |
| Chondroitin Pentamer | 20 µg | 6,690 |

Thus, it can be seen that the pmHAS$^{1-703}$ can utilize molecules other than the naturally occurring acceptors or primer molecules as the basis for forming a polysaccharide polymer chain.

Figure 2:
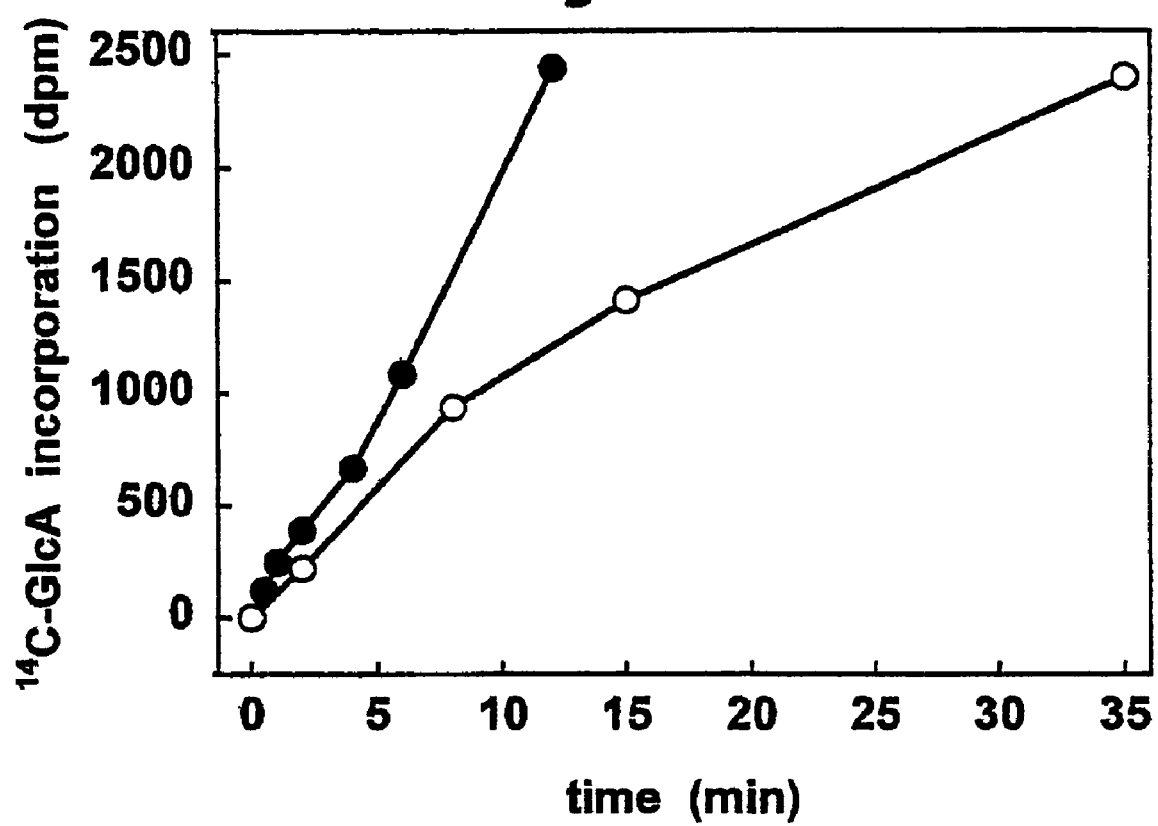
FIG. 2 is a graphical plot showing that HA polymerization is effected by HA oligosaccharides.

The HA polymerizing activity of recombinant pmHAS$^{1-703}$ is dependent on the simultaneous incubation with both UDP-sugar precursors and a Mn$^{2+}$ ion. The level of incorporation is dependent on protein concentration, on HA oligosaccharide concentration, and on incubation time as shown in FIG. 2. In FIG. 2, two parallel reactions containing pmHAS$^{1-703}$ with even-numbered HA oligosaccharides (105 µg membrane protein/point with a mixture of HA hexamer, octamer, and decamer, 4.4. µg total; solid circles) or six-fold more pmHAS$^{1-703}$ without oligosaccharide acceptor (630 µg protein/point; open circles) were compared. The enzyme preparations were added to prewarmed reaction mixtures containing UDP-[$^{14}$C]GlcUA (240 µM 6×10$^4$ dpm/point) and UDP-GlcNAc (600 µM) in assay buffer. At various times, 50 µl aliquots were withdrawn, terminated, and analyzed by paper chromatography. The exogenously supplied acceptor accelerated the bulk incorporation of sugar precursor into polymer product by pmHAS$^{1-703}$, but the acceptor was not absolutely required.

HA synthesized in the presence or the absence of HA oligosaccharides is sensitive to HA lyase (>95% destroyed) and has a molecular weight of ~1-5×10$^4$ Da (~50-250 monosaccharides). No requirement for a lipid-linked intermediate was observed as neither bacitracin (0.5 mg/ml) nor tunicamycin (0.2 mg/ml) alter the level of incorporation in comparison to parallel reactions with no inhibitor.

Figure 3:
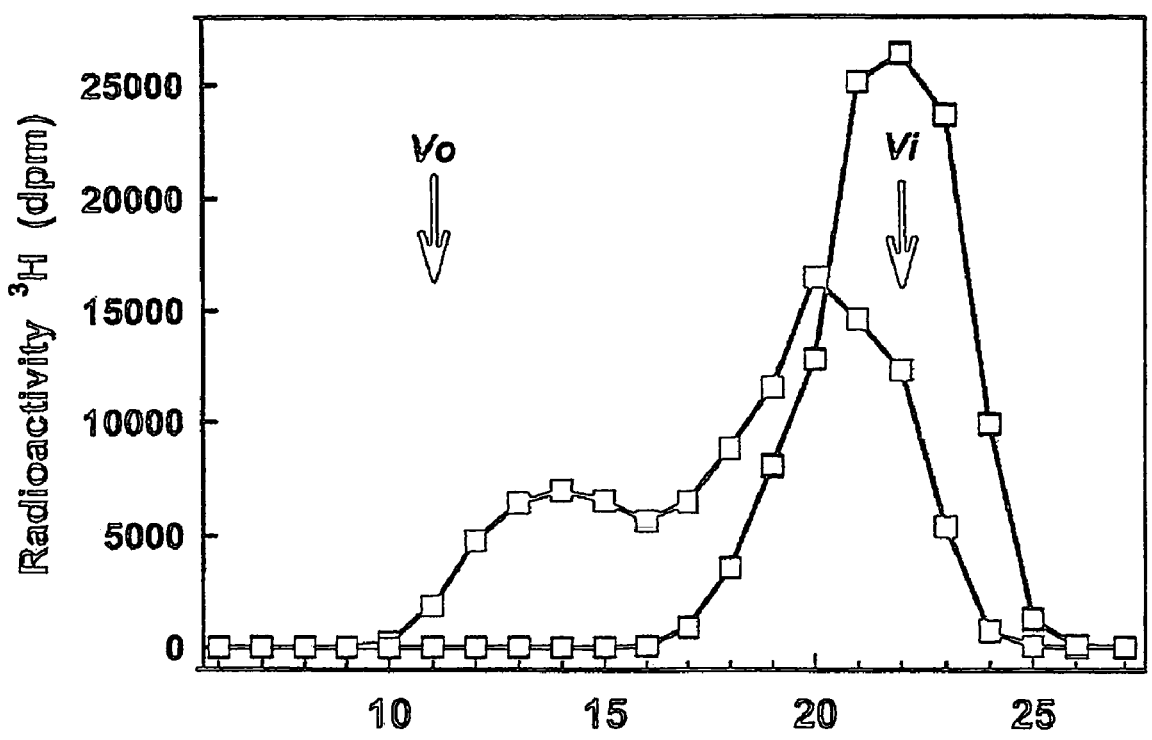
FIG. 3 is a graphical plot showing HA tetramer elongation into larger polymers by pmHAS.

Gel filtration chromatography analysis of reactions containing recombinant pmHAS$^{1-703}$, $^3$H-HA tetramer, UDP-GlcNAc and UDP-GlcUA show that labeled polymers from ~0.5 to 5×10$^4$ Da (25-250 monosaccharides) are made as shown in FIG. 3. In FIG. 3, gel filtration analysis on Sephacryl S-200 (20 ml column, 0.7 ml fractions) shows that pmHAS$^{1-703}$ makes HA polysaccharide using HA tetramer acceptor and UDP-sugars. Dextrans of greater than or equal to 80 kDa (~400 monosaccharides) elute in the void volume (Vo arrow). The starting tetramer elutes in the included volume (Vi arrow). Membranes (190 µg total protein), UDP-GlcUA (200 µM), UDP-GlcNAc (600 µM), and radiolabeled $^3$H-HA tetramer (1.1×10$^5$ dpm) were incubated for 3 hours before gel filtration (solid squares). As a negative control, a parallel reaction containing all the components except for UDP-GlcNAc was analyzed (open squares). The small primer was elongated into higher molecular weight product if both precursors were supplied. In a parallel reaction without UDP-GlcNAc, the elution profile of the labeled tetramer is not altered.

The activity of the native pmHAS$^{1-703}$ from *P. multocida* membranes, however, is not stimulated by the addition of HA oligosaccharides under similar conditions. The native pmHAS$^{1-703}$ enzyme has an attached or bound nascent HA chain that is initiated in the bacterium prior to membrane isolation. The recombinant enzyme, on the other hand, lacks such a nascent HA chain since the *E. coli* host does not produce the UDP-GlcUA precursor needed to make HA polysaccharide. Therefore, the exogenous HA-derived oligosaccharide has access to the active site of pmHAS$^{1-703}$ and can be elongated.

The tetramer from bovine testicular hyaluronidase digests of HA terminates at the nonreducing end with a GlcUA residue and this molecule served as an acceptor for HA elongation by pmHAS$^{1-703}$. On the other hand, the tetramer and hexamer oligosaccharides produced by the action of *Streptomyces* HA lyase did not stimulate HA polymerization as shown in FIG. 1; "unsHA4/6". As a result of the lyase eliminative cleavage, the terminal unsaturated sugar is missing the C4 hydroxyl of GlcUA which would normally be extended by the HA synthase. The lack of subsequent polymerization onto this terminal unsaturated sugar is analogous to the case of dideoxynucleotides causing chain termination if present during DNA synthesis. A closed pyranose ring at the reducing terminus was not required by pmHAS$^{1-703}$ since reduction with borohydride did not affect the HA tetramer's ability to serve as an acceptor thus allowing the use of borotritide labeling to monitor the fate of oligosaccharides.

Neither Yeast-derived recombinant Group A HasA nor recombinant DG42 produced elongated HA-derived oligosaccharides into larger polymers. First, the addition of HA tetramer (or a series of longer oligosaccharides) did not significantly stimulate nor inhibit the incorporation of radiolabeled UDP-sugar precursors into HA (<5% of control value) by these Class I HA synthases. In parallel experiments, the HAS activity of HasA or DG42 was not affected by the addition of chitin-derived oligosaccharides. Second, the recombinant Class I enzymes did not elongate the radiolabeled HA tetramer in the presence of UDP-sugars (Table IV). These same preparations of enzymes, however, were highly active in the conventional HAS assay in which radiolabeled UDP-sugars were polymerized into HA.

TABLE IV

| Enzyme | Units[a] | EDTA | Incorporation of HA4 into polymer (pmoles) |
|---|---|---|---|
| PmHAS[1-703] | 6[b] | − | 240 |
|  |  | + | 1.7 |
| HasA | 9,800 | − | ≦0.2 |
|  |  | + | ≦0.2 |
| DG42 | 11,500 | − | ≦0.1 |
|  |  | + | ≦0.3 |

[a] pmoles of GlcUA transfer/hr in the conventional HAS assay
[b] measured without HA tetramer; 360 units with 100 μM HA tetramer.

As shown in Table IV, the various recombinant enzymes were tested for their ability to convert HA tetramer into molecular weight products. The reactions contained radiolabeled HA tetramer (5-8×10$^5$ dpm), 750 μM UDP-GlcNAc, 360 μM UDP-GlcUA, 20 mM XCl$_2$, 50 mM Tris, pH 7-7.6 (the respective X cation and pH values used for each enzyme were: pmHAS[1-703], Mn/7.2; Xenopous DG42, Mg/7.6; Group A streptococcal HasA, Mg/7.0), and enzyme (units/reaction listed). As a control, parallel reactions in which the metal ion was chelated (22 mM ethylenediaminetetraacetic acid final; EDTA column, rows with +) were tested; without free metal ion, the HAS enzymes do not catalyze polymerization. After 1 hour incubation, the reactions were terminated and subjected to descending paper chromatography. Only pmHAS[1-703] could elongate HA tetramer even though all three membrane preparations were very active in the conventional HAS assay (incorporation of [$^{14}$C]GlcUA from UDP-GlcUA into polymer when supplied UDP-GlcNAc).

Figure 4:
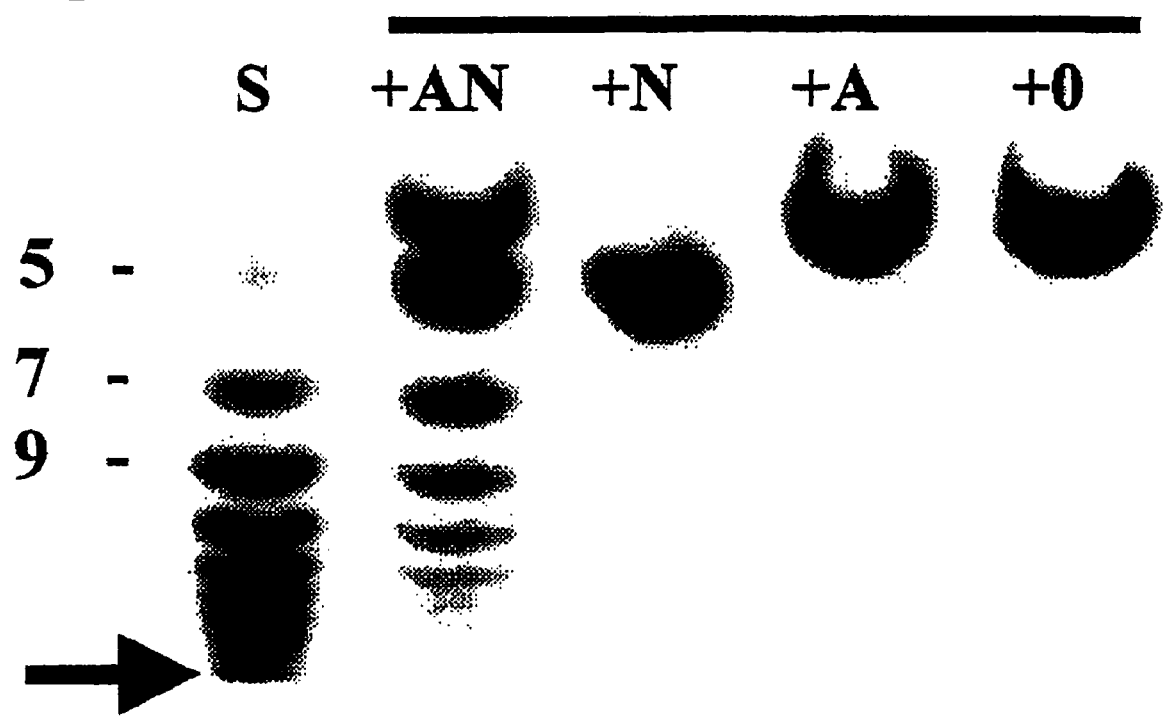
FIG. 4 is a graphical representation of a thin layer chromatography analysis of pmHAS extension of HA tetramer.

Thin layer chromatography was utilized to monitor the pmHAS-catalyzed elongation reactions containing $^3$H-labeled oligosaccharides and various combinations of UDP-sugar nucleotides. FIG. 4 demonstrates that pmHAS[1-703] elongated the HA-derived tetramer by a single sugar unit if the next appropriate UDP-sugar precursor was available in the reaction mixture. GlcNAc derived from UDP-GlcNAc was added onto the GlcUA residue at the nonreducing terminus of the tetramer acceptor to form a pentamer. On the other hand, inclusion of only UDP-GlcUA did not alter the mobility of the oligosaccharide. If both HA precursors are supplied, various longer products are made. In parallel reactions, control membranes prepared from host cells with a vector plasmid did not alter the mobility of the radiolabeled HA tetramer under any circumstances. In similar analyses monitored by TLC, pmHAS[1-703] did not utilize labeled chitopentaose as an acceptor.

As shown in FIG. 4, pmHAS extended an HA tetramer. In FIG. 4, radiolabeled HA tetramer (HA4 8×10$^3$ dpm $^3$H) with a GlcUA at the nonreducing terminus was incubated with various combinations of UDP-sugars (A, 360 μM UDP-GlcUA; N, 750 μM UDP-GlcNAc; 0, no UDP-sugar), and pmHAS (55 μg membrane protein) in assay buffer for 60 minutes. The reactions (7 μl total) were terminated by heating at 95° C. for 1 minute and clarified by centrifugation. Portions (2.5 μl) of the supernatant were spotted onto the application zone of a silica TLC plate and developed with solvent (1.25:1:1 butanol/acetic acid/water). The beginning of the analytical layer is marked by an arrow. The positions of odd-numbered HA oligosaccharides (S lane) are marked as number of monosaccharide units. The autoradiogram of FIG. 4 (4 day exposure) shows the single addition of a GlcNAc sugar onto the HA tetramer acceptor to form a pentamer when only the subsequent precursor is supplied (N). The mobility of the labeled tetramer is unchanged if only the inappropriate precursor, UDP-GlcUA (A), or no UDP-sugar (0) is present. If both UDP-sugars are supplied, then a ladder of products with sizes of 5, 7, 9, 11, and 13 sugars is formed (+AN). In a parallel experiment, chitopentaose (8×10$^4$ dpm $^3$H) was tested as an acceptor substrate. Under no condition was this structurally related molecule extended by pmHAS.

Figure 5:
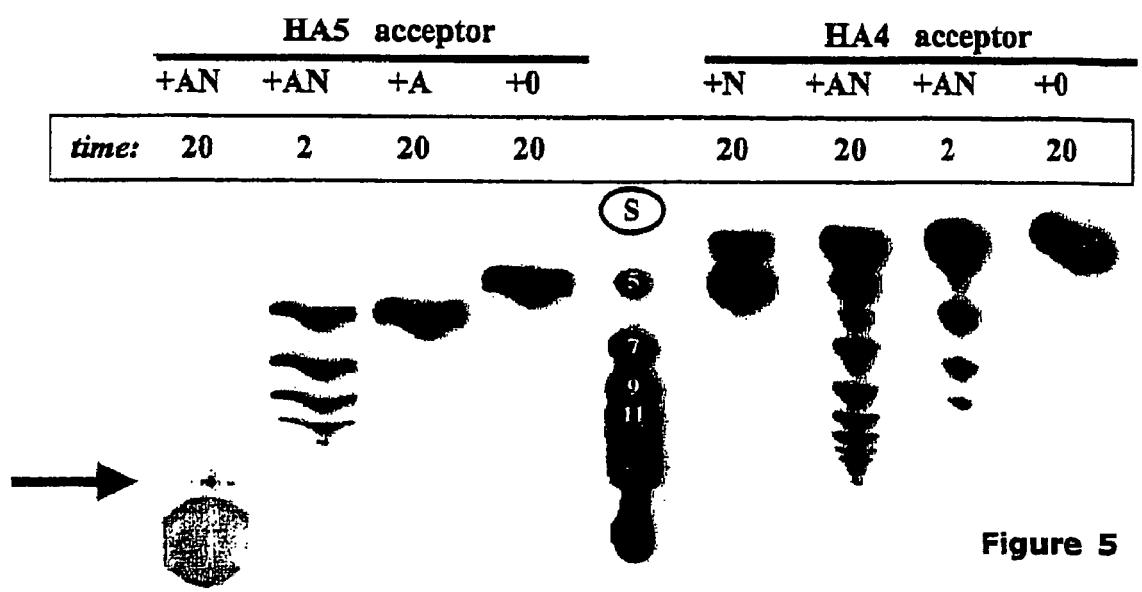
FIG. 5 is a graphical representation of thin layer chromatography analysis of the early stages of HA elongation.

HA-derived oligosaccharides with either GlcUA or GlcNAc at the nonreducing terminus served as acceptors for pmHAS[1-703] (FIG. 5). In FIG. 5, radiolabeled HA pentamer (HA5, 5×10$^3$ dpm $^3$H) or HA tetramer (HA4, 25×10$^3$ dpm $^3$H) was incubated with pmHAS[1-703] and various combinations of UDP-sugars (as in FIG. 4) for 2 or 20 minutes. Portions (1.5 μl) of the supernatant were spotted onto the TLC plate and developed in 1.5:1:1 solvent. This autoradiogram (1 mo. exposure) shows the single addition of a sugar onto an acceptor when only the appropriate precursor is supplied (HA4, N lane and HA5, A lane). If both UDP-sugars are supplied (+AN lanes), then a ladder of products with final sizes of 6, 8, and 10 sugars is formed from either HA4 or HA5 in 2 minutes. After 20 minutes, a range of odd- and even-numbered product sugars are observed in reactions with HA4 and both UDP-sugars. In the 20 minute reaction with HA5 and both UDP-sugars, the HA products are so large that they do not migrate from the application zone.

Within two minutes, 2 to 6 sugar units were added, and after 20 minutes, at least of from about 9 to about 15 sugar units were added. In the experiments with the HA tetramer and both sugars, a ladder of even- and odd-numbered products is produced at the 20 minute time point. Therefore, in combination with the results of the single UDP-sugar experiments, the pmHAS[1-703] enzyme transfers individual monosaccharides sequentially during a polymerization reaction.

Methods and Reagents

Membrane preparations containing recombinant pmHAS (GenBankAF036004) (SEQ. ID NOS: 1 and 2) were isolated from E. coli SURE(pPmHAS). Membrane preparations containing native pmHAS were obtained from the P. multocida strain P-1059 (ATCC #15742). pmHAS was assayed in 50 mM Tris, pH 7.2, 20 mM MnCl$_2$, and UDP-sugars (UDP-[$^{14}$C]GlcUA, 0.3 μCi/mmol, NEN and UDP-GlcNAc) at 30° C. The reaction products were analyzed by various chromatographic methods as described below. Membrane preparations containing other recombinant HAS enzymes, Group A streptococcal HasA or Xenopus DG42 produced in the yeast Saccharomyces cerevisiae, were prepared.

Uronic acid was quantitated by the carbazole method. Even-numbered HA oligosaccharides [(GlcNAc-GlcUA)$_n$] were generated by degradation of HA (from Group A Streptococcus) with either bovine testicular hyaluronidase Type V (n=2-5) or Streptomyces hyaluroniticus HA lyase (n=2 or 3) in 30 mM sodium acetate, pH 5.2, at 30° C. overnight. The latter enzyme employs an elimination mechanism to cleave the chain resulting in an unsaturated GlcUA residue at the nonreducing terminus of each fragment. For further purification and desalting, some preparations were subjected to gel filtration with P-2 resin (BioRad) in 0.2 M ammonium formate and lyophilization. Odd-numbered HA oligosaccharides [GlcNAc(GlcUA-GlcNAc)$_n$] ending in a GlcNAc residue were prepared by mercuric acetate-treatment of partial HA digests generated by HA lyase (n=2-7). The masses of the HA oligosaccharides were verified by matrix-assisted laser desorption ionization time-of-flight mass spectrometry. Sugars in water were mixed with an equal volume of 5 mg/ml 6-azo-2-thiothymine in 50% acetonitrile/0.1% trifluoroacetic acid, and rapidly air-dried on the target plate. The negative ions produced by pulsed nitrogen laser irradiation were analyzed in linear mode (20 kV acceleration; Perceptive Voyager).

Other oligosaccharides that are structurally similar to HA were also tested in HAS assays. The structure of heparosan pentamer derived from the *E. coli* K5 capsular polysaccharide is β4GlcUA-α4GlcNAc; this carbohydrate has the same composition as HA but the glycosidic linkages between the monosaccharides are different. The chitin-derived oligosaccharides, chitotetraose and chitopentaose, are β4GlcNAc polymers made of 4 or 5 monosaccharides, respectively.

Various oligosaccharides were radiolabeled by reduction with 4 to 6 equivalents of sodium borotritide (20 mM, NEN; 0.2 μCi/mmol) in 15 mM NaOH at 30° C. for 2 hrs. $^3$H-oligosaccharides were desalted on a P-2 column in 0.2 M ammonium formate to remove unincorporated tritium and lyophilized. Some labeled oligosaccharides were further purified preparatively by paper chromatography with Whatman 1 developed in pyridine/ethyl acetate/acetic acid/$H_2O$ (5:5:1:3) before use as an acceptor.

Paper chromatography with Whatman 3M developed in ethanol/1M ammonium acetate, pH 5.5 (65:35) was used to separate high molecular weight HA product (which remains at the origin) from UDP-sugars and small acceptor oligosaccharides. In the conventional HAS assay, radioactive UDP-sugars are polymerized into HA. To obtain the size distribution of the HA polymerization products, some samples were also separated by gel filtration chromatography with Sephacryl S-200 (Pharmacia) columns in 0.2 M NaCl, 5 mM Tris, pH 8. Columns were calibrated with dextran standards. The identity of the polymer products was assessed by sensitivity to specific HA lyase and the requirement for the simultaneous presence of both UDP-sugar precursors during the reaction. Thin layer chromatography [TLC] on high performance silica plates with application zones (Whatman) utilizing butanol/acetic acid/water (1.5:1:1 or 1.25:1:1) development solvent separated $^3$H-labeled oligosaccharides in reaction mixes. Radioactive molecules were visualized after impregnation with EnHance spray (NEN) and fluorography at ~80° C.

An anti-pmHAS monospecific antibody reagent has also been identified that routinely monitors the protein by Western blots or immunoassays; this reagent can be used to normalize protein expression levels. The DNA inserts encoding the enzyme sequence from interesting mutants picked up in screens can be subcloned and completely sequenced to verify and to identify the mutation site.

A series of truncated versions of pmHAS (normally a 972-residue membrane protein) were created and are tabulated (with functionality) in Table V that produce proteins with altered physical properties (i.e., proteins that are more conducive to high-level expression and purification) and altered function (i.e., single transferase activity). Polymerase chain reaction [PCR] was used to amplify a portion of the pmHAS gene using a primer corresponding to the authentic N-terminus sequence and a primer corresponding to an internal coding region which ended in a stop codon. The coding regions for the truncated proteins were cloned into an *Escherichia coli* expression plasmid (pKK223-3; Pharmacia) under control of the tac promoter. The DNA sequence was verified by automated sequencing.

The truncation series was generated and tested for activity. All proteins were made at the expected molecular weight, but not all proteins were active.

TABLE V

| Name | Residues of pmHAS-D | Activity | SEQ ID NO: |
|---|---|---|---|
| pmHAS$^{437-972}$ | 437-972 | N.D. | 13 |
| pmHAS$^{437-756}$ | 437-756 | N.D. | 14 |
| pmHAS$^{1-756}$ | 1-756 | HA Synthase | 20 |
| pmHAS$^{1-703}$ | 1-703 | HA Synthase | 9, 71 |
| pmHAS$^{1-650}$ | 1-650 | GlcNAc Transferase | 10 |
| pmHAS$^{152-756}$ | 152-756 | N.D. | 15 |

N.D. - no activity detected.

Figure 6:
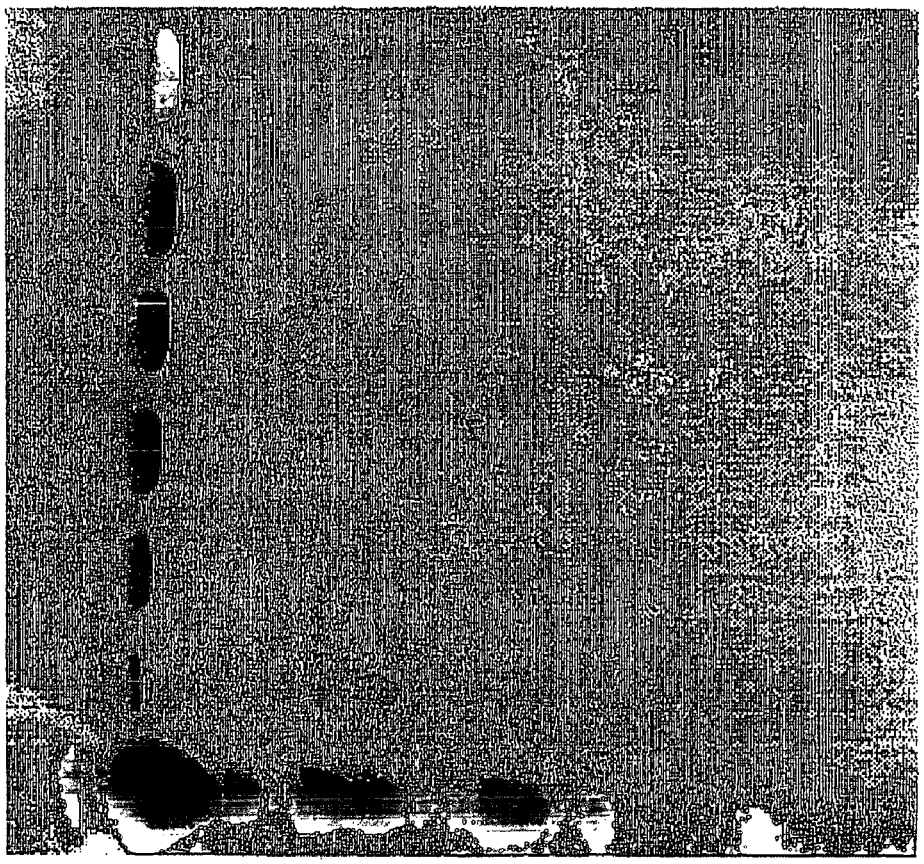
FIG. 6 is an electrophoresis gel showing the purification of pmHAS$^{1-703}$.

Analysis of induced cell cultures containing the plasmid with a 703-residue open reading frame revealed that a new 80-kDa protein, named pmHAS$^{1-703}$, was produced in large quantities. Furthermore, functional pmHAS$^{1-703}$ was present in the soluble fraction of the cell lysate; thus allowing for rapid extraction and assay of the enzyme. pmHAS$^{1-703}$ was purified by sequential chromatography steps shown in FIG. 6. In FIG. 6, a soluble, active form of the HA synthase was constructed with molecular biological techniques. The recombinant enzyme from *E. coli* was purified by conventional chromatography with yields of up to 20 mg/liter of cell culture. FIG. 6 is a stained electrophoretic gel loaded with samples of pmHAS$^{1-703}$ (marked with an arrow) during different stages of chromatography. This catalyst (and improved mutant versions) can be used to prepare HA coatings on artificial surfaces or HA extensions on suitable acceptor molecules.

The pmHAS$^{1-703}$ is highly active and at least 95% pure as assessed by denaturing polyacrylamide gel electrophoresis. Mass spectrometric analysis indicates that the pmHAS$^{1-703}$ is the desired protein due to the close agreement of the calculated and the observed mass values. A buffer system has also been developed to stabilize the enzymatic activity in the range of 0° to 37° C.

Site-directed mutagenesis was then used to prepare versions of pmHAS$^{1-703}$ with altered enzymatic activity. Synthetic DNA oligonucleotides and multiple rounds of extension with Pfu DNA polymerase were used to add mutations to the coding region using the Quick-Change system from Stratagene. Through use of primers with mixed bases at certain positions, a wide variety of amino acid changes were generated. DNA sequencing was then employed to identify the changed residue. Several pmHAS$^{1-703}$ mutants have also been obtained having altered sugar transferase activity. Similar methodology has also been used to alter the HA-acceptor binding site of pmHAS$^{1-703}$.

Two positions of the pmHAS$^{1-703}$ sequence were mutated in the initial trials. Conserved aspartates at residue 196 or 477 were critical for HAS activity. Results are shown in Table VI.

TABLE VI

| Mutation (*) | HAS Activity | GlcNActase | GlcUAtase | SEQ. ID NO: |
|---|---|---|---|---|
| D196E | W/O | W/O | YES | 16 |
| D196N | W/O | W/O | YES | 12 |
| D196K | W/O | W/O | YES | 17 |
| D477E | W/O | YES | W/O | 18 |
| D477N | W/O | YES | W/O | 11 |
| D477K | W/O | YES | W/O | 19 |
| WILD TYPE CONTROL | YES | YES | YES | 2 |

(*) Single letter code for amino acid changes at position 196 or 477 (as noted) in which wild type aspartate (D) is exchanged with an asparagine (N), glutamate (E), or lysine (K).
"W/O" weak (<8% of wild-type) or no activity.

Figure 7:
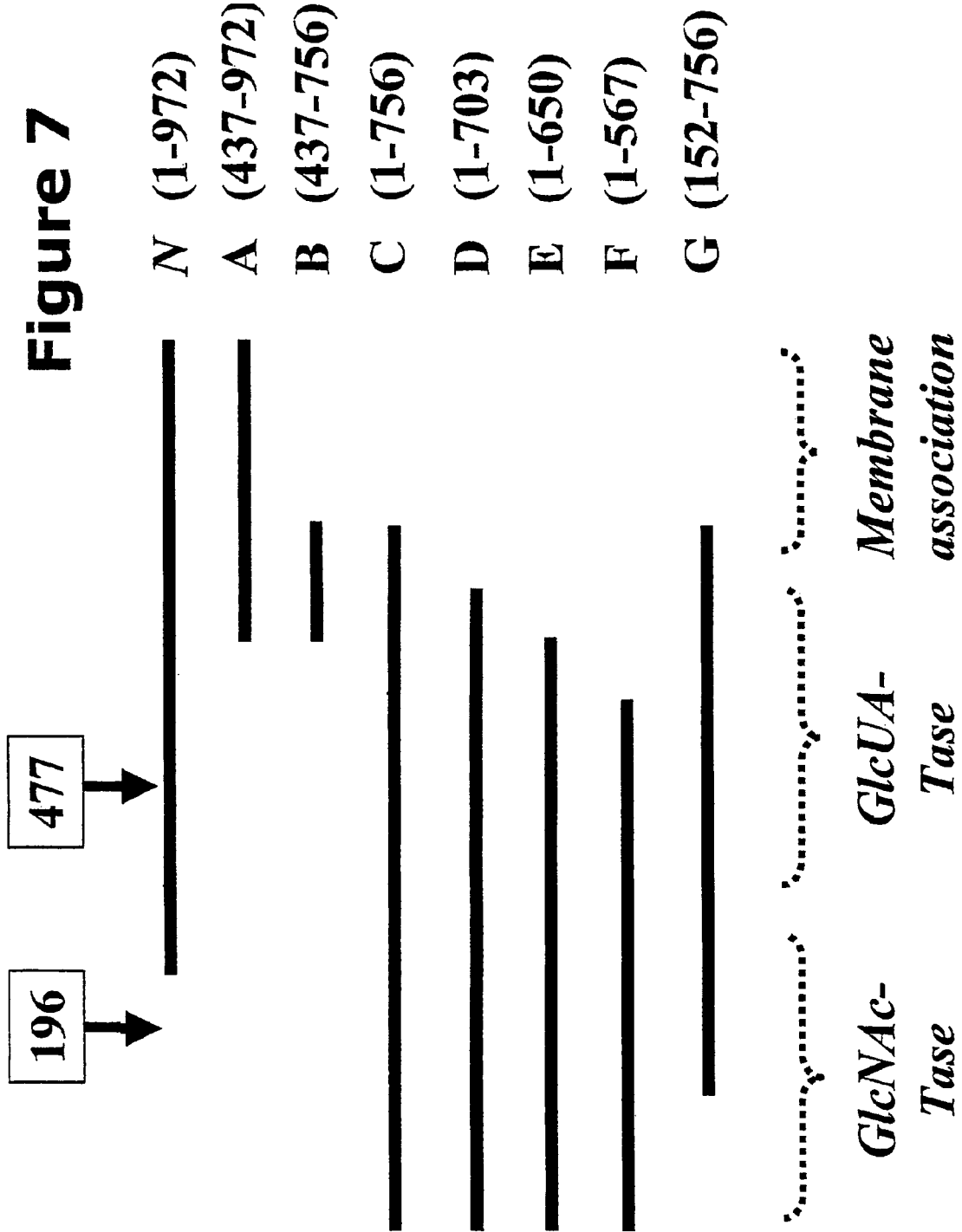
FIG. 7 is a pictorial representation of the pmHAS truncation mutants.

The mutant enzymes are useful for adding on a single GlcNAc or a single GlcUA onto the appropriate acceptor oligosaccharide. It appears that pmHAS$^{1-703}$ has two domains or two modules for transferring each sugar. One of ordinary skill in the art, given this specification, would be able to shift or to combine various domains to create new polysaccharide synthases capable of producing new polysaccharides with altered structures. Within such use, a variety of grafting techniques arise which utilize pmHAS$^{1-703}$ as the prototype. A graphical representation of each mutant as it relates to the pmHAS$^{1-703}$ sequence is shown in FIG. 7.

Figure 8:
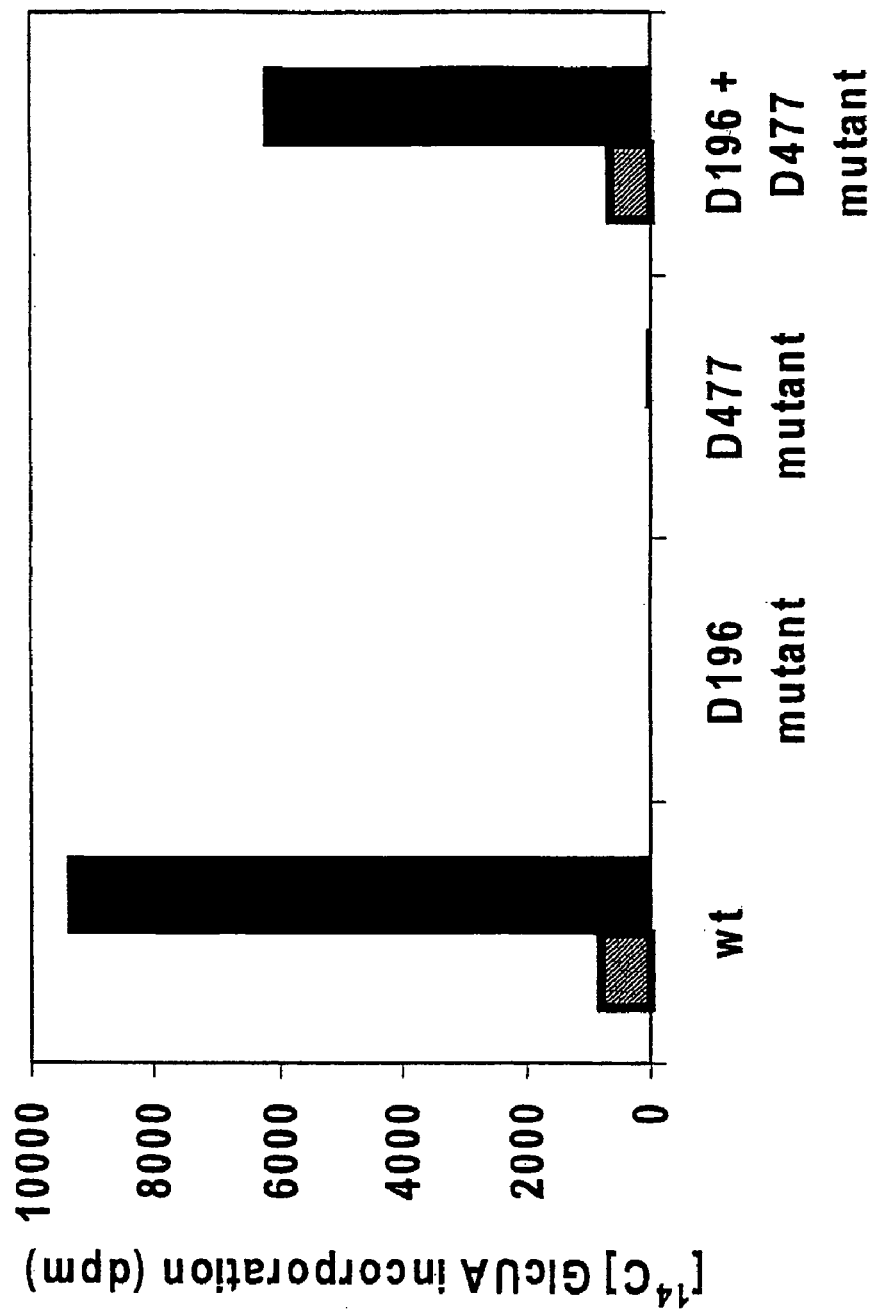
FIG. 8 is a graphical representation of a mutant combination assay.

FIG. 8 is a graphical representation of an experiment where combining two single action mutants rescued dual enzymatic activity. HAS enzyme assays were performed in the presence of wild type pmHAS$^{1-703}$ alone, D196 mutant alone, D477 mutant alone, or in the presence of both D196 and D477 mutants. Equal amounts of each enzyme were tested with a small amount of HA acceptor sugar in the typical reaction buffer at 30° C. Two time points were measured (cross-hatched, 25 minutes; black, 1.5 hours) for each assay. The two mutants work together to make HA polymer; by itself, a single mutant cannot make HA polymer. Enzyme activity of the pmHAS$^{1-703}$ mutants is shown in FIG. 9. Extracts of the mutants were used for all three kinds of assays: for HA polymer production, for GlcUA-Tase activity and for GlcNAc-Tase activity. Equivalent amounts of pmHAS$^{1-703}$ proteins (based on Western blot analysis) were assayed. The activities were indicated as the percentage of the activity of wild type pmHAS$^{1-703}$.

Additionally, HA, chondroitin, heparin, or chimeric or hybrid molecules that include any or all of the previous GAGs may be attached to other substrates by using the polymer grafting technology of the presently claimed and disclosed invention. These additional substrates may be metal or metalized—i.e., having a metal coating on the surface of a second material (or a laminate material) such as plastic or silica. The metal substrate may be, but is not limited to: gold, copper, stainless steel, nickel, aluminum, titanium, vanadium, chromium, thermosensitive metal alloys, and combinations thereof to name but a few. One of ordinary skill in the art would appreciate that any metal could be used as the substrate as long as it had a surface layer capable of having an activated surface or activated surface group with a functional acceptor molecule.

In particular, gold is an exceptional metal substrate to which a functional acceptor may be attached by using the polymer grafting technology of the presently claimed and disclosed invention. This biologically inert metal acts to elongate the functional acceptor as well as to create a glycosidic bond between the functional acceptor and at least one of GlcUA and GlcNAc.

The procedure for elongating a functional acceptor includes: providing a functional acceptor having at least two sugar units selected from the group consisting of GlcUA, GlcNAc, and hexosamine, and attaching the functional acceptor to a substrate such as gold; providing a hyaluronic acid synthase capable of elongating the functional acceptor, wherein the hyaluronic acid synthase has an amino acid sequence encoded by a nucleotide sequence capable of hybridizing under standard conditions to a nucleotide sequence encoding the hyaluronic acid synthase, such as pmHAS pr pmHAS$^{1-703}$; and providing UDP-GlcUA and UDP-GlcNAc sugars such that the hyaluronic acid synthase elongates the functional acceptor.

Other acceptable substrates include, but are not limited to, silica, silicon, glass, polymers, organic compounds, metals and combinations thereof. Other metals that may act as a substrate include, but are not limited to, copper, stainless steel, nickel, aluminum, titanium, thermosensitive alloys and combinations thereof.

The procedure for creating a glycosidic bond between a functional acceptor and at least one of GlcUA and GlcNAc includes: providing a hyaluronic acid synthase capable of making a glycosidic bond between a functional acceptor and at least one of GlcUA and GlcNAc wherein the functional acceptor has at least two sugar units selected from the group consisting of GlcUA, GlcNAc, and hexosamine, and wherein the hyaluronic acid synthase has an amino acid sequence encoded by a nucleotide sequence capable of hybridizing under standard conditions to the nucleotide sequence encoding hyaluronic acid synthase, such as pmHAS pr pmHAS$^{1-703}$, and wherein the functional acceptor is attached to a substrate such as gold; and incubating the hyaluronic acid synthase with at least one of UDP-GlcUA and UDP-GlcNAc in the presence of the functional acceptor so as to create the glycosidic bond between the functional acceptor and at least one of GluUA and GlcNAc.

Other acceptable substrates include, but are not limited to, silica, silicon, glass, polymers, organic compounds, metals and combinations thereof. Other metals that may act as a substrate include, but are not limited to, copper, stainless steel, nickel, aluminum, titanium, thermosensitive alloys and combinations thereof.

The procedure for attachment of HA, chondroitin, heparin, or chimeric or hybrid molecule chains onto metal is the same as any other type of substrate and includes: combining the metal particle-NHS ester i.e. activated metal surface (NanoGold from NanoProbes, Inc.) and 10 molar equivalents of amino-HA4 (reactive pmHAS$^{1-703}$ acceptor oligosaccharide) in 0.03 M borate buffer, pH 8.5, 20% DMSO for 2 hours at 20° C.; separating the free unused acceptor from the metal particle-HA4 product by P-2 (BioRad) gel filtration column in TBS buffer (50 mM Tris, pH 7.5, 0.15 M NaCl), harvesting the void gold peak; adding the metal particle-HA4 to the reaction with below components at a final concentration of: 1 M ethylene glycol, 50 mM Tris, pH 7.2, 15 mM MnCl$_2$, 0.05 mM UDP-[$^{14}$C]Glc-UA, 0.05 mM UDP-[3H]GlcNAc, and pmHAS$^{1-703}$ enzyme extract.

The *E coli* host cells containing the pmHAS$^{1-703}$ cloned into the expression vector pKK223-3 (Pharmacia) are grown on Luria broth (LB) plates with ampillicin at 30° C. A colony is used to seed a 40 ml starter culture in enriched LB broth (1.0 g LB broth powder [Difco], 0.4 g Casamino acids, 40 ml water) with ampicillin in a 250 ml Erlenmeyer flask. After overnight culture, the starter is split and used to inoculate four 2 L Erlenmeyer flasks with 400 ml enriched LB broth containing Ampicillin and Carbinicillin and trace elements. When the OD-600 nm reaches 0.5-0.8, the inducer IPTG is added to a concentration of 0.2 mM. After 1 hour, fructose is added to 12.8 mM. After overnight growth, cells are harvested by centrifugation, and frozen at −80° C. The cells are extracted with 30 ml of lysis buffer (1% n-Octyl-b-D-Thioglucopyranoside, 1 M ethylene glycol, 50 mM HEPES, pH 7, Pepstatin (14.6 uM), Leupeptin (20 uM), E-64 (2 uM), AEBSF (0.4 mM), Benzamidine (2 mM), DNAse/RNAse (1 mg of ea/ml). The suspension is stirred at 4° C. for 1 hour; the cells are removed by centrifugation at 3,000×g, for 30 min @ 4° C. The supernatant containing the pmHAS$^{1-703}$ is clarified by high-speed centrifugation at 30,000×g and applied to a dye affinity column. The pmHAS$^{1-703}$ is eluted with a salt gradient. The relevant fractions with enzyme are pooled and dialyzed into a reaction buffer for use in polymer grafting.

Creation of HA/Chondrotin sulfate chimeric or hybrid polysaccharides—The pmHAS catalyst (pmHAS$^{1-703}$-1 microgram) was mixed with either (a) no polymer acceptor or with various amounts of chondroitin sulfate (shark, Sigma)—either (b) 5 or (c) 25 micrograms—in a 20 ul reaction. All reactions contained 50 mM Tris, pH 7.2, 1 M ethylene glycol, 20 mM MnCl2, 2.5 mM UDP-GlcUA. Half of the reactions also contained 2.5 mM UDP-GlcNAc; for grafting of long HA chains, both UDP-sugars need to be present. All reactions were allowed to incubate at 30° C. for 16 hours. A sample of all the reactions were analyzed on a 0.8% agarose gel in 1×TAE buffer with a DNA standard (1 kb ladder, Stratagene). After the run, the gel was stained with the dye Stains-all according to Lee and Cowman (Analytical Biochemistry, v. 219, p. 278-287. 1994). The slower running HA/CS hybrids are obvious in reactions containing both UDP-sugars and the chondroitin sulfate acceptor.

One example of polymer grafting comprises incubating all components together for 16 hours at 20° C.; removing the unincorporated HA precursor sugars with ultrafiltration with a Micron 3 (3,000 Da MW cutoff; Amicon) and repeated washing with TBS buffer; and counting the retained samples (e.g., big polymers and particles) by liquid scintillation counting for both $^3$H and $^{14}$C labels. Various formulations, buffers, and procedures can be used for polymer grafting.

TABLE VII

| gold particle-A4 present? | PmHAS$^{1-703}$ catalyst present? | [$^3$H]GlcNAc (dpm) | [$^{14}$C]GlcUA (dpm) |
|---|---|---|---|
| Yes | Yes | 12,000 | 5,000 |
| Yes | No | 80 | 40 |
| No | Yes | 420 | 190 |

As can be observed from the above-described results (Table VII), (1) HA was grafted by pmHAS$^{1-703}$ onto gold particles via the HA4 acceptor—i.e. both sugars were added to the gold particles in presence of enzyme; and (2) along with previous demonstrations of attaching HA to various disparate entities (including glass, plastic, polymers, and organic molecules) by polymer grafting technology, one of ordinary skill in the art may attach HA onto any substrate by attaching the initial acceptor to the target and then contacting the acceptor-target complex with pmHAS$^{1-703}$ and UDP-sugars.

Due to the relative absence of foreign components or artificial moieties, no immunological problems occur if the polymer grafted product is introduced into the body. Depending on the particular application, the polymer length and the chain orientation can be controlled with precision. The polysaccharide surface coatings of the present invention improve the biocompatibility of the artificial material, lengthen the lifetime of the device in the cellular environment, and encourage natural interactions with host tissues.

With regard to surface coatings on solid materials, polyacrylamide beads have been coated with the HA polymer using pmHAS$^{1-703}$ as the catalyst. First, aminoethyl-beads were chemically primed with HA oligosaccharide (a mixture of 4, 6, and 8 sugars long) by reductive amination. Beads, HA oligosaccharide, and 70 mM NaCNBH$_4$ in 0.2 M borate buffer, pH 9, were incubated at 42° C. for 2 days. The beads were washed with high and low salt buffers before use in the next step. Control beads without priming sugar or with chitopentaose [(GlcNAc)$_5$] were also prepared; beads without HA would not be expected to prime HA synthesis and the chitopentaose does not serve as an acceptor for pmHAS-D. Second, the various preparations of beads (15 µliters) were incubated with pmHAS$^{1-703}$ (3 µz), 150 mM UDP-[$^3$H] GlcNAc, 60 mM UDP-[$^{14}$C]GlcUA, 20 mM MnCl$_2$, in 50 mM Tris, pH 7.2, at 30° C. for 60 min. The beads were then washed with high and low salt buffers. Radioactivity linked to beads (corresponding to the sugars) was then measured by liquid scintillation counting and are reported in Table VIII.

TABLE VIII

| Bead Type | Enzyme Added? | Bound GlcUA ($^{14}$C dpm) | Bound GlcNAc ($^3$H dpm) |
|---|---|---|---|
| HA primer | Yes | 990 | 1140 |
| HA primer | No | 10 | 10 |
| Chito primer | Yes | 24 | 18 |
| No primer | Yes | 5 | 35 |

Only HA beads primed with the HA oligosaccharide and incubated with pmHAS$^{1-703}$ incorporated the radiolabel from both UDP-sugar precursors indicating that the short HA sugar attached to the bead was elongated into a longer HA polymer by the enzyme. Thus far, no other known HA synthase possesses the desired catalytic activity to apply an HA polymer coating onto a primed substrate.

Thus, as shown above, an authentic HA oligosaccharide primer was chemically coupled to a polyacrylamide surface and then this primer was further elongated using the pmHAS$^{1-703}$ enzyme and UDP-sugars. Depending on the substrate, the reaction conditions can be optimized by one of ordinary skill in the art. For example, the mode of substrate modification, buffer conditions, HA elongation reaction time and stoichiometry can be varied to take into account any single or multiple reaction variation. The resulting coatings can then be evaluated for efficacy and use.

In order to scale-up and to facilitate the biocompatible HA coating process to a level practical for medical devices in the future, (a) a new synthetic molecule that would substitute for the HA oligosaccharide with the original pmHAS$^{1-703}$ enzyme will be used; or (b) a mutant form of the pmHAS$^{1-703}$ enzyme that will utilize a "simpler" organic molecule as the primer will be used.

The critical structural elements of the HA oligosaccharide acceptor or primer molecule are currently being tested and identified. The smallest acceptor molecule with activity tested thus far is an HA disaccharide, although it is anticipated that molecules as short as a monosaccharides will be suitable for use with the present invention.

Chemically synthesized oligosaccharides (ref. Halkes, K. M. et al., 1998, Carbohydrate Research, 309, p. 161-174) were tested to see if they could be elongated by pmHAS$^{1-703}$. Each sugar was added individually to a final concentration of 0.05 mM to a series of 50 µL reaction mixtures containing 50 mM Tris, pH 7.2, 1 M ethylene glycol, 0.1 M ammonium sulfate, 10 mM MnCl$_2$, 800 µM UDP-GlcNAc, 600 µM UDP-[$^{14}$C]GlcUA (6×10$^4$ dpm), and 2.5 µg pf pmHAS$^{1-703}$. After 20 minutes at 30° C., the HA polymer produced was quantitated by paper chromatography (polymer at the origin of the paper strip) and liquid scintillation counting (Jing and DeAngelis, 2000, Glycobiology, 10, p. 883-889).

TABLE IX

| Sugar* | [$^{14}$C]GlcUA incorporation (dpm) |
|---|---|
| 0 | 18 |
| N-MP | 16 |
| AN-MP | 24 |
| NA-MP | 140 |
| ANA-MP | 3540 |
| NAN-MP | 250 |
| ANAN-MP | 4000 |
| NANA-MP | 1710 |

TABLE IX-continued

| Sugar* | [$^{14}$C]GlcUA incorporation (dpm) |
|---|---|
| NANAN-MP | 2620 |
| ANANAN-MP | 3720 |

*Note: The sugar composition symbols: MP, methoxyphenyl group at the reducing end; N, GlcNAc; A, GlcUA.

It is obvious that the trisaccharide ANA (GlcUA-GlcNAc-GlcUA) is sufficient for high efficiency elongation by pmHAS, but certain disaccharides such as NA (GlcNAc-GlcUA), as well as certain monosaccharides (such as N or A), are also functional acceptors albeit at a lower efficiency than the longer sugars. Of course, one skilled in that art would expect that other sugar acceptors would be possible in light of the fact that pmHAS will elongate hyaluronic acid or chondroitin or chondroitin sulfate or heparin polysaccharides. The identity of the hexosamine and the availability of the hydroxyls (e.g. sulfated) may also be altered.

Recent data suggests that the pmHAS$^{1-703}$ enzyme has some flexibility with respect to the identity of the hexosamine group; i.e. other isomers will substitute for the GlcNAc sugar. For example, chondroitin pentamer [GalNAc-GlcUA-GalNAc-GlcUA-GalNAc], serves as an effective acceptor for pmHAS$^{1-703}$. Therefore, a synthetic molecule consisting of several hydroxyl groups, a pair of negatively charged groups (corresponding to the carboxyl groups of GlcUA sugar), and hydrophobic patches (analog of the carbon-rich side of the sugar ring) will work as a functional primer for pmHAS. Such an approach is not unprecedented as the polymerization of heparin, a glycosaminoglycan, can be primed with a rather simple aromatic xyloside instead of a complex proteoglycan core in vertebrate cells.

Computer modeling of HA oligosaccharides can visualize potential molecular shape. However, some proteins distort the sugar chains upon binding, thus making computer modeling somewhat more complicated. The most efficacious method of finding an artificial primer is a combinatorial chemistry approach. Closely related series of molecules are screened by high-throughput assay methodologies in order to detect HA elongation. pmHAS$^{1-703}$ is then tested for the ability to add an HA polymer onto synthetic primer candidates in a typical 96-well plate format. For example, a series of synthetic peptides (1 to 8 residues) terminating with a GlcNAc group using conventional F$_{moc}$ chemistry can be generated. Such peptides are particularly promising because they can adopt a variety of conformations and fit within the pmHAS$^{1-703}$ HA-binding pocket via an induced fit mechanism. Synthetic peptide chemistry is also much less cumbersome than carbohydrate chemistry. One of ordinary skill in the art, given the present specification, would be capable of using the known synthetic peptide chemistry techniques.

The amino acids are chosen with the goal of mimicking the properties of the GlcNAcGlcUA sugar repeats of HA. For example, glutamate or aspartate may be used as a substitute for the acid group of GlcUA, or glutamine or asparagine may be used as a substitute for the amide group of GlcNAc. Serine, threonine, or tyrosine can be used as substitutes for the hydroxyl groups and sugar rings in general. The peptide library terminates with a GlcNAc or GlcUA sugar group so that the demands on the pmHAS$^{1-703}$ enzyme's binding site and catalytic center are not overly burdensome. A vast variety of distinct peptides are made in parallel with a combinatorial approach; for example, with a hypothetical 6-7 residue peptide containing 1 to 3 different amino acids at each position, there are hundreds of possible peptides. The peptide combinatorial libraries will either be immobilized on plastic pins or plates.

The present invention also encompasses the development of a mutant version of pmHAS that utilizes a simpler molecule than an HA oligosaccharide as a primer. Chitopentaose ($\beta$1,4-GlcNAc homopolymer) is one such variant primer. Native pmHAS does not utilize chitopentaose as a primer, but a mutant pmHAS but a mutant pmHAS as disclosed herein, elongates chitopentaose, a more readily available substance. The chitopentaose primer is attached to the solid phase by reductive amination to an amino-containing plate or to a carrier protein (albumin) for immobilization on a normal plastic plate. Various mutants could then be screened for function. Other potential non-sugar mimics contemplated for use are short poly(ethleneglycol)-based copolymers containing styrene, sulfonate, acrylate, and/or benzoate groups.

Certain experiments are useful for detecting a protein's binding sites. Photoaffinity labeling is used to cross-link a radioactive HA oligosaccharide analog containing an aryl azide to the pmHAS$^{1-703}$ protein. The binding site of the pmHAS$^{1-703}$ protein is obtained through peptide mapping and Edman sequencing. With this information, mutants are prepared with alterations at the binding site. In the chitopentaose example, removal of some of the basic residues of the HA-binding site (which normally contact the carboxylate of GlcUA) and substitution of neutral polar residues would be chosen. As described above, a variety of site-directed mutants using a mutagenic oligonucleotide with mixed bases at certain positions have been generated. Such a mixed-base approach economizes on the number of custom oligonucleotides and transformations required. A high-throughput screen is then used to assess the ability of the mutant pmHAS to elongate the synthetic primer with a HA chain. An empirical approach can also be used to randomly mutate pmHAS$^{1-703}$ (either chemical mutagens or with a passage through a mutator strain) and then screen.

Figure 10:
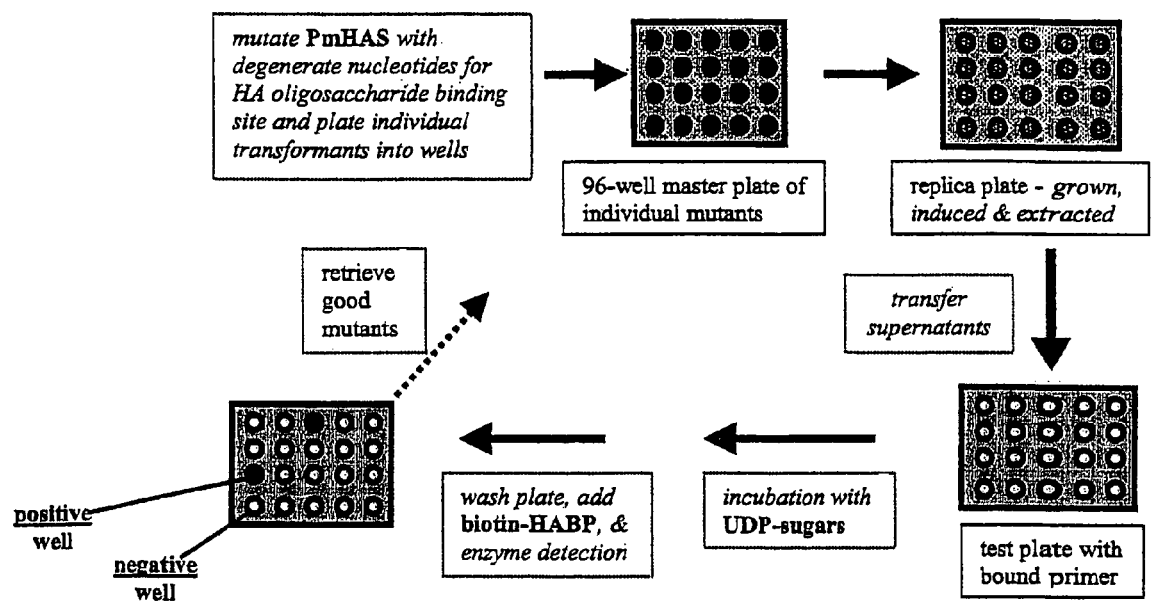
FIG. 10 is a graphical representation of a high-throughput assay for pmHAS mutants.

An assay has been designed to measure successful HA elongation reactions in a 96-well format (FIG. 10). The assay is shown in FIG. 10 in a graphical representation. Utilizing this assay many mutants can be screened in parallel. This screening method is facilitated by the fact that (i) a protocol to readily extract functional recombinant pmHAS$^{1-703}$ from E. coli cultures in a 96-well plate format with minimal processing exists and (ii) sensitive methods to detect HA on solid-phase microtiter plates exists. Cultures and extracts are transferred in parallel with multi-channel pipettes. HAS activity produced by 10-30 µl of induced cell culture (with an absorbance=1 at 600 nm) is routinely detected and the wells have a working volume of 200-300 µl, thus multiple assays or detection of low HA production is possible. Other components in the cell lysate do not interfere with the HAS assay. The extracts are stable at ~80° C. for long-time storage. For detection of HA elongation, specificity of a HA-binding protein [HABP] probe, biotinylated aggrecan, is capitalized upon. This probe binds elongated HA chains with high affinity but not small HA primers (4-6 sugars long). The bound HABP probe is detected by virtue of the biotin tag that is measured with fluorescent, radiolabeled, or enzyme-conjugated avidin (a biotin-binding protein). Alternatively, radioactive sugar incorporation from UDP-sugars onto the wells will signify HA elongation; this method is more direct than HABP.

In order to identify enzymes with low activities or reactions with poor primers, radioactive sugar incorporation (from UDP-[$^3$H]GlcNAC or UDP-[$^{14}$C]GlcUA) is measured instead of using the HABP probe. Of course, the majority of mutants and primers will not possess desirable characteristics, but the high-throughput screen allows those rare target molecules that facilitate the HA-coating process to be easily identified.

The pmHAS$^{1-703}$ polypeptide contains duplicated sequence elements that are sugar-transfer sites; one site transfers a GlcNAc sugar and the other site transfers a GlcUA sugar to form the alternating HA polymer backbone. If a aspartate residue (D196) in the first domain, is mutated, then the enzyme only transfers GlcUA. On the other hand, if a residue (D477) in the second domain, is mutated, then the enzyme only transfers GlcNAc. Thus the pmHAS$^{1-703}$ enzyme has been molecularly dissected into its two catalytic components. Based on the protein sequence, the chondroitin synthase (pmCS) and the heparin synthases (pmHS and PgIA), also have 2 domains that can be modified and mutated as well to give distinct sugar transferases.

Further mutagenesis transformed the low expression level (~0.1% of protein) pmHAS membrane protein found in nature to a high expression level (~10% of protein) soluble protein. This alteration of pmHAS allows both (i) the generation of more catalyst and (ii) the purification of catalyst by standard chromatographic means. Several strategies have been developed to purify milligram-level quantities of pmHAS mutant proteins by conventional protein chromatography. 90-95% pure enzyme was obtained in one or two steps. All phases of purification are readily scaled up. Soluble versions of the chondroitin synthase, pmCS, and the heparin synthases pmHS and PgIA, have also been made.

The pmHAS$^{1-703}$ enzyme was found to respond very favorably with a linear increase in reaction rate when tested with the high UDP-sugar concentrations (10-15 mM) predicted to be useful for "industrial" scale synthesis; the presence of two similar UDP-sugars simultaneously does not cause cross-inhibition (data not shown). A property of many enzymes is that their reaction products or downstream metabolites often regulate the catalysis rate. In the live cell, this control makes sense because if sufficient product is made, then it is not logical to consume more starting materials. In biotechnology, however, this feedback inhibition prematurely shuts the enzyme system down reducing yields. HA synthases from both *Streptococcus* bacteria and human are turned off or inhibited by low levels of the unavoidable by-product of HA synthesis, UDP (0-5% activity at 0.1-0.4 mM). On the other hand, pmHAS$^{1-703}$ is not very susceptible to UDP inhibition (approximately 60% activity at 15 mM). This fortunate circumstance allows higher production yields because UDP does not need to be vigorously removed during the reaction.

Expression of the single 972-residue pmHAS protein has allowed *Escherichia coli* host cells to produce HA capsules in vivo; normally *E. coli* does not make HA. Overall, the deduced pmHAS sequence is very different from the other known HA synthases. There appears to be only two short potential sequence motifs ([D/N]DGS[S/T]; DSD[D/T]Y) in common between pmHAS and Group A spHAS. Instead, a portion of the central region of the pmHAS enzyme is more homologous to the amino termini of other bacterial glycosyl-transferases that produce different capsular polysaccharides or lipopolysaccharides. Furthermore, pmHAS is about twice as long as any other HAS enzyme. Using the pmHAS enzyme, it was found that pmHAS (and pmCS and pmHS and the PgIA) enzymes add sugars to the nonreducing end of the growing polymer chain. Likewise, it was shown that the correct monosaccharides are added in a sequential stepwise fashion to the nascent chain. These results form the theoretical and scientific underpinnings of the presently claimed and disclosed invention.

In the case of the biosynthesis of the other glycosaminoglycan polysaccharides, heparin and chondroitin, some details of the vertebrate enzymes are available. Both heparin and chondroitin are synthesized by addition of sugar units to the non-reducing end of the polymer chain. In vivo, the glycosyltransferases initiate chain elongation on primers such as tetrasaccharides [xylose-galactose-galactose-GlcUA] that are attached to serine residues of proteoglycan core molecules. In vitro, enzyme extracts transfer a single sugar to exogenously added heparin or chondroitin oligosaccharides; unfortunately, the subsequent sugar of the disaccharide unit is usually not added and processive elongation to longer polymers does not occur. Therefore it is likely that some component is altered or missing in the in vitro system. In the case of heparin biosynthesis, a single enzyme, EXT1 or 2 (isozymes), transfers both GlcUA and GlcNAc sugars to the glycosaminoglycan chain based on co-purification or expression studies, described hereinbelow.

Recent work with the *E coli* K5 KfiA and KfiC enzyme complex, which together polymerizes heparosan, differ from the hereinafter described pmHS and PgIA, which are both single proteins that can transfer both sugars to the nonreducing end of acceptor molecules in vitro. In 2002, an *E. coli* K4 enzyme, called KfoC which is 60% identical to pmCS and that hybridizes to pmCS, SEQ ID NO:3, under standard stringency hybridizations conditions, was described as being a chondroitin polymerase that adds on chains to chondroitin acceptors. In particular, the present applicants used the pmCS gene DNA as a hybridization probe for detecting other chondroitin synthase genes and in particular, the *E. coli* K4 kfoC gene DNA. In general, a commercial Southern blot kit (Dig Hi-Prime, Roche) was used to label restriction fragments containing pmCS with digoxigenin probe. This probe was used to analyze a Southern blot (FIG. 10A) containing a PstI/EcoRI digest of Type F *Pasteurella multocida* genomic DNA (a positive control; P lane), a PCR product of the kfoC gene (corresponding to product of Ninomiya et al, 2002; lane K), or Lambda HindIII standard (lane L). The hybridization was carried out at 37° C. overnight in the manufacturer's buffer (Dig Easy Hyb) at 37° C. overnight. The blot was washed with 2×SSC, 0.1% SDS at 30° C. for 15 min twice, then for 30 min in 0.5×SSC, 0.1% SDS at 30° C. before using the manufacturer's Dig-antibody protocol for colorimetric detection. The kfoC band is apparent (KfoC black arrow) as well as the native *Pasteurella* gene (white arrow). No spurious hybridization signals were seen from other irrelevant DNA species. Therefore, the knowledge of the pmCS sequence can be used to identify other chondroitin synthase candidates by known standard methodology.

Preparation of Mutant PmHAS Enzymes.

One of the early dogmas of glycobiology was that one glycosyltransferase protein transfers only one specific sugar, the "one enzyme, one linkage" hypothesis of Hagopian and Eylar (1968). However, several enzymes consisting of a single type of polypeptide chain have been demonstrated or suspected to catalyze the transfer of at least two distinct sugars. Perhaps the most documented examples are the hyaluronan synthases [HASs] that polymerize a polysaccharide composed of repeating disaccharide β1,4GlcUAβ1,3GlcNAc units. The HAS polypeptides from certain pathogenic bacteria, vertebrates, and an algal virus have been shown to be both selective β-GlcNAc-transferases and β-GlcUA-transferases by molecular genetic and/or biochemical methods. Transformation of a HAS gene on a plasmid into foreign hosts that normally do not synthesize HA conferred the recombinant cells with the ability to produce HA polymer in vivo or their extracts to synthesize HA in vitro. Immunopurified *Strepto-* coccal HAS protein or mouse HAS1 protein produced HA in vitro when supplied with the appropriate UDP-sugar precursors.

Certain potential sequence motifs of 5-14 amino acid residues in length are similar among the Group A and C *Streptococcus* bacteria, vertebrate, and viral HA synthases (Class I). The unique HAS from Type A *Pasteurella multocida* bacteria (Class II) has a set of motifs that are more similar to sequences found in other glycosyltransferases that make other bacterial capsular polysaccharides or lipopolysaccharides, but possesses 2 motifs in common with the Class I HA synthases. These conserved residues between the two classes are involved in catalysis or substrate binding. As described hereinabove, a specific residue in a Class 1 motif, (S/G)GPL(G/S)xY(R/K), is associated with the β3-GlcUA-transferase catalytic activity of a HA synthase. Substitution of the leucine at position 314 of mouse HAS1 with a valine also results in a loss of HA synthase activity, but the mutant protein can still make chitin-like GlcNAc-polymers in vitro.

Work on the *E. coli* K5 two enzyme complex KfiA and KfiC that synthesize the structurally related heparosan polysaccharide [α1,4GlcUAβ1,4GlcNAc] has suggested that these proteins coordinate the transfer of two different monosaccharides to the appropriate acceptor oligosaccharide; KfiA is the GlcNAc-transferase while KfiC is the GlcUA transferase. However, repeated polymerization to an acceptor chain has not been demonstrated in vitro; only one GlcNAc or one GlcUA monosaccharide can be transferred to a GlcUA-terminating or a GlcNAc-terminating oligosaccharide, respectively.

A family of glycosyltransferases that synthesize β-linked polysaccharides has been proposed based largely on amino acid sequence comparisons and knowledge of the transferase reactions. Two types of domain, named "A" and "B", have been tentatively identified by hydrophobic cluster analysis. One or two of these putative domains may exist within a single polypeptide depending on the enzyme. Proteins with domains A and B appear to be associated with processive polymerization. On the other hand, nonprocessive enzymes only appear to possess domain A. These observations have led to mechanistic hypotheses invoking multiple binding sites for nucleotide-sugar precursors and simultaneous disaccharide formation by enzymes such as cellulose synthase and HA synthase. In the case of pmHAS, an enzyme with two Domain A units, single sugars are added individually to the nascent HA chain; the fidelity of the two transferase activities yields the disaccharide repeats of the polymer. As described hereinabove, the two distinct transferase activities of the pmHAS enzyme were dissected by molecular genetic means. The results indicate that the pmHAS polypeptide contains two relatively independent transferase sites.

In order, to identify the important domains of the 972-residue pmHAS polypeptide, the protein was truncated at the amino- and/or the carboxyl-termini. Polymerase chain reaction with primers corresponding to various internal sequences was used to generate a series of recombinant proteins for expression (Table X).

TABLE X

| | | Enzyme Activity | | | |
|---|---|---|---|---|---|
| Protein* | Localization | HAS | GlcNAc-Tase | GLCUA-Tase | SEQ ID NO: |
| -972 | Membrane | + | + | + | 2 |
| 437-972 | Inclusion body | − | − | − | 13 |
| 437-756 | Inclusion body | − | − | − | 14 |
| 1-756 | Membrane | + | + | + | 20 |
| 1-703 | Soluble | + | + | + | 9 |
| 1-650 | Soluble | − | + | − | 10 |
| 1-567 | Inclusion body | − | − | − | 21 |
| 152-756 | Inclusion body | − | − | − | 15 |

+, active;
−, inactive
*The different truncated proteins are described by their constituent amino acid residues.

Figure 11:
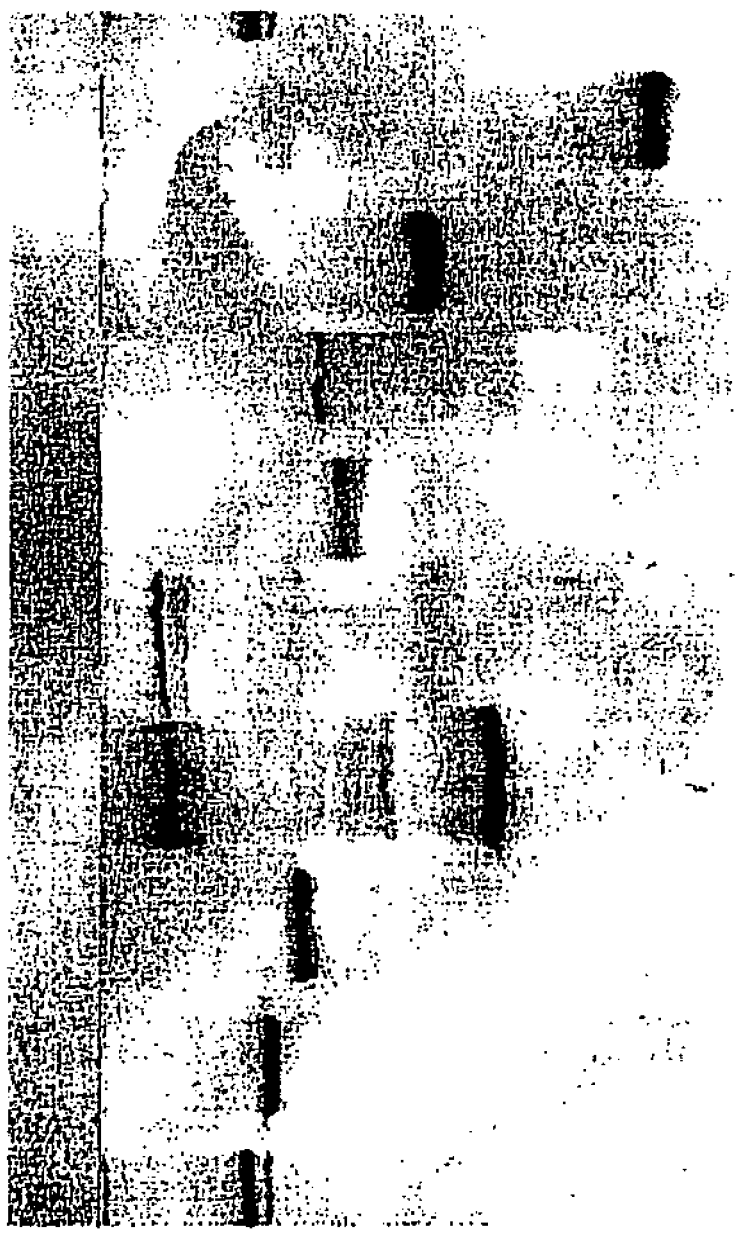
FIG. 11 is a Western Blot analysis showing the expression of pmHAS and its truncated forms. Either whole cell lysates (pmHAS$^{437-972}$, pmHAS$^{1-567}$, and pmHAS$^{152-756}$) or membrane preparations (pmHAS$^{437-756}$, pmHAS$^{1-567}$, r1-972, n1-972) or B-Per extract (pmHAS$^{1-703}$) were analyzed by Western blot (r, recombinant from *E. coli*; n, native from P-1059). The bars on the left denote the position of molecular weight standards (from top to bottom: 112, 95, 55, and 29 kDa).

The truncated polypeptides were expressed well in *E. coli* and the experimentally determined molecular weight corresponded to the predicted size (FIG. 11). In vitro assays were utilized to assess the HA synthase activity, or the two half-reactions, either GlcNAc-Tase or GlcUA-Tase, that comprise HA polymerization (Table X). Some of the truncations were inactive. pmHAS$^{1-756}$ (SEQ ID NO:20), which lacks the carboxyl-terminal 216 amino acid residues, was an active HA synthase and, for the most part, membrane-associated. An interesting observation was that pmHAS$^{1-703}$ (SEQ ID NO:9), which lacks a larger portion of the carboxyl terminus, retained HAS activity but was transformed into a cytoplasmic protein accounting for up to ~10% of the total cellular protein. Thus the carboxyl-terminus, especially residues 703-756, is responsible for the association of native pmHAS with the membrane. With the further deletion from carboxyl-terminus, pmHAS$^{1-650}$ (SEQ ID NO: 10) was still expressed at a high level as a soluble protein, yet was inactive as a HA synthase. However, pmHAS$^{1-650}$ was capable of transferring GlcNAc to the nonreducing terminal GlcUA of HA-derived oligosaccharides. As expected from the lack of HAS activity, pmHAS$^{1-650}$ did not transfer GlcUA to HA oligosaccharides, which terminated with a GlcNAc residue. Thus residues 650-703 are required, either directly or indirectly, for transferring GlcUA to the HA chain. pmHAS$^{1-567}$ (SEQ ID NO:21), with a further truncation at the carboxyl terminus, and pmHAS$^{152-756}$ (SEQ ID NO: 15) were insoluble, inactive proteins. These latter mutant proteins are likely to be misfolded inclusion bodies as they were not dissolved by a buffer containing the detergents NP-40, sodium deoxycholate and SDS unless boiled; in contrast, full-length pmHAS was readily solubilized by this buffer at room temperature.

Site-directed Mutagenesis of pmHAS$^{1-703}$

Based on similarities in the amino acid sequence and predicted topology, two families of HASs have been proposed. The only member of Class II, pmHAS, possesses motifs similar to two out of the seven putative conserved motifs of Class I HASs; these motifs contain DGS and DxD sequences. The pmHAS sequence has a duplication of a ~100-residue long element in the regions from residue 161-267 and from residue 443-547 with these conserved motifs. These two elements of pmHAS that contain the conserved motif are named domain A1 and domain A2, respectively. This nomenclature is based on the similarity of these pmHAS domains to the "A" domain proposed for other glycosyltransferases that make β-linked carbohydrates. FIG. 12 shows the amino acid alignment of the two putative domains and their relative position in pmHAS$^{1-703}$. The above truncation results show that the GlcNAc-transferase activity can be separated from the HA synthase activity of pmHAS. Therefore, the domain A1 is responsible for the GlcNAc-transferase function of HA synthase while domain A2 is responsible for GlcUA-transferase activity. pmHAS$^{1-703}$, a short polypeptide with complete HAS activity, was subjected to site-directed mutagenesis in order to further refine the results. We mutated the conserved aspartate residues (residue 196 and 477; underlined, FIG. 12) of the two DGS motifs in the two domains were mutated.

Six different mutants were produced containing the following changes: domain A1-D196E, D196N, D196K, and domain A2-D477N, D477E, D477K. Upon sequence verification of the complete open reading frame, it was found that mutants with D196K, D196N, or D477N also had spontaneous mutation of D702I. As it was the penultimate residue of pmHAS$^{1-703}$, and as pmHAS$^{1-650}$ was a functional GlcNAc-Tase, this undesired mutation does not greatly affect the interpretation of the results of the desired point mutations (as the results below demonstrate, the mutants with substitutions at D196 or D477 sharing the same D702I mutation had different transferase activities supporting this conclusion). All of the mutant proteins were produced at similar levels. All of the mutants were either inactive or made long HA polymer with low efficiency as measured by the full HAS assay (Table XI).

TABLE XI

| Mutants | Enzyme Specific Activity | | |
|---|---|---|---|
| | HAS | GlcNAc-Tase | GlcUA-Tase |
| D477N | 2 | 200% | 2% |
| D477K | 0.3 | 70% | 2% |
| D477E | 4 | 50% | 4% |
| D196N | 0.1 | 0% | 74% |
| D196K | 0.01 | 3% | 100% |
| D196E | 0.3 | 7% | 60% |

Specific activities of various pmHAS$^{1-703}$ mutants. Equivalent amounts of pmHAS$^{1-703}$ proteins (based on Western blot) were assayed. The specific activities (average of duplicate determinations) are indicated as the percentage of the wild-type sequence pmHAS$^{1-703}$ (set as 100%). The specific activities (picomoles of monosaccharide transfer/mg of protein/min) for wild-type enzyme in the three different assays were: HAS, 37; GlcNAc-Tase, 63; GlcUA-Tase, 76.

However, pmHAS$^{1-703}$ domain A1 mutants containing D196E, D196K or D196N maintained high levels of GlcUA-transferase activity. On the other hand, pmHAS$^{1-703}$ domain A2 mutants containing D477E, D477K or D477N had high levels of GlcNAc-transferase activity implying that the two aspartate residues were critical for HA synthase function. Thus, two distinct transferase domains exist in the pmHAS enzyme; domain A1 is the GlcNAc-transferase and domain A2 is the GlcUA-transferase.

$K_M$ Analysis of Mutants

In order to detect potential interaction or cross-talk between the two putative domains of pmHAS, the apparent affinity of the wild-type and the pmHAS$^{1-703}$ mutants were compared for the UDP-GlcNAc or for the UDP-GlcUA substrates by measuring their Michaelis constants ($K_M$) for the functional transferase activity. Titration of the UDP-sugars in the half assays for the GlcUA and GlcNAc transferases were performed (Table XII).

TABLE XII

| Enzyme | $K_M$ for UDP-GlcNAc (mM) | $K_M$ for UDP-GlcUA (mM) |
|---|---|---|
| D477K | +/−40 | ND |
| D477E | 150 +/− 30 | ND |
| D196K | ND | 115 +/− 45 |
| D196E | ND | 140 +/− 35 |

$K_M$ values for UDP-sugar precursors of pmHAS$^{1-703}$ and mutant proteins. The results ± standard deviation is shown. The apparent affinities of the functional glycosyltransferase activities of the various enzymes are similar. The typical level of radiolabel incorporation at the saturating UDP-sugar concentration using 1 mg of total protein/assay point was 500-1000 dpm [$^{14}$C]GlcA or 200-800 dpm [$^3$H]GlcNAc for the UDP-GlcNAc or UDP-GlcUA $K_M$ values, respectively.
ND, not done.

The results indicate that the $K_M$ values of the domain A1 or A2 mutants were not very different from the wild-type sequence pmHAS$^{1-703}$. Thus, the functional disruption of one glycosyltransferase domain of pmHAS does not affect greatly the other domain.

Complementation of HAS Activity with Two Mutant Proteins in vitro

Figure 13:
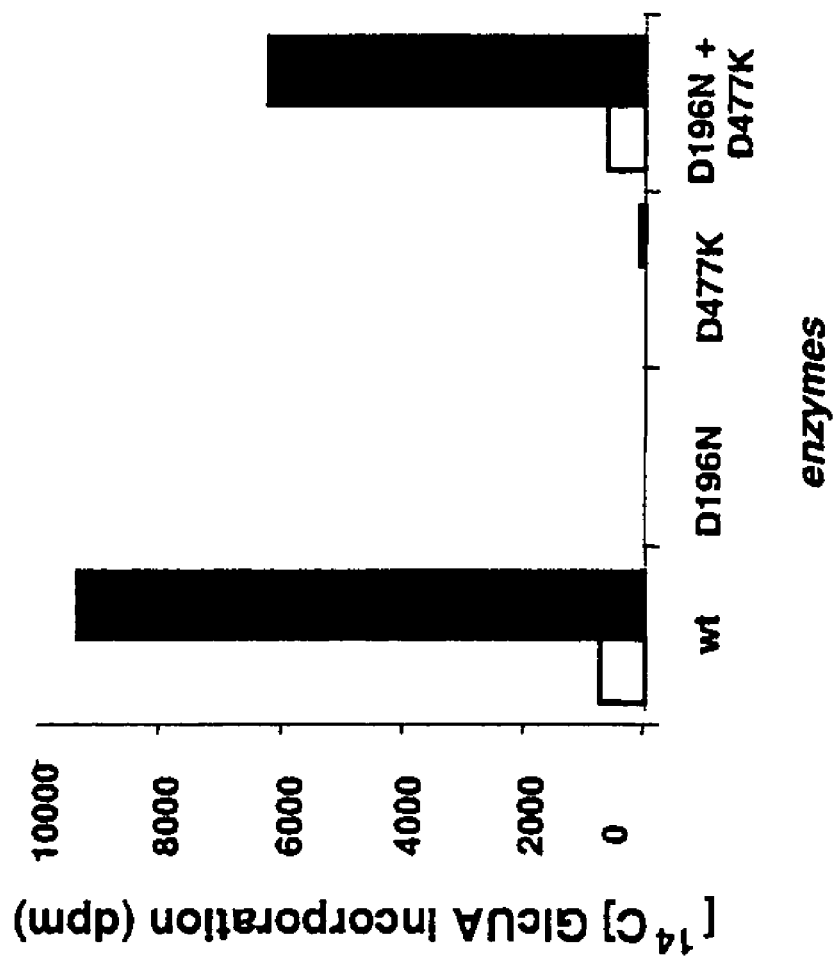
FIG. 13 is a graphical representation of the complementation of the HAS activity of mutant enzymes in vitro. HAS enzyme assays with HA-derived acceptor were performed in the presence of either wild type pmHAS$^{1-703}$ alone, or D196 mutant alone, or D477 mutant alone or in the presence of both D196 and D477 mutants, for either 25 minutes (open bars) or 1.5 hours (solid bars).

The domain A1 and the domain A2 mutants fulfill the complete function of a HAS even if present on separate polypeptide molecules if the mutants are mixed together in the same reaction. The standard HA synthesis assay was performed with extracts containing either the truncated wild-type sequence pmHAS$^{1-703}$ enzyme, or a GlcNAc-Tase mutant enzyme (D196N) alone, or a GlcUA-Tase mutant enzyme (D477K) alone, or a mixture of the two mutant enzymes. These two mutants were selected as they were the least active in the HA synthase assay (Table XI). Equivalent amounts of wild-type pmHAS$^{1-703}$ polypeptide (2 μg of total protein) or mutant pmHAS$^{1-703}$ polypeptide (based on Western blot analysis) were used for these assays. In the mixture, the same amount of each mutant polypeptide was added (equivalent to 4 μg of total protein of wild-type extract). The D196N mutant alone or the D477K mutant alone did not produce detectable amounts of HA chains (FIG. 13), but when the mutant polypeptides were incubated together, along with a HA oligosaccharide acceptor (4-10 sugars long), longer HA polymers were made. The amount and the rate of HAS activity of the combination of the two mutants was similar to the parallel reaction containing the wild-type pmHAS$^{1-703}$. Without HA oligosaccharide acceptor, the wild-type pmHAS$^{1-703}$ enzyme could still make HA, albeit with lower efficiency (2 μg total protein in 3 hr assay incorporated 220 dpm). The combination of the two mutant extracts, however, did not make detectable amounts of HA polymer in absence of the HA acceptor (incorporation ≦4 dpm). These results suggest that in the presence of HA oligosaccharide acceptor, the two kinds of transferases could work together and sequentially transfer GlcNAc and GlcUA monosaccharides to an existing HA chain in an alternating fashion. Apparently chain initiation requires two active transferases to be present on the same polypeptide.

Gel filtration chromatography studies were performed to analyze the size of the HA products polymerized by reaction mixtures containing either the wild-type pmHAS$^{1-703}$ or a combination of the GlcUA-transferase and the GlcNAc-transferase mutant enzymes. The results show that the size distribution of the HA products from either reaction were similar; polymers with an average peak size of ~28-30 kDa (~150 sugars) were detected after a three minute incubation. Therefore, the two individual mutant transferase polypeptides worked together with almost the same efficiency as the wild-type enzyme consisting of a single polypeptide chain.

Putative Membrane Localization or Anchor Domain of pmHAS

Figure 14:
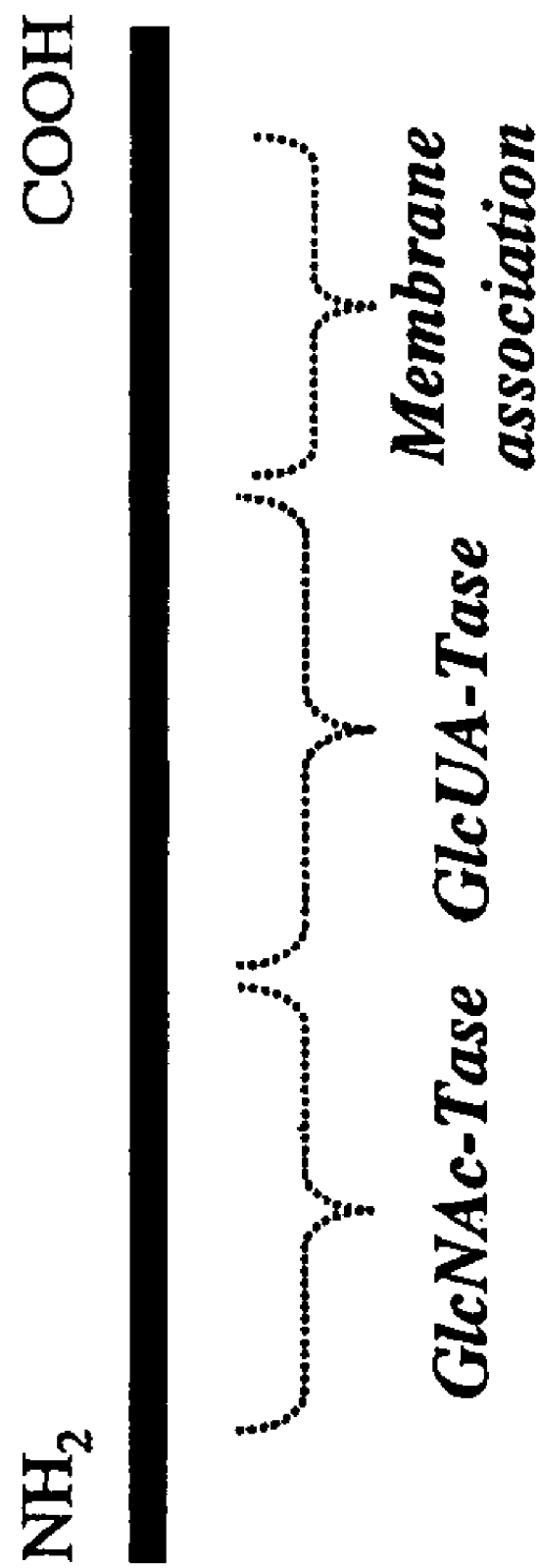
FIG. 14 is a pictorial representation of a model of the two putative glycosyltransferase sites and the potential membrane association region of the pmHAS polypeptide.

All known native HASs are found in membrane preparations upon lysis and fractionation of cells. Class I HASs, which include the *streptococcal*, vertebrate and viral enzymes, have similar predicted topology with five to seven membrane-associated regions in the membrane bilayer. On the other hand, pmHAS, the only member of Class II, is predicted to have two transmembrane helices by some computer analysis programs (TmPRED), while other algorithms (SOSUI) classify the enzyme as a soluble protein. In any case, the majority of the pmHAS polypeptide chain is not predicted to be associated with the membrane based on its amino acid sequence alone. After removal of the residues from 703 to 756, a membrane-associated form of pmHAS was transformed into a soluble cytoplasmic protein. The most simplistic hypothesis is that the carboxyl terminus is required to target or to bind pmHAS to the membrane (FIG. 14). However, this region of pmHAS is predicted neither to be membrane-associated (TmPRED, SOSUI, and HMMTOP) nor serve as a site for a post-translational lipidation (as assessed by PROSITE) based on its sequence. It can be deduced, however, that some of the residues in the region of residues 703-972 of pmHAS interact with another membrane bilayer-associated protein to mediate the localization to the membrane.

Role of Conserved Aspartate Residues in the DGS Motif of pmHAS

Several acidic aspartate and/or glutamate residues are conserved in the putative β-glycosyltransferase family members which utilize nucleotide-sugars as precursors to make polysaccharides. These carboxylate sidechains are likely to play roles as catalytic acids or bases, in precursor binding, or in complexing essential metal ions. The amino acid sequence of the pmHAS polypeptide is distinct from the sequences of Class I HASs. All known HASs, however, share the DGS sequence motif containing an aspartate residue that appears to also be conserved among other-glycosyltransferase family members. Presently after the aspartate residue of the DGS motif was mutated in domain A1 or domain A2, these pmHAS mutants almost completely lost HA synthase function by losing the ability to transfer either GlcNAc or GlcUA, respectively. The X-ray crystal structure of the putative UDP-sugar transferase SpsA of *Bacillus subtilis* with bound UDP recently became available. One region of this protein (residues 1-117) has some similarity to the pmHAS A1 and A2 domains (32% and 31% identity, respectively; Multalin). Their results show that the aspartate residue in the DGS motif is involved in binding the UDP-sugar by interacting with the N3 group of the uracil ring. Unfortunately, the sugar transferase specificity of the SpsA enzyme is currently unknown. The pmHAS aspartate mutants lost the ability to bind one of the precursor sugars and, therefore, do not incorporate the monosaccharide into the HA chain. The mutant proteins with asparagine or glutamate substitutions at D196 or D477 were inactive or very poor transferases, indicating that both the size and the charge of the aspartate side chain of this motif is very important for interaction with uracil.

The data from the activity analyses of the truncated versions and the point mutants of pmHAS shows that two relatively independent active sites on one polypeptide are responsible for the alternating addition of GlcUA and GlcNAc monosaccharides during HA polymerization. The selective disruption of either the GlcNAc-transferase or the GlcUA-transferase does not perturb significantly the remaining transferase activity as measured by $K_M$ values. Likewise, the successful rescue of HA synthase activity in vitro by mixing two different mutants supports the two-site model. The simplest explanation for the reconstitution of HA synthase activity is that the nascent HA chain is extended by one functional transferase, released, and extended by the other transferase in a repetitive fashion.

It is not believed that two pmHAS polypeptides form a dimer to create the active HA synthase species in vivo. Preliminary data from radiation inactivation studies of native or recombinant full-length pmHAS yields a target size of ~110 kDa for the functional size of the HA synthase which corresponds to the mass of one pmHAS monomer. An alternative model in which a single transferase site on the polypeptide is responsible for transferring both of the GlcNAc and GlcUA monosaccharides in an alternating fashion also seems much less likely in view of the mutagenesis data and the domain organization of pmHAS. The exact demarcation of the domain A1 and A2 boundaries requires further analysis by molecular biological, biochemical, and possibly, structural means.

The precise identification of the putative HA acceptor-binding site of pmHAS has not yet been defined, but as judged by the activity of the various mutants in the half-reaction assays, the site probably resides in the first 650 residues. This acceptor binding site is probably responsible for maintaining the nonreducing terminus of the nascent HA chain in close proximity to the residues involved in transferase activity. The number and nature of residues required for polymer binding awaits analysis.

As disclosed herein, the molecular dissection of a glycosyltransferase enzyme that normally forms a repeating heteropolysaccharide into its two functional constituent transferases is demonstrated. In the case of pmHAS it is shown that the glycobiology dogma of "one transferase protein, one linkage" does not hold; a single polypeptide can contain two separate UDP-sugar binding and transferase sites. As pmHAS is rather distinct from the Class I enzymes, it is unclear as yet which lessons may be applied to the Class I enzymes. It is likely, however, that the DGS motif is responsible in part for UDP-sugar binding in both classes of HAS.

Materials and Methods

Molecular biology reagents were from Promega unless noted. Custom oligonucleotides were from The Great American Gene Company. All other reagents were the highest grade available from either Sigma or Fisher unless otherwise noted.

A series of truncated polypeptides were generated by amplifying the pPm7A insert (DeAngelis et al., 1998) by 13 cycles of PCR with Taq polymerase (Fisher) and synthetic oligonucleotide primers corresponding to various portions of the pmHAS open reading frame. The primers contained EcoRI and PstI restriction sites to facilitate cloning into the expression plasmid pKK223-3 (tac promoter; Pharmacia). The resulting recombinant constructs were transformed into *E coli* TOP 10F' cells (Invitrogen) and maintained on Luria-Bertani media with ampicillin selection. Mutations were made using the QuickChange site-directed mutagenesis method (Stratagene) with the plasmid pKK/pmHAS DNA as template. The sequences of the mutant open reading frames were verified by automated DNA sequencing (Oklahoma State University Recombinant DNA/Protein Resource Facility).

Membrane preparations containing recombinant full length pmHAS, $pmHAS^{437-972}$, $pmHAS^{437-756}$, $pmHAS^{1-756}$, $pmHAS^{1-567}$ and $pmHAS^{152-756}$ were isolated from *E coli* as described. For soluble truncated pmHAS proteins, $pmHAS^{1-703}$, $pmHAS^{1-650}$, and $pmHAS^{1-703}$-derived mutants, cells were extracted with B-Per™ II Bacterial Protein Extraction Reagent (Pierce) according to the manufacturer's instruction except that the procedure was performed at 7° C. in the presence of protease inhibitors. Membrane preparations of P. multocida P-1059 (ATCC 15742) were made as described. In order to test whether the truncated recombinant polypeptides were formed as insoluble inclusion bodies, membrane preparations were suspended in RIPA buffer (1% NP-40, 1% sodium deoxycholate and 0.1% SDS in 50 mM Tris, pH 7.2) for 20 minutes at room temperature. After centrifugation at 20,000×g for 10 minutes, the supernatants were saved and the pellets were resuspended in RIPA buffer. The supernatants and the pellets were analyzed by SDS-polyacrylamide gel electrophoresis and Western blot analysis as described later.

Three assays were designed to detect either (a) the polymerization of long HA chains, or (b) the addition of a single GlcNAc to a GlcUA-terminated a HA oligosaccharide acceptor, or (c) the addition of a single GlcUA to a GlcNAc-terminated HA oligosaccharide acceptor. The complete HAS activity was assayed in 50 mM Tris, pH 7.2, 20 mM $MnCl_2$, 0.1 M $(NH_4)_2SO_4$, 1 M ethylene glycol, 0.12 mM UDP-[$^{14}$C] GlcUA (0.01 µCi; NEN), 0.3 mM UDP-GlcNAc, and even-numbered HA oligosaccharides (1 µg uronic acid) derived from testicular hyaluronidase [$(GlcNAc-GlcUA)_n$; n=4-10] at 30° C. for 25 minutes in a reaction volume of 50 µl. GlcNAc-transferase activity was assayed for 4 minutes in the same buffer system with even-numbered HA oligosaccharides but with only one precursor sugar, 0.3 mM UDP-[$^3$H] GlcNAc (0.2 µCi; NEN). GlcUA-transferase activity was assayed for 4 minutes in the same buffer system but with only 0.12 mM UDP-[$^{14}$C]GlcUA (0.02 µCi) and odd-numbered HA oligosaccharides [$GlcNAc(GlcUA-GlcNAc)_n$; n=7-20] (3.5 µg uronic acid) prepared by mercuric acetate treatment of Streptomyces HA lyase digests. Reactions were terminated by the addition of SDS to 2% (w/v). The reaction products were separated from substrates by descending paper (Whatman 3M) chromatography with ethanol/1 M ammonium acetate, pH 5.5, development solvent (65:35 for the HAS and GlcUA-Tase assays; 75:25 for the GlcNAc-Tase assay). For the HAS assay, the origin of the paper strip was eluted with water and the incorporation of radioactive sugars into HA polymer was detected by liquid scintillation counting with BioSafe II cocktail (RPI). For the half-assay reactions, the origin and the downstream 6 cm of the strip were counted in 2 cm pieces. All assays were adjusted to be linear with regard to incubation time and to protein concentration. For the $K_M$ studies, the UDP-sugar concentration was titrated in the half-assay reactions (0-2000 µM UDP-GlcNAc or 0-1260 µM UDP-GlcUA) and 6-fold more HA oligosaccharide acceptor was utilized.

Membranes and extracts were analyzed using standard 8% polyacrylamide SDS gels. Following electrophoresis, proteins were transferred with a semi-dry apparatus to nitrocellulose membranes (S&S) and detected with a monospecific antibody directed against a synthetic peptide corresponding to residues 526 to 543 of pmHAS. The peptide, acetyl-LDS-DDYLEPDAVELCLKE-amide (SEQ ID NO: 22) (Quantum), was coupled to ovalbumin to form the initial immunogen for injection into female New Zealand white rabbits (HTI Bioscience protocols). In the subsequent boosts, free peptide was utilized. The specific antipeptide IgG was purified from ammonium sulfate fractionated sera (after third boost) using an immobilized peptide column (internal cysteine coupled to Iodoacetyl beads; Pierce). The desired IgG was eluted with 0.1 M glycine, pH 2.5, neutralized, and exchanged into phosphate-buffered saline. Immunoreactive bands on Western blots were detected with a protein A-alkaline phosphatase conjugate and were visualized with 5-bromo-4-chloro-3-indolyl phosphate and nitroblue tetrazolium reagent.

The size of HA polymers was analyzed by chromatography on a Phenomenex PolySep-GFC-P 3000 column (300×7.8 mm) eluted with 0.2 M sodium nitrate at 0.6 ml/min on a Waters 600E system. The column was standardized with various size fluorescent dextrans (580, 50, and 12 kDa). Radioactive components were detected with a LB508 Radioflow Detector (EG & G Berthold) and Zinsser cocktail (1.8 ml/min). In comparison to the full HAS assay using paper chromatography described above, these 3 minute reactions contained twice the UDP-sugar concentrations, 0.06 µCi UDP-[$^{14}$C]GlcUA, and 0.25 µg even-numbered HA oligosaccharide. Also, addition of ethylenediamine tetracetic acid (final conc. 22 mM) and boiling (2 min) was employed to terminate the reactions instead of addition of SDS.

P. multocida Chondroitin Synthase pmCS

As mentioned previously, chondroitin [$\beta(1,4)GlcUA-\beta(1,3)GalNAc]_n$, heparin/heparan [$\alpha(1,4)GlcUA-\beta(1,4)GlcNAc]_n$, and hyaluronan [$\beta(1,4)GlcUA-\beta(1,3)GlcNAc]_n$ are the three most prevalent GAGs found in humans. In the former two polymers, usually n=20 to 100 while in the case of HA, n=$10^{3-4}$. Chondroitin and heparin/heparan, but not HA, are synthesized as glycoproteins and are sulfated at various positions in vertebrates. A substantial fraction of the GlcUA residues of heparin are epimerized to form iduronic acid. Many lower animals possess these same GAGs or very similar molecules. A chondroitin synthase from P. multocida (pmCS) is described and enabled in copending U.S. Ser. No. 09/842,484 which is expressly incorporated herein in its entirety by reference.

The studies of GAG biosynthesis have been instrumental in understanding polysaccharide production in general. The HA synthases were the first GAG glycosyltransferases to be identified at the molecular level. These enzymes utilize UDP-sugar nucleotide substrates to produce large polymers containing thousands of disaccharide repeats. The genes encoding bacterial, vertebrate, and viral HAS enzymes have also been cloned. In all these cases, expression studies demonstrated that transformation with DNA encoding a single HAS polypeptide conferred the ability of foreign hosts to synthesize HA. Except for pmHAS, these proteins have similar amino acid sequences and predicted topology in the membrane.

The biochemical study of chondroitin biosynthesis in vertebrates was initiated in the 1960s. Only recently have the mammalian enzymes for elongation of the polysaccharide backbone of chondroitin been tentatively identified by biochemical means. An 80-kDa GlcUA-transferase found in vertebrate cartilage and liver was implicated in the biosynthesis of the chondroitin backbone by photoaffinity labeling with an azidoUDP-GlcUA probe. A preparation from bovine serum with the appropriate GalNAc- and GlcUA-transferase activities in vitro was obtained by conventional chromatography, but several bands on SDS-polyacrylamide gels (including a few migrating ~80 kDa) were observed. The gene has been designated CHSY1 (Kitagawa H, Uyama T, Sugahara K. J Biol Chem 2001 Oct. 19:276(42):38721-6), which is expressly incorporated herein in its entirety by reference). The expression of a soluble recombinant form of the CHSY1 (human chondroitin synthase) protein in COS-1 cells produced an active enzyme, GenBank™ accession number AB023207 which transferred not only the glucuronic acid (GlcUA) from UDP-[(14)C]GlcUA but also N-acetylgalactosamine (GalNAc) from UDP-[(3)H]GalNAc to the polymer chondroitin. Identification of the reaction products demonstrated that the enzyme was chondroitin synthase, with both β1,3-GlcUA transferase and β1,4-GalNAc transferase activities. It was demonstrated that analogous to *Pasteurella* chondroitin synthase, pmCS, and human heparan sulfate polymerases, the single polypeptide chondroitin synthase possesses two glycosyltransferase activities required for chain polymerization.

With respect to related microbial GAG synthases other than the HASs, the *E. coli* K5 glycosyltransferase two enzyme complexes, KfiC and KfiA, that synthesizes heparosan has been identified by genetic and biochemical means. In contrast to the HASs, it appears that KfiA, a GlcNAc-tase and KfiC a GlcUA-tase, alternate transferring a sugar to the disaccharide repeat of the growing polymer chain. The chondroitin-backbone synthesizing enzyme of *E. coli* K4 has been enzymatically characterized, and recently the gene KfoC encoding the relevant glycosyltransferases was identified; this enzyme is approximately 60% identical to pmCS (Ninomiya T, Sugiura N, Tawada A, Sugimoto K, Watanabe H, Kimata K. J Biol Chem 2002 Jun. 14:277(24):21567-75, which is expressly incorporated herein in its entirety by reference).

*Escherichia coli* strain K4 produces the K4 antigen, a capsule polysaccharide consisting of a chondroitin backbone (GlcUA β(1-3)-GalNAc β(14)) to which beta-fructose is linked at position C-3 of the GlcUA residue. The region 2 of the K4 capsular gene cluster essential for biosynthesis of the polysaccharide was cloned, and identified a gene encoding a bifunctional glycosyltransferase that polymerizes the chondroitin backbone. The enzyme, containing two conserved glycosyltransferase sites, showed 61% identity at the amino acid level to the chondroitin synthase from *Pasteurella multocida*. The soluble enzyme expressed in a bacterial expression system transferred GalNAc and GlcUA residues alternately, and polymerized the chondroitin chain up to a molecular mass of 20 kDa when chondroitin sulfate hexasaccharide was used as an acceptor. KfoC absolutely required acceptors of chondroitin sulfate polymers and oligosaccharides at least longer than a tetrasaccharide. In addition, chondroitin polymers and oligosaccharides and hyaluronan polymers and oligosaccharides served as acceptors for chondroitin polymerization, but dermatan sulfate and heparin did not.

As mentioned above, many *P. multocida* isolates produce GAG or GAG-like molecules as assessed by enzymatic degradation and removal of the capsule of living bacterial cells. Type A *P. multocida*, the major fowl cholera pathogen, makes a capsule that is sensitive to hyaluronidase. Subsequent NMR structural studies of capsular extracts confirmed that HA was the major polysaccharide present. A specific HA-binding protein, aggrecan, also interacts with HA from Type A *P. multocida*. Two other distinct *P. multocida* types, a swine pathogen, Type D, and a minor fowl cholera pathogen, Type F, produce polymers that are chondroitin or chondroitin-like based on the observation that their capsules are degraded by *Flavobacterium* chondroitin AC lyase. After enzymatic removal of the capsule, both types were more readily phagocytosed by neutrophils in vitro. The capsule of Type D cells, but not Type F cells, is also reported to be degraded by heparinase III.

Hereinafter the monosaccharide composition of the *P. multocida* Type F polysaccharide and the DNA sequence information of the Type A HA biosynthesis locus is described and was used to obtain the homologous region from the Type F chromosome. Thus, pmCS, the first chondroitin synthase to be identified and molecularly cloned from any source is hereinafter described.

Experimental Procedures

Unless otherwise noted, all chemicals were from Sigma or Fisher, and all molecular biology reagents were from Promega. The wild-type encapsulated Type F *P. multocida* strains, P-4679 and P-3695, were obtained from Dr. Richard Rimler (USDA, Ames, Iowa). These strains were isolated from turkeys with fowl cholera. P-4679 had a slightly larger capsule than P-3695 as judged by light microscopy and India ink staining. The latter strain also possessed an endogenous uncharacterized plasmid.

The anionic polymer in the capsule of Type F bacteria was purified by urea extraction and cetylpyridinium chloride precipitation. P-4679 was grown in complete defined media (150 ml) with mild shaking overnight at 37° C. Cells were harvested by centrifugation (3,000×g, 10 min) and washed twice with 0.1 M NaCl by repeated centrifugation and resuspension. The capsule was removed by extraction with 3 ml of 8 M urea for 8 min at 98° C. The cells were removed by high-speed centrifugation (15,000×g, 10 min) and the urea solution was extracted with one volume of chloroform thrice at 22° C. GAGs in the aqueous extract were precipitated by the addition of cetylpyridinium chloride (1% w/v final concentration). After standing for 10 min, the precipitate was collected by high-speed centrifugation and redissolved in 2.5 M NaCl. The mixture was clarified by high-speed centrifugation and the supernatant was precipitated with 3 vol of ethanol. The precipitate was washed with 70% ethanol, dried slightly, and resuspended in 2.5 M NaCl. The ethanol precipitation procedure was repeated and the pellet was redissolved in water. Another round of ethanol precipitation (2 vol) was performed. The final GAG pellet was dissolved in water. The yield (0.6 mg uronic acid) was determined with the carbazole assay for uronic acid using a glucuronolactone standard.

The monosaccharide composition of the GAG extract was determined by acid hydrolysis (2 N HCl, 4 hrs, 100°) and high pH anion exchange chromatography. The hydrolyzate was repeatedly diluted in water and dried under vacuum to remove HCl, then mixed with a rhamnose standard, and clarified using a 0.2 μm spin filter. Portions of the hydrolyzate (~5 nmoles of uronic acid) were injected onto a PA-1 column (Dionex) equilibrated with 12 mM NaOH. After isocratic elution (25 min) to separate the neutral sugars, a gradient of sodium acetate (0 to 0.18 M in 30 min) was utilized to separate the acidic sugars. Eluted compounds were detected by pulsed amperometric detection. In parallel runs, the Type F sample was spiked with known monosaccharide standards or authentic chondroitin sulfate C (derived from shark cartilage) hydrolyzate. HA and heparin hydrolyzate standards were also run. Retention times relative to the rhamnose internal standard were calculated.

Preliminary data from Southern blot analysis using pmHAS hybridization probes suggested that the Type A and the Type F microbes were very homologous at the capsule locus. PCR was utilized to verify these findings. Type F chromosomal DNA (0.1 μg) served as a template in PCR reactions (20 μl) utilizing oligonucleotide primers corresponding to various regions of the Type A capsule locus genes. After 40 cycles of PCR (94° C. 30 s; 42° C. 30 s; 72° C. 4 min) with Taq DNA polymerase in the supplied buffer (Fisher), the samples were separated by agarose gel electrophoresis. Many primer pairs, but not all, amplified Type F DNA to yield products of the predicted size assuming that Type A and Type F loci were homologous. Two primers (Pm10, 5=-CACTGTCTAACTTTATTGTTAGCC-3=(SEQ ID NO: 23); Pm21, 5=-TTTTTAACGAATAGGCTGTC-3= (SEQ ID NO:24)) were chosen to amplify a 3.6 kb portion of the Type F locus predicted to contain the DNA encoding carboxyl-terminal half of the KfaA homolog and the amino-terminal portion of the putative polysaccharide synthase. The product from a PCR reaction (26 cycles) was cloned into a TA vector (Invitrogen) according to the manufacturer guidelines. The plasmid was analyzed by cycle sequencing (ThermoSequenase system with $^{33}$P-terminators, Amersham) with the Pm10 or the Pm21 primer. The preliminary sequence data from the PCR product derived from Type F DNA was highly homologous to the sequence of the Type A locus. Therefore, the 3.6-kb insert was excised from the plasmid, gel-purified, and labeled with digoxigenin (High Prime system, Boehringer Mannheim) to serve as a hybridization probe.

A lambda library of Sau3A partially digested P-4679 DNA (~4-9 kb average length insert) was made using the BamHI-cleaved "Zap Express" vector system (Stratagene). The plaque lifts were screened by hybridization (5×SSC, 50° C.; 16 hrs) with the digoxigenin-labeled probe using the manufacturer guidelines for colorimetric development. E. coli XLI-Blue MRF' was co-infected with the purified, individual positive lambda clones and ExAssist helper phage to yield phagemids. The resulting phagemids were transfected into E coli XLOLR cells to recover the plasmids. Sequence analysis of the plasmids revealed a novel open reading frame, which we called pmCS, with high homology to pmHAS.

In previous studies with pmHAS, it was found that a functional, soluble enzyme would be created if a portion of the carboxyl terminus was truncated by molecular genetic means. Therefore, a portion of the pmCS ORF (residues 1-704) in the insert of one of the excised lambda clones, pPmF4A, was amplified by 20 cycles of PCR with Taq polymerase. The sense primer corresponded to the sequence at the deduced amino terminus of the ORF and the antisense primer encoded the new carboxyl terminus followed by an artificial stop codon. The resulting PCR product was purified and concentrated using GeneClean. This insert was cloned using the pETBlue-1 Acceptor system (Novagen) according to the manufacturer's instructions. The Taq-generated single A overhang is used to facilitate the cloning of the open reading frame downstream of the T7 promoter and the ribosome binding site of the vector. The ligated products were transformed into E. coli NovaBlue and plated on LB carbenicillin (50 μg/ml) under conditions for blue/white screening. White or light blue colonies were analyzed by restriction digestion. A clone containing a plasmid with the desired truncated ORF, pPm-CS$^{1-704}$, was transformed into E coli Tuner, the T7 RNA polymerase-containing expression host, and maintained on LB media with carbenicillin and chloramphenicol (34 μg/ml) at 30° C. Log phase cultures were induced with β-isopropylthiogalactoside (0.2 mM final) for 5 hrs. The cells were harvested by centrifugation, frozen, and extracted for 20 min with a mild detergent (bper II reagent, Pierce) at 7° C. in the presence of a broad-range protease inhibitor cocktail. The cells were removed by centrifugation and the soluble extract was used as the source of CS enzyme for in vitro assays.

A monospecific polyclonal antibody was generated against a synthetic peptide (SEQ ID NO:25) (acetyl-LDSDDYLEP-DAVELCLKEF-amide) corresponding to residues 526 to 544 of the pmHAS protein. The bPer extracts of various recombinant E coli strains were heated at 42° C. for 10 min in sample buffer before loading. After electrophoresis, semi-dry transfer to a nitrocellulose membrane was performed. The Western blots were blocked with bovine serum albumin and incubated with the affinity-purified antibody before detection with a Protein A-alkaline phosphatase conjugate and colorimetric development with bromochloroindolyl phosphate and nitro blue tetrazolium.

Incorporation of radiolabeled monosaccharides from UDP-[$^{14}$C]GlcUA and/or UDP-[$^{3}$H]GalNAc precursors (NEN) was used to monitor chondroitin synthase activity. Samples were usually assayed in a buffer containing 50 mM Tris, pH 7.2, 20 mM MnCl$_2$, 0.1 M (NH$_4$)$_2$SO$_4$, 1 M ethylene glycol, 0-0.6 mM UDP-GlcUA, and 0-0.6 mM UDP-GalNAc in the presence of a chondroitin-6-sulfate acceptor oligosaccharide, GalNAc-6-SO$_4$[GlcUA-GalNAc-6-SO$_4$]$_n$ (n=1 or 2; gift of Dr. Geetha Sugumaran), at 30° C. The reaction products were separated from ubstrates by descending paper (Whatman 3M) chromatography with ethanol/1 M ammonium acetate, pH 5.5, development solvent (65:35). The origin of the paper strip was cut out, eluted with water, and the incorporation of radioactive sugars into HA polymer was detected by liquid scintillation counting with BioSafe II cocktail (RPI). To test the transfer specificity of pmCS$^{1-704}$ (SEQ ID NO:26), various UDP-sugars (UDP-GlcNAc, UDP-GalUA, UDP-Glc) were substituted for the authentic chondroitin precursors.

Gel filtration chromatography was used to analyze the size distribution of the labeled polymers. Separations were performed with a Polysep-GFC-P 5000 column (300×7.8 mm; Phenomenex) eluted with 0.2 M sodium nitrate at 0.6 ml/min. Radioactivity was monitored with an in-line Radioflow LB508 detector (EG & G Berthold) using Unisafe I cocktail (1.8 ml/min; Zinsser). The column was standardized with fluorescein-labeled dextrans of various sizes. To identify the radiolabeled polymers, portions of some reactions were dialyzed into water (3 kDa cutoff) and the high molecular weight product was digested with various glycolytic enzymes for 7 hours at 37° C. The enzyme concentrations and digestion buffers were: *Flavobacterium* chondroitin AC lyase, 1 milliunit/μl, 50 mM Tris-acetate, pH 7.5; *Proteus* chondroitin AC lyase, 1 milliunit/μl, 50 mM Tris-acetate, pH 8; *Streptomyces* HA lyase, 266 milliunits/μl, 50 mM sodium acetate, pH 5.4.

Previous work by others had shown that the Type F capsule was removed from bacterial cells by treatment with chondroitin AC lyase. We found that a fragment of the specific HA-binding protein, aggrecan, in the HA-TEST assay (Pharmacia) did not cross-react with extracts of the Type F polymer, but readily detected the HA in parallel extracts from Type A bacteria (data not shown). Acid hydrolysis and monosaccharide analysis of the Type F polymer showed that it contained the sugars galactosamine and GlcUA (Table XIII).

TABLE XIII

| Sugar | Polysaccharides | | | | |
|---|---|---|---|---|---|
| | C | C/F mix | F | HA | HEP |
| | Retention Time Relative to Rhamnose | | | | |
| glucosamine | ND* | ND | ND | 1.38 | 1.38 |
| galactosamine | 1.14 | 1.12 | 1.12 | ND | ND |

TABLE XIII-continued

| Sugar | Polysaccharides | | | | |
|---|---|---|---|---|---|
| | C | C/F mix | F | HA | HEP |
| | Retention Time (min) | | | | |
| uronic acid | 14.87 | 14.87 | 14.87 | 14.85 | 14.58 |

*NOT DETECTED
Monosaccharide Composition of Type F Polymer and Various GAGs. Acid hydrolysis and high pH ion exchange chromatography were utilized to determine the sugar components of the Type F polymer (F). The polysaccharides chondroitin sulfate C (C), hyaluronan (HA), and heparin (HEP), and pure monosaccharides were used as standards. Under these hydrolysis conditions, deacetylation and desulfation as well as the desired fragmentation of glycosidic bonds occur. Retention times relative to the internal standard rhamnose elution time (10.7 min; set to 1) are presented for the relevant hexosamines. Acidic sugars were eluted with a sodium acetate gradient; the retention time of the major uronic acid peak from the start of the gradient is presented. Type F polysaccharide and chondroitin sulfate possess the identical monosaccharide composition, galactosamine and glucuronic acid.

The ion exchange profile of the chondroitin sulfate C hydrolyzate was indistinguishable from the Type F hydrolysate; mixing experiments demonstrated that the component peaks migrated identically. No other sugars were detected in the Type F polymer including glucosamine, mannose, galactose, glucose, and fucose. Hydrolysates of the HA and heparin standards clearly contained glucosamine but not galactosamine. Preliminary NMR studies are consistent that the amino sugar of the Type F polymer is present in an acetylated form (NAc $CH_3$ chemical shift at 2.02 ppm in $D_2O$; University of Georgia Complex Carbohydrate Research Center).

PCR products were obtained utilizing Type F chromosomal DNA as a template and various oligonucleotide primers corresponding to the Type A capsule locus. A 3.6 kb PCR product, which contained large portions of the Type F KfaA homolog (a putative polysaccharide transporter of *E. coli*) and the putative pmCS gene, was used as a hybridization probe to obtain an intact *P. multocida* capsular locus from a lambda library. Two positively hybridizing plaques were found after screening ~$10^4$ plaques, and this phage were converted into plasmids. We found that both plasmids contained a novel open reading frame of 965 residues, which we named pmCS (SEQ ID NO: 4), that was highly homologous to the Type A HA synthase, pmHAS (FIG. 15). The level of identity was 90% at both the DNA and protein levels. The differences in amino acid sequence were mainly localized to several regions of the polypeptide in the amino terminal half of the molecules. There is an excellent overall alignment of the enzymes (according to Multalin) except for a 7-residue insertion in the pmHAS sequence in the position corresponding to residue 53 of the pmCS sequence.

The central portion of both the pmCS and the pmHAS polypeptides (residues 430-530) is most homologous to bacterial glycosyltransferases from a wide variety of genera, including *Streptococcus, Vibrio, Neisseria* and *Staphylococcus*, which form exopolysaccharides or the carbohydrate portions of lipopolysaccharides. The most notable sequence similarities are the DGSTD and the DXDD motifs. Directly downstream of the pmCS gene, a putative UDP-glucose dehydrogenase gene was found. Therefore, the relative gene order [KfaA homolog—polysaccharide synthase gene—UDP-glucose dehydrogenase gene] in this portion of the *Pasteurella* Type F capsule operon is the same as that found in Type A.

Figure 16:
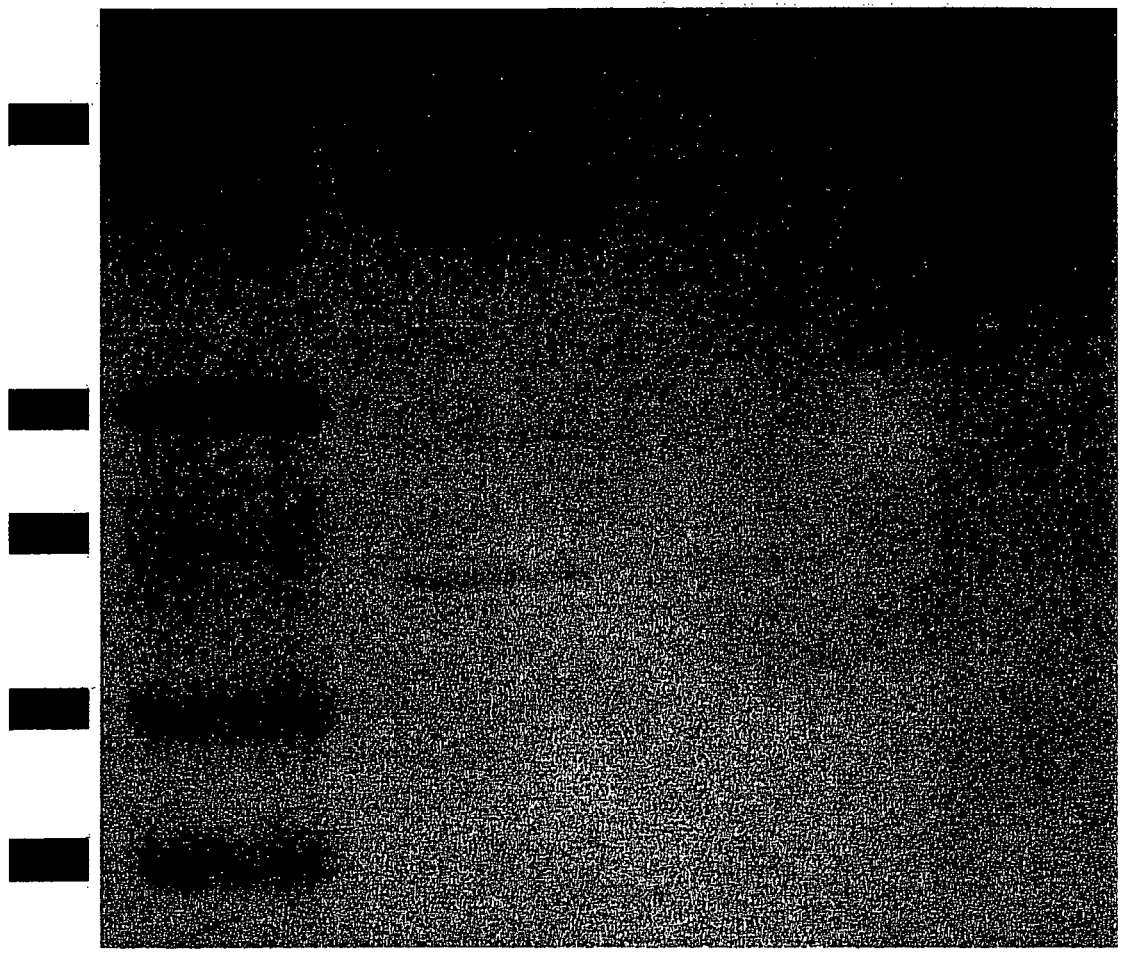
FIG. 16 is a Western Blot Analysis of Truncated Recombinant *Pasteurella* GAG Synthases. Immunoreactive bands at the predicted size of 80 kDa correspond to pmCS$^{1-704}$ (CS) or pmHAS$^{1-703}$ (HAS). No similar band is seen for the vector control (V). Prestained standards (Std) are shown for size comparison (from top to bottom: 95.5, 55, 43, 36, 29 kDa).

Western blot analysis using a monospecific antipeptide antibody was used to detect the production of pmCS$^{1-704}$ (SEQ ID NO: 26) or pmHAS$^{1-703}$ (SEQ ID NO:9) polypeptide (FIG. 16). Both enzymes contain a sequence that corresponds exactly to the synthetic peptide used to generate the antibody. Extracts derived from *E. coli* Tuner cells containing the pmCS$^{1-704}$ plasmid contained an immunoreactive band of the appropriate size (i.e. predicted to be 80 kDa), but this band was not present in samples from cells with the vector alone control. The use of soluble pmCS$^{1-704}$ protein provided increased expression levels and facilitated preparation of enzyme in comparison to use of the native-length membrane protein.

Extracts derived from *E. coli* Tuner cells containing the pPmCS$^{1-704}$ plasmid, but not samples from cells with the vector alone, synthesized polymer in vitro when supplied with both UDP-GlcUA and UDP-GalNAc simultaneously (Table XIV).

TABLE XIV

| Second Sugar nucleotide present | Incorporation of first sugar | |
|---|---|---|
| dpm % | [$^{14}$C]GlcUA | [$^3$H]GalNAc |
| None | 60 (0.9) | 250 (7.5) |
| UDP-GlcUA | ND | 3,310 (100) |
| UDP-GalUA | ND | 315 (9.5) |
| UDP-GalNAc | 6,590 (100) | ND |
| UDP-GlcNAc | 85 (1.2) | ND |
| UDP-Glc | 60 (0.9) | 370 (11) |

ND, not determined.

Transferase Specificity of Recombinant pmCS$^{1-704}$ for Sugar Nucleotides. Crude bPer extract (150 mg of total protein) was incubated in 50 ml of assay buffer containing 0.5 mg of chondroitin oligosaccharide acceptor for 20 min either with UDP-[$^{14}$C]GlcUA or UDP-[$^3$H]GalNAc. The radiolabeled sugar (300 mM, 0.04 mCi) was used in the presence of the indicated second unlabeled sugar nucleotide (600 mM). The incorporation into polymer was assessed by paper chromatography. The relative percentage of incorporation in comparison to the assay containing the authentic precursor (set to 100%) is shown in parentheses. A representative experiment is shown. The recombinant pmCS$^{1-704}$ incorporated only the authentic chondroitin precursors into polysaccharide.

No incorporation of radiolabeled [$^{14}$C]GlcUA into polymer was observed if UDP-GalNAc was omitted, or if UDP-GlcNAc was substituted for UDP-GalNAc. Conversely, in experiments using UDP-[$^3$H]GalNAc, substantial incorporation of radiolabel into polymer was only noted when UDP-GlcUA was also present. UDP-GalUA or UDP-Glc did not substitute for UDP-GlcUA. No polymerization or transferase activity was detected if the divalent metal ions were chelated with EDTA. The addition of the chondroitin oligosaccharide acceptor increased sugar incorporation catalyzed by pmCS$^{1-704}$ at least 50- to 100-fold in comparison to parallel reactions without acceptor in analogy to observations of pmHAS.

Figure 17:
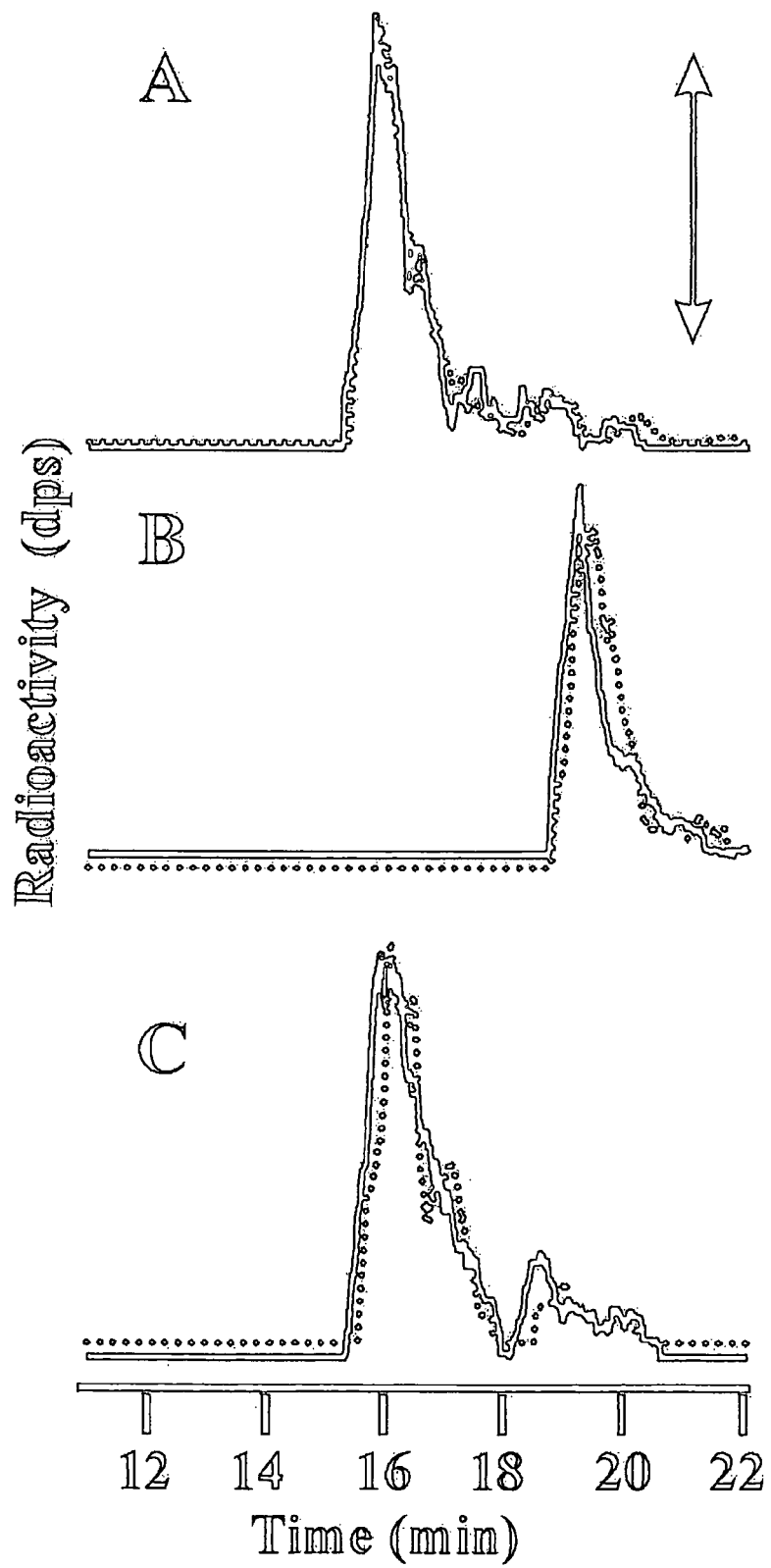
FIG. 17 is a graphical plot of gel filtration analysis of radiolabeled polymer synthesized in vitro. The pmCS$^{1-704}$ extract (1 mg total protein) was incubated with chondroitin acceptor oligosaccharide (5 mg), UDP-[$^{14}$C]GlcUA and UDP-[$^{3}$H]GalNAc (580 mM, 0.16 mCi each) in a reaction volume of 200 ml for 30 min. The reaction product was split into five aliquots and treated with various GAG glycosidases as described in *Experimental Procedures*. Portions (60%) of the samples were then analyzed on the PolySep column (calibration elution times in minutes: void volume, 12.7; 580 kDa dextran, 15.4; 145 kDa dextran, 16.0, totally included volume, 19.3 min). Radioactivity ($^{14}$C, solid line; $^{3}$H, dotted line) measured by the in-line detector is presented as disintegrations per second (dps). The double-headed arrow corresponds to a response of 20 dps. A, untreated polymer, peak 15.9 min; B, *Flavobacterium* chondroitinase AC lyase-treated polymer, peak, 19.2 min; C, HA lyase-treated polymer, peak 15.9 min. The polymer peak with a size of –100 to 400 kDa contained both radiolabeled sugars at a 1:1 ratio and was degraded only by the appropriate enzyme, chondroitin AC lyase.

Analysis by gel filtration chromatography indicated that recombinant pmCS produced polymer chains of ~$10^3$ monosaccharides long (~100 to 400 kDa) in vitro. Radioactivity from both labeled GlcUA and GalNAc sugars co-migrated as a single peak (FIG. 17A). No radiolabel was incorporated into high molecular weight polymer if both UDP-sugars were not present during the assay. The identity of the polymer as chondroitin was verified by its sensitivity to *Flavobacterium* or *Proteus* chondroitin AC lyase (FIG. 17B) and its resistance to the action of *Streptomyces* HA lyase (FIG. 17C).

*P. multocida* Type F produces a chondroitin or chondroitin-like capsule. The glycosyltransferase responsible for polymerizing the chondroitin backbone component of the capsular polysaccharide has also been molecularly cloned. The pmCS enzyme appears to be a close homolog of the pmHAS enzyme. In pmHAS one domain, called A1, is responsible for GlcNAc transfer and the other domain, called A2, is responsible for GlcUA transfer. Comparison of the pmHAS and the pmCS sequences reveals that the majority of the sequence differences exist in the A1 domain. The pmCS enzyme transfers a different hexosamine, GalNAc, thus this observation is consistent with the two-domain structure for pmHAS.

Mutant enzymes derived from the soluble pmCS$^{1-704}$ parental dual-action chondroitin synthase were also created with the ability to elongate HA or chondroitin-based oligosaccharides by adding a single β3-GalNAc monosaccharide to the non-reducing terminus. The mutants were formed by targeting the DXD motif in Domain A2 (also found in pmHAS) by site-directed mutagenesis (same general procedure as with pmHAS); the two aspartate (D) groups were converted into asparagine (N) residues forming the "NXN" mutants. It was predicted by the Applicants that this genetic procedure would eliminate the GlcUA-transferase of Domain A2 and leave the remaining GalNAc-transferase of Domain A1 intact.

Several independent clones producing mutant pmCS$^{1-704}$ NXN enzyme were assayed individually for the ability to transfer [$^3$H]GalNAc to HA oligosaccharides using UDP-GalNAc in analogy to pmHAS transferring [$^3$H]GalNAc to HA oligosaccharides using UDP-GlcNAc as described hereinabove. The NXN mutants could transfer a single GalNAc sugar like the wild-type sequence pmCS$^{1-704}$ enzyme.

The NXN mutants could not, however, make long chondroitin chains when assayed in a different system that only detected the addition of both GlcUA and GalNAc. This system utilizes leech hayluronidase-generated HA8-12mer oligosaccharide (this acceptor has a non-reducing end GlcNAc; 1.5 ug), 15 mM UDP-GlcUA, 0.1 mM UDP-[$^3$H]GalNAc (4.4×10$^5$ dpm) in 20 μL reaction mixtures containing 50 mM Tris, pH 7.2, 1 M ethylene glycol, 0.1 M ammonium sulfate, 10 mM MnCl$_2$. Extracts containing either the wild-type pmCS$^{1-704}$ (CS-WT) or the NXN mutant extracts were assayed for 120 minutes at 30° C. After the reaction, the labeled polymer produced was quantitated by paper chromatography (polymer at the origin of the paper strip) and liquid scintillation counting. The NXN mutants (3 different clones: 2, 3, or 7) do not display high incorporation in this assay because these single-action enzymes cannot add the required GlcUA to the acceptor terminus: without prior GlcUA transfer, the radioactive GalNAc is never added. (See Table XV.) In contrast, the parental dual-action pmCS enzyme can perform GlcUA addition thus allowing the radioactive GalNAc to be added; furthermore, multiple rounds of GlcUA and GalNAc addition are possible with wild-type enzyme yielding a very high signal. Overall, such controllable single-action enzymes are useful for bioreactor systems for oligosaccharide syntheses or for construction of sugar libraries.

TABLE XV

| Enzyme | [$^3$H]GalNAc (dpm) |
| --- | --- |
| None | 2 |
| CS-NXN-2 | 141 |
| CS-NXN-3 | 152 |
| CS-NXN-7 | 242 |
| CS-WT | 173,000 |

The bacterial chondroitin synthase and the putative mammalian are not related based on sequence comparisons. Both bacterial pmCS and the vertebrate chondroitin synthase utilize UDP-sugars to extend acceptor carbohydrates in vitro. In most cases, the mammalian enzyme in cell-free extracts, however, does not produce long chondroitin chains and only the half-reaction (e.g., adding a single GlcUA to a GalNAc-terminated oligosaccharide or vice versa) is readily observed in vitro. In vertebrate tissues, other enzymes modify chondroitin extensively by sulfation and/or epimerization.

Additional pmHAS Mutants pmHAS and pmCS both utilize two relatively independent glycosyltransferase sites. Other sequence motifs are also discussed with respect to their roles in polysaccharide biosynthesis. Hereinafter is the analysis of truncated pmHAS proteins used to delineate essential regions.

In order to analyze the contribution of the amino terminal region of pmHAS, various recombinant truncated polypeptides (pmHAS$^{46-703}$ SEQ ID NO:27, pmHAS$^{72-703}$ SEQ ID NO:28, pmHAS$^{96-703}$ SEQ ID NO: 29 and pmHAS$^{118-703}$ SEQ ID NO:30) were produced in *E. coli*. The experimentally determined molecular weights corresponded to the predicted sizes. The truncated versions pmHAS$^{46-703}$ and pmHAS$^{72-703}$ were as active as pmHAS$^{1-703}$, a soluble polypeptide with complete HAS activity. pmHAS$^{96-703}$ expressed at a very low level compared with other constructs but was active. pmHAS$^{118-703}$ expressed better than pmHAS$^{96-703}$ and still elongated HA chains. Therefore, further deletion beyond residue 72 appears to affect the overall folding efficiency of the entire polypeptide. Observation of lower molecular weight degradation bands derived from pmHAS$^{118-703}$ on Western blots also suggests that improper folding occurs to some extent. Overall, these findings suggest that the amino-terminal 117 residues are not required for HA synthase activity.

It was discussed herein above that pmHAS$^{1-650}$ (SEQ ID NO:10) lostitsGlcUA-transferase activity. To further delineate the GlcUA-transferase domain within the carboxyl terminal region, two slightly longer mutants, pmHAS$^{1-668}$ SEQ ID NO: 31 and pmHAS$^{1-686}$ SEQ ID NO: 32 were created. Both mutants also could not polymerize HA due to the loss of GlcUA-transferase activity, indicating that the carboxyl-terminal boundary of the GlcUA-transferase resides between residues 686 and 703.

Others of ordinary skill in the art have used hydrophobic cluster analysis to identify two types of domains conserved in a variety of β-linked glycosyltransferases that use nucleotide diphospho sugar as donors, termed Domain A and Domain B. Characterization of two conserved DGS motifs in the two A domains of pmHAS indicate that the two aspartate residues are essential for HAS activity. The existence of a third potential DGS sequence motif in pmHAS is also located at position 563-565. In order to determine if this motif is critical for synthase activity in the same manner as the other two DGS motifs, D563 of pmHAS$^{1-703}$ was mutated into a glutamate, asparagine or lysine residue. All of the mutants behaved like wild-type pmHAS$^{1-703}$ indicating that the third motif DGS is not essential for the catalytic activity of pmHAS. This also demonstrates that certain residues may be changed, but the enzyme remains a functional synthase—i.e., with respet to the "functionality" language of the hereafter appended claims.

The DXD motif is found in many glycosyltransferases. pmHAS has two DXD motifs, one in domain A1 and another in domain A2 (FIG. 12). X-ray crystallography of the *Bacillus* SpsA protein/UDP-complex suggests that the DXD motif is involved in binding metal ion coordinated with the beta phosphate and the ribose moiety of the UDP-sugar. The involvement of the individual aspartate residues of DXD in pmHAS, therefore, is characterized. The aspartate residues (residue 247, 249, 527 or 529; FIG. 12) of the two DXD motifs of pmHAS$^{1-703}$ were mutated in the two domains. Mutants were produced containing the following changes in domain A1-D247E (SEQ ID NO:33), D247N (SEQ ID NO:34), D247K (SEQ ID NO:35), D249E (SEQ ID NO:36), D249N (SEQ ID NO:37), or D249K (SEQ ID NO:38) and in domain A2-D527N (SEQ ID NO:39), D527E (SEQ ID NO:40), D527K (SEQ ID NO:41), D529E (SEQ ID NO:42), D529N (SEQ ID NO:43), or D529K (SEQ ID NO:44). Upon sequence verification of the complete open reading frame, mutants with D247N, D249K, D529E and D527K were found to also have a mutation of D7021 that did not affect HAS activity. All of the mutant proteins were produced at similar levels in soluble form. In vitro assays were utilized to assess the HA synthase activity (e.g. polymerization of long HA chains), or the two half-reactions, either GlcNAc-transferase or GlcUA-transferase activity. All of the mutants were inactive as HA synthases except D529E which had only 10% of the wild type activity (Table XVI).

TABLE XVI

| | Specific Activity | | |
|---|---|---|---|
| Enzyme | HAS | GlcNAc-Transferase | GlcUA-Transferase |
| D247N | <0.1 | <0.1% | 110% |
| D247K | <0.1 | <0.1% | 130% |
| D247E | <0.1 | <0.1% | 90% |
| D249K | <0.1 | <0.1% | 100% |
| D249E | <0.1 | <0.1% | 105% |
| D527K | <0.1 | 115% | <0.1% |
| D527E | <0.1 | 120% | 0.1% |
| D529N | <0.1 | 230% | <0.1% |
| D529K | 5% | 360% | <0.1% |
| D529E | 10% | 110% | 15% |

Specific activities of the various pmHAS$^{1-703}$ DXD mutants. Equivalent amounts of pmHAS$^{1-703}$ proteins (based on Western blot) were assayed. The specific activities are indicated as the percentage of the wild-type sequence pmHAS$^{1-703}$ (set as 100%). The specific activities for wild-type enzyme in the three assays were 6-34 picomole of monosaccharide transfer/mg/min. The DXD motif of each domain is involved in HA polymerization.

As predicted, the enzymes containing mutations at position 247 or 249 (domain A1 mutants) maintained high levels of GlcUA-transferase activity. On the other hand, the enzymes containing mutations at position 527 or 529 (domain A2 mutants) had high levels of GlcNAc-transferase activity. Therefore, all of the four aspartate residues were critical for HA synthase function. These results confirm the model of two distinct transferase sites in a single pmHAS polypeptide; domain A1 is essential for GlcNAc-transferase activity and domain A2 is essential for GlcUA-transferase activity.

The two DXD motifs of pmHAS are predicted to be involved in metal ion binding based on the SpsA structure. Experiments were designed to examine (a) if other metal ions could rescue mutant activity and (b) if the two separate active sites have similar metal ion preference. The presence of Co$^{2+}$, Mg$^{2+}$ or Ca$^{2+}$ did not convert the DXD mutants into functional HASs. GlcNAc-transferase or GlcUA-transferase assays were performed with wild-type pmHAS$^{1-703}$ in the presence of 20 mM Mn$^{2+}$, Co$^{2+\ or\ Mg2+}$. Although the highest activities were obtained in the presence of 20 mM of Mn$^{2+}$, the GlcNAc-transferase activity preferred Co$^{2+}$ over Mg$^{2+}$ while the GlcUA-transferase activity preferred Mg$^{2+}$ over Co$^{2+}$ (Table XVII).

TABLE XVII

| | Specific Activity | | | |
|---|---|---|---|---|
| | GlcNAc-Transferase | | GlcUA-Transferase | |
| Enzyme | Co$^{2+}$ | Mg$^{2+}$ | Co$^{2+}$ | Mg$^{2+}$ |
| D247N | | | 15% | 52% |
| D247K | | | 1% | 37% |
| D247E | | | 9% | 55% |
| D249N | | | 14% | 58% |
| D249K | | | 10% | 46% |
| D527E | 87% | 27% | | |
| D529N | 75% | 59% | | |
| Wt | 77% | 39% | 18% | 66% |

Metal ion preference of the GlcNAc-transferases and the GlcA-transferase activities. Equivalent amounts of wild type pmHAS$^{1-703}$ protein (wt) or DXD mutants were assayed in the presence of 20 mM of Mn$^{2+}$, Co$^{2+}$ or Mg$^{2+}$. The activities are indicated as the percentage of their activities in the presence of Mn$^{2+}$ (set as 100%). Overall, Mn$^{2+}$ is the best cofactor, but in its absence, the GlcNAc-transferase preferred Co$^{2+}$ while the GlcUA-transferase preferred Mg$^{2+}$. The active sites of domain A1 and A2 are similar yet distinct.

Similar results were obtained when assays were performed with the pmHAS$^{1-703}$ mutants that have only a single transferase activity. In a preferred embodiment, both Ds (aspartates) are mutated to Ns (asparagines): one D can be changed to N but the resulting mutant enzyme may retain some "sloppiness"—i.e. the enzyme may incorporate both natural sugars. As such, it may be preferred to mutate both Ds of the DXD motif to Ns in order to truly "kill" or knock-out the enzymatic activity of the domain.

In the pmHAS polypeptide sequence, there is a segment similar to portions of mammalian UDP-GalNAc: polypeptide N-acetylgalactosaminyltransferases (ppGaNTransferases) that catalyzes the initial step for making the oligosaccharide moiety on O-linked glycoproteins. The W366GGED370 motif, which resides between the putative domain A1 and domain A2, does not exist in the sequences of other HA synthases from Streptococcus, vertebrates, or Chlorella virus. To study the function of the WGGED motif in pmHAS, E369 or D370 were mutated. Six different mutants were produced each containing one of the following changes, E369D (SEQ ID NO:45), E369Q (SEQ ID NO:46), E369H (SEQ ID NO:47), D370E (SEQ ID NO:48), D370N (SEQ ID NO:49), or D370K (SEQ ID NO:50). All the mutants were expressed at comparable levels with the wild type enzyme. Based on the results of the HAS assays and the two half assays, mutation at either of these two sites resulted in the loss of only GlcNAc-transferase activity, but not the GlcUA-transferase activity (Table XVIII), suggesting that the WGGED motif in pmHAS-D is essential for GlcNAc-transferase activity.

TABLE XVIII

| | Specific Activity | | |
|---|---|---|---|
| Enzyme | HAS | GlcNAc-Transferase | GlcUA-Transferase |
| D370N | <0.1 | 1% | 80% |
| D370K | <0.1 | 2% | 80% |

TABLE XVIII-continued

| Enzyme | Specific Activity | | |
|---|---|---|---|
| | HAS | GlcNAc-Transferase | GlcUA-Transferase |
| D370E | 1% | <0.1% | 105% |
| E369H | <0.1 | 5% | 130% |
| E369D | <0.1 | 1% | 55% |
| E369Q | 1% | 1% | 60% |

Specific activities of the pmHAS$^{1-703}$ WGGED mutants. Equivalent amounts of pmHAS$^{1-703}$ proteins (based on Western blot) were assayed. The activities are indicated as the percentage of the wild type pmHAS$^{1-703}$ (100%). The WGGED motif is involved in the transfer of GlcNAc.

As described hereinabove, a combination of two DGS motif mutants, D196N, a GlcUA-transferase and D477K, a GlcNAc-transferase, fulfill the complete function of a HAS when mixed together in the same reaction along with a HA oligosaccharide acceptor. Hereinafter the standard HA synthesis activity assay was performed with several different combinations of DXD or WGGED mutants. One GlcNAc-transferase mutant enzyme (a D527 or D529 mutant) and one GlcUA-transferase mutant enzyme (a D247, D249, E370, or D369 mutant) were combined in these tests. When the mutant polypeptides were incubated together, along with a HA oligosaccharide acceptor (4-10 sugars long), HA polymers were made. This demonstration further enables the proposition that two independent transferase sites sequentially transfer GlcNAc and GlcUA monosaccharides to an existing HA chain in an alternating fashion.

The chondroitin synthase, pCS, from Type F *P. multocida* is about 90% identical to pmHAS at the protein level. The majority of sequence differences exist in the vicinity of the domain A1 of pmHAS while their carboxyl-terminal halves are almost identical (described hereinabove). This is to be expected because the carboxyl-terminal half of pmHAS contains domain A2 which has the GlcUA-transferase active site. The pmCS also possesses two separate transferase sites with respect to pmCS, but the amino-terminal half is a GalNAc-transferase while the carboxyl-terminal half is a GlcUA-transferase. Thus, swapping the carboxyl-terminal GlcUA-transferase site between pmHAS and pmCS does not affect the sugar polymerizing activity. On the other hand, swapping of the amino-half of either pmHAS or pmCS changes the hexosamine transfer specificity. In order to test such "swapping" abilities, domain swapping between pmHAS and pmCS was performed by the PCR-overlapping-extension method (as described in Horton et al., 1989, which is expressly incorporated herein by reference in its entirety). The active truncated versions of the synthases, pmCS$^{1-704}$ and pmHAS$^{1-703}$, were used as the starting materials for the construction. Residues 427/428 of pmHAS and the equivalent site of pmCS, residues 420/421, were chosen as the initial splicing site based on comparisons of the amino acid sequences of pmHAS, pmCS and other GlcNAc-transferases.

The combination of residues 1-427 from pmHAS and residues 421-704 from pmCS (pmAC construct: SEQ ID NO:51) resulted in an active HAS. The opposite combination, consisting of residues 1-420 from pmCS and residues 428-703 from pmHAS (pmBD construct: SEQ ID NO:52), resulted in an active chondroitin synthase (Table XIX).

TABLE XIX

| Enzyme Synthase | Chondroitin | HA synthase |
|---|---|---|
| pmHAS$^{1-703}$ | − | + |
| pmCS$^{1-704}$ | + | − |
| pm-AC | − | + |
| pm-BD | + | − |

Activity of chimeric or hybrid *Pasteurella* synthases. The wild type enzymes and the chimeric or hybrid constructs (pm-AC, pmHAS$^{1-427}$-pmCS$^{421-704}$; pm-BD, pmCS$^{1-420}$-pmHAS$^{428-703}$) were tested in the HA or the chondroitin synthase assays. Domain A1 is responsible for hexosamine transfer and domain A2 is responsible for GlcUA transfer.

This finding indicates that the domain A1 dictates hexosamine transfer specificity. Also, the source of the GlcUA-transferase domain A2 does not affect the specificity of either the GalNAc-transferase or the GlcNAc-transferase activity. The two single-action transferase sites of pmHAS and pmCS are relatively independent.

The DXD motif is conserved in many glycosyltransferases from different families and the aspartates have been shown to be crucial for activity in enzymes whose function and sequences are highly divergent. pmHAS possesses a DXD motif in both domain A1 and domain A2. Mutagenesis of any of these four aspartates indicates that they are involved in HA polymerization in agreement with the presumed critical role of the motif. Mutation of the domain A1 DXD results in the loss of only GlcNAc-transferase activity while mutation of the domain A2 DXD results in the loss of only GlcUA-transferase activity.

Although the importance of the DXD motif was previously hypothesized, its function was not clear until very recently. Based on an X-ray crystal structure of SpsA, a family 2 glycosyltransferase, the DXD motif is now known as a nucleotide-binding element. The first aspartate forms a hydrogen bond with the ribose ring and the second aspartate coordinates with the metal cation bound to the phosphate to assist leaving group departure. The involvement of the DXD motif in nucleotide binding and in metal ion interaction is supported by several other available glycosyltransferase structures which were solved later, including bovine β4-galactosytransferase, rabbit N-acetylglucosaminyltransferase I (in which the motif is in the form of EDD and the last aspartate, D213, makes the only direct interaction with the bound Mn$^{2+}$), and human β1,3-glucuronyltransferase I. A retaining enzyme, bovine β1,3-galactosyltransferase, contains a DXD motif with a similar structure for UDP-binding.

In the case of pmHAS, which possesses two separate transferase sites each with a DXD motif, each transferase site contains a set of UDP-precursor-binding sites and catalytic residues. The two DXD motifs of each site are similar but not identical. The two half-activities of pmHAS prefer Mn$^{2+}$, but the two sites differ in their relative preference for Co$^{2+}$ and Mg$^{2+}$. The underlying reason for this selectivity is not known, but it can be speculated that various metal ions confer different coordination angles and geometry to the sugar nucleotide/enzyme binding site complex. Indeed, the X-ray crystal structure of SpsA showed that the two phosphate groups of UDP are ordered differently in the presence of Mn$^{2+}$ or Mg$^{2+}$.

The WGGED motif was first noted among β4-galactosyltransferases and a similar motif, WGXEXXE, was found among UDP-GalNAc:polypeptide N-acetylgalactosaminyl-transferases. Residues in this Gal/GalNAcT motif have been shown to be essential for enzyme activity. The X-ray crystal structure of bovine β4-galactosyltransferase showed that E317D residues in WGGE317D segment are located at the bottom of the proposed UDP-Gal binding pocket. It was speculated that the E or the D residue was a good candidate for making the nucleophilic attack on the 4-hydroxyl group of the acceptor substrate GlcNAc ring. The assignment of the role of catalytic base to an E or D residue is supported by structural studies on several other glycosyltransferases. There is only one WGGED motif in pmHAS. The GlcNAc-transferase, but not the GlcUA-transferase, activity of pmHAS depends on the WGGED motif. The homologous pmCS enzyme also possesses this motif. The WGGED motif plays the same role in the hexosamine transfer reaction of the *Pasteurella* synthases as it does in the Gal-/GalNAc-transferases.

Saxena proposed two types of putative domains, Domain A and Domain B, among many beta-glycosyltransferases that use nucleotide diphospho sugars as donors. Saxena noticed that processive enzymes, which add a number of sugar residues without releasing the nascent chain, possess both Domains A and B, while those enzymes that add a single sugar residue have only Domain A. In general, Domain A resides in the N-terminal half of the polypeptide and possesses two invariant Asp residues, while Domain B resides in the C-terminal half and with an invariant Asp residue along with a characteristic QXXRW motif. Saxena, et al. hypothesized that the production of heteropolysaccharides with alternating sugar residues, such as HA, is fulfilled by specializing Domain A for one sugar and Domain B for a different sugar.

The only known member of Class II HA synthases, pmHAS, possesses two tandem copies of Domain A and does not contain Domain B. Data from the activity analysis of the truncated versions and the point mutants of pmHAS indicate that two active sites coexist in one polypeptide. Overall, pmHAS appears to be a polypeptide with two coordinated but intrinsically nonprocessive activities. Support for this characterization is found in the pmHAS mutant in vitro complementation study; two distinct polypeptide molecules can act together to polymerize HA chains in a rapid fashion. The HA chain must be released by one mutant to be acted on by the other mutant. The distinct Class I HA synthases, however, do not appear to release the nascent chain during synthesis.

Figure 18:
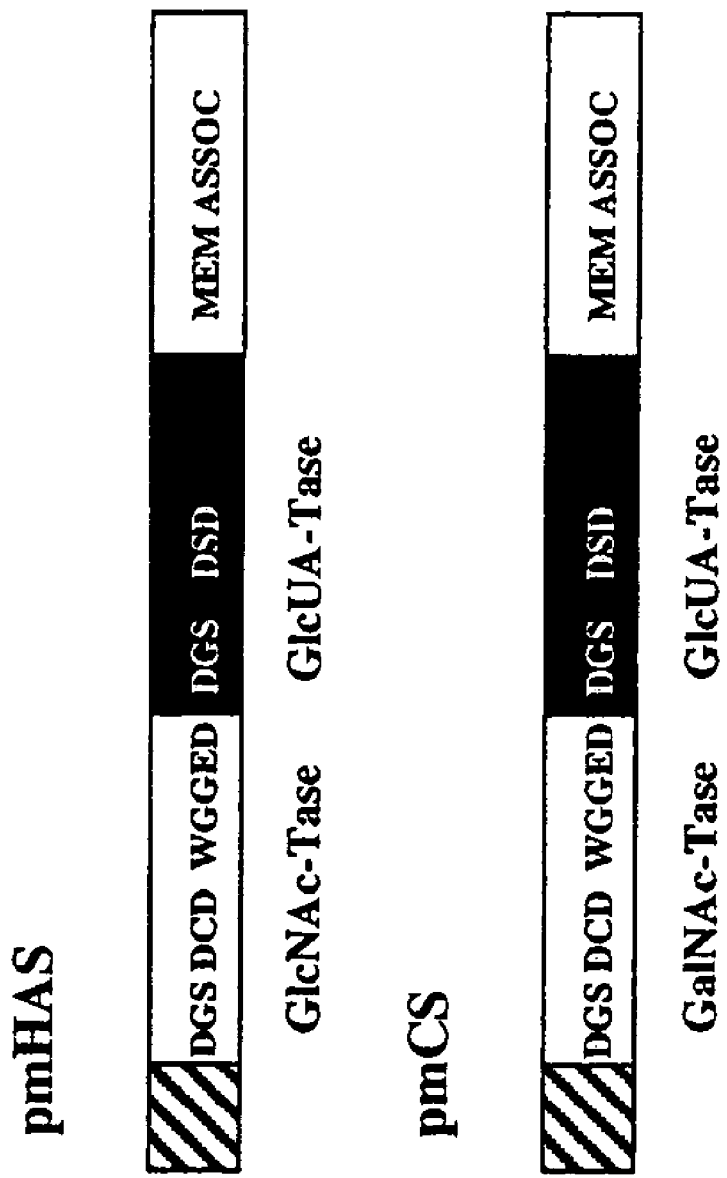
FIG. 18 is a pictorial representation of a model of the two putative glycosyltransferase sites of pmHAS and pmCS. PmHAS and pmCS contain two distinct and relatively independent glycosyltransferase sites. Each site possesses a DGS and a DXD amino acid motif. A WGGED motif is found near the junction of the two domains, and is involved in hexosamine-transferase activity. The carboxyl-terminus is involved in membrane association (MEM ASSOC), but is not required for catalytic activity. Residues 1-117 (cross-hatched) appear dispensable for catalysis of sugar transfer but may contain structure scaffolding or play other roles.

PmCS is 90% identical to pmHAS and possesses two similar sets of putative nucleotide-binding elements. Therefore, pmCS utilizes the same structural organization and general catalytic mechanism as pmHAS. Dissection of the two transferase activities in pmHAS provides direct evidence for a two-active center model (FIG. 18). The *E. coli* K4 chondroitin polymerase (named a "polymerase" rather than "synthase" due to its apparent absolute requirement for an acceptor chain), KfoC, was recently reported (Ninomiya, et al., 2002). This protein is about 60% identical to pmHAS and pmCS, and thus probably utilizes similar motifs and domains. Another case of the "one polypeptide, two active center" model is the eukaryotic glycosyltransferase FT85, an enzyme involved in the glycosylation of Skp1 protein in Dictyostelium. This bifunctional glycosyltransferase mediates the ordered addition of β1,3-linked Gal and α1,2-linked Fuc to the Skp1 glycomoiety. The overall architecture of FT85 resembles pmHAS in that it contains two glycosyltransferase domains.

In the live bacterium, the pmHAS or the pmCS polypeptide engages with the polysaccharide export apparatus. In order to retain the nascent chain during polymerization in vivo, other proteins may help maintain the interaction of the transferase with the elongating GAG chain. The catalytic reaction mechanism and/or the intrinsic nature of pmHAS or pmCS are probably not the major chain retaining mechanisms.

In recent years, a large number of glycosyltransferases have been identified at DNA level, but the knowledge about their donor and acceptor specificity is limited to empirical testing and/or identification of their natural reaction products. Enzymes even within the same family can have rather broad range of donor and acceptor specificity, making it more difficult to identify the selectivity determinants. There are several X-ray crystal structures for glycosyltransferases, but these static snapshots of catalysis have not provided a clear interpretation of the mechanism of substrate specificity. Although Q289 of *E. coli* MurG is suggested to play a role in discriminating between UDP-GlcNAc and UDP-GalNAc, this result is limited and the contribution of a single residue might not be sufficient. Hyaluronan and chondroitin are polysaccharide chains composed of disaccharide repeats that differ at only one sugar; HA contains GlcNAc while chondroitin contains GalNAc, the C4 epimer of GlcNAc. The molecular cloning and the ability to dissect the highly homologous pmHAS and pmCS enzymes provides a potential strategy to identify the specific determinants that differentiate GlcNAc and GalNAc during catalysis of sugar transfer.

Reagents and Methods

Molecular biology reagents were from Promega unless noted. Custom oligonucleotides were from The Great American Gene Company. Oligonucleotides for mutagenesis were trityl purified. All other reagents were the highest grade available from either Sigma or Fisher unless otherwise noted.

Truncated polypeptides were generated by amplifying the pPm7A insert by 13 cycles of PCR with Taq polymerase (Fisher) and synthetic oligonucleotide primers corresponding to various portions of the pmHAS open reading frame. Except for the construction of pmHAS$^{1-668}$ and pmHAS$^{1-668}$, the primers contained EcoRI and PstI restriction sites to facilitate cloning into the expression plasmid pKK223-3 (tac promoter; Pharmacia). The resulting recombinant constructs were transformed into *E. coli* TOP 10F' cells (Invitrogen) and maintained on Luria-Bertani media with ampicillin selection. The DNA encoding pmHAS$^1$ 686 and pmHAS$^{1-668}$ were cloned into pETBlue-1 plasmid and expressed in Tuner (DE3)pLacI cells (Novagen) according to manufacturing instructions; these cells were maintained on Luria-Bertani media with carbenicillin and chloramphenicol selection.

Point mutations were made using the QuickChange site-directed mutagenesis method (Stratagene) with the plasmid pKK223/pmHAS$^{1-703}$ DNA as template. The sequences of the mutant open reading frames were verified by automated DNA sequencing (Oklahoma State University Recombinant DNA/Protein Resource Facility).

Recombinant *E. coli* were grown in Luria-Bertani media with drug selection until $OD_{600}$ was 0.3-0.6 when cells were induced with 0.5 mM isopropyl-1-thio-β-D-galactoside. Cells were harvested 5 hours after induction. For soluble truncated proteins and pmHAS$^{1-703}$-derived mutants expressed in *E. coli* TOP10F' cell, cells were extracted with B-Per™ II Bacterial Protein Extraction Reagent (an octylthioglucoside-based solution; Pierce) according to the manufacturer's instruction except that the procedure was performed at 7° C. in the presence of protease inhibitors. For proteins expressed in Tuner(DE3)pLacI, lysis by ultrasonication followed by subcellular fractionation was performed and the supernatant after centrifugation at 100,000×g was used.

Five assays were designed to detect either (a) the polymerization of long HA chains, (b) the addition of a single GlcNAc to a GlcUA-terminated HA oligosaccharide acceptor, (c) the addition of a single GlcUA to a GlcNAc-terminated HA oligosaccharide acceptor, (d) the polymerization of long chondroitin chains, or (e) the addition of a single GalNAc to a GlcUA-terminated HA oligosaccharide acceptor. The first three assays were described hereinabove. For the chondroitin synthase assay, the same conditions as the HA synthase assay were used except that the other hexosamine precursor, UDP-GalNAc, was employed and there is no ammonium sulfate or ethylene glycol in the assay system. GalNAc-transferase activity was assayed under the same conditions as the GlcNAc-transferase assay except that 0.3 mM UDP-[$^3$H]Gal-NAc (0.2 µCi; NEN) was used instead of UDP-[$^3$H]GlcNAc. Reactions were terminated by the addition of SDS to 2% (w/v). The reaction products were separated from substrates by descending paper (Whatman 3M) chromatography with ethanol/1 M ammonium acetate, pH 5.5, development solvent (65:35 for the HAS, chondroitin synthase, and GlcUA-transferase assays; 75:25 for GlcNAc-transferase and GalNAc-transferase assay). All assays were adjusted to be linear with regard to incubation time and to protein concentration. Radiolabeled products were quantitated by liquid scintillation counting (Biosafe II, Research Products International).

The pmHAS polypeptides in membranes and extracts were analyzed using standard 8% polyacrylamide SDS gels and Western blotting utilizing a monospecific antibody directed against a synthetic peptide corresponding to residues 526 to 543 of pmHAS (acetyl-LDSDDYLEPDAVELCLKE-amide) as described hereinabove.

The DNA encoding different segments of pmHAS-D or pmCS were generated by amplifying the pPm7A insert or pPmF4A insert, respectively, by 15 cycles of PCR with Taq polymerase (Fisher) and synthetic oligonucleotide primers corresponding to various portions of the pmHAS-D or pmCS open reading frame. Each internal primer contained overlaps with the other segment to allow joining of the two desired segments. The forward and reverse primers for pmHAS residue 1427 (A segment) were P1=5'-ATGAACACATTATCA-CAAGCAATAAAAGC-3' (SEQ ID NO:53) and P2=5'-GC-GAATCTTCTATTGGTAAAAGYTTTC-3' (SEQ ID NO:54) (Y=C/T), respectively. The forward and reverse primers for pmCS residue 421-704 (C segment) were P3=5'-CTTTTACCAATAGAAGATTCGCATAT-3' (SEQ ID NO:55) and P4=5'-GAAGACGTCTTAGGCATCTTTAT-TCTGAATGAG-3' (SEQ ID NO:56), respectively. The forward and reverse primers for pmCS residue 1-420 (D segment) were P1 and P2. The forward and reverse primers for pmHAS residue 428-703 (B segment) were P3 and P5=5'-GGGAATTCTGCAGTTAAATATCTTTTAA-GATATCAATCTCTTC-3' (SEQ ID NO:57), respectively. The chimeric or hybrid synthases were created by 15 cycles of PCR with the gel-purified (GeneClean; Biol 01) segments and outer primers (pm-AC used A and C segments with primer P1 and P4; pm-BD used B and D segments with primer P1 and P5). The purified PCR products were cloned into pETBlue-1 vector and the chimeric or hybrid proteins were expressed in Tuner(DE3)pLacI cells (Novagen). The complete open reading frames of multiple clones of both constructs were sequenced. A pmAC construct that was perfect, was found but both of the two pmBD constructs that we had sequenced completely had secondary undesired mutations (#1, E695 and 1697F; #2, 1302V). However, these mutations were in different locations and the enzyme transferase activities were identical. Several other pmBD clones have the identical phenotype but their complete sequences were not determined.

pmHS and PgIA Identification and Molecular Cloning.

As stated hereinabove, *Pasteurella multocida* Type D, a causative agent of atrophic rhinitis in swine and pasteurellosis in other domestic animals, produces an extracellular polysaccharide capsule that is a putative virulence factor. It has been reported that the capsule of Type D was removed by treating microbes with heparin lyase III. A 617-residue enzyme, pmHS (SEQ ID NOS: 5 and 70), and a 651-residue enzyme, PgIA (SEQ ID NO: 8), which are both authentic heparosan (unsulfated, unepimerized heparin) synthase enzymes have been molecularly cloned and are presently claimed and disclosed in copending U.S. application Ser. No. 10/142,143. Recombinant *Escherichia co*/1-derived pmHS or PgIA catalyzes the polymerization of the monosaccharides from UDP-GlcNAc and UDP-GlcUA. Other structurally related sugar nucleotides do not substitute. Synthase activity was stimulated about 7- to 25-fold by the addition of an exogenous polymer acceptor. Molecules composed of ~500 to 3,000 sugar residues were produced in vitro. The polysaccharide was sensitive to the action of heparin lyase III but resistant to hyaluronan lyase. The sequence of pmHS enzyme is not very similar to the vertebrate heparin/heparan sulfate glycosyltransferases, EXT1/2 (SEQ ID NOS: 65/66), or to other *Pasteurella* glycosaminoglycan synthases that produce hyaluronan or chondroitin. Certain motifs do exist however, between the pmHS, pgIA, and KfiA (SEQ ID NO:65) and KfiC (SEQ ID NO:64) thereby leading to deduced amino acid motifs that are conserved throughout this class of GAG synthases for the production of heparin/heparosan. The pmHS and PgIA enzymes are the first microbial dual-action glycosyltransferase to be described that form a polysaccharide composed of $\beta$4GlcUA-$\alpha$4GlcNAc disaccharide repeats. In contrast, heparosan biosynthesis in *E. coli* K5 requires at least two separate polypeptides, KfiA and KfiC, to catalyze the same polymerization reaction.

Glycosaminoglycans [GAGs] are long linear polysaccharides consisting of disaccharide repeats that contain an amino sugar. Heparin/heparan [$\beta$4GlcUA-$\alpha$4GlcNAc]$_n$, chondroitin [$\beta$4GlcUA-$\beta$3GalNAc]$_n$, and hyaluronan [$\beta$4GlcUA-$\beta$3GlcNAc]$_n$ are three prevalent GAGs and the only known acidic GAGs. In the former two polymers, usually n=20 to 100 while in the case of HA, typically n=103-4. In vertebrates, one or more modifications including O-sulfation of certain hydroxyls, deacetylation and subsequent N-sulfation, or epimerization of glucuronic acid to iduronic acid are found in most GAGs except HA.

The invasiveness and pathogenicity of certain *Escherichia coli* strains has been attributed to their polysaccharide capsule. Two *E. coli* capsular types, K5 and K4, make polymers composed of GAG-like polymers. The K5 capsular material is a polysaccharide called heparosan, N-acetylheparosan, or desulfoheparin, which are identical to mammalian heparin/heparin sulfate except that the bacterial polymer is unsulfated and there is no epimerization of GlcUA to iduronic acid. The *E. coli* K4 polymer is an unsulfated chondroitin backbone decorated with fructose side-branches on the C3 position of the GlcUA residues.

The *E. coli* K5 capsule biosynthesis locus contains the open reading frames KfiA-D (also called Kfa in some reports; GenBank Accession Number X77617). At first, KfiC was stated to be a dual-action glycosyltransferase responsible for the alternating addition of both GlcUA and GlcNAc to the heparosan chain. However, a later report by the same group reported that another protein, KfiA, was actually the $\alpha$GlcNAc-transferase required for Heparosan polymerization. Therefore, at least these two enzymes, KfiA and KfiC, the $\beta$GlcUA-transferase, work in concert to form the disaccharide repeat and the first report, that KfiC was a dual-action enzyme, was in error. Another deduced protein in the operon, KfiB, was suggested to stabilize the enzymatic complex during elongation in vivo, but perhaps not participate directly in catalysis. The identity and the sequence of the *E coli* K4 capsular glycosyltransferase(s) has recently been reported.

This enzyme, KfoC, is approximately 60% identical to the *Pasteurella* chondroitin synthase (pmCS) (and hybridized to pmCS under standard straingency hybridization conditions) and is also a dual-action enzyme.

Many *P. multocida* isolates produce GAG or GAG-like molecules as assessed by enzymatic degradation and removal of the capsule of living bacterial cells. Carter Type A *P. multocida*, the major causative agent of fowl cholera and pasteurellosis, makes an HA capsule. A single polypeptide, the HA synthase, pmHAS, polymerizes the HA chain by transferring both GlcUA and GlcNAc. Type F *P. multocida*, the minor fowl cholera pathogen, produces a capsule composed of an unsulfated chondroitin sensitive to *Flavobacterium* chondroitin AC lyase. Again, a dual-action chondroitin synthase, pmCS, polymerizes the chondroitin chain. The capsule of another distinct *P. multocida*, Type D, was reported to be sensitive to heparin lyase III which thereby led to the presently claimed and disclosed invention—the identification and characterization of pmHS(*P. multocida* heparin/heparosan synthase) and PglA, the first and only known bacterial dual-action heparosan synthases.

Prior to recombinantly obtaining the pmHS gene and heterologously expressing it in a recombinant system, activity assays of *P. multocida* Type D enzymes were completed. Native membranes were prepared from a wild-type encapsulated Type D strain (P-3881; DeAngelis et al., 1996, the entirety of which is expressly incorporated herein in its entirety). The membranes were tested for in vitro sugar incorporation monitored by paper chromatography analysis. Characterization of the ability to co-polymerize the two sugars and utilize metal ions was performed. First, detection of co-polymerization activity of the Type D *P. multocida* strain was determined in vitro. The membranes+UDP-[$^{14}$C]GlcUA (300 pM; $1.5\times10^5$ dpm)+various combinations of the 2$^{nd}$ sugar (UDP-GlcNAc, 900 μM) and/or EDTA chelator (45 mM) were mixed in 50 mM Tris, pH 7.2 with 20 mM $MnCl_2$ and 20 mM $MgCl_2$ reaction buffer. All reactions were performed at 30 degrees Celsius for 2.5 hours. The incorporation was measured by paper chromatography as disclosed in DeAngelis et al., 1996. The results of this co-polymerization activity are summarized in Table XX.

TABLE XX

| UDP-GlcNAc Added? | EDTA Added? | Incorporation (dpm) |
|---|---|---|
| No | No | 520 |
| Yes | No | 9150 |
| No | Yes | 35 |
| Yes | Yes | 160 |

Thus, it is apparent that the Type D *P. multocida* strain P-3881 has a metal-dependent enzyme that copolymerized both heparin precursors into a polymer.

Second, the metal requirement of the Type D *P. multocida* HS activity was tested in vitro. Membranes+UDP-[$^{14}$C]GlcUA+UDP-GlcNAc and buffer without the metals were mixed in a similar fashion as the preceding experiment except that various metals or EDTA (20 mM) were added as noted in Table XXI. The results of this metal specificity are summarized in Table XXI.

TABLE XXI

| Metal | dpm |
|---|---|
| None | 13 |
| Mg | 2960 |
| Mn | 3070 |
| Mn + Mg | 3000 |
| Co | 120 |

Thus, it is apparent that the Type D *P. multocida* HS requires either manganese or magnesium ion for enzymatic activity.

Further, the sugar specificity of the Type D *P. multocida* strain was determined in vitr in similar experiments. The ability to co-polymerize the sugars that compose the authentic backbone was tested by performing two parallel reactions:

UDP-[$^{14}$C]GlcUA+various combinations of 2$^{nd}$ UDP-sugars.

UDP-[$^{3}$H]GlcNAc+various combinations of 2$^{nd}$ UDP-sugars

The results of these experiments are summarized in Table XXII. Significant $^{14}$C-GlcUA incorporation required UDP-GlcNAc and, conversely, significant $^{3}$H-GlcNAc incorporation required UDP-GlcUA; the enzyme copolymerizes the polysaccharide chain with both authentic heparin UDP-sugar precursors.

TABLE XXII

| A. Hexosamine-transfer | |
|---|---|
| 2$^{nd}$ Sugar Added | $^{14}$C dpm incorporation |
| None | 330 |
| UDP-GlcNAc | 2290 |
| UDP-GalNAc | 2790 |
| UDP-Glc | 450 |
| B. Uronic Acid Transfer | |
| 2$^{nd}$ Sugar Added | $^{3}$H dpm incorporation |
| None | 170 |
| UDP-GlcUA | 1000 |
| UDP-GalUA | 290 |
| UDP-Glc | 185 |

It should be added that the above-described results show that the native Type D *P. multocida* membrane enzymes have relaxed hexosamine transfer specificity in vitro. Such relaxed hexosamine transfer specificity is an advantage for syntheses where the UDP-sugar supplied can be manipulated. In such a manner, novel and non-naturally occurring polymers can be created. These novel, non-naturally occurring polymers have significant utility and novel biological properties.

Experimental Procedures for Isolating HS Genes and Testing Function

Materials and *Pasteurella* Strains—Unless otherwise noted, all chemicals were from Sigma or Fisher, and all molecular biology reagents were from Promega. The wild-type encapsulated Type D *P. multocida* isolates, P-934 (swine), P-3881 (bovine), P-4058 (rabbit), and P-5695 (swine), were obtained from the USDA collection (Ames, Iowa). The strains were grown in brain heart infusion (Difco) at 37° C.

Analysis of Genomic DNA and Isolation of Capsule Biosynthesis Locus DNA—Preliminary data from Southern blot analysis using pmHAS-based hybridization probes (12) suggested that the Type A synthase and the putative Type D synthase were not very similar at the DNA level. However, PCR suggested that the UDP-glucose dehydrogenase genes, which encode an enzyme that produces the UDP-GlcUA precursor required for both HA and heparin biosynthesis, were very homologous. In most encapsulated bacteria, the precursor-forming enzymes and the transferases are located in the same operon. To make a hybridization probe predicted to detect the capsule locus, Type D chromosomal DNA served as a template in PCR reactions utilizing degenerate oligonucleotide primers (sense: GARTTYBTIMRIGARG-GIAARGCIYTITAYGAY (SEQ ID NO:58); antisense: RCARTAICCICCRTAICCRAAISWXG-GRTTRTTRTARTG (SEQ ID NO:59), where I=inosine; R=A or G; S=C or G; W=A or T; Y=C or T) corresponding to a conserved central region in many known UDP-glucose dehydrogenase genes. The ~0.3-kb amplicon was generated using Taq DNA polymerase (Fisher), gel-purified, and labeled with digoxigenin (High Prime system, Boehringer Mannheim).

A lambda library of Sau3A partially digested P-3881 DNA (~4-9 kb average length insert) was made using the BamHI-cleaved λZap Express™ vector system (Stratagene). The plaque lifts were screened by hybridization (5×SSC, 50° C.; 16 hrs) with the digoxigenin-labeled probe using the manufacturer guidelines for colorimetric development. E. coli XLI-Blue MRF' was co-infected with the purified, individual positive lambda clones and ExAssist helper phage to yield phagemids. The resulting phagemids were transfected into E. coli XLOLR cells to recover the plasmids. Sequence analysis of the plasmids using a variety of custom primers as well as the GPS-1 Genome Priming System (New England Biolabs) revealed a novel open reading frame, which we called pmHS (DNA sequence facilities at Oklahoma State University and University of Oklahoma HSC). We amplified and sequenced the ORF from several highly encapsulated isolates (see hereinbelow); very similar sequences were obtained.

Expression of Recombinant P. multocida Heparosan Synthase—The pmHS ORF (617 amino acids) was amplified from the various Type D genomic DNA template by 18 cycles of PCR with Taq polymerase. For constructing the full-length enzyme, the sense primer (ATGAGCTTATTTAAACGTGC-TACTGAGC—SEQ ID NO:58) corresponded to the sequence at the deduced amino terminus of the ORF and the antisense primer (TTTACTCGTTATAAAAAGATAAACACGGAATAAG—SEQ ID NO:59) encoded the carboxyl terminus including the stop codon. In addition, a truncated version of pmHS was produced by PCR with the same sense primer but a different antisense primer (TATATTTACAGCAGTATCATTTTCTAAAGG—SEQ ID NO:60) to yield a predicted 501-residue protein, DcbF (SEQ ID NO:61) (GenBank Accession Number AAK17905); this variant corresponds to residues 1-497 of pmHS followed by the residues TFRK.

The amplicons were cloned using the pETBlue-1 Acceptor system (Novagen) according to the manufacturer's instructions. The Taq-generated single A overhang is used to facilitate the cloning of the open reading frame downstream of the T7 promoter and the ribosome binding site of the vector. The ligated products were transformed into *E. coli* NovaBlue and plated on LB carbenicillin (50 μg/ml) and tetracycline (13 μg/ml) under conditions for blue/white screening. White colonies were analyzed by PCR-based screening and by restriction digestion. Plasmids with the desired ORF were transformed into *E. coli* Tuner, the T7 RNA polymerase-containing expression host, and maintained on LB media with carbenicillin and chloramphenicol (34 μg/ml) at 30° C. Mid-log phase cultures were induced with P-isopropylthiogalactoside (0.2 mM final) for 5 hrs. The cells were harvested by centrifugation, frozen, and membranes were prepared according to a cold lysozyme/sonication method except 0.1 mM mercaptoethanol was included during the sonication steps. Membrane pellets were suspended in 50 mM Tris, pH 7.2, 0.1 mM EDTA and protease inhibitors.

Assays for Heparosan Synthase Activity—Incorporation of radiolabeled monosaccharides from UDP-[$^{14}$C]GlcUA and/or UDP-[$^{3}$H]GlcNAc precursors (NEN) was used to monitor heparosan synthase activity. Samples were assayed in a buffer containing 50 mM Tris, pH 7.2, 10 mM $MgCl_2$, 10 mM $MnCl_2$, 0-0.6 mM UDP-GlcUA, and 0-0.6 mM UDP-GlcNAc at 30° C. Depending on the experiment, a Type D acceptor polymer processed by extended ultrasonication of a capsular polysaccharide preparation (isolated by cetylpyridinium chloride precipitation of the spent Type D culture media) was also added to the reaction mixture. The reaction products were separated from substrates by descending paper (Whatman 3M) chromatography with ethanol/1 M ammonium acetate, pH 5.5, development solvent (65:35). The origin of the paper strip was cut out, eluted with water, and the incorporation of radioactive sugars into polymer was detected by liquid scintillation counting with BioSafe II cocktail (RPI).

The metal preference of pmHS was assessed by comparing the signal from a "no metal" control reaction (0.5 mM EDTA) to reactions containing 10 to 20 mM manganese, magnesium, or cobalt chloride. To test the transfer specificity of pmHS, various UDP-sugars (UDP-GalNAc, UDPGalUA, or UDP-Glc) were substituted for the authentic heparosan precursors. The data from the recombinant construct containing pmHS gene from the P-4058 strain is presented, but the results were similar to constructs derived from the P-934 or P-5695 strains.

Size Analysis and Enzymatic Degradation of Labeled Polymers—Gel filtration chromatography was used to analyze the size distribution of the labeled polymers. Separations were performed with a Polysep-GFC-P 4000 column (300×7.8 mm; Phenomenex) eluted with 0.2 M sodium nitrate at 0.6 ml/min. Radioactivity was monitored with an in-line Radioflow LB508 detector (EG & G Berthold; 500 μl flow cell) using Unisafe I cocktail (1.8 ml/min; Zinsser). The column was standardized with fluorescein-labeled dextrans of various sizes. To further characterize the radiolabeled polymers, depolymerization tests with specific glycosidases was performed. The high molecular weight product was purified by paper chromatography. The origin of the strips was washed with 80% ethanol, air-dried, then extracted with water. The water extract was lyophilized, resuspended in a small volume of water and split into three aliquots. Two aliquots were treated with glycolytic enzymes for 2 days at 37° C. (*Flavobacterium* heparin lyase III, 6.7 mU/il, 50 mM sodium phosphate, pH 7.6, or *Streptomyces* HA lyase, 333 milliunits/il, 50 mM sodium acetate, pH 5.8). The last aliquot was mock-treated without enzyme in acetate buffer. The aliquots were quenched with SDS, subjected to paper chromatography, and the radiolabel at the origin was measured by liquid scintillation counting.

Results

Molecular Cloning of the Type D *P. multocida* Heparosan Synthase—A PCR product which contained a portion of the Type D UDP-glucose dehydrogenase gene was used as a hybridization probe to obtain the rest of the Type D *P. multocida* capsular locus from a lambda library. We found a functional heparosan synthase, which we named pmHS, in several distinct Type D strains from different host organisms isolated around the world (i.e. A2 clone SEQ ID NOS:5 and 6; bioclone SEQ ID NOS:69 and 70). In every case, an open reading frame of 617 residues with very similar amino acid sequence (98-99% identical) was obtained. In the latter stages of our experiments, another group deposited a sequence from the capsular locus of a Type D organism in GenBank [15]. In their annotation, the carboxyl terminus of the pmHS homolog is truncated and mutated to form a 501-residue protein that was called DcbF (GenBank Accession Number AAK17905) (SEQ ID NOS:61 and 62). No functional role for the protein except "glycosyltransferase" was described and no activity experiments were performed. As described herein, membranes or cell lysates prepared from *E coli* with the recombinant dcbF gene do not possess heparosan synthase activity. The gene annotated as DcbF (SEQ ID NO:62) is truncated at the carboxyl terminus in comparison to the presently claimed and described *P. multocida* HS clones. The truncated (T) or the full-length (FL) open reading frames of DcbF were cloned into the expression system pETBlue-1 vector, as described hereinabove. Membranes isolated from the same host strain, *E. coli* Tuner with the various recombinant plasmids were tested in HS assays with both radiolabeled UDP-sugars. The results of these experiments are summarized in Table XXIII.

TABLE XXIII

| Clone | [14C]GlcUA Incorp. (dpm) | [3H]GlcNAc Incorp. (dpm) |
|---|---|---|
| Negative Control | 160 | 40 |
| B1(FL) | 710(*) | 1040(*) |
| 012(T) | 40 | 265 |
| 013(T) | 70 | 1610 |
| 019(T) | 55 | 1105 |
| N2(T) | 70 | 1910 |
| N4(T) | 70 | 880 |
| N5(T) | 80 | 650 |

Five-fold less FL enzyme than T enzymes were tested in these parallel assays. At most, only a single GlcNAc sugar is added to the exogenously supplied acceptor in the truncated enzymes (T). Full-length HS from Type D *P. multocida*, however, adds both sugars (*) to the nascent chain. Thus, the previously annotated and deposited DcbF gene is not a functional heparosan synthase.

Another deduced gene was recently uncovered by the University of Minnesota in their Type A *P. multocida* genome project, called PgIA (GenBank Accession Number AAK02498), encoding 651 amino acids that are similar to pmHS (73% identical in the major overlapping region). However, the PgIA gene (SEQ ID NO:7) is not located in the putative capsule locus. This group made no annotation of the function of PgIA. Our studies show that this PgIA protein (SEQ ID NO:8) also polymerizes GlcUA and GlcNAc residues to form heparosan. We also found that a Type D strain and a Type F strain also appear to contain a homologous PgIA gene as shown by PCR and activity analysis.

As mentioned before, during the pmHS cloning project in the present Applicant(s)' laboratory, investigators at the Univ. of Minnesota published the complete genome of a *Pasteurella multocida* isolate. The fragments of the presently claimed and disclosed pmHS gene were utilized as the query in a BLAST search against this *P. multocida* genome. A gene annotated as pgla, but with no ascribed, predicted or demonstrated function was found to be very similar to the pmHS gene. The pglA gene is not in the main capsule locus found by either the DeAngelis or the Adler groups. The pglA open reading frame was obtained from two different encapsulated strains: Type A (P-1059 from a turkey—this strain is not the same as the Univ. of Minnesota strain—clones denoted as "A") and Type D (P-3881 from a cow—clones denoted as "D"). The pglA gene was amplified from chromosomal templates prepared by method of Pitcher et al (*Letters in Applied Microbiology,* 1989 which is expressly incorporated herein by reference in its entirety). PCR with Taq polymerase (18 cycles) using custom flanking oligonucleotide primers that correspond to the region of the start codon and the stop codon of pglA. An appropriate size amplicon corresponding to the pglA gene was found in both Type A and D strains; this result was rather unexpected if one considers that the capsular compositions are HA and N-acetylheparosan polysaccharides, for Type A and Type D strains, respectively. The resulting ~1.9 kilobase PCR amplicons were ligated into an expression vector, pET-Blue-1 (Novagen), transformed into the cloning host, *E coli* Novablue (Novagen), and selected on LB carbenicillin and tetracycline plates at 30° C. The colonies were screened for the presence of insert in the proper orientation by PCR with a combination of vector and insert primers. Clones were streak isolated, small cultures were grown, and preparations of the plasmid DNA were made. The plasmids were transformed into the expression host, *E. coli* Tuner (Novagen), and selected on LB with carbenicillin and chloramphenicol.

After streak isolation, small cultures were grown at 30° C. as the starting inoculum (1:100) for larger cultures (50 ml) for protein expression and activity assay. These cultures were grown in the same LB supplemented with 1% casein amino acids and trace element solution with vigorous shaking (250 rpm) at 30° C. The cells were grown to mid-logarithmic phase (2.5 hours), induced with 0.5 mm IPTG, and grown for 4.5 hours. Cells were collected by centrifugation and frozen at −80° C. overnight. The membrane preparations were isolated by cold lysozyme/ultrasonication method of DeAngelis et. al (*J. Biol. Chem.,* 1998; pmHAS isolation the contents of which are expressly incorporated herein in their entirety) except that 0.1 mM mercaptoethanol was used as the reducing agent. The membranes were assayed for radioactive sugar incorporation and descending paper chromatography (according to the methodology of DeAngelis and Padget-McCue, *J. Biol. Chem.,* 2000, the contents of which are expressly incorporated herein in their entirety).

In general, a mixture with membranes, 50 mM Tris, pH 7.2, 10 mM $MgCl_2$, 10 mM $MnCl_2$, 0.4 mM UDP-[$^3$H]GlcNAc, 0.2 mM UDP-[$^{14}$C]GlcUA, and heparin oligosaccharide acceptor (2 μg uronic acid) were incubated at 30° C. for 2.5 hours before analysis by paper chromatography. As expected for a polysaccharide synthase, both sugars were incorporated into polymer (Table XXIV). Negative controls using membranes from a plasmid with an irrelevant control insert did not show incorporation. Therefore, PglA is a dual-action synthase capable of sugar biosynthesis as shown by functional expression of activity of one recombinant gene in a foreign host that normally does not make GlcUA/GlcNAc polymers. The relaxed specificity of UDP-sugar incorporation of PglA should be of use for the design and production of new polymers with altered characteristics.

TABLE XXIV

In vitro incorporation of sugar by membranes containing recombinant pglA.

| CLONE | [$^3$H]GlcNAc (dpm) | [$^{14}$C]GlcUA (dpm) |
|---|---|---|
| PglA-A2 | 50,400 | 54,900 |
| PglA-A4 | 39,100 | 41,000 |
| PglA-D4 | 32,500 | 34,200 |
| PglA-D7 | 44,800 | 46,600 |

The typical background for negative controls is less than 200 dpm incorporation. Type A and Type D isolates have the PgIA, a synthase that incorporates both GlcUA and GlcNAc sugars. (A=Type A; D=Type D; #=independent clone number).

Table XXV shows PgIA Sugar Specificity test results. The experiments summarized in Table XXV are similar to the experiments summarized in Table XXIV (with less enzyme) except that other UDP-sugars that are not normally found in heparin or heparosan were also tested (note ~60 minute incubation times, 50 µl reactions). The Type A and the Type D enzymes behave in a similar fashion with relaxed sugar specificity in this test. The PgIA system can add a glucose instead of a GlcNAc sugar. The ability to co-polymerize the sugars that compose the authentic heparin backbone were tested by performing two parallel reactions:

UDP-[$^{14}$C]GlcUA+various combinations of $2^{nd}$ UDP-sugars.

UDP-[$^3$H]GlcNAc+various combinations of $2^{nd}$ UDP-sugars.

TABLE XXV $2^{nd}$ Sugar

Panel I. Type A PgIA-A2

[$^3$H]GlcNAc Incorporated into Polymer (dpm)

| | |
|---|---|
| none | 450 |
| UDP-GlcUA | 12,900 |
| UDP-GalUA | 400 |
| UDP-Glc | 430 |

[$^{14}$C]GlcUA Incorporated into Polymer (dpm)

| | |
|---|---|
| none | 60 |
| UDP-GlcNAc | 7,700 |
| UDP-GalNAc | 60 |
| UDP-Glc | 985 |

Panel II. Type D PgIA-D7

[$^3$H]GlcNAc Incorporated into Polymer (dpm)

| | |
|---|---|
| None | 570 |
| UDP-GlcUA | 13,500 |
| UDP-GalUA | 530 |
| UDP-Glc | 500 |

[$^{14}$C]GlcUA Incorporated into Polymer (dpm)

| | |
|---|---|
| None | 60 |
| UDP-GlcNAc | 6,500 |
| UDP-GalNAc | 40 |
| UDP-Glc | 660 |

TABLE XXVI

Acceptor Usage of PgIA from Types A and D
The Type A and the Type D clones were tested for stimulation by addition of the Type D polysaccharide acceptor (described hereinbefore with respect to pmHS). Weaker stimulation of activity by acceptor on PgIA was observed in comparison to pmHS (comparison is not shown here).
[$^{14}$C-GlcUA] incorporation

| Clone | Acceptor | NO Acceptor |
|---|---|---|
| A2 | 1560 | 1210 |
| D7 | 1240 | 1080 |

*P. multocida* Type F-derived recombinant pgIA is thus also a heparosan synthase. As shown in the following Table XXVII, the Type F PgIA can incorporate the authentic heparin sugars.

TABLE XXVII

Activity of pgIA from Type F

| Membranes | Acceptor | $^3$H-GlcNAc (dpm) | $^{14}$C-GlcUA (dpm) |
|---|---|---|---|
| Blank | 0 | 8 | 8 |
| PgIA F 3 | + | 7100 | 3100 |
| PgIA F 4 | 0 | 6100 | 3800 |
| PgIA F 4 | + | 11000 | 6400 |
| PgIA F 18 | 0 | 20000 | 10000 |
| PgIA F 18 | + | 23000 | 12000 |
| PgIA D 7 | 0 | 36000 | 17000 |

The pgIA homolog of *P. multocida* Type F strain P-4218 was amplified with flanking primers as described for the Type A and D strains. The ORF was subcloned into the pETBlue-1 system in *E coli* Tuner cells for use as a source of membrane preparations as described. Three independent clones (F 3,4, 18) were assayed under standard HS assay measuring radiolabeled sugar incorporation with paper chromatography. A negative control, membranes from "Blank" vector and a positive control, the Type D pgIA clone D7, were tested in parallel. Reactions plus/minus the Type D polymer acceptor were assayed.

Figure 19:
FIG. 19 graphically depicts Sequence Similarity of pmHS with KfiA and KfiC. Elements of the *Pasteurella* heparosan synthase, HS1 (containing residues 91-240) and HS2 (containing residues 441-540) are very similar to portions of two proteins from the *E coli* K5 capsular locus (A, residues 75-172 of KfiA; C, residues 262-410 of KfiC) as shown by this modified Multalin alignment (ref. 21; numbering scheme corresponds to the pmHS sequence). The HS1 and HS2 elements may be important for hexosamine transferase or for glucuronic acid transferase activities, respectively. (con, consensus symbols: asterisks, [K or R] and [S or T]; %, any one of F,Y,W; $, any one of L,M; !, any one of I,V; #, any one of E,D,Q,N).
Figure 20:
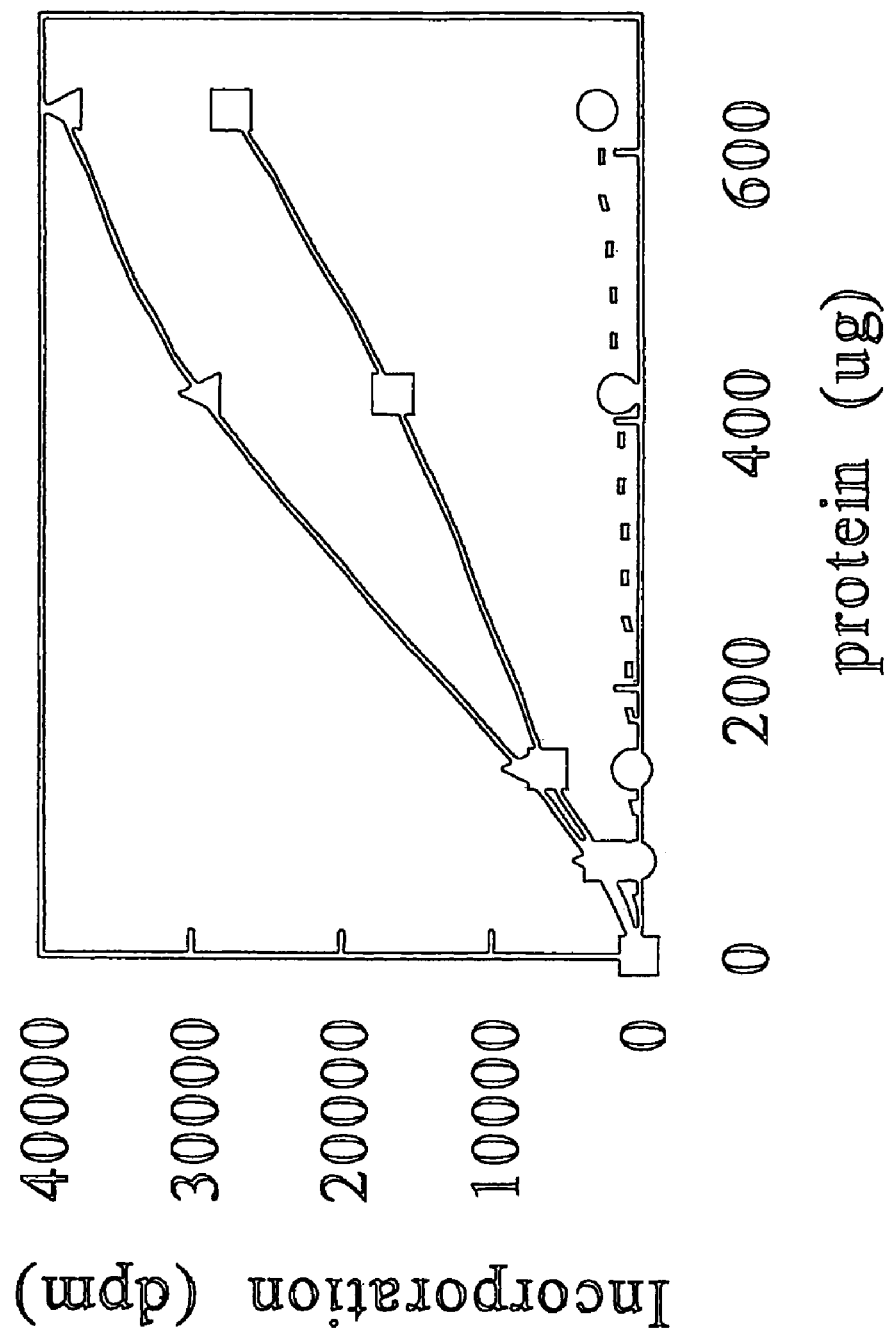
FIG. 20 depicts pmHS Activity Dependence on Acceptor and Enzyme Concentration. Various amounts of crude membranes containing the full-length enzyme, pmHS1-617, were incubated in 50 □l of buffer containing 50 mM Tris, pH 7.2, 10 mM MgCl$_2$, 10 mM MnCl$_2$, 500 □M UDP-[$^{14}$C]GlcUA (0.15 □Ci), and 500 □M UDP-GlcNAc. Three parallel sets of reactions were performed with either no acceptor (circles) or two concentrations of heparosan polymer acceptor (uronic acid: 0.6 □g, squares; 1.7 □g, triangles). After 40 min, the reaction was terminated and analyzed by paper chromatography. The background incorporation due to vector membranes alone (630 □g total protein; not plotted) with the high concentration of acceptor was 75 dpm [$^{14}$C]GlcUA. The activity of pmHS is greatly stimulated by exogenous acceptor.
Figure 22A:
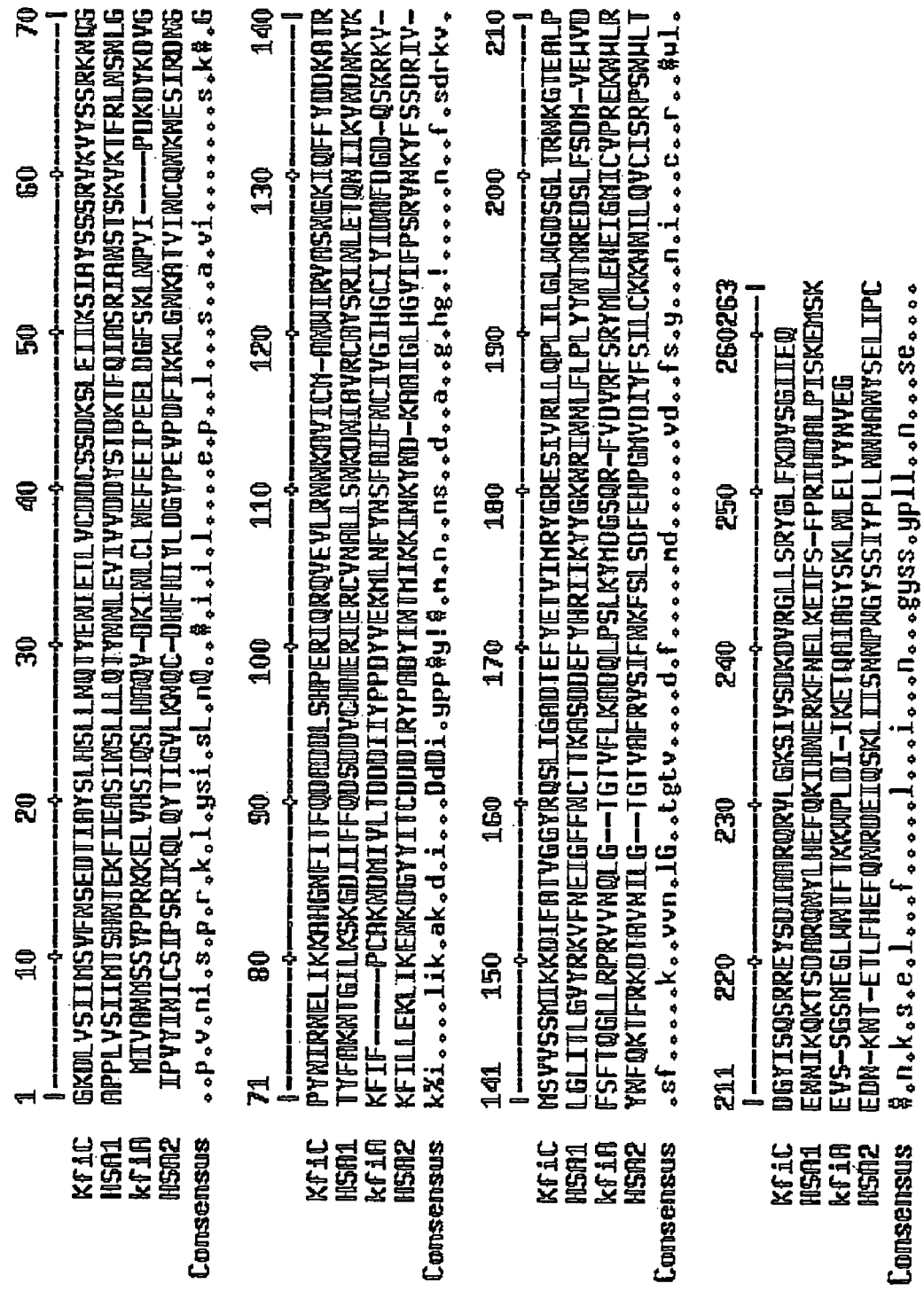
FIG. 22(A-D) graphically depicts the alignment of the pmHS (two clones: A2, B10) with PglA, KfiA, KfiC, and DcbF. pmHS is shown in various forms: HSA1 and HSA2 are the two putative domains of pmHS; pORF=partial open reading frame which was obtained before complete sequence determined; recon=reconstructed open reading frame with sequence from multiple sources.

The next best heterologous matches for the pmHS enzyme in the Genbank database are KfiA and KfiC proteins from *E coli* K5; these two proteins work together to make the heparosan polymer. There is a good overall alignment of the enzyme sequences if smaller portions of pmHS ORF are aligned separately with KfiA (pmHS2, SEQ ID NO:63) and KfiC (pmHS1, SEQ ID NO:64) (FIG. 19). The MULTALIN alignment program (Corpet, 1988) identified regions that were very similar. Some of the most notable sequence similarities occur in the regions containing variants of the DxD amino acid sequence motif. Indeed, the first 1-360 residues of pmHS1 align with an approximate 38% identity to the *E. coli* KfiC, a single action GlcUA-transferase, while the 361-617 residues of pmHS2 align with an approximate 31% identity to the *E coli* KfiA, a GlcNAc-transferase. Thus, the pmHS is a naturally occurring fusion of two different glycosyltransferase domains. The pmHS is a dual action enzyme that alone makes heparin/heparosan polymers because both sugar transferase sites exist in one polypeptide enzyme.

Heterologous Expression of a Functional *P. multocida* Heparosan Synthase Membrane extracts derived from *E. coli* Tuner cells containing the plasmid encoding pmHS, but not samples from cells with the vector alone, synthesized polymer in vitro when supplied with both UDP-GlcUA and UDP-GlcNAc simultaneously. The identity of the polymer as heparosan was verified by its sensitivity to *Flavobacterium* heparin lyase III (~97% destroyed after treatment) and its resistance to the action of *Streptomyces* HA lyase. No substantial incorporation of radiolabeled [$^{14}$C]GlcUA into polymer was observed if UDP-GlcNAc was omitted, or if UDP-GalNAc was substituted for UDP-GlcNAc. Conversely, in experiments using UDP-[$^{3}$H]GlcNAc, substantial incorporation of radiolabel into polymer was only noted when UDP-GlcUA was also present. UDP-GalUA or UDP-Glc did not substitute for UDP-GlcUA. No polymerization or transferase activity was detected if the divalent metal ions were chelated with EDTA. Maximal activity was observed in reactions that contained Mn ion, but Mg also supported substantial incorporation (65%-85% maximal). Cobalt was a poorer cofactor (~30% maximal). The addition of the heparosan polymer acceptor increased sugar incorporation catalyzed by pmHS at least 7- to 25-fold in comparison to parallel reactions without acceptor (FIG. 20) in analogy to observations of pmHAS and pmCS. The acceptor stimulation of activity is due to the lower efficiency or slower rate of initiation of a new polymer chain in comparison to the elongation stage in vitro. The exogenous acceptor sugar associates with the recombinant enzyme's binding site for the nascent chain and then is elongated rapidly.

Analysis by gel filtration chromatography indicated that recombinant pmHS produced long polymer chains (~1-3× 103 monosaccharides or ~200-600 kDa) in vitro without acceptor (FIG. 21). If acceptor polymer was supplied to parallel reaction mixtures, then higher levels of shorter chains (~0.1-2×103 monosaccharides or ~20-400 kDa added to acceptor) were more rapidly produced. Radioactivity from both labeled GlcUA and GlcNAc sugars co-migrated as a single peak in all chromatography profiles. Some chains also appear to be initiated de novo in reactions with acceptor as evidenced by the small peak of higher molecular weight material near the void volume. Apparently, once pmHS either starts a new chain or binds an existing chain, then rapid elongation is performed.

We found in parallel tests that membranes or lysates prepared from recombinant cells containing the predicted Dcb gene (SEQ ID NO:62), a truncated version of pmHS, in the same expression vector, do not exhibit heparosan synthase activity. Even with large amounts of total protein, repeated polymerization was not observed and no significant radiolabel incorporation above background levels was noted.

We have molecularly cloned a dual-action glycosyltransferase responsible for polymerizing the heparosan backbone component of the Type D *P. multocida* capsular polysaccharide. As discussed earlier, the first 497 residues of the pmHS protein are virtually identical to the hypothetical DcbF sequence. We have sequenced the DNA from the equivalent P-934 isolate obtained from the same USDA collection as reported, as well as several other Type D strains, but our results do not agree with the dcbF open reading frame. The Adler group appears to have made a sequencing error that resulted in a frame-shift mutation; a conceptual premature termination led to the creation of the erroneously truncated dcbF annotation. Recently, we have determined that the *Pasteurella* hyaluronan synthase, pmHAS, contains two active sites in a single polypeptide by generating mutants that transfer only GlcUA or only GlcNAc. Interestingly, mixing the two different mutant pmHAS proteins reconstituted the HA synthase activity. We hypothesized that one domain, called A1, is responsible for GlcNAc transfer and the other domain, called A2, is responsible for GlcUA transfer. The chondroitin synthase, pmCS, transfers a different hexosamine, GalNAc, and also appears to contain a similar two-domain structure[14]. The amino acid sequence of the heparosan synthase, pmHS, however, is very different from other *Pasteurella* GAG synthases, pmHAS and pmCS. The pmHAS and pmHS enzymes both perform the task of polymerizing the identical monosaccharides; HA and heparin only differ with respect to their linkages. The creation of different anomeric linkages probably requires very distinct active sites due to the disparity between a retaining (to form α-linkages) and an inverting (to form β-linkages) transfer mechanism. The putative dual-action vertebrate heparin synthases, EXT1 (SEQ ID NO:65) and EXT 2 (SEQ ID NO:66), also appear to have two transferase domains, but the amino acid sequences are not similar to pmHS. Thus, by aligning pglA, pmHS (B10 and A2 clones), KfiA, or KfiC, deduced amino acid sequence motifs have been identified. Such motifs are listed below and the alignment is shown in FIG. 22A-D.

Two distinct regions of pmHS (pmHS1 and pmHS2) are similar to the *E. coli* K5 KfiA or KfiC proteins suggesting the limits of the sugar transfer domains (FIG. 19). On the basis of sequence similarity, if the Kfi studies are correct, then GlcUA transfer and GlcNAc transfer occur at the amino and carboxyl portions of pmHS, respectively. The pmHS protein may be the result of the fusion of two ancestral single-action enzymes. The efficiency and convenience of combining the two required enzyme activities into a single polypeptide seems clear, but as a counterexample, the *E. coli* KfiA and KfiC proteins remain separate entities. Interestingly, pglA, a gene with no reported function from a Type A isolate is (~70%) similar to the pmHS gene of a Type D strain. In parallel expression experiments, PglA from Type A or D or F strains also appear to be heparosan synthases, as shown hereinabove. It is quite puzzling that the Type A strain would have a heparosan synthase as well as the known HA synthase. The major Type A capsular polymer was shown to be HA, but in retrospect, a small amount of heparosan would be difficult or impossible to detect in these characterization studies. A possible scenario for the presence of a heparosan synthase in the Type A bacteria is that the pglA gene is repressed or silent and not expressed in this host under laboratory conditions. The pglA gene could also be a cryptic remnant from an ancestral organism (i.e., before Types A and D and F diverged) that has been maintained and the gene product is still functional. Another interesting possibility is that in Type A organisms either the pmHAS or the pglA gene is utilized at different times depending on conditions or stage of infection; using different capsular polymers could serve as a phase-shift mechanism.

Comparisons of the two known sets of heparin/heparosan biosynthesis enzymes from the *E. coli* K5 Kfi locus, the PglA enzyme, and the pmHS from Type D capsular locus, allows for the initial assessment and bioinformatic prediction of new enzymes based on the amino acid sequence data. The closer the match (% identity) in a single polypeptide for the two sequence motifs described hereinafter (corresponding to the critical elements of the GlcUA-transferase and the GlcNAc-transferase), the higher the probability that the query enzyme is a new heparin/heparosan synthase (a single dual-action enzyme). The closer the match (% identity) in two polypeptides (especially if encoded in the same operon or transcriptional unit) for the two sequence motifs, the higher the probability that the query enzymes are a pair of single-action glycosyltransferases. Thus, one of ordinary skill in the art would appreciate that given the following motifs, one would be able to ascertain and ascribe a probable heparin synthase function to a newly discovered enzyme and then test this ascribed function in a manner to confirm the enzymatic activity. Thus, single dual-action enzymes possessing enzymatic activity to produce heparin/heparosan and having at least one of the two disclosed motifs are contemplated as being encompassed by the presently claimed and disclosed invention.

Motif I: (SEQ ID NO:67)

$QTYXN(L/I)EX_4DDX(S/T)(S/T)D(K/N)(T/S)X_6IAX(S/T)(S/T)(S/T)(K/R)V(K/R)X_6NXGXYX_{16}FQDXDDX(C/S)H(H/P)ERIXR$

Motif II: (SEQ ID NO:68)

$(K/R)DXGKFIX_{12-17}DDDI(R/I)YPXDYX_3MX_{40-50}VNXLGTGTV$

Motif I corresponds to the GlcUA transferase portion of the enzyme, while Motif II corresponds to the GlcNAc transferase portion of the enzyme. With respect to the motifs: X=any residue; parentheses enclose a subset of potential residues [separated by a slash] that may be at a particular position (e.g.,—(K/R) indicates that either K or R may be found at the position—i.e. there are semiconserved residues at that position.

The consensus X spacing is shown with the number of residues in subscript (e.g., $X_{12-17}$), but there are weaker constraints on these particular residues, thus spacing may be longer or shorter. Conserved residues may be slightly different in a few places especially if a chemically similar amino acid is substituted (e.g., K for a R, or E for a D). Overall, at the 90% match level, the confidence in this predictive method is very high, but even a 70-50% match level without excessive gap introduction (e.g., altered spacing between conserved residues) or rearrangements (miss-positioning with respect to order of appearance in the amino to carboxyl direction) would also be considered to be within the scope of these motifs. One of ordinary skill in the art, given the present specification, general knowledge of the art, as well as the extensive literature of sequence similarity and sequence statistics (e.g., the BLAST information website at www.ncbi.nim.mih.gov), would appreciate the ability of a practitioner to identify potential new heparin/heparosan synthases based upon sequence similarity or adherence to the motifs presented herein and thereafter test for functionality by means of heterozologous expression, to name but one example.

Bacteria-derived heparosan may be converted by epimerization and sulfation into a polymer that resembles the mammalian heparin and heparan sulfate because all the modifying enzymes have been identified[3]. In general, sulfation with chemical reagents ($SO_3$, chlorosulfonic acid) or sulfo-transferases (i.e., 2-O-GlcUA-sulfotransferase, etc.) And PAPs precursor is possible. N-sulfation can be done by using either chemical means (hydrazinolysis and subsequent N-sulfation) or enzymatic means with dual function deacetylase/N-sulfotransferase. For creation of iduronic acid, epimerization can be performed enzymatically with heparin epimerase or chemically with super-critical carbon dioxide. The art is replete with articles, methods, and procedures for sulfating and epimerizing heparosan to form heparin. Example, include Leali, et al., Fibroblast Growth Factor-2 Antagonist Activity and Angiostatic Capacity of Sulfated *E. coli* KS Polysaccharide Derivatives, J. Biol. Chem., Vol. 276, No. 41, Oct. 12, 2001, pp. 37900-902; Esko, et al., Molecular Diversity of Heparin Sulfate, J. Clin. Invest. 108: 169-173 (2001); and Crawford, et al., Cloning, Golgi Localization, and Enzyme Activity of the Full-Length Heparin/Heparosan Sulfate-Glucuronic Acid C5-Epimerase, J. Biol. Chem., Vol. 276, No. 24, Jun. 15, 2001, pp. 21530-543, the contents of each being hereby expressly incorporated by reference in their entirety. Thus, given the present specification which discloses and teaches methods for the recombinant production of Heparosan, one of ordinary skill in the art would be capable of producing Heparin therefrom. As such, Heparin obtained through the process of sulfating and epimerizing Heparosan is contemplated as falling within the scope of the presently disclosed and claimed invention.

pmHS or PglA (or an improved recombinant version) may be a more economical and useful sources of heparosan than *E. coli* K5 for several reasons. pmHS and PglA have a higher intrinsic biosynthetic capacity for capsule production. The *Pasteurella* capsule radius often exceeds the cell diameter when observed by light microscopy of India ink-prepared cells. On the other hand, visualization of the meager *E coli* K5 capsule often requires electron microscopy. From a safety standpoint, *E. coli* K5 is a human pathogen, while Type D *Pasteurella* has only been reported to cause disease in animals. Furthermore, with respect to recombinant gene manipulation to create better production hosts, the benefits of handling only a single gene encoding pmHS or PglA, dual action synthases, in comparison to utilizing KfiA and C (and probably KfiB) are obvious. The in vitro properties of pmHS and pglA are also superior; these enzymes can make large chains in vitro either with or without an exogenous acceptor sugar, but KfiA and KfiC do not.

The discovery of pmHS and PglA expands the known GAG biosynthesis repertoire of *P. multocida*. Depending on the Carter capsular type, this widespread species produces HA, heparosan, or chondroitin.

pmHS and PgIA Polymer Grafting and Use of Chimeric or Hybrid or Mutant Transferases.

As mentioned hereinabove, it was first discovered and disclosed that the molecular directionality of pmHAS synthesis was unique in comparison to all other existing HA synthases of *Streptococcus*, bacteria, humans or an algal virus. Specifically, recombinant pmHAS can elongate exogenously supplied functional acceptors (described herein) into longer glycosaminoglycans. The pmHAS synthase adds monosaccharides one at a time in a step-wise fashion to the growing chain. The pmHAS' exquisite sugar transfer specificity results in the repeating sugar backbone of the GAG chain. The pmCS enzyme, which is 90% identical at the amino acid level to pmHAS, performs the same synthesis reactions but incorporates GalNAc instead of GlcNAc. The pmHS and PglA enzymes can also add heparosan chains onto exogenous supplied functional acceptors such as long or short heparosan polymers. The method of action for pmHAS is that pmHAS possesses two independent active sites in one polypeptide.

The *Pasteurella* GAG synthases (pmHAS, pmCS, pmHS and PgIA) are very specific glycosyltransferases with respect to the sugar transfer reaction: usually only the authentic sugar is added onto acceptors. The epimers or closely structurally related molecules (e.g., UDP-glucose) are not utilized. However, these GAG synthases from *Pasteurella* do utilize heterologous acceptor sugars. For example, pmHAS elongates short chondroitin acceptors with HA chains. Additionally, pmHS adds heparosan chains onto HA acceptor oligosaccharides. Thus, a diverse range of hybrid of chimeric or hybrid GAG oligosaccharides can be made with the disclosed GAG synthases (i.e., pmHAS, pmCS, pmHS, and PglA). The chemoenzymatic methodology can be used in either a liquid-phase synthesis of soluble, free sugars or in a solid-phase synthesis to build sugars on surfaces (as disclosed hereinafter).

TABLE XXVIII

Acceptor Sugar Usage of pmHS Test

| | PmHS | | Vector | |
|---|---|---|---|---|
| Acceptor Sugar | $^3$H-GlcNAc (dpm) | $^{14}$C-GlcUA (dpm) | $^3$H-GlcNAc (dpm) | $^{14}$C-GlcUA (dpm) |
| None | 690 | 580 | 55 | 60 |
| Type D (0.38 µg) sonicated | 4400 | 4500 | 80 | 60 |
| Heparin (10 µg) porcine | 570 | 560 | 50 | 65 |
| HA$_4$ (12.5 µg) | 5900 | 6500 | 85 | 65 |
| HA$_4$ (0.5 µg) | 2200 | 2600 | 60 | 75 |
| HA$_{4-10}$ (25 µg) | 7400 | 6900 | 75 | 70 |
| HA$_{4-10}$ (1 µg) | 2300 | 2200 | 120 | 70 |
| HA$_4$ leech (12.5 µg) | 880 | 670 | 45 | 85 |

TABLE XXVIII-continued

Acceptor Sugar Usage of pmHS Test

| Acceptor Sugar | PmHS | | Vector | |
|---|---|---|---|---|
| | $^3$H-GlcNAc (dpm) | $^{14}$C-GlcUA (dpm) | $^3$H-GlcNAc (dpm) | $^{14}$C-GlcUA (dpm) |
| HA$_{8-14}$ leech (25 μg) | 1100 | 1000 | 70 | 90 |
| Hep2 (1 μg) | 1800 | 1700 | 70 | 95 |
| Hep3 (25 μg) | 5800 | 5600 | 55 | 75 |
| Hep3 (1 μg) | 9700 | 10000 | 45 | 90 |

Synthase activity assays (2.5 hours, 30° C.) with subsequent paper chromatography separations and liquid scintillation counting of the origin zone. Typical reaction buffer (Tris & Mn ion; DeAngelis & White 2001) contained both radioactive UDP-GlcNAc and UDP-GlcUA and various acceptor sugars (as noted in table). Unless noted, the HA was from testicular Haase digestions (Leech means leech HAase). Hep2 or Hep2 are synthetic heparosan disaccharide or trisaccharide analogs, respectively (Haller & Boons, 2001). Recombinant E. coli derived membranes from cell with plasmids containing pmHS gene or no insert (vector). With no membranes and no acceptor sugar, the background was 70 and 35 dpm, respectively.

Thus, chimeric or hybrid GAGS can be made using the Pasteurella GAG synthases of the presently claimed and disclosed invention. As shown in Table XXVIII, synthetic di- and tri-saccharides of heparosan, chondroitin and HA can be elongated. Naturally derived HA tetramers can also be elongated. The reducing end is not required to be in a free state (aglycons are not a problem), therefore, the reducing end can serve as the tether site onto a surface, drug, or other synthetic or natural molecule. Exemplary compounds that can be made using the Pasteurella GAGs of the presently claimed and disclosed invention include, but are not limited to:

HA-C CS-HA C-HA HA-HP C-HP
HA-C-HA CS-HA-C C-HA-C HA-C-HP
CS-HA-HP C-HA-HP and so forth, and one of ordinary skill in the art given this specification would appreciate and be able to construct any number of chimeric or hybrid GAG molecules using the Pasteurella GAG synthases disclosed and claimed herein. With respect to the above-referenced chimeric or hybrid GAGs, HA=hyaluronan; C=chondroitin; CS=chondroitin sulfate; and HP=heparosan or heparin like molecules.

The C-terminal halves of pmHAS and pmCS (the putative GlcUA-transferase) can be switched and the sugar-transfer specificity for GlcNAc and GalNAc is not disturbed. This finding suggested that the hexosamine specificity determinants of the enzymes between GlcNAc- and GlcUA-transfer are located in their amino-terminal halves. To define the critical residues or regions that specify sugar transfer, further domain swapping was performed by PCR-overlap-extension (FIG. 23).

Certain chimeric or hybrid constructs, such as pm-EG and pm-IK (FIG. 23), are not dual-action enzymes and do not have either pmHAS or pmCS activities. But pm-FH, which possesses pmCS residues 1-258, is an active pmCS, although its remaining part is from pmHAS residues 266-703. When more of the pmCS sequence is replaced by pmHAS sequence as in pm-JL enzyme construct (which possesses pmCS residues 1-214 at the amino-terminal and pmHAS residues 222-703 at the carboxyl-terminal), the enzyme is converted into a catalyst with HAS activity. The conversion of GalNAc-transferring activity into GlcNAc-transferring activity indicated that residues 222-265 of pmHAS and probably the corresponding residues 215-258 of pmCS play critical role in the selectivity between binding and/or transferring of GalNAc and GlcNAc substrate.

Site-directed mutagenesis of region HAS222-265/CS215-258: none of the residues tested in this region are sufficient alone to switch the sugar transfer specificity between pmHAS and pmCS. In the above identified regions, there are 14 residues that are different between pmHAS and pmCS. We checked the primary sequences of the predicted chondroitin synthases from several independent type F Pasteurella multocida in the region of 215 to 258. Based on the comparison of these amino acid sequences, most of the differences between pmHAS and pmCS are conserved among those independent strains (FIG. 24). To identify possible critical individual residues that might be important for the selectivity between GalNAc and GlcNAc substrate, we utilized site-directed mutagenesis to change a single or multiple residues in this region. We used either pmHAS$^{1-703}$ DNA (for I243-, I243/G244/L245-containing mutants) or pmCS$^{1-704}$ DNA (for Y216-, L220-, or C221-containing mutants) as templates and replaced the target residue(s) with the corresponding one(s) in the other enzyme (FIG. 24). Results from enzymatic assays showed that all pmCS$^{1-704}$ mutants transfer GalNAc instead of GlcNAc and all pmHAS$^{1-703}$ mutants transfer GlcNAc instead of GalNAc. This finding indicates that none of the residues that we tested here are sufficient alone to switch the sugar transfer specificity between pmHAS and pmCS.

Domain swapping between pmHAS and pmCS: pmCS$^{1-214}$-HAS$^{222-265}$-CS$^{258-704}$ transfers both GlcNAc and GalNAc.

Figure 25:
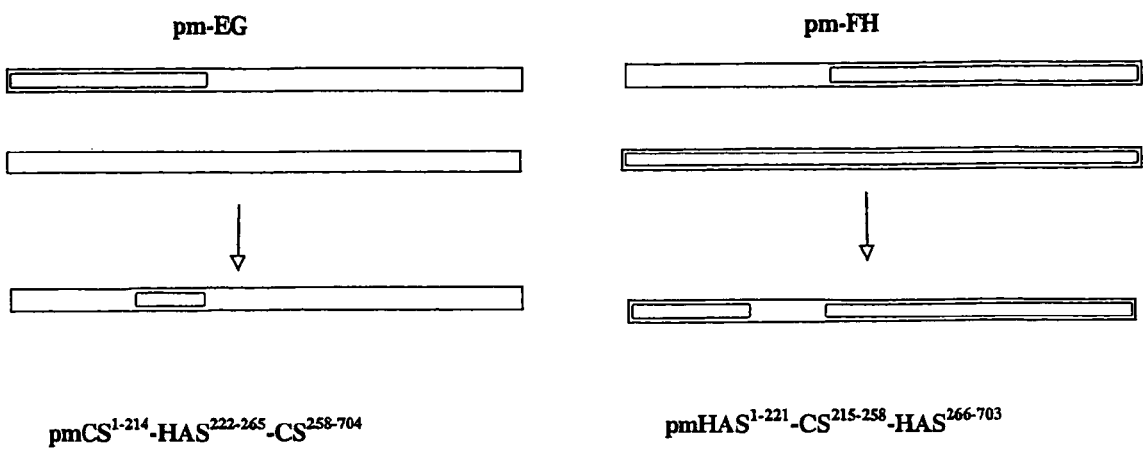
FIG. 25 depicts chimeric constructs of pmHAS$^{1-221}$-CS$^{215-258}$-HAS$^{266-703}$ and pmCS$^{1-214}$-HAS$^{222-265}$-CS$^{258-704}$. Pm-FH and pPm7A DNA were used to create pmHAS$^{1-221}$CS$^{215-258}$-HAS$^{266-703}$. A very interesting result was that pmCS$^{1-214}$-HASM$^{222-265}$-CS$^{258-704}$ can transfer both GalNAc and GlcNAc to HA oligomer acceptor; this enzyme displays relaxed sugar specificity.

Based on the above studies, we hypothesized that additional residues in the 44-residues region were important for the selectivity between GalNAc and GlcNAc transferase. To prove our hypothesis, this region was swapped between pmHAS$^{1-703}$ and pmCS$^{1-704}$ by PCR-overlap-extension. Pm-EG and pPmF4A (a C library clone containing pmCS gene locus) DNAs were used to create pmCS$^{1-214}$-HAS$^{222-265}$-CS$^{258-704}$. Pm-FH and pPm7A (a C library clone containing pmHAS gene locus) DNAs were used to create pmHAS$^{1-221}$-CS$^{215-258}$-HAS$^{266-703}$ (FIG. 25). PmHAS$^{1-221}$-CS$^{215-258}$-HAS$^{266-703}$ did not express. Interestingly, pmCS$^{1-214}$-HAS$^{222-265}$-CS$^{258-704}$ could transfer both GlcNAc and GalNAc with preference for UDP-GalNAc as judged by HAS assay and CS assay, supporting our conclusion that this region in pmHAS and pmCS plays a critical role in determination of sugar substrate specificity. We also obtained a pmCS$^{1-214}$-HAS$^{222-265}$-CS$^{258-704}$ clone that possesses an additional mutation of I243V; this clone lost GlcNAc-transferring activity and was switched back into a chondroitin synthase. This finding suggests that I243 in pmHAS, and probably V236 in pmCS, plays important yet unknown roles in the determination of sugar substrate specificity.

In order to examine whether pmCS$^{1-214}$-HAS$^{222-265}$-CS$^{258-704}$ could transfer sugars other than GlcNAc and GalNAc, different sugar substrates, including UDP-glucose, UDP-galactose, UDP-mannose, UDP-xylose and UDP-glucosamine (GlcN), along with isotope-labeled GlcUA and HA oligosaccharide acceptor, were included when performing the polymerization assay. The results demonstrated that pmCS$^{1-214}$-HAS$^{222-265}$-CS$^{258-704}$ will use UDP-GlcNAc, UDP-GalNAc, or UDP-glucosamine Table XXIX. This observation indicated that although swapping of the small region between pmCS and pmHAS resulted in relaxation of substrate selectivity, the enzyme is not so promiscuous that all UDP-sugars will substitute.

We exploited the possibility that the chimeric or hybrid enzyme could synthesize hybrid polymers with a blend of HA- and chondroitin-like sugars. We performed reactions containing $^3$H-UDP-GalNAc, $^{14}$C-UDP-GlcNAc, UDP-GlcUA and HA acceptor. The ratio of the incorporation of $^3$H-GalNAc and $^{14}$C-GlcNAc changed according to the UDP-sugar ratio in the reaction mixture included in the reaction. Gel filtration analysis of the polymerization products demonstrated that the molecules contain both $^3$H and $^{14}$C. The characterization of all the chimeric or hybrid proteins is summarized in FIG. 26.

TABLE XXIX

Sugar substrate specificity of pmCS$^{1-214}$-HAS$^{222-265}$-CS$^{258-704}$
Standard polymerization assay were performed in the presence of isotope-labeled GlcUA, HA oligosaccharide acceptor, and one of the following sugar substrates. The sugar incorporation was indicated as the percentage of the incorporation of UDP-GalNAc.
pmCS$^{1-214}$-HAS$^{222-265}$-CS$^{258-704}$
can transfer GalNAc, GlcNAc, and Glucosamine.

| substrate sugar | incorporation |
| --- | --- |
| UDP-GalNAc | 100% |
| UDP-GlcNAc | 28% |
| UDP-Glucosamine | 2% |
| UDP-Galactose | not detectable |
| UDP-Glucose | not detectable |
| UDP-Mannose | not detectable |
| UDP-Xylose | not detectable |

Thus, pmHAS is unique compared to all other known HASs.

Truncation analysis of pmHAS has identified a carboxyl-terminal region that appears to be responsible for the membrane association of pmHAS. Site-directed mutagenesis studies focused on several conserved motifs indicated that these conserved residues are critical for function. Evidence is provided that pmHAS and pmCS each contain two separate glycosyltransferase sites (FIG. 18). Thus the novel "one polypeptide, two active sites" theory has been confirmed. A 44-residue region of the enzymes has been demonstrated to be critical for sugar-transfer specificity. Based on this discovery, an enzyme that can transfer GalNAc, GlcN, and GlcNAc has been engineered.

Type A *Pasteurella multocida* produces a hyaluronan [HA] capsule to enhance infection. The 972-residue hyaluronan synthase, pmHAS, polymerizes the linear HA polysaccharide chain composed of GlcNAc and GlcUA. PmHAS possesses two separate glycosyltransferase sites. Protein truncation studies demonstrated that residues 1-117 can be deleted without affecting catalytic activity. The carboxyl-terminal boundary of the GlcUA-transferase resides within residues 686-703. Both sites contain a D×D motif. All four aspartate residues are essential for HA synthase activity. D247 and D249 mutants possessed only GlcUA-transferase activity while D527 and D529 mutants possessed only GlcNAc-transferase activity. These results further confirm our previous assignment of the active sites within the synthase polypeptide. The WGGED sequence motif appears to be involved in GlcNAc-transferase activity because E396 mutants and D370 mutants possessed only GlcUA-transferase activity.

Type F *P. multocida* synthesizes an unsulfated chondroitin GalNAc and GlcUA capsule. Domain swapping between pmHAS and the homologous chondroitin synthase, pmCS, was performed. A chimeric or hybrid enzyme consisting of residues 1-427 of pmHAS and residues 421-704 of pmCS was an active HA synthase. On the other hand, the converse chimeric or hybrid enzyme consisting of residues 1-420 of pmCS and residues 428-703 of pmHAS was an active chondroitin synthase. Overall, these findings support the model of two independent transferase sites within a single polypeptide as well as further delineate the site boundaries.

pmHAS utilizes two separate glycosyltransferase sites to catalyze the transfer of GlcNAc and GlcUA to form the HA polymer. Within the pmHAS sequence, there is a pair of duplicated domains which are similar to the "Domain A" proposed by Saxena. Both domains of pmHAS possess a short sequence motif containing DGS that is conserved among many β-glycosyltransferases. Changing the aspartate in either motif to asparagines, glutamate, or lysine significantly reduced or eliminated the HAS activity. However, the D196 mutants and the D477 mutants maintain high level of GlcUA-transferase and GlcNAc-transferase activity, respectively.

pmCS contains 965 amino acid residues and is about 90% identical to pmHAS. A soluble recombinant *Escherichia coli*-derived pmCS$^{1-704}$ catalyzes the repetitive addition of sugars from UDP-GalNAc and UDP-GlcUA to chondroitin oligosaccharide acceptors in vitro.

In order to analyze the contribution of the amino terminal region of pmHAS, various recombinant truncated polypeptides were produced (pmHAS$^{46-703}$, pmHAS$^{72-703}$, pmHAS$^{96-703}$ and pmHAS$^{1-703}$) in *E. coli*. The truncated versions pmHAS$^{46-703}$ and pmHAS$^{72-403}$ were as active as pmHAS$^{1-703}$, a soluble polypeptide with complete HAS activity. PmHAS$^{96-703}$ expressed at a very low level compared with other constructs but was active. PmHAS$^{118-703}$ expressed better than pmHAS$^{96-703}$ and still elongated HA chains. Therefore, it is probable that further deletion beyond residue 72 affected the overall folding efficiency of the entire polypeptide. Observation of lower molecular weight degradation bands derived from pmHAS$^{118-703}$ on Western blots also suggests that improper folding occurs to some extent. Overall, these findings suggest that the amino-terminal 117 residues are not required for HA synthase activity.

pmHAS$^{1-650}$ loses its GlcUA-transferase activity. To further delineate the GlcUA-transferase domain within the carboxyl terminal region, two slightly longer mutants, pmHAS$^{1-668}$ and pmHAS$^{1-686}$ were created. Both mutants also could not polymerize HA due to the loss of GlcUA-transferase activity, indicating that the carboxyl-terminal boundary of the GlcUA-transferase resides between residues 686 and 703.

Materials and Methods

Molecular biology reagents were from Promega unless noted. Custom oligonucleotides were from The Great American Gene Company. Oligonucleotides for mutagenesis were trityl purified. All other reagents were the highest grade available from either Sigma or Fisher unless otherwise noted.

Truncated polypeptides were generated by amplifying the pPm7A insert by 13 cycles of PCR with Taq polymerase (Fisher) and synthetic oligonucleotide primers corresponding to various portions of the pmHAS open reading frame. Except for the construction of pmHAS$^{1-686}$ and pmHAS$^{1-668}$, the primers contained EcoRI and PstI restriction sites to facilitate cloning into the expression plasmid pKK223-3 (tac promoter; Pharmacia). The resulting recombinant constructs were transformed into *E. coli* TOP 10F' cells (Invitrogen) and maintained on Luria-Bertani media with ampicillin selection. The DNA encoding pmHAS$^{1-686}$ and pmHAS$^{1-686}$ were cloned into pETBlue-1 plasmid and expressed in Tuner (DE3)pLacI cells (Novagen) according to manufacturing instructions; these cells were maintained on Luria-Bertani media with carbenicillin and chloramphenicol selection.

Point mutations were made using the QuickChange site-directed mutagenesis method (Stratagene) with the plasmid pKK223/pmHAS$^{1-703}$ DNA as template. The sequences of the mutant open reading frames were verified by automated DNA sequencing (Oklahoma State University Recombinant DNA/Protein Resource Facility).

Recombinant E coli were grown in Luria-Bertani media with drug selection until $OD_{600}$ was 0.3-0.6 when cells were induced with 0.5 mM isopropyl-1-thio-β-D-galactoside. Cells were harvested 5 hours after induction. For soluble truncated proteins and pmHAS$^{1-703}$-derived mutants expressed in E. coli TOP10F' cell, cells were extracted with B-Per™ II Bacterial Protein Extraction Reagent (an octylthioglucoside-based solution; Pierce) according to the manufacturer's instruction except that the procedure was performed at $7_cC$ in the presence of protease inhibitors. For proteins expressed in Tuner(DE3)pLacI, lysis by ultrasonication followed by subcellular fractionation was performed and the supernatant after centrifugation at $100,000_C$ g was used.

Five assays were designed to detect either (a) the polymerization of long HA chains, (b) the addition of a single GlcNAc to a GlcUA-terminated HA oligosaccharide acceptor, (c) the addition of a single GlcUA to a GlcNAc-terminated HA oligosaccharide acceptor, (d) the polymerization of long chondroitin chains, or (e) the addition of a single GalNAc to a GlcUA-terminated HA oligosaccharide acceptor. The first three assays were described previously (Jing and DeAngelis, 2000). For the chondroitin synthase assay, the same conditions as the HA synthase assay were used except that the other hexosamine precursor, UDP-GalNAc, was employed and there is no ammonium sulfate or ethylene glycol in the assay system. GalNAc-transferase activity was assayed under the same conditions as the GlcNAc-transferase assay except that 0.3 mM UDP-[$^3$H]GalNAc (0.2 $_c$Ci; NEN) was used instead of UDP-[$^3$H]GlcNAc. Reactions were terminated by the addition of SDS to 2% (w/v). The reaction products were separated from substrates by descending paper (Whatman 3M) chromatography with ethanol/1 M ammonium acetate, pH 5.5, development solvent (65:35 for the HAS, chondroitin synthase, and GlcUA-transferase assays; 75:25 for GlcNAc-transferase and GalNAc-transferase assay). All assays were adjusted to be linear with regard to incubation time and to protein concentration. Radiolabeled products were quantitated by liquid scintillation counting (Biosafe II, Research Products International).

The pmHAS polypeptides in membranes and extracts were analyzed using standard 8% polyacrylamide SDS gels and Western blotting utilizing a monospecific antibody directed against a synthetic peptide corresponding to residues 526 to 543 of pmHAS (acetyl-LDSDDYLEPDAVELCLKE-amide) as described hereinabove.

The DNA encoding different segments of pmHAS or pmCS were generated by amplifying the pPm7A insert (DeAngelis et al., 1998) or pPmF4A insert (DeAngelis and Padgett-McCue, 2000), respectively, by 15 cycles of PCR with Taq polymerase (Fisher) and synthetic oligonucleotide primers corresponding to various portions of the pmHAS or pmCS open reading frame. Each internal primer contained overlaps with the other segment to allow joining of the two desired segments. The forward and reverse primers for pmHAS residue 1-427 (A segment) were P1=5'-ATGAACA-CATTATCACAAGCAATAAAAGC-3' and P2=5'-GC-GAATCTTCTATTGGTAAAAGYTTTC-3' (Y=C/T), respectively. The forward and reverse primers for pmCS residue 421-704 (C segment) were P3=5'-CTTTTACCAATA-GAAGATTCGCATAT-3' and P4=5'-GAAGACGTCTTAG-GCATCTTTATTCTGAATGAG-3', respectively. The forward and reverse primers for pmCS residue 1-420 (D segment) were P1 and P2. The forward and reverse primers for pmHAS residue 428-703 (B segment) were P3 and P5=5'-GGGAATTCTGCAGTTAAATATCTTTTAA-GATATCAATCTCTTC-3', respectively. The chimeric or hybrid synthases were created by 15 cycles of PCR with the gel-purified (GeneClean; Bio101) segments and outer primers (pm-AC used A and C segments with primer P1 and P4; pm-BD used B and D segments with primer P1 and P5). The purified PCR products were cloned into pETBlue-1 vector and the chimeric or hybrid proteins were expressed in Tuner (DE3)pLacI cells (Novagen). We sequenced the complete open reading frames of multiple clones of both constructs. We found a pm-AC construct that was perfect, but both of the two pm-BD constructs that we had sequenced completely had secondary undesired mutations (#1, E695 and I697F; #2, I302V). However, these mutations were in different locations and the enzyme transferase activities were identical. Several other pm-BD clones have the identical phenotype but their complete sequences were not determined.

Microarrays and Bioreactors Utilizing GAGs.

Production and Purification of a Practical GAG Synthase Catalyst.

Mutagenesis transformed the low expression level (~0.1% of membrane protein) 972-residue pmHAS membrane protein found in nature to a high expression level (~10% of total cell protein) 703-residue soluble protein. This alteration of pmHAS allows both (i) the generation of more catalyst and (ii) the purification of catalyst by standard chromatographic means. Several strategies have been developed to purify milligram-level quantities of pmHAS mutant proteins by conventional protein chromatography. We obtain 90-95% pure enzyme in one to three steps. A soluble version of the chondroitin synthase, pmCS, has also been produced by truncating residues 705-965 from the 965 residue pmCS.

Solid-Phase Synthesis of Oligosaccharides.

Microarrays are emerging as powerful, high-throughput tools in genomics and proteomics research. Sugar-based microarrays are generated (and are encompassed by the presently claimed and disclosed invention) to test a wide variety of novel GAG oligosaccharides for interaction with essential proteins. HA polymers have been applied to a glass slide compatible for analysis with conventional DNA-based microarray detection instrumentation. The pmHAS enzyme was used to add medium-sized radioactive HA polymer chains to glass slides as well.

A two-step process was used to form a "spot" containing a polymer on the sugar array: (i) a short acceptor or primer oligosaccharide is chemically attached to an activated glass substrate, and (ii) the acceptor is elongated enzymatically with anyone of the Pasteurella GAG synthases (e.g., pmHAS, pmCS, pmHS, and PgIA) and UDP-sugar precursors. The acceptor sugar was a hyaluronan tetramer modified at the reducing end with a free amino group by reductive amination of the tetramer with diaminoethane. The tetramer was coupled to commercially available activated glass slides. Several chemistries were investigated but epoxy-activated glass and N-hydroxysuccinimide [NHS] glass were optimal. The chemical coupling step was performed at room temperature in 0.1 M sodium borate buffer, pH 8.5, for 40 min. The solution was removed, the remaining activated groups on the glass were quenched with 0.1 M Tris, pH 8.0, and the slide was washed with water. For the second step, enzymatic elongation, we employed radiolabeled sugars were employed to monitor the immobilization of both HA sugars on to the glass.

A reaction mixture containing pmHAS$^{1-703}$ enzyme, UDP-[$^{14}$C]GlcUA, UDP-[$^3$H]GlcNAc, 10 mM MnCl$_2$, 50 mM Tris, pH 7.2, 1 M ethylene glycol was incubated on the spot coupled with the HA tetramer. As a negative control, a similar spot without acceptor sugar was also tested. After 40 min, the enzyme mixture was removed and the slide was washed extensively to remove any free radiolabeled sugar. The radiolabeled sugars attached to the glass slide were measured by liquid scintillation counting. Both GlcNAc and GlcUA, the sugar components of the HA chain, were shown to be added to the glass slide in a specific fashion. Thus, the use of any functional acceptor and the pmHAS, pmCS, or pmHS enzymes and/or derivatives of these enzymes can be used to create a GAG sugar microarray.

Synthesis of GAG Compound in Bioreactor Format.

Acceptor sugars were shown to be elongated by the *P. multocida* GAG synthases if supplied in a free state in a liquid solution or covalently immobilized to a surface. To be truly useful, a method for production of defined lead molecules in larger amounts for animal or cultured cell tests is required. Molecules with good output from the microarray (e.g., bind strongly or selectively) are subsequently synthesized in the bioreactor format and then assayed for activity. Any molecule used in the microarray and that is of particular interest may be manufactured in the bioreactor format as described herein.

A series of bioreactors is employed with each containing a different genetically engineered catalyst capable of only single sugar transfer e.g. pmHAS domain A2 mutant, capable of transferring β3GlcNAc; pmCS domain A2 mutant, capable of transferring β3GalNAc; pmHS mutant, capable of transferring α4GlcNAc; or pmHAS domain A1 mutant, capable of transferring β4GlcUA. Percolating the acceptor sugar through various bioreactors produces the desired GAG-oligosaccharides. Multiple passes through the bioreactors results in longer oligosaccharide chains. The major technical and cost benefits of this process is that the challenging purification of the intermediate oligosaccharide products and unused UDP-sugar after each step is not required due to the synthases' exquisite transfer specificity. Furthermore, each step is driven to completion after long reaction time by recirculation on a given column before applying on the next column.

Two bioreactors were prepared with immobilized mutant pmHAS enzymes. One column only transferred GlcNAc (i.e. pmHAS$^{1-703}$) while the other column transferred only GlcUA (i.e., pmHAS$^{1-703}$ mutant D196N). As an easily monitorable test, a series of fluorescent HA oligosaccharides were prepared for use with the bioreactors. Larger oligosaccharides were made as expected. A desirable HA dodecamer (12-mer) molecule was made, the appropriate size for anticancer activity, in a single afternoon. The identity of the product was verified by the most rigorous analytical method, mass spectrometry.

Experimental Design and Methods.

Oligosaccharide synthesis may occur in either the solid phase (for microarray construction) or in the liquid phase (for bioreactor synthesis).

Oligosaccharide potency is improved by the presently claimed and disclosed invention. Novel oligosaccharides that readily form the special binding shape or conformation recognized by a particular GAG-binding protein (without the prior assistance of the binding protein) is produced according to the methodology of the presently claimed and disclosed invention, then such novel oligosaccharides will bind with even higher affinity than the regular GAG-oligosaccharide. This model draws upon numerous examples of protein/ligand interactions in which a complementary fit yields high affinity binding.

Oligosaccharide selectivity is also improved by the presently claimed and disclosed invention. Since the novel molecules bind strongly to one class of GAG-binding protein, but not to the other classes, then more specific drugs can be created. From a practical standpoint, less side-effects or undesirable consequences would be expected if such a selective therapeutic is developed. The scientific rationale for selectivity is based on NMR-based structural analyses of HA-binding proteins, such as TG-6 link module and CD44, in the act of binding small HA-oligosaccharides. Each protein binds HA, but the bound sugar molecule exists in different shapes or conformations for the two proteins. Different critical elements of the sugar chain are bound by each of the proteins. In a specific example of the desired selectivity requirements for a potential GAG-based drug, certain forms of CD44 found in cancer cells have been strongly implicated in more virulent, invasive disease; thus perturbing this system with oligosaccharides is a logical and natural use of the oligosaccharides of the presently disclosed and claimed invention. On the other hand, a different system such as aggrecan, a type of proteoglycan which is critical for stabilizing and organizing normal tissues (especially cartilage and connective tissue), should not be perturbed or weakened. Therefore, a CD44-binding oligosaccharide that does not interact with aggrecan is a more desirable therapeutic agent.

Synthesis of Sugar-Based Microarrays.

The methodology of the presently disclosed and claimed invention includes the creation of specifically designed GAG oligosaccharides with distinct properties optimized for medical uses. The process of the presently claimed and disclosed invention builds the sugar chain in a step-wise process, thus allowing a particular sugar to be added at various desired points in the chain. A library of related GAG compounds is synthesized in a microarray format. DNA-based microarrays have been used with much success and protein-based arrays have recently been reported, but this technology has not yet been reported for carbohydrate analyses. A slide is produced according to the methodology of the present invention with a series of spots each containing molecules of a single unique member of a family of related oligosaccharides. Each sugar differs in chain size (e.g., 6- to 5-mers) and/or sequence.

One array includes a library composed of a numerous HA/chondroitin-like hybrids. Combinations of GalNAc or GlcNAc are placed at various locations of the oligosaccharide chain. One example of a novel sugar is a HA-like 10-mer variant with a GalNAc sugar substituting for the penultimate sugar that is normally a GlcNAc. Each isomer adopts a different preferred set of conformations from that of HA$_{10}$. An additional array embodiment includes (a) HA/chondroitin-like hybrid libraries with heparin-like sugar substitutions and (b) libraries of sulfated and/or epimerized heparin and chondroitin sugars.

The array devices are made by chemically linking the acceptor (e.g., amino-HA4) to epoxy- or N-hydroxysuccinimide-glass (NoAb, Inc.) and then elongating the acceptor with various combinations of substrate and the appropriate enzyme (e.g. UDP-GlcNAc+pmHAS-D or UDP-GalNAc+pmCS or UDP-GlcUA+pmHAS-D). The reaction at each step is controlled by limiting the UDP-sugar that is available with the chosen enzyme. After a coupling step, the slide is washed and the next sugar is coupled. GAG linkages that may be prepared include those listed hereinabove.

The initial optimization of sugar elongation is monitored by measuring incorporation of radiolabeled sugars (e.g.

$^3$H-GlcNAc, $^{14}$C-GlcUA). Manual application of the reaction mixture to the solid substrate may be employed at this stage (1-2 mm spots produced with 0.5-2 µl reaction mixtures). Each oligosaccharide spot is prepared in duplicate to make sure that even spotting and processing is performed. The use of larger spots may avoid problems associated with stray signals caused by dust, scratches, or uneven spotting. Automated printing may be used if identical microarrays or higher density arrays are desired: this technology is adapted to facilitate multiple incubation and washing steps. Additionally, sugar libraries may be manufactured in 96-well or 384-well or 1536-well microtiter plates to counter sensitivity problems. The GAG synthase technology of the presently claimed and disclosed invention also works on plastic surfaces and many types of activated plastic plates with a high surface capacity are commercially available.

For example, an activated 96-well plate, "Protein Immobilizer" (Exiqon, Denmark) suitable for covalently binding HA4-amine acceptor may be (and has been) used to form the sugar library in a microtiter format. The HA4-amine acceptor in a non-amine buffer (50 mM Hepes, pH 7-9) is added to all of the activated wells. After 30-60 min, the well is rinsed with water, quenched with Tris buffer, blocked with albumin, and is then ready for multiple steps of synthase-catalyzed sugar addition. Basically, a synthase or transferase plus the appropriate UDP-sugar is added to the well, incubated, rinsed, then the next synthase or transferase plus the appropriate UDP-sugar is added and so on. In analogy to the spots of the microarray slide, each well will have a different structure dictated by the choice and the exact sequence of steps with the synthase/transferases and UDP-sugars utilized in the construction.

Post-Polymerization Modification of GAGs—Sulfation.

Heparin, a sulfated heparosan, interacts with high affinity to several distinct proteins. In many cases if heparin is desulfated, then much of its binding activity is lost. Similarly, most chondroitin molecules in humans are sulfated. Sulfates are added to the polymer chain during biosynthesis in a wide variety of patterns. The sulfate addition to any particular hydroxyl or amine group is catalyzed by distinct sulfotransferases in vivo. All of the relevant sulfation enzymes have been cloned and overexpressed. Active extracts or overexpression clones may be obtained from many sources known to those of ordinary skill in the art. The sulfotransferases and PAPS, the sulfate donor, are incubated with various immobilized oligosaccharides. Only small amounts of the modification enzymes are required at this stage because each spot contains only a small amount of sugar. The precise sugar by sugar control of the sulfation positions along a particular oligosaccharide chain is not possible in this scenario because the sulfotransferase will add a sulfate onto any available, appropriate hydroxyl or amino group. But if desired, an oligosaccharide with a block of sulfated groups can be prepared; for example, the first third, the first half, or the entire oligosaccharide can be sulfated. For microarray purposes, a series of differently sulfated molecules is useful especially when compared in parallel. Treating some spots with multiple sulfotransferases is used to increase the array diversity. The activity of certain sulfotransferases depends on the preexisting sulfation or epimerization state of the sugar and this array design must proceed in an appropriate manner.

Epimerization.

The epimerization of GAGs results in the conversion of GlcUA groups into IdoUA groups. The IdoUA allows more conformational flexibility and certain proteins require this modification for high affinity binding. The heparin epimerase gene (Crawford, et al.) has been identified, but the chondroitin epimerase gene is still unknown (but functional extracts are available to those of ordinary skill in the art). The heparin epimerase converts heparin or heparosan into more IdoUA-rich polymer and the chondroitin epimerase will convert chondroitin into dermatan. As with sulfation, a gradient of IdoUA residues can be formed by adding epimerase at different times in the oligosaccharide synthesis.

After the desired syntheses (i.e., array build-up), the microarray slide is incubated with one of the various GAG-binding proteins of interest in a buffer to prevent non-specific adsorption. After washing away the unbound target protein, a fluorescent detection reagent (e.g., labeled antibody or avidin) is used to locate the bound protein on an oligosaccharide spot. The GeneTac2000 instrument, for example, is set up for detection of cyanine dyes (e.g., Cy5, Cy3). In the near future, rare earth fluorophores (e.g., europium, terbium) may be more suitable in specific applications due to their improved photostability, larger Stokes shifts, and narrower emission spectra. The simultaneous testing of multiple proteins uses detection reagents with distinct fluorophores with non-overlapping emission spectra. Alternatively, radioactive or enzyme-based (colorimetric or chemoluminescent monitoring) are also useful for detection of protein binding.

Activity screens with HA-binding proteins are facilitated by the availability of aggrecan (biotinylated form; Calbiochem) and CD44 (IgG-fusion) in tagged forms, and antibodies to RHAMM and TG-6 link module. Likewise, useful antibody reagents for the heparin-binding targets antithrombin III, fibroblast growth factor 2, and vascular endothelium growth factor as well as the chondroitin/dermatan target heparin cofactor II are available.

Specificity of binding is gauged by observing the position of the spots (the sequence and the composition of the oligosaccharide are known for each spot in the array) that bind the various proteins. Incubations are also conducted in the presence of soluble natural GAGs. In the array described hereinabove, for example, HA polymer or pure $HA_{10}$ oligosaccharide is used as a competitor molecule to gauge the specificity of the interaction. If a HA-binding protein truly binds with higher affinity to the novel sugar, then the signal from its spot does not fade significantly in the presence of HA.

A strong interaction between oligosaccharide and protein is due to a better bonding network (e.g. more bonds or better geometry or higher overlap). To compare binding potency of the various sugars on the array, the protein and microarray is incubated at more stringent, harsher conditions (e.g., higher temperature, and/or buffers with suboptimal pH or salt concentrations); these conditions break or weaken the noncovalent bonds holding the complex together. For example, in many affinity chromatography purifications of proteins, a salt or pH gradient is used to elute the bound material from the resin. The output of this potency assay is to determine which spot retains the protein either longer or under more harsh conditions. Duplicate arrays tested under optimal or stringent conditions are compared in parallel.

Poor fluorescence signals in glass slide microarray screening trials can be overcome by using 96-well or 384-well or 1536-well microtiter plates. The plates have a higher surface capacity thus more oligosaccharide is available per assay. Also, the plates have bigger working volumes (50 to 400 µl/well) to allow incubations with more reagents. The microtiter plates are also suitable for signal amplification using reporter enzymes such as peroxidase or alkaline phosphatase conjugates in order to provide chemoluminescent, fluorescent or calorimetric readout. Automated microplate readers are not quite as high-throughput as the microarray readers, but the automated microplate readers still serve as useful substitutes for drug discovery processes. Utilizing the microarrays of the presently disclosed and claimed invention.

Carbohydrate synthesis is a difficult and demanding undertaking. Hexamers are the largest GAG oligosaccharides reported to have been chemically synthesized. Typically, as the sugar chain gets longer, the chemical synthesis rate and yield plummets. For certain protein/GAG interactions, a hexamer may be sufficient, but quite often slightly longer forms of the same GAG have increased activity or potency. The speed of transfer to the oligosaccharide acceptor actually increases as the chain gets bigger than 6 sugars utilizing the GAG synthases of the presently claimed and disclosed invention.

Monosaccharides have many potential reactive functional groups and thus many combinations of sugars are possible. Therefore all conventional syntheses involve the coupling of protected sugar donor subunits and protected sugar acceptor subunits. Protecting groups are required because only one functional group from each of the two compounds will be coupled. At the conclusion of the reaction in a chemical synthesis, all of the protecting groups must be removed, but this process is not perfect; as a result, a fraction of the product molecules retain these unnatural moieties. Also, monosaccharides can be connected with either $\alpha$ or $\beta$ anomeric linkages. In a chemical synthesis, a 1:10 to 1:100 ratio of the desired anomer is considered a good reaction. However, if a dodecamer is made with a 1:100 ratio, then only ~90% of the reaction products is the desired sugar with a wide variety of contaminating analogs. In the case of longer sugars, the cumulative effect is even greater. The issues of residual protection groups, racemization, and side-products from chemical synthesis are not problematic for the high-fidelity GAG synthase catalysts of the presently disclosed and claimed invention.

A distinct method for producing novel GAG sugars uses certain degradative enzymes to generate small molecules by "running in reverse" (transglycosylation) on mixtures of HA and chondroitin polymers. This method has some potential for novel synthesis, but it only makes a very limited scope of products with a block pattern (no single or specifically spaced substitutions possible) using slow reactions that cannot easily be customized or controlled. At this point, heparin-like compounds cannot be made by this reaction because the appropriate enzyme is not known—i.e. heparin lyase will not transglycosylate.

Immobilization of Functional Enzymes.

Figure 27:
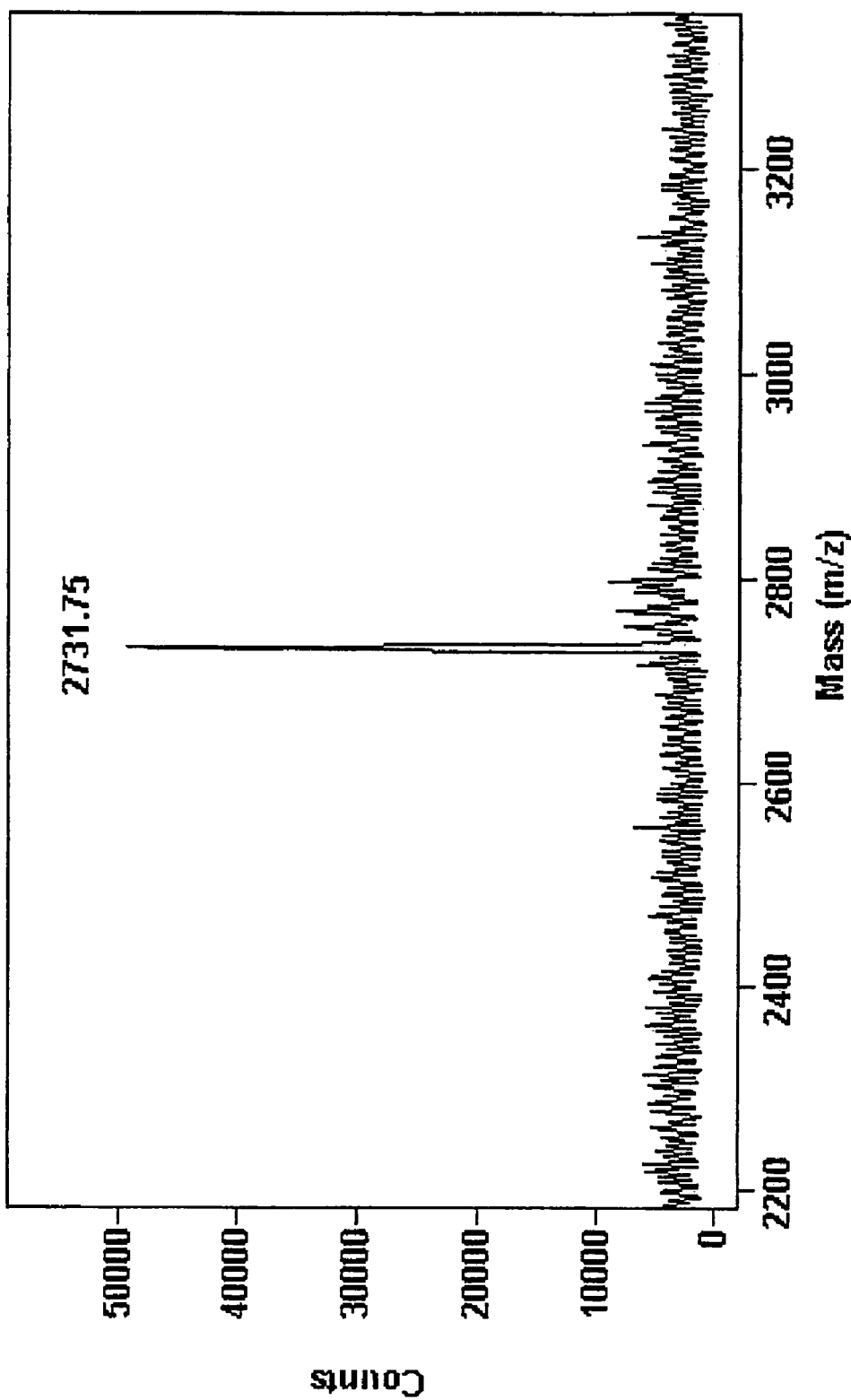
FIG. 27 depicts a mass spectra of F-HA12 product. This fluorescent HA oligosaccharide was synthesized using the twin bioreactor scheme. A peak with the predicted mass is apparent; no shorter HA11 sugar is observed.

Large-scale synthesis mediated by catalysts can be performed in a variety of formats. Perhaps the most useful and advantageous method is the catalytic bioreactor format: FIG. 27. For example, processing often involves passing the starting material through a reactor column packed with catalyst. This column serves to hold or to immobilize the catalyst (often an extremely expensive material) so that it can contact all of the starting material in a serial fashion. After the reaction occurs in the column bed, the product exits the column. A good column (i.e., one that does not lose the catalyst or does not allow the catalyst to fail) allows repetitive (multiple use allows cost-savings) or continuous reactions to occur.

The biocatalytic system for sugar synthesis of the presently claimed and disclosed invention was designed with several issues in mind. First the pmHAS$^{1-703}$ enzyme and its mutant derivatives were tested to see if they could be immobilized to a bead suitable for use in a column. Chemistry was found that will allow virtually 100% of the purified enzyme to be attached to a bead with minimal loss of catalytic activity. Generally, pmHAS$^{1-703}$ is purified (as described hereinabove) transferred into a non-amine buffer (Hepes, pH 7-8), and mixed 2 hours with NHS-ester activated beads (agarose). The enzyme couples to the bead. Residual NHS-esters are quenched with Tris. The beads are stored in typical buffer.

The beads with wild-type dual-action pmHAS$^{1-703}$ made long HA polymer chains. The mutant versions of pmHAS$^{1-703}$ possessing only a single functional transfer site transferred only one type of sugar. Furthermore, the immobilized enzyme was extremely stable and retained catalytic function even if maintained at useful functional temperatures (i.e., 30° C.) for at least a week in reaction buffer.

Laboratory-Scale Synthesis with Bioreactors.

Figure 28:
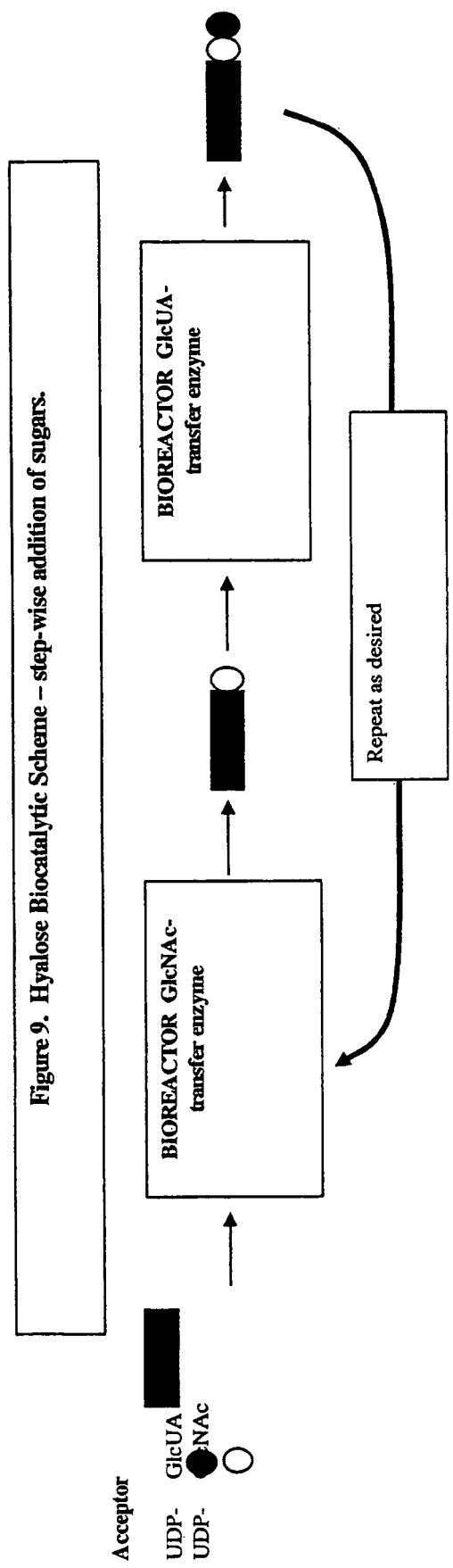
FIG. 28 is a pictorial representation of a hyalose biocatalytic scheme depicting the step-wise addition of sugars.

Two bioreactors were prepared with immobilized mutant pmHAS$^{1-703}$ enzymes (described hereinabove). One column only transferred GlcNAc while the other column transferred only GlcUA. As an easily monitorable test, a series of fluorescent HA oligosaccharides were prepared utilizing these bioreactors. As a feedstock, a fluorescent HA4 [F-HA4] acceptor was first made in a two-step chemical synthesis. The HA4 tetrasaccharide is coupled by reductive amination with diaminobutane and NaCNβH$_4$ in borate buffer. The resulting amino-HA4 is coupled to fluorescein-NHS (oregon green, molecular-probes) in borate buffer. This acceptor and the two required UDP-sugars, UDP-GlcNAc and UDP-GlcUA (0.8 mM each), together in a suitable reaction buffer (1 M ethylene glycol, 10 mM MnCl$_2$, 50 mM Tris, pH 7.2) were applied to the two enzyme columns in a repetitive fashion 8 times (4 cycles each column). Samples of the reaction mixture were analyzed by thin layer chromatography at every step. Larger oligosaccharides were observed to be made as expected. A desirable nanoHA molecule, a F-HA12 sugar, was made in a single afternoon. The identity of this F-HA12 product was verified by the most rigorous analytical method, maldi-tof mass spectrometry FIG. 28. The theoretical molecular weight for the F-HA12 sugar agreed with the observed experimental molecular weight (2731.8 Da).

In addition to being a sensitive test molecule for the synthesis process of the presently claimed and disclosed invention, this fluorescent reagent has an added bonus for use as a probe. The fluorescent tag allows for sensitive visualization of the location and the fate (e.g. stick to cell surface, internalized, etc.) of HA oligosaccharides or chimeric or hybrid molecules on live cancer cells. The fluorescent tag allows for sensitive visualization of the location and the fate (e.g., stick to cell surface, internalized, etc.) of HA oligosaccharides or chimeric or hybrid molecules on live cancer cells.

Synthesis of Microarrays.

Microarrays are emerging as powerful, high-throughput tools in genomics and proteomics research. Sugar-based microarrays utilizing the processes of the present invention can be used to test a wide variety of novel oligosaccharides for interaction with proteins essential for tissue integrity or recognition/signaling events. Information from such screening microarrays leads directly to the development of second generation sugars having increased potency and/or increased selectivity. These second generation sugars are also synthesized in the bioreactor. HA polymers have been applied to a glass slide (described hereinbelow) compatible for analysis with conventional microarray detection instrumentation. For oligosaccharide production, the individual sugars would be added in a controlled, stepwise fashion to build custom oligosaccharides.

Preparation of nanoHA Catalysts.

Normally, the natural wild-type enzyme catalysts (pmHAS$^{1-703}$, pmCS, pmHS, or PgIA) adds sugars to a long HA polymer chain or chondroitin chain or heparin chain without stopping resulting in HA chondroitin or heparin chain lengths that cannot be controlled (and are not unique). Therefore, the two important catalytic activities of pmHAS$^{1-703}$, pmCS$^{1-70}$, pmHS, and PgIA, (i.e., GlcNAc transfer, GalNAc, and GlcUA transfer) were dissected in order to make two controllable enzymes each of which can only add one type of sugar in a step-wise fashion. By utilizing these mutant enzymes there is no need to purify or to separate the intermediate products between each sugar addition step (resulting in significant time and cost savings). Useful mutants have been produced that form single-action catalysts.

Biomaterials and Methods of Making Same.

Biomaterials also play a pivotal role in the field of tissue engineering. Biomimetic synthetic polymers have been created to elicit specific cellular functions and to direct cell-cell interactions both in implants that are initially cell-free, which may serve as matrices to conduct tissue regeneration, and in implants to support cell transplantation. Biomimetic approaches have been based on polymers endowed with bioadhesive receptor-binding peptides and mono- and oligosaccharides. These materials have been patterned in two- and three-dimensions to generate model multicellular tissue architectures, and this approach may be useful in future efforts to generate complex organizations of multiple cell types. Natural polymers have also played an important role in these efforts, and recombinant polymers that combine the beneficial aspects of natural polymers with many of the desirable features of synthetic polymers have been designed and produced. Biomaterials have been employed to conduct and accelerate otherwise naturally occurring phenomena, such as tissue regeneration in wound healing in the otherwise healthy subject; to induce cellular responses that might not be normally present, such as healing in a diseased subject or the generation of a new vascular bed to receive a subsequent cell transplant; and to block natural phenomena, such as the immune rejection of cell transplants from other species or the transmission of growth factor signals that stimulate scar formation.

Approximately 10 years ago, the concept of bioadhesion was introduced into the pharmaceutical literature and has since stimulated much research and development both in academia and in industry. The first generation of bioadhesive drug delivery systems (BBDS) were based on so-called mucoadhesive polymers, i.e. natural or synthetic macromolecules, often already well accepted and used as pharmaceutical excipients for other purposes, which show the remarkable ability to 'stick' to humid or wet mucosal tissue surfaces. While these novel dosage forms were mainly expected to allow for a possible prolongation, better localization or intensified contact to mucosal tissue surfaces, it had to be realized that these goals were often not so easily accomplished, at least not by means of such relatively straightforward technology. However, although not always convincing as a "glue", some of the mucoadhesive polymers were found to display other, possibly even more important biological activities, namely to inhibit proteolytic enzymes and/or to modulate the permeability of usually tight epithelial tissue barriers. Such features were found to be particularly useful in the context of peptide and protein drug delivery.

The primary goal of bioadhesive controlled drug delivery is to localize a delivery device within the body to enhance the drug absorption process in a site-specific manner. Bioadhesion is affected by the synergistic action of the biological environment, the properties of the polymeric controlled release device, and the presence of the drug itself. The delivery site and the device design are dictated by the drug's molecular structure and its pharmacological behavior.

One such bioadhesive known in the art is a fibrin "glue" and compositions which include one or more types of fibrin glue in combination with a medicament have been studied. For example, in order to test the effect on the handling properties of two component fibrin glue, the viscosity of the fibrin glue was increased with sodium hyaluronate and the glue was applied to a microvascular anastomosis in rats. The femoral artery of each rat was anastomosed with three conventional sutures and then sealed with the fibrin glue. Three glues with different viscosities were tested: original Tisseel fibrin glue (Immuno AG, Vienna); Tisseel with 0.9% sodium chloride added to the fibrinogen component; and Tisseel with a high molecular weight sodium hyaluronate (10 mg/ml, Healon, Pharmacia, Sweden) added to the fibrinogen component. The increased viscosity of the fibrin glue to which hyaluronate had been added resulted in a significantly higher patency rate 20 minutes after completion of the anastomosis (p<0.01), and reduced the amount of fibrin that entered the vessels. Wadstrom et al. "Fibrin glue (Tisseel) added with sodium hyaluronate in microvascular anastomosing." Scand J Plast Reconstr Surg Hand Surg 1993 December:27(4):257-61.

The typical properties of the bioadhesive fibrin system described above ensue from its physiological properties. Filling the wound enhances natural biological processes of healing. The tissue reaction to the applied tissue fibrin coagulum is favorable. The treated parenchymatous organs, liver and spleen, heal with a smooth scar. The number of adhesions in the peritoneal cavity in all known treated experimental animals after treatment of the spleen was similar. Fewer adhesions are also observed when using a bioadhesive for repairing liver injuries in rabbits. The macroscopic appearance of the scar was similar; the scar was less visible in the liver parenchyma. The histological appearance was similar. The bioadhesive did not damage the tissue surrounding the parenchyma and did not act as a foreign body. These results confirm the biocompatibility of the fibrin glue as well as tissue tolerance and satisfactory healing without a reaction to the bioadhesive. After healing the bioadhesive is typically replaced by natural fibrous tissue.

Despite the effectiveness and successful use of the fibrin glue by medical practitioners in Europe, neither fibrin glue nor its essential component fibrinogen is widely used in the United States at the present time because of the general risks and problems of infection from pooled blood products contaminated with lipid-enveloped viruses such as HIV, associated with AIDS, and the hepatitis causing viruses such as HBV and HCV, as well as cytomegalovirus (CMV), Epstein-Barr virus, and the herpes simplex viruses in fibrinogen preparations. Thus, a naturally occurring or recombinantly produced bioadhesive which is not derived from pooled blood sources is actively being sought. The bioadhesive of the present invention fulfills such a need.

For example, one embodiment of the present invention is the use of sutures or bandages with HA-chains grafted on the surface or throughout the material in combination with the fibrinogen glue. The immobilized HA does not diffuse away as in current formulations, but rather remains at the wound site to enhance and stimulate healing.

Organic materials have also been postulated for use as bioadhesives. Bioadhesive lattices of water-swollen poly (acrylic acid) nano-and microparticles have been synthesized using an inverse (W/O) emulsion polymerization method. They are stabilized by a co-emulsifier system consisting of Span™ 80 and Tween™ 80 dispersed in aliphatic hydrocarbons. The initial polymerization medium contains emulsion droplets and inverse micelles which solubilize a part of the monomer solution. The polymerization is then initiated by free radicals, and particle dispersions with a narrow size distribution are obtained. The particle size is dependent on the type of radical initiator used. With water-soluble initiators, for example ammonium persulfate, microparticles are obtained in the size range of 1 to 10 micrometer, indicating that these microparticles originate from the emulsion droplets since the droplet sizes of the W/O emulsion show similar distribution. When lipophilic radical initiators, such as azo-bis-isobutyronitrile, are used, almost exclusively nanoparticles are generated with diameters in the range of 80 to 150 nm, due to the limited solubility of oligomeric poly(acrylic acid) chains in the lipophilic continuous phase. These poly(acrylic acid) micro- and nanoparticles yielded excellent bioadhesive properties in an in-vitro assay and may, therefore, be suitable for the encapsulation of peptides and other hydrophilic drugs.

In the present invention, HA or chondroitin chains would be the natural substitute for poly(acrylic-acid) based materials. HA is a negatively-charged polymer as is poly(acrylic-acid), but HA is a naturally occurring molecule in the vertebrate body and would not invoke an immune response like a poly(acrylic-acid) material.

The interest in realizing 'true' bioadhesion continues: instead of mucoadhesive polymers, plant or bacterial lectins, i.e. adhesion molecules which specifically bind to sugar moieties of the epithelial cell membrane, are now widely being investigated as drug delivery adjuvants. These second-generation bioadhesives not only provide for cellular binding, but also for subsequent endo- and transcytosis. This makes the novel, specifically bioadhesive molecules particularly interesting for the controlled delivery of DNA/RNA molecules in the context of antisense or gene therapy.

For the efficient delivery of peptides, proteins, and other biopharmaceuticals by nonparenteral routes, in particular via the gastrointestinal, or GI, tract, novel concepts are needed to overcome significant enzymatic and diffusional barriers. In this context, bioadhesion technologies offer some new perspectives. The original idea of oral bioadhesive drug delivery systems was to prolong and/or to intensify the contact between controlled-release dosage forms and the stomach or gut mucosa. However, the results obtained during the past decade using existing pharmaceutical polymers for such purposes were rather disappointing. The encountered difficulties were mainly related to the physiological peculiarities of GI mucus. Nevertheless, research in this area has also shed new light on the potential of mucoadhesive polymers. First, one important class of mucoadhesive polymers, poly(acrylic acid), could be identified as a potent inhibitor of proteolytic enzymes. Second, there is increasing evidence that the interaction between various types of bio(muco)adhesive polymers and epithelial cells has direct influence on the permeability of mucosal epithelia. Rather than being just adhesives, mucoadhesive polymers may therefore be considered as a novel class of multifunctional macromolecules with a number of desirable properties for their use as biologically active drug delivery adjuvants.

In the present invention, HA or other glycosaminoglycan polysaccharides are used. As HA is known to interact with numerous proteins (i.e., RHAMM, CD44) found throughout the healthy and diseased body, then naturally occurring adhesive interactions can be utilized to effect targeting, stabilization, or other pharmacological parameters. Similarly, chondroitin interacts with a different subset of proteins (i.e., platelet factor 4, thrombin); it is likely that this polymer will yield properties distinct from HA and widen the horizon of this technology.

In order to overcome the problems related to GI mucus and to allow longer lasting fixation within the GI lumen, bioadhesion probably may be better achieved using specific bioadhesive molecules. Ideally, these bind to surface structures of the epithelial cells themselves rather than to mucus by receptor-ligand-like interactions. Such compounds possibly can be found in the future among plant lectins, novel synthetic polymers, and bacterial or viral adhesion/invasion factors. Apart from the plain fixation of drug carriers within the GI lumen, direct bioadhesive contact to the apical cell membrane possibly can be used to induce active transport processes by membrane-derived vesicles (endo- and transcytosis). The nonspecific interaction between epithelia and some mucoadhesive polymers induces a temporary loosening of the tight intercellular junctions, which is suitable for the rapid absorption of smaller peptide drugs along the paracellular pathway. In contrast, specific endo- and transcytosis may ultimately allow the selectively enhanced transport of very large bioactive molecules (polypeptides, polysaccharides, or polynucleotides) or drug carriers across tight clusters of polarized epi- or endothelial cells, whereas the formidable barrier function of such tissues against all other solutes remains intact.

Bioadhesive systems are presently playing a major role in the medical and biological fields because of their ability to maintain a dosage form at a precise body-site for a prolonged period of time over which the active principle is progressively released. Additional uses for bioadhesives include: bioadhesives/mucoadhesives in drug delivery to the gastrointestinal tract; nanoparticles as a gastroadhesive drug delivery system; mucoadhesive buccal patches for peptide delivery; bioadhesive dosage forms for buccal/gingival administration; semisolid dosage forms as buccal bioadhesives; bioadhesive dosage forms for nasal administration; ocular bioadhesive delivery systems; nanoparticles as bioadhesive ocular drug delivery systems; and bioadhesive dosage forms for vaginal and intrauterine applications.

The bioadhesive may also contain liposomes. Liposomes are unilamellar or multilamellar lipid vesicles which entrap a significant fraction of aqueous solution. The vesicular microreservoirs of liposomes can contain a variety of water-soluble materials, which are thus suspended within the emulsion. The preparation of liposomes and the variety of uses of liposomes in biological systems has been disclosed in U.S. Pat. Nos. 4,708,861, 4,224,179, and 4,235,871. Liposomes are generally formed by mixing long chain carboxylic acids, amines, and cholesterol, as well as phospholipids, in aqueous buffers. The organic components spontaneously form multilamellar bilayer structures called liposomes. Depending on their composition and storage conditions, liposomes exhibit varying stabilities. Liposomes serve as models of cell membranes and also are used as drug delivery systems.

Most attempts to use liposomes as drug delivery vehicles have envisioned liposomes as entities which circulate in blood, to be taken up by certain cells or tissues in which their degradation would slowly release their internal aqueous drug-containing contents. In an effort to aid in their up-take by a given target tissue, some liposomes have been Atailored@ by binding specific antibodies or antigens to the outer surface. Liposomes have also been devised as controlled release systems for the delivery of their contents in vivo. Compositions in which liposomes containing biologically active agents are maintained and immobilized in polymer matrices, such as methylcellulose, collagen and agarose, for sustained release of the liposome contents, are described in U.S. Pat. No. 4,708,861 to Popescu et al.

In this manner, the present invention contemplates a bioadhesive comprising HA or chondroitin or heparin produced from pmHAS, pmCS, pmHS, or PglA. The present invention also contemplates a composition containing a bioadhesive comprising HA or chondroitin or heparin produced from pmHAS, pmCS, pmHS, or PgIA and an effective amount of a medicament, wherein the medicament can be entrapped or grafted directly within the HA or chondroitin or heparin bioadhesive or be suspended within a liposome which is entrapped or grafted within the HA or chondroitin or heparin bioadhesive. These compositions are especially suited to the controlled release of medicaments. Such compositions are useful on the tissues, skin, and mucus membranes (mucosa) of an animal body, such as that of a human, to which the compositions adhere. The compositions so adhered to the mucosa, skin, or other tissue slowly release the treating agent to the contacted body area for relatively long periods of time, and cause the treating agent to be sorbed (absorbed or adsorbed) at least at the vicinity of the contacted body area. Such time periods are longer than the time of release for a similar composition that does not include the HA bioadhesive.

The treating agents useful herein are selected generally from the classes of medicinal agents and cosmetic agents. Substantially any agent of these two classes of materials that is a solid at ambient temperatures may be used in a composition or method of the present invention. Treating agents that are liquid at ambient temperatures, e.g. nitroglycerine, can be used in a composition of this invention, but are not preferred because of the difficulties presented in their formulation. The treating agent may be used singly or as a mixture of two or more such agents.

One or more adjuvants may also be included with a treating agent, and when so used, an adjuvant is included in the meaning of the phrase "treating agent" or "medicament." Exemplary of useful adjuvants are chelating agents such as EDTA that bind calcium ions and assist in passage of medicinal agents through the mucosa and into the blood stream. Another illustrative group of adjuvants are the quaternary nitrogen-containing compounds such as benzalkonium chloride that also assist medicinal agents in passing through the mucosa and into the blood stream.

The treating agent is present in the compositions of this invention in an amount that is sufficient to prevent, cure and/or treat a condition for a desired period of time for which the composition of this invention is to be administered, and such an amount is referred herein as "an effective amount." As is well known, particularly in the medicinal arts, effective amounts of medicinal agents vary with the particular agent involved, the condition being treated and the rate at which the composition containing the medicinal agent is eliminated from the body, as well as varying with the animal in which it is being used, and the body weight of that animal. Consequently, effective amounts of treating agents may not be defined for each agent. Thus, an effective amount is that amount which in a composition of this invention provides a sufficient amount of the treating agent to provide the requisite activity of treating agent in or on the body of the treated animal for the desired period of time, and is typically less than that amount usually used.

Inasmuch as amounts of particular treating agents in the blood stream that are suitable for treating particular conditions are generally known, as are suitable amounts of treating agents used in cosmetics, it is a relatively easy laboratory task to formulate a series of controlled release compositions of this invention containing a range of such treating agent for a particular composition of this invention.

The second principle ingredient of this embodiment of the present invention is a bioadhesive comprising an amount of hyaluronic acid (HA) from pmHAS or chondroitin from PmCS or heparin from pmHS or PgIA. Such a glycosaminoglycan bioadhesive made from a HA or chondroitin or heparin chain directly polymerized onto a molecule with the desired pharmacological property or a HA or chondroitin or heparin chain polymerized onto a matrix or liposome which in turn contains or binds the medicament.

Although the foregoing invention has been described in detail by way of illustration and example for purposes of clarity of understanding, it will be obvious to those skilled in the art that certain changes and modifications may be practiced without departing from the spirit and scope thereof, as described in this specification and as defined in the appended claims below.

REFERENCES

The following references, to the extent that they provide exemplary procedural or other details supplementary to those set forth herein, are specifically incorporated herein by reference in their entirety as though set forth herein particular.

Altschul, S. F., W. Gish, W. Miller, E. W. Meyers and D. J. Lipman. (1990) *J. Mol. Biol.* 215, 403-410.

Arrecubieta, C., T. C. Hammarton, B. Barrett, S. Chareonsudjai, N. Hodson, D. Rainey, and I. S. Roberts. (2001) The transport of the Group 2 capsular polysaccharides across the periplasmic space in *Escherichia coli. J. Biol. Chem.*, 276, 4245-4250.

Asplund, T., J. Brinck, M. Suzuki, M. J. Briskin, and P. Heldin. (1998) *Biochim. Biophys.* Acta. 1380, 377-388.

Atkinson, E. M. and S. R. Long. (1992) *Mol. Plant-Microbe Interact.* 5, 439-442.

Ausubel, F. M., R. Brent, R. E. Kingston, D. D. Moore, J. G. Seidman, J. A. Smith, and K. Struhl. (1995) *Short Protocols in Molecular Biology*, 3$^{rd}$ Ed., John Wiley & Sons Inc., New York.

Azad, A. K., J. G. Coote, and R. Parton. Construction of conjugative shuttle and suicide vectors for *Pateurella haemolytica* and *P. Multocida. Gene* 1994; 145: 81-5.

Bertram, J., M. Stratz, and P. Durre. Natural transfer of conjugative transposon Tn916 between Gram-positive and Gram-negative bacteria. *J. Bact* 1991; 173: 443-8.

Bitter, T. and H. M. Muir. (1962) *Anal. Biochem.* 4, 330-334.

Bradford, M. M., (1976) *Anal. Biochem.* 72, 248-254.

Breton, C. and A. Imberty. (1999) *Curr. Opin. Struc. Biol.* 9, 563-571.

Bulawa, C. E. (1992) *Mol. Cell. Biol.* 12, 1764-1776.

Busch, C., F. Hofmann, J. Seizer, S. Munro, S. Jeckel, and K. Aktories. (1998) A common motif of eukaryotic glycosyltransferases is essential for the enzyme activities of large clostridial cytotoxins. *J. Biol. Chem.*, 273, 19566-19572.

Campbell, R. E., S. C. Mosimann, I. van de Rijn, M. E. Tanner, and N. C. J. Strynadke. (2000) *Biochemistry* 39, 7012-7023.

Carter, G. R. and E. Annau. (1953) *Am. J. Vet Res.* 14, 475-478.

Charnock, S. J. and G. J. Davies. Structure of the nucleotide-diphospho-sugar transferases, spsA from *Bacillus subtilis*, in native and nucleotide complexed forms. *Biochemistry*, 38, 6380-6385, 1999.

Charnock, S. J. and G. J. Davies. (1999) Structure of the nucleotide-diphospho-sugar transferases, spsA from *Bacillus subtilis*, in native and nucleotide-complexed forms. *Biochemistry*, 38, 6380-6385.

Chung, J. Y., I. Wilkie, J. D. Boyce, K. M. Townsend, A. J. Frost, M. Ghoddusi, and B. Adler. (2001) Role of capsule in the pathogenesis of fowl cholera caused by *Pasteurella multocida* Serogroup A. *Infect. Immun.*, 69, 2487-2492.

Cleary, P. P., and A. Larkin. (1979) Hyaluronic acid capsule: strategy for oxygen resistance in Group A Streptococci. *J. Bacteriol*, 140, 1090-1097.

Corpet, F. (1998) *Nucleic Acids Res.* 16, 10881-10890.

Crater, D. L., and I. van de Rijn. (1995) *J. Biol. Chem.* 270, 18452-18458.

DeAngelis, P. L., M. H. Graves, and J. L. Van Etten, unpublished results.

DeAngelis, P. L., J. Papaconstantinou, and P. H. Weigel. Isolation of a *Streptococcus pyogenes* gene locus that directs hylauronan biosynthesis in acapsular mutants and in heterologous bacteria. *J. Biol. Chem.,* 268, 14568-14571, 1993.

DeAngelis, P. L., J. Papaconstantinou, and P. H. Weigel. Molecular cloning, identification and sequence of the hyaluronan synthase gene from Group A *Streptococcus pyogenes*. *J. Biol. Chem.,* 268, 19181-19184, 1993.

DeAngelis, P. L., N. Yang, and P. H. Weigel. (1994) *Biochem. Biophys. Res. Commun.* 199, 1-10.

DeAngelis, P. L. and P. H. Weigel. Immunochemical confirmation of the primary structure of *streptococcal* hyaluronan synthase and synthesis of high molecular weight product by the recombinant enzyme. *Biochemistry,* 33, 9033-9039, 1994.

DeAngelis, P. L. and P. H. Weigel. (1994) *Diagn. Microbio. Infect Dis.* 20, 77-80.

DeAngelis, P. L., W. Jing, M. V. Graves, D. E. Burbank, and J. L. Van Etten. Hyaluronan synthase of chlorella virus PBCV-1. *Science,* 278, 1800-1803, 1997.

DeAngelis, P. L. Hyaluronan synthases: fascinating glycosyltransferases from vertebrates, bacterial pathogens and algal viruses. *Cell. Mol. Life Sci.,* 56, 670-682, 1999.

DeAngelis, P. L. Microbial glycosoaminoglycan glycosyltransferases. *Glycobiology.* 12(1):9R-16R. Review. 2002.

DeAngelis, P. L., and C. L. White. Identification and molecular cloning of a heparosan synthase from *Pasteurella multocida* type D. *J. Biol. Chem.* 277(9):7209-13, 2002.

DeAngelis, P. L. Polysachharide labeling with N-methylisatioic anyhydride: generation of ultraviolet chromophores and blue fluorophores. *Anal. Biochem.* 284(1):167-9, 2000.

DeAngelis, P. L. and A. J. Padgett-McCue. Identification and molecular cloning of a chondroitin synthase from Pasteurelia multocida type F. *J. Biol. Chem.* 275(31):24124-9, 2000.

DeAngelis, P. L. Molecular directionality of polysaccharide polymerization by the *Pasteurella multocida* hyaluronan synthase. *J. Biol. Chem.* 274(37); 26557-62, 1999.

DeAngelis, P. L. *J. Biol. Chem.* 274, 26557-26562, 1999.

DeAngelis P. L. Transposon Tn916 insetional mutagenesis of *Pasteurella multocida* and direct sequencing of disruption site. *Microb. Pathog.* 24(4):203-9, 1998.

DeAngelis, P. L., W. Jing, R. R. Drake, and A. M. Achyuthan. Identification and molecular cloning of a unique hyaluronan synthase from *Pasturella multocida*. *J. Biol. Chem.* 273(14):8454-8, 1998.

DeAngelis, P. L., W. Jing, M. V. Graves, D. E. Burbank, and J. L. Van Etten. Hyaluronan synthase of chlorella virus PBCV-1. *Science.* 278(5344):1800-3, 1997.

DeAngelis, P. L., and A. M. Achyuthan. Yeast-derived recombinant DG42 protein of *Xenopus* can synthesize hyaluronan in vitro. *J. Biol. Chem.* 271(39):23657-60, 1996.

DeAngelis, P. L. Enzymological characterization of the *Pasteurella multocida* hyaluronic acid synthase. *Biochemistry.* 35(30):9768-71, 1996.

DeLuca, S. and J. E. Silbert. (1968) *J. Biol. Chem.* 243, 2725-2729.

Doughtery, B. A., and I. van de Rijn. (1994) Molecular characterization of hasA from an operon required for hyaluronic acid synthesis in Group A Streptococci. J. Biol. Chem., 269, 169-175.

Drake, C. R., I. S. Roberts, B. Jann, K. Jann, and G. J. Boulnois (1990) Molecular cloning and expression of the genes encoding the *Escherichia coli* K4 capsular polysaccharide, a fructose-substituted chondroitin. *FEMS Microbiol. Lett.,* 54, 227-230.

Duncan, G., C. McCormick, and F. Tufaro. (2001) The link between heparan sulfate and hereditary bone disease: finding a function for the EXT family of the putative tumor suppressor proteins. *J. Clin. Invest.,* 108, 511-516.

Ehtesham, N. Z., and S. E. Hasnain. Direct in-gel hybridization without blotting, using nick-translated cloned DNA probe. *BioTechniques* 1991; 11: 718-21.

Esko, J. D. and U. Lindahl. (2001) Molecular diversity of heparan sulfate. *J. Clin. Invest.* 108, 169-173.

Finke, A., D. Bronne, A. V. Nikolaev, B. Jann, and K. Jann. (1991) Biosynthesis of the *Escherichia coli* K5 polysaccharide, a representative of group II capsular polysaccharides: polymerization in vitro and characterization of the product. *J. Bacteriol.,* 173, 4088-4094.

Fleischmann, R. D., M. D. Adams, and O. White, et al. Whole genome random sequencing and assembly of *Haemophilus influenzae* Rd. *Science* 1995; 269: 496-512.

Franke, A. E. and D. B. Clewell. Evidence for chromosome-borne resistance transposon in *Streptococcus faecalis* capable of >conjugal=transfer in the absence of conjugative plasmid. *J. Bact.* 1981; 145: 494-502.

Gastinel, L. N., C. Cambillau, and Y. Bourne. (1999) *EMBO J.* 18, 3546-3557.

Gastinel, L. N., C. Bignon, A. K. Misra, O. Hindsgaul, J. H. Shaper, and D. H. Joziasse. (2001) *EMBO J.* 20, 638-649.

Gawron-Burke, C. And D. B. Clewell. Regeneration of insertionally inactivated *streptococcal* DNA fragments after excision of transposon Tn916 in *Escherichia coli*: strategy for targeting and cloning of genes from gram positive bacteria. *J. Bact.* 1984; 159: 214-21.

Gherezghiher, T., M. C. Koss, R. E. Nordquist, and C. P. Wilkinson. (1987) *J. Chromatogr.* 413, 9-15.

Gietz, R. D., R. H. Schiestl, A. R. Willems, and R. A. Woods. (1995) *Yeast* 11, 355-360.

Graves, M. H., D. D. Landstein, J. L. Van Etten, unpublished results.

Griffiths, G., N. J. Cook, E. Gottfridson, T. Lind, K. Lidholt, and I. S. Roberts. Characterization of the glycosyltransferase enzyme from the *Escherichia coli* K5 capsule gene cluster and identification and characterization of the flucuronyl active site. *J. Biol. Chem.,* 273, 11752-11757, 1998.

Hagopian, A. and E. H. Eylar. Glycoprotein biosynthesis: studies on the receptor specificity of the polypeptidyl: N-acetylgalactosaminyl transferase from bovine submaxillary glands. *Arch. Biochim. Biophys.,* 128, 422-433.

Hall, N. A. and A. D. Patrick. (1989) *Anal. Biochem.* 178, 378-384.

Hansen, L. M. and D. C. Hirch. (1989) *Vet. Microbiol.* 21, 177-184.

Hardingham, T. E. and A. J. Fosang. (1992) *FASEB J.* 6, 861-870.

Harmon, B. G., J. Glisson, K. S. Latimer, W. L. Stephens, and J. C. Nunnally. (1991) *Am. J. Vet. Res.* 52, 1507-1511.

Hascall, V. C. and G. K. Hascall. (1981) in Cell Biology of *Extracellular Matrix* (Hay, E. D., ed) pp. 39-78, Plenum Publishing Corp. New York.

Heldermon, C. D., P. L. DeAngelis, and P. H. Weigel. (1997) *Glycobiology* 7, 1032.

Heldermon, C., P. L. DeAngelis, and P. H. Weigel. (2001) Topological organization of the hyaluronan synthase from *Streptococcus pyogenes*. *J. Biol. Chem.*, 276, 2037-2046.

Hempel, J., J. Perozich, H. Romavacek, A. Hinich, I. Kuo, and D. S. Feingold. (1994) *Protein Sci.* 3, 1074-1080.

Herias, M. V., T. Midtvedt, L. A. Hanson, and A. E. Wold. (1997) *Escherichia coli* K5 capsule expression enhances colonization of the large intestine in the gnotobiotic rat. Infect. Immun., 65, 531-536.

Hodson, N., G. Griffiths, N. Cook, M. Pourhossein, E. Gottfridson, T. Lind, K. Lindholt, and I. S. Roberts. (2000) Identification that KfiA, a protein essential for the biosynthesis of the *Escherichia coli* K5 capsular polysaccharide, is an alpha-UDP-GlcNAc glycosyltransferase. The formation of a membrane-associated K5 biosynthetic complex requires KfiA, KfiB, and KfiC. J. Biol. Chem., 275, 27311-27315.

Hofmann, K. and W. Stoffel. (1993) *Biol. Chem.* Hoppe-Seyler 347, 166 (abstr.)

Holland, J., K. J. Towner, and P. Williams. Tn916 insertion mutagenesis in *Escherichia coli* and *Haemophilus influenzae* type b following conjugative transfer. J. Gen. Microb. 1992; 138: 509-515.

Husmann, L. K., D. L. Yung, S. K. Hollingshead, and J. R. Scott. (1997) Role of putative virulence factors of *Streptococcus pyogenes* in mouse models of long-term throat colonization and pneumonia. *Infect. Immun.*, 65, 1422-1430.

Itano, N., T. Sawai, M. Yoshida, P. Lenas, Y. Yamada, M. Imagawa, T. Shinomura, M. Hamaguchi, Y. Yoshida, Y. Ohnuki, S. Miyauchi, A. P. Spicer, J. A. McDonald, and K. Kimata. (1999) *J. Biol. Chem.* 274, 25085-25092.

Jablonski, L., N. Sriranganathan, S. M. Bole, and G. R. Carter. Conditions for transformation of *Pasteurella multocida* by electroporation. *Microb. Pathog.* 1992; 12: 63-8.

Jing, W. and P. L. DeAngelis. Dissection of the two transferase activities of the *Pasturella multocida* hyaluronan synthase: two active sites exist in one polypeptide. *Glycobiology.* 10(9):883-9, 2000.

Kass, E. H. and C. V. Seastone. (1944) J. Exp. Med. 79, 319-330. Kathariou, S., P. Metz, H. Hof, and W. Goebel. Tn916 induced mutations in the hemolysin determinant affecting virulence of *Listeria monocytogenes. J. Bact.* 1987; 169: 1291-7.

Kauc, L. and S. H. Goodgal. Introduction of transposon Tn916 DNA into *Haemophilus influenzae* and *Haemophilus parainfluenzae. J. Bact.* 1989; 171: 6625-8.

Kendall, F. E., M. Heidelberger, and M. H. Dawson. (1937) A serologically inactive polysaccharide elaborated by mucoid strains of Group A *Streptococcus. J. Biol. Chem.*, 118, 61-69.

Kitagawa, H., T. Uyama, and K. Sugahara. (2001) Molecular cloning and expression of a human chondroitin synthase. *J. Biol. Chem.*, 276, 38721-38726.

Knudson, C. B. and W. Knudson (1993) *FASEB. J.* 7, 1233-1241.

Koyama, M., W. Helbert, T. Imai, J. Sugiyama, and B. Henrissat. (1997) *Proc. Natl. Acad. Sci. U.S.A.* 94, 9091-9095.

Kroll, J. S., B. Loynds, L. N. Brophy, and E. R. Moxon. (1990) *Mol. Microbiol.* 4, 1853-1862.

Kumari, K. and P. H. Weigel. (1997) Molecular cloning, expression, and characterization of the authentic hyaluronan synthase from Group C *Streptococcus equisimilis. J. Biol. Chem.*, 272, 32539-32546.

Kumari, K., Tlapak-Simmons, V. L., B. A. Baggenstoss, and P. H. Weigel. (2002) J. Biol. Chem. 277, 13943-13951.

Landstein, D., P. L. DeAngelis, and J: L. Van Etten, in preparation.

Laurent, T. C., and J. R. E. Fraser. (1992) *FASEB J.* 6, 2397-2404.

Lee, C. J. (1987) Bacterial capsular polysaccharides-biochemistry, immunity and vaccine. *Mol. Immunol.*, 24, 1005-1019.

Lee, M. D. and A. D. Henk. Tn10 insertional mutagenesis in *Pasteurella multocida. Vet. Microbiol.* 1996; 50:143-8.

Li, J., D. M. Rancour, M. L. Allende, C. A. Worth, D. S. Darling, J. B. Gilbert, A. K. Menon and W. W. Young Jr. (2001) The DxD motif is required for GM2 synthase activity but is not critical for nucleotide binding. *Glycobiology*, 11, 217-229.

Lidholt, K. (1997) *Biochem. Soc. Trans.* 25, 866-870.

Lidholt, K. and M. Fjelstad. (1997) Biosynthesis of the *Escherichia coli* K4 capsule polysaccharide. A parallel system for sutdies of gylcosyl-transferases in chondroitin formation. *J. Biol. Chem.* 272, 2682-2687.

Lidholt, K. and U. Lindahl. (1992) *Biochem J* 287, 21-29.

Lindahl, U. and M. Hook. (1978) *Annu. Rev. Biochem.* 47, 385-417.

Lind, T., U. Lindahl, and K. Lidholt. (1993) *J. Biol. Chem.* 268, 20705-20708.

Lind, T., Tufaro, F., McCormick, C., Lindahl, U., and K. Lidholt. (1998) *J. Biol. Chem.* 273, 11752-11757.

Ludwigs, U., A. Elgavish, J. D. Esko, E. Meexan, and L. Roden. Reaction of unsaturated uronic acid residues with mercuric salts. Cleavage of the hyaluronic acid disaccharide 2-acetamido-2-deoxy-3-O-(β-D-gluco-4-enepyranosyluronic acid)-D-glucose. *Biochem. J.*, 245, 795-804, 1987.

Marks, D. L., M. Dominguez, K. Wu, and R. E. Pagano. (2001) *J. Biol. Chem.* 276, 26492-26498.

Markovitz, A., J. A. Cifonelli, and A. Dorfman. (1959) *J. Biol. Chem.* 234, 2343-2350.

May, B. J., Q. Zhang, L. Li, M. L. Paustian, T. S. Whittam, and V. Kapur. (2001) *Proc. Natl. Acad. Sci. U.S.A.* 98, 3460-3465.

Meyer, M. F., and G. Kreil (1996) *Proc. Natl. Acad. Sci. U.S.A.* 93, 4543-4547.

Morera, S., A. Imberty, U. Aschke-Sannenborn, P. S. Freemont, J. Janin, and W. Ruger. (1999) *J. Mol. Biol.* 311, 569-577.

Morera, S. L. Lariviere, J. Kurzeck, U. Aschke-Sannenborn, P. S. Freemont, J. Janin, and W. Ruger. (2001) *J. Mol. Biol.*, 311, 569-577.

Nnalue, N. A., and B. A. Stocker. Transfer and properties of some natural and suicide replicons in *Pasteurella multocida. J. Gen. Microb.* 1989; 135: 3345-52.

Nnalue, N. A. Tn7 inserts in both orientations at a single chromosomal location and apparently forms co-integrates in *Pasteurella multocida. Mol. Microbiol.* 1990; 4: 107-17.

Norgren, M. and J. R. Scott. The presence of conjugative transposon Tn916 in the recipient strain does not impede transfer of a second copy of the element. *J. Bact.* 1991; 173: 319-324.

Ohya, T. and Y. Kaneko. (1970) *Biochim. Biophys. Acta* 198, 607-609.

Ohman. (1987) Bacterial virulence versus host resistance in the urinary tracts of mice. *Infect Immun.*, 55, 1224-1232.

Pedersen, L. C., K. Tsuchida, H. Kitagawa, K. Sugahara, T. A. Darden, and M. Negishi. (2000) Heparan/chondroitin sulfate biosynthesis. Structure and mechanism of human glucuronyltransferase I. *J. Biol. Chem.*, 275, 34580-34585.

Persson, K., H. D. Ly, M. Dieckelmann, W. W. Wakarchuk, S. G. Withers, and N. C. J. Strynadka. (2001) *Nat. Struct. Biol.* 8, 166-175.

Petit, C., G. P. Rigg, C. Pazzani, A. Smith, V. Sieberth, M. Stevens, G. Boulnois, K. Jann, and I. S. Roberts. Region 2 of the *Escherichia coli* K5 capsule gene cluster encoding proteins for the biosynthesis of the K5 polysaccharide. *Mol. Microbiol.*, 17, 611-620.

Prehm, P. (1983) *Biochem. J.* 211, 181-189.

Prehm, P. (1983) *Biochem. J.* 211, 191-198.

Pruimboom, I. M., R. B. Rimler, and M. R. Ackerman. (1999) Enhanced adhesion of *Pasteurella multocida* to cultured turkey peripheral blood monocytes. *Infect Immun.*, 67, 1292-1296.

Pummill, P. E., and P. L. DeAngelis. Evaluation of Critical Structural Elements of UDP-Sugar Substrates and Certain Cysteine Residues of a Vertebrate Hyaluronan Synthase. *J. Biol. Chem.* 277(24):21610-6, 2002.

Pummill P. E., A. M. Achyuthan, and P. L. DeAngelis. Enzymological characterization of recombinant xenopus DG42, a vertebrate hyaluronan synthase. *J. Biol. Chem.* 273(9): 4976-81, 1998.

Quinn, A. W., and K. P. Sing. (1957) *Proc. Soc. Exp. Biol. Med.* 95, 290-294.

Radominska, A. and R. R. Drake. (1994) *Methods Enzymol.* 230, 330-339.

Rahemtulla, F. and S. Lovtrup. (1975) *Comp. Biochem. Physiol.* 50B, 631-635.

Ramakrishnan, B. and P. Qasba. (2001) *J. Mol. Biol.* 310, 205-218.

Rimler, R. B. (1994) Presumptive identification of *Pasteurella multocida* Serogroups A, D and F by capsule depolymerisation with mucopolysaccharidases. *Vet. Rec.* 134, 191-192.

Rimler, R. B. and K. R. Rhodes. (1987) *J. Clin. Microbiol.* 25, 615-618.

Rimler, R. B. (1994) *Vet Rec.* 134, 191-192.

Rimler, R. B., K. B. Register, T. Magyar, and M. R. Ackermann. (1995) *Vet. Microbiol.* 47, 287-294.

Roberts, I. S. (1996) The biochemistry and genetics of capsular polysaccharide production in bacteria. *Annu. Rev. Microbiol.* 50, 285-315.

Roberts, I. S., R. Mounfford, R. Hodge, K. B. Jann, and G. Boulnois. (1988) *J. Bacteriol.* 170, 1305-1310.

Roden, L. (1980) in *The Biochemistry of Glycoproteins and Proteoglycans* (Lennarz, W. J., ed) pp. 267-371, Plenum Publishing Corp. New York.

Rodriguez, M. L, B. Jann, and K. Jann. (1988) Structure and serological characteristics of the capsular K4 antigen of *Escherichia coli* O5: K4: H4, a fructose-containing polysaccharide with a chondroitin backbone. *Eur. J. Biochem.* 177, 117-124.

Rohozinski, J., L. E. Girton, and J. L. Van Etten. *Virology* 168, 363 (1989).

Rosa, F., T. D. Sargent, M. L. Rebbert, G. S. Michaels, M. Jamrich, H. Grunz, E. Jonas, J. A. Winkles, and I. B. Dawid. (1988) *Dev. Biol.* 129, 114-123.

Rosner, H., H. D. Grimmecke, Y. A. Knirel, and A. S. Shashkov. (1992) *Carbohydr. Res.* 223, 329-333.

Sambrook, J., E. F. Fritshc, and T. Maniatis. *Molecular Cloning: A Laboratory Manual*, $2^{nd}$ edn. Cold Spring Harbor, N.Y.: Cold Spring Laboratory Press. 1989.

Saxena, I. M., R. M. Brown, M. Fevre, R. A. Geremia, and B. Henrissat. Multidomain architecture of β-glycosyl transferases: implications for mechanism of action. *J. Bacteriol.*, 177, 1419-1424, 1995.

Scott, J. R. Sex and the single circle: conjugative transposition. *J. Bact* 1992; 174: 6005-10.

Semino, C. E. and P. W. Robbins. (1995) *Proc. Natl. Acad. Sci. U.S.A.* 92, 3498-3501.

Semino, C. E., C. A. Specht, A. Raimondi, and P. W. Robbins. (1996) *Proc. Natl. Acad. Sci. U.S.A.* 93, 4548-4553.

Senghas, E., J. M Jones, M. Yamamoto, C. Gawron-Burke, and D. B. Clewell. Genetic organization of the bacterial conjugative transposon Tn916. *J. Bact* 1988; 170: 245-9.

Semino, C. E., C. A. Specht, A. Raimondi, and P. W. Robbins. (1996) Proc. Natl. Acad. Sci. U.S.A. 93, 4548-4553.

Silbert, J. E. and S. DeLuca. (1968) *J. Biol. Chem.* 243, 2725-2729.

Silver, R. P., K. Prior, C. Nsahlai, and L. F. Wright. (2001) ABC transporters and the export of capsular polysaccharides from gram-negative bacteria. *Res. Microbiol.*, 152, 357-364.

Skrdla, M. P., D. E. Burbank, Y. Xia, R. H. Meints, and J. L. Van Etten. *Virology* 135, 308 (1984); I.-N Wang et al., *Proc. Natl. Acad. Sci. U.S.A.* 90, 3840 (1993).

Snipes, K. P., G. Y. Ghazikhanian, and D. C. Hirch. (1986) *Avian Dis.* 31, 254-259.

Spicer, A. P. and J. A. McDonald. (1998) *J. Biol. Chem.* 273, 1923-1932.

Stoolmiller, A. C. and A. Dorfman. (1969) The biosynthesis of hyaluronic acid by *Streptococcus*. *J. Biol. Chem.* 244, 236-346.

Sugahara, K., N. B. Schwartz and A. Dorfman. (1979) Biosynthesis of hyaluronic acid by *Streptococcus*. *J. Biol. Chem.* 254, 6252-6261.

Sugarman, G., M. Katsman, P. Sunthankar, and R. R. Drake. (1997) *J. Biol. Chem.* 272, 14399-14403.

Sunthankar, P. I. Pastuszak, A. Rooke, A. D. Elbein, I. van de Rijn, W. M. Canfield, and R. R. Drake. (1998) Synthesis of 5-azido-UDP-N-acetylhexosamine photoaffinity analogs and radiolabeled UDP-N-acetylhexosamines. *Anal. Biochem.*, 258(2): 195-201.

Svanborg-Eden, C., L. Hagberg, R. Hull, S. Hull, K. E. Magnusson, and L. Tarbouriech, N., S. J. Charnock, and G. J. Davies. (2001) *J. Mol. Biol.* 314, 655-661.

Taylor, K. A., and J. G. Buchanan-Smith. (1992) *Anal. Biochem.* 201, 190-196.

Telser, A., H. C. Robinson, and A. Dorfman. (1965) *Proc. Natl. Acad. Sci. U.S.A.* 54, 912-919.

Tengblad, A. (1980) *Biochem. J.* 185, 101-105.

Tlapak-Simmons, V. L., E. S. Kempner, B. A. Baggenstoss, and P. H. Weigel. (1998) The active *streptococcal* hyaluronan synthases (HASs) contain a single HAS monomer and multiple cardiolipin molecules. *J. Biol. Chem.*, 273, 26100-26109.

Tlapak-Simmons, V. L., B. A. Baggenstoss, K. Kumari, C. Heldermon, and P. H. Weigel. (1999) *J. Biol. Chem.* 274, 4246-4253.

Townsend, K. M., J. D. Boyce, J. Y. Chung, A. J. Frost, and B. Adler. (2001) Genetic organization of *Pasteurella multocida* cap loci and develpment of a multiplex capsular PCR typing system. *J. Clin. Microbiol.*, 39, 924-929.

Tsuchida, K., T. Lind, H. Kitagawa, U. Lindahl, K. Sugahara, and K. Lindholt. (1999) *Eur. J. Biochem.* 264, 461-467.

Unligil, U. M. and J. M. Rini. (2000) *Curr. Opin. Struct. Biol.* 10, 510-517.

Unligil, U. M., S. Zhou, S. Yuwaraj, M. Sarkar, H. Schachter, and J. M. Rini. (2000) *EMBO J.* 19, 5269-5280.

van de Rijn, I. and R. R. Drake (1992) *J. Biol. Chem.* 267, 24302-24306.

van de Rijn, I. and R. E. Kessler. (1980) *Infect Immun.* 27, 444-448.

Van Etten, J. L., D. E. Burbank, A. M. Schuster, and R. H. Meints, *Virology*, 140, 135 (1985).

Vann, W. F., M. A. Schmidt, B. Jann, and K. Jann. (1981) The structure of the capsular polysaccharide (K5 antigen) of urinary-tract-inefective *Escherichia coli* O10: K5: H4. A polymer similar to desulfo-heparin. *Eur. J. Biochem.* 116, 359-364.

Varki, A. (1996) *Proc. Natl. Acad. Sci. U.S.A.* 93, 4523-4525.

Vimr, E. R., W. Aaronson, and R. P. Silver. (1989) *J. Bacteriol.* 171, 1106-1117.

Vrielink, A., W. Ruger, H. P. C. Driessen, and P. S. Freemont. (1994) *EMBO J.* 15, 3413-3422.

Watson, D. A. and D. M. Musher. Interruption of capsule production in *Streptococcus pneumoniae* serotype 3 by insertion of transposon Tn916. *Infect. Immun.* 1990; 58: 3135-8.

Weigel, P. H., V. C. Hascall, and M. Tammi. Hyaluronan synthases. *J. Biol. Chem.*, 272, 13997-14000, 1997.

Wessels, M. R., A. E. Moses, J. B. Goldberg, and T. J. DiCesare. (1991) *Proc. Natl. Acad. Sci. U.S.A.* 88, 8317-8321.

Wessels, M. R., J. B. Goldberg, A. E. Moses, and T. J. DiCesare. (1994) Effects on virulence of mutations in a locus essential for hyaluronic acid capsule expression in Group A Streptococci. *Infect. Immun.*, 62, 433-441.

Whitfield, C. and I. S. Roberts. (1999) Structure, assembly and regulation of expression of capsules in *Escherichia coli*. *Mol. Microbiol.*, 31, 1307-1319.

Wiggins, C. A. R., and S. Munro. (1998) *Proc. Natl. Acad. Sci. U.S.A.* 95, 7945-7950.

Wilson, K. Preparation of genomic DNA from bacteria. In: Ausbel F M, Brent R, Kingston R E, et al., Eds. *Current Protocols in Molecular Biology*. New York: Wiley Interscience Publishing, 1987:2.4.1-2.4.5.

Wilson, M. A., M. J. Morgan, and G. E. Barger. Comparison of DNA fingerprinting and serotyping for identification of avian *Pasteurella multocida* isolates. *J. Clin. Microbiol.* 1993; 31: 255-9.

Yamada, T., T. Higashiyama, and T. Fukuda, *Appl. Environ. Microbiol.* 57, 3433 (1991).

Yoshida, M., N. Itano, Y. Yamada, and K. Kimata. In vitro synthesis of hyaluronan by a single protein derived from mouse HAS1 gene and characterization of amino acid residues essential for the activity. *J. Biol. Chem.,* 255, 497-506, 2000.

Zhang, Y., P. Strasser, R. Grabherr, and J. L. Van Eften. *Virology* 202, 1079 (1994).

What is claimed is:

1. A method for enzymatically producing a hyaluronic acid polymer in vitro, wherein the hyaluronic acid polymer is composed of less than about 150 sugars, comprising the steps of:
   providing a functional acceptor, wherein the functional acceptor has at least two sugar units selected from the group consisting of uronic acid and hexosamine;
   providing a hyaluronic acid synthase capable of elongating the functional acceptor, wherein the hyaluronic acid synthase is selected from the group consisting of:
   (a) a hyaluronic acid synthase having the amino acid sequence as set forth in SEQ ID NO:2;
   (b) a hyaluronic acid synthase encoded by the nucleotide sequence as set forth in SEQ ID NO:1;
   (c) a truncated form of (a) encoded by the nucleotide sequence as set forth in any of SEQ ID NOS:20, 27-30 and 71;
   (d) a truncated form of (a) having the amino acid sequence as set forth in SEQ ID NO:9;
   (e) a mutated form of (a) encoded by the nucleotide sequence as set forth in SEQ ID NO:42; and
   (f) a hyaluronic acid synthase encoded by a nucleotide sequence capable of hybridizing to the complement of the nucleotide sequence of SEQ ID NO:1 under hybridization conditions selected from the group consisting of:
      (i) 5×SSC/5× Denhardt's solution/1.0% SDS at 68° C., followed with washing in 0.2×SSC/0.1% SDS at room temperature;
      (ii) 1.8×HPB at about 30° C. to about 45° C. followed by washing in 0.2-0.5×HPB at about 45° C.; and
      (iii) 5×SSC/5× Denhardt's solution/1% SDS at 68° C., followed with washing in 3×SSC at 42° C.; and
   providing UDP-GlcUA and UDP-GlcNAc sugars such that the hyaluronic acid synthase elongates the functional acceptor to provide a hyaluronic acid polymer wherein the hyaluronic acid polymer is composed of less than about 150 sugars.

2. The method of claim 1 wherein, in the step of providing a functional acceptor, uronic acid is further defined as a uronic acid selected from the group consisting of GlcUA, IdoUA, and GalUA, and hexosamine is further defined as a hexosamine selected from the group consisting of GlcNAc, GalNAc, GlcN and GalN.

3. The method of claim 1, wherein the hyaluronic acid polymer is composed of from about 50 to about 150 sugars.

4. The method of claim 1, wherein the hyaluronic acid polymer is composed of from about 15 to 50 sugars.

5. The method of claim 1, wherein the hyaluronic acid polymer is composed of from about 10 to 14 sugars.

6. The method of claim 1 wherein, in the step of providing the functional acceptor, the functional acceptor has at least three sugar units.

7. The method of claim 1 wherein the hyaluronic acid synthase is immobilized and the at least one of UDP-GlcUA and UDP-GlcNAc are in liquid phase.

8. The method of claim 1 wherein the functional acceptor is immobilized and the at least one of UDP-GlcUA and UDP-GlcNAc and the hyaluronic acid synthase are in liquid phase.

9. The method of claim 1, further comprising the step of providing a divalent metal ion selected from the group consisting of manganese, magnesium, cobalt, nickel and combinations thereof, and wherein the method occurs in a buffer having a pH of from about 6 to about 8.

10. A method for producing a chimeric or hybrid glycosaminoglycan having a non-natural structure, wherein the chimeric or hybrid glycosaminoglycan comprises at least one sugar not found in a single naturally occurring glycosaminoglycan, the method comprising the steps of:
   providing a functional acceptor, wherein the functional acceptor has at least two sugar units selected from the group consisting of uronic acid and hexosamine, and wherein at least one of the at least two sugar units is a sugar unit other than GlcUA and GlcNAc;
   providing at least one hyaluronic acid synthase selected from the group consisting of:
   (a) a hyaluronic acid synthase having the amino acid sequence as set forth in SEQ ID NO:2;
   (b) a hyaluronic acid synthase encoded by the nucleotide sequence as set forth in SEQ ID NO:1;
   (c) a truncated form of (a) encoded by the nucleotide sequence as set forth in any of SEQ ID NOS:20, 27-30 and 71;
   (d) a truncated form of (a) having the amino acid sequence as set forth in SEQ ID NO:9;
   (e) a mutated form of (a) encoded by the nucleotide sequence as set forth in SEQ ID NO:42;
   (f) a hyaluronic acid synthase encoded by a nucleotide sequence capable of hybridizing to the complement of the nucleotide sequence of SEQ ID NQ:1 under hybridization conditions selected from the group consisting of:
      (i) 5×SSC/5× Denhardt's solution/1.0% SDS at 68° C., followed with washing in 0.2×SSC/0.1% SDS at room temperature;
      (ii) 1.8×HPB at about 30° C. to about 45° C. followed by washing in 0.2-0.5×HPB at about 45° C.; and
      (iii) 5×SSC/5× Denhardt's solution/1% SDS at 68° C., followed with washing in 3×SSC at 42° C.; and
   (g) at least one modified hyaluronic acid synthase, wherein the at least one modified hyaluronic acid synthase is a single action glycosyltransferase capable of adding only one of GlcUA or GlcNAc to a functional acceptor, and wherein the at least one modified hyaluronic acid synthase is selected from the group consisting of:
      (i) a modified hyaluronic acid synthase having the nucleotide sequence as set forth in any of SEQ ID NQS:10-12, 16-19, 31-41, and 43-50; and
      (ii) a modified hyaluronic acid synthase encoded by a nucleotide sequence capable of hybridizing to the complement of the nucleotide sequence of SEQ ID NO:1 under the hybridization conditions of (f);
   providing at least one of UDP-GlcUA and UDP-GlcNAc such that the at least one hyaluronic acid synthase elongates the functional acceptor in a manner so as to provide a chimeric or hybrid glycosaminoglycan having a non-natural structure whereby the chimeric or hybrid glycosaminoglycan comprises at least one sugar not found in a naturally occurring hyaluronic acid polymer.

* * * * *

UNITED STATES PATENT AND TRADEMARK OFFICE
CERTIFICATE OF CORRECTION

PATENT NO. : 7,741,091 B2
APPLICATION NO. : 11/698311
DATED : June 22, 2010
INVENTOR(S) : Paul L. DeAngelis and Wei Jing Page 1 of 4

It is certified that error appears in the above-identified patent and that said Letters Patent is hereby corrected as shown below:

In the Drawings:
Replace Figures 3, 23 & 25 in their entirety.

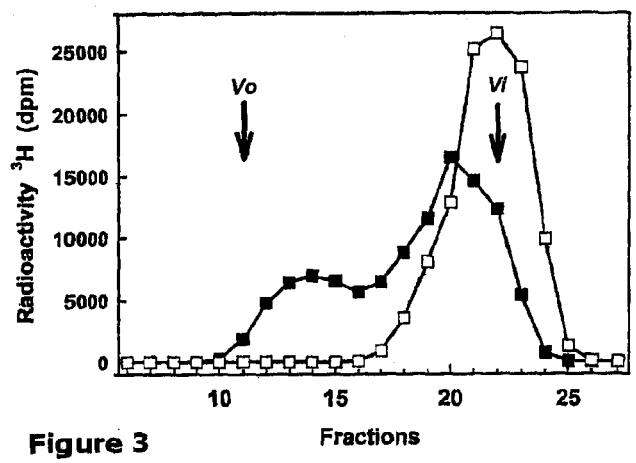

Figure 3

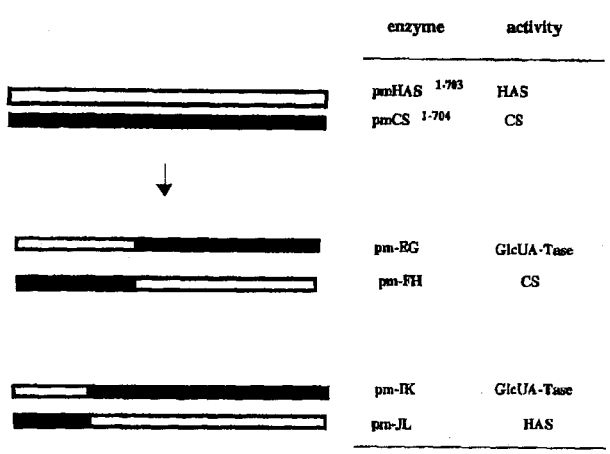

Figure 23

Signed and Sealed this
Eighth Day of February, 2011

David J. Kappos
*Director of the United States Patent and Trademark Office*

Figure 25

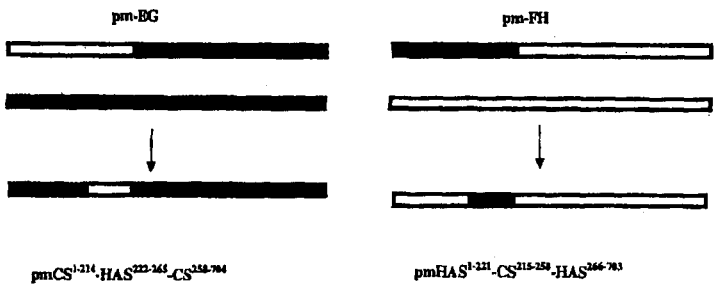

Column 5, line 19: Delete "PgIA)" and replace with -- PglA) --
Column 5, line 20: Delete "PgIA" and replace with -- PglA --
Column 5, line 56: Delete "PgIA" and replace with -- PglA --
Column 6, line 2: Delete "PgIA" and replace with -- PglA --
Column 6, line 4: Delete "PgIA," and replace with -- PglA, --
Column 6, line 24: Delete "PgIA" and replace with -- PglA --
Column 6, line 30: Delete "PgIA" and replace with -- PglA --
Column 6, line 35: Delete "PgIA" and replace with -- PglA --
Column 6, line 40: Delete "PgIA" and replace with -- PglA --
Column 6, line 50: Delete "PgIA" and replace with -- PglA --
Column 7, line 8: Delete "PgIA" and replace with -- PglA --
Column 7, line 12: Delete "PgIA" and replace with -- PglA --
Column 8, line 9: Delete "PgIA" and replace with -- PglA --
Column 8, line 14: Delete "PgIA" and replace with -- PglA --
Column 8, line 20: Delete "PgIA" and replace with -- PglA --
Column 8, line 27: Delete "PgIA" and replace with -- PglA --
Column 9, line 20: Delete "PgIA," and replace with -- PglA, --
Column 13, line 11: Delete "PgIA," and replace with -- PglA, --
Column 17, line 37: Delete "PgIA)." and replace with -- PglA). --
Column 17, line 52: Delete "PgIA" and replace with -- PglA --
Column 17, line 56: Delete "PgIA" and replace with -- PglA --
Column 18, line 3: Delete "PgIA," and replace with -- PglA, --
Column 18, line 35: Delete "PgIA" and replace with -- PglA --
Column 18, line 44: Delete "PgIA" and replace with -- PglA --
Column 19, line 3: Delete "PgIA" and replace with -- PglA --
Column 19, line 20: Delete "PgIA" and replace with -- PglA --
Column 20, line 6: Delete "(I) IIc" and replace with -- (I) Ile --
Column 20, line 7: Delete "Gin," and replace with -- Gln --
Column 20, line 42: Delete "PgIA," and replace with -- PglA, --
Column 20, line 44: Delete "PgIA" and replace with -- PglA --

CERTIFICATE OF CORRECTION (continued)
U.S. Pat. No. 7,741,091 B2

Column 25, line 38: Delete "PgIA)" and replace with -- PglA) --
Column 28, line 55: Delete "PgIA" and replace with -- PglA --
Column 41, line 29: Delete "PgIA," and replace with -- PglA, --
Column 41, line 62: Delete "PgIA)" and replace with -- PglA) --
Column 42, line 21: Delete "PgIA," and replace with -- PglA, --
Column 42, line 31: Delete "Southem" and replace with -- Southern --
Column 45, line 13: Delete "D7021." and replace with -- D702I. --
Column 45, line 18: Delete "D7021" and replace with --D702I --
Column 53, line 54: Delete "(bper II" and replace with -- (bPer II --
Column 54, line 13: Delete "ubstrates" and replace with -- substrates --
Column 59, line 14: Delete "D7021" and replace with -- D702I --
Column 65, line 47: Delete "Biol 01)" and replace with -- Bio 101 --
Column 65, line 62: Delete "PgIA" and replace with -- PglA --
Column 66, line 3: Delete "PgIA" and replace with -- PglA --
Column 66, line 7: Delete "co/1-derived" and replace with -- coli-derived --
Column 66, line 20: Delete "PgIA," and replace with -- PglA, --
Column 66, line 23: Delete "PgIA" and replace with -- PglA --
Column 66, line 26: Delete "P4GlcUa-α4GlcNAc" and replace with -- β4GlcUA-α4GlcNAc --Column 67, line 20: Delete "PgIA," and replace with -- PglA, --
Column 67, line 34: Delete "pM;" and replace with -- μM; --
Column 69, line 65: Delete "P-isopropylthiogalactiside" and replace with
       -- β-isopropylithiogalactodide --
Column 70, line 50: Delete "mU/il," and replace with -- mU/μl, --
Column 70, line 51-52: Delete "333 milliunits/il," and replace with -- 333 milliunits/μl. --
Column 71, line 43: Delete "PgIA" and replace with -- PglA --
Column 71, line 46: Delete "PgIA" and replace with -- PglA --
Column 71, line 48: Delete "PgIA." and replace with -- PglA, -- and before "protein" delete "PgIA"
       and replace with -- PglA --
Column 71, line 51: Delete "PgIA" and replace with -- PglA --
Column 71, line 59: Delete "pgla," and replace with -- pglA, --
Column 72, line 51: Delete "PgIA" and replace with -- PglA --
Column 73, line 1: Delete "PgIA," and replace with -- PglA, --
Column 73, line 4: Delete "PgIA" and replace with -- PglA --
Column 73, line 11: Delete "PgIA" and replace with -- PglA --
Column 73, line 66: Delete "PgIA" and replace with -- PglA --
Column 76, line 12: Delete "PgIA" and replace with -- PglA --
Column 76, line 31: Delete "PgIA" and replace with -- PglA --
Column 77, line 16: Delete "www.ncbi.nim.mih.gov)," and replace with -- www.ncbi.nlm.nih.gov), --
Column 77, line 27: Delete "2-O-GlcUA-sulfotransferase," and replace with
       -- 2-0-GlcUA-sulfotransferase, --
Column 77, line 53: Delete "PgIA" and replace with -- PglA --
Column 77, line 55: Delete "PgIA" and replace with -- PglA --
Column 77, line 65: Delete "PgIA," and replace with -- PglA, --

CERTIFICATE OF CORRECTION (continued)
U.S. Pat. No. 7,741,091 B2

Column 78, line 8: Delete "PgIA" and replace with -- PglA --
Column 78, line 24: Delete "PgIA" and replace with -- PglA --
Column 78, line 30: Delete "PgIA)" and replace with -- PglA) --
Column 78, line 40: Delete "PgIA)." and replace with -- PglA). --
Column 84, line 54: Delete "PgIA)" and replace with -- PglA) --
Column 88, line 65: Delete "calorimetric" and replace with -- colormetric --
Column 90, line 64: Delete "PgIA)" and replace with -- PglA) --
Column 91, line 2: Delete "PgIA," and replace with -- PglA, --
Column 94, line 65: Delete "PgIA." and replace with -- PglA. --
Column 95, line 66: Delete "PgIA." and replace with -- PglA. --

In the References:
Column 96, line 46: Delete "Seizer," and replace with -- Seltzer, --
Column 97, line 43-44: Delete "Pasteurelia" and replace with -- Pasteurella --
Column 101, line 43: Delete "Mounfford," and replace with -- Mountford, --
Column 104, line 23: Delete "Van Eften." and replace with -- Van Etten. --

SEQUENCE LISTING

```
<160> NUMBER OF SEQ ID NOS: 71

<210> SEQ ID NO 1
<211> LENGTH: 2920
<212> TYPE: DNA
<213> ORGANISM: Pasteurella multocida

<400> SEQUENCE: 1
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
```

-continued

```
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatatta aaatcatcca gaataaagat gccaaaatcg cagtcagtat tttttatccc   2160
aatacattaa acggcttagt gaaaaaacta aacaatatta ttgaatataa taaaaatata   2220
ttcgttattg ttctacatgt tgataagaat catcttacac cagatatcaa aaaagaaata   2280
ctagccttct atcataaaca tcaagtgaat attttactaa ataatgatat ctcatattac   2340
acgagtaata gattaataaa aactgaggcg catttaagta atattaataa attaagtcag   2400
ttaaatctaa attgtgaata catcattttt gataatcatg acagcctatt cgttaaaaat   2460
gacagctatg cttatatgaa aaaatatgat gtcggcatga atttctcagc attaacacat   2520
gattggatcg agaaaatcaa tgcgcatcca ccatttaaaa agctcattaa aacttatttt   2580
aatgacaatg acttaaaaag tatgaatgtg aaaggggcat cacaaggtat gtttatgacg   2640
tatgcgctag cgcatgagct tctgacgatt attaaagaag tcatcacatc ttgccagtca   2700
attgatagtg tgccagaata taacactgag gatatttggt tccaatttgc acttttaatc   2760
ttagaaaaga aaaccggcca tgtatttaat aaaacatcga ccctgactta tatgccttgg   2820
gaacgaaaat tacaatggac aaatgaacaa attgaaagtg caaaaagagg agaaaatata   2880
cctgttaaca agttcattat taatagtata actctataaa                         2920
```

<210> SEQ ID NO 2
<211> LENGTH: 972
<212> TYPE: PRT
<213> ORGANISM: Pasteurella multocida

<400> SEQUENCE: 2

```
Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45
```

-continued

```
His Pro Ser Val Asn Ser Ala His Leu Ser Val Asn Lys Glu Glu Lys
     50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
                100                 105                 110

Val Arg Ala Val Ala Leu Val Pro Lys Asp Phe Pro Lys Asp Leu Val
            115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
                180                 185                 190

Val Thr Asp Asp Gly Ser Gln Glu Asp Leu Ser Pro Ile Ile Arg Gln
            195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
                260                 265                 270

Ile Gly Pro Arg Lys Tyr Ile Asp Thr Gln His Ile Asp Pro Lys Asp
            275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
                340                 345                 350

Leu Asn Lys Ser Gly Phe Phe Asp Glu Glu Phe Asn His Trp Gly Gly
            355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
                420                 425                 430

Asp Ser His Ile Asn Arg Val Pro Leu Val Ser Ile Tyr Ile Pro Ala
            435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
```

```
                465                 470                 475                 480
Asp Asn Thr Leu Glu Val Ile Asn Lys Leu Tyr Gly Asn Asn Pro Arg
                    485                 490                 495
Val Arg Ile Met Ser Lys Pro Asn Gly Gly Ile Ala Ser Ala Ser Asn
                    500                 505                 510
Ala Ala Val Ser Phe Ala Lys Gly Tyr Tyr Ile Gly Gln Leu Asp Ser
                    515                 520                 525
Asp Asp Tyr Leu Glu Pro Asp Ala Val Glu Leu Cys Leu Lys Glu Phe
                    530                 535                 540
Leu Lys Asp Lys Thr Leu Ala Cys Val Tyr Thr Thr Asn Arg Asn Val
545                 550                 555                 560
Asn Pro Asp Gly Ser Leu Ile Ala Asn Gly Tyr Asn Trp Pro Glu Phe
                    565                 570                 575
Ser Arg Glu Lys Leu Thr Thr Ala Met Ile Ala His His Phe Arg Met
                    580                 585                 590
Phe Thr Ile Arg Ala Trp His Leu Thr Asp Gly Phe Asn Glu Lys Ile
                    595                 600                 605
Glu Asn Ala Val Asp Tyr Asp Met Phe Leu Lys Leu Ser Glu Val Gly
                    610                 615                 620
Lys Phe Lys His Leu Asn Lys Ile Cys Tyr Asn Arg Val Leu His Gly
625                 630                 635                 640
Asp Asn Thr Ser Ile Lys Lys Leu Gly Ile Gln Lys Lys Asn His Phe
                    645                 650                 655
Val Val Val Asn Gln Ser Leu Asn Arg Gln Gly Ile Thr Tyr Tyr Asn
                    660                 665                 670
Tyr Asp Glu Phe Asp Asp Leu Asp Glu Ser Arg Lys Tyr Ile Phe Asn
                    675                 680                 685
Lys Thr Ala Glu Tyr Gln Glu Glu Ile Asp Ile Leu Lys Asp Ile Lys
                    690                 695                 700
Ile Ile Gln Asn Lys Asp Ala Lys Ile Ala Val Ser Ile Phe Tyr Pro
705                 710                 715                 720
Asn Thr Leu Asn Gly Leu Val Lys Lys Leu Asn Asn Ile Ile Glu Tyr
                    725                 730                 735
Asn Lys Asn Ile Phe Val Ile Val Leu His Val Asp Lys Asn His Leu
                    740                 745                 750
Thr Pro Asp Ile Lys Lys Glu Ile Leu Ala Phe Tyr His Lys His Gln
                    755                 760                 765
Val Asn Ile Leu Leu Asn Asn Asp Ile Ser Tyr Tyr Thr Ser Asn Arg
                    770                 775                 780
Leu Ile Lys Thr Glu Ala His Leu Ser Asn Ile Asn Lys Leu Ser Gln
785                 790                 795                 800
Leu Asn Leu Asn Cys Glu Tyr Ile Ile Phe Asp Asn His Asp Ser Leu
                    805                 810                 815
Phe Val Lys Asn Asp Ser Tyr Ala Tyr Met Lys Lys Tyr Asp Val Gly
                    820                 825                 830
Met Asn Phe Ser Ala Leu Thr His Asp Trp Ile Glu Lys Ile Asn Ala
                    835                 840                 845
His Pro Pro Phe Lys Lys Leu Ile Lys Thr Tyr Phe Asn Asp Asn Asp
                    850                 855                 860
Leu Lys Ser Met Asn Val Lys Gly Ala Ser Gln Gly Met Phe Met Thr
865                 870                 875                 880
Tyr Ala Leu Ala His Glu Leu Leu Thr Ile Ile Lys Glu Val Ile Thr
                    885                 890                 895
```

-continued

```
Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
        915                 920                 925

Phe Asn Lys Thr Ser Thr Leu Thr Tyr Met Pro Trp Glu Arg Lys Leu
    930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970
```

<210> SEQ ID NO 3
<211> LENGTH: 2979
<212> TYPE: DNA
<213> ORGANISM: Pasteurella multocida

<400> SEQUENCE: 3
```
ttataaactg attaaagaag gtaaacgatt caagcaaggt taatttttaa aggaaagaaa      60
atgaatacat tatcacaagc aataaaagca tataacagca atgactatga attagcactc     120
aaattatttg agaagtctgc tgaaacctac gggcgaaaaa tcgttgaatt ccaaattatc     180
aaatgtaaag aaaaactctc gaccaattct tatgtaagtg aagataaaaa aaacagtgtt     240
tgcgatagct cattagatat cgcaacacag ctcttacttt ccaacgtaaa aaaattaact     300
ctatccgaat cagaaaaaaa cagtttaaaa aataaatgga aatctatcac tgggaaaaaa     360
tcggagaacg cagaaatcag aaaggtggaa ctagtaccca aagattttcc taaagatctt     420
gttcttgctc cattgccaga tcatgttaat gattttacat ggtacaaaaa tcgaaaaaaa     480
agcttaggta taaagcctgt aaataagaat atcggtcttt ctattattat tcctacattt     540
aatcgtagcc gtattttaga tataacgtta gcctgtttgg tcaatcagaa aacaaactac     600
ccatttgaag tcgttgttgc agatgatggt agtaaggaaa acttacttac cattgtgcaa     660
aaatacgaac aaaaacttga cataaagtat gtaagacaaa aagattatgg atatcaattg     720
tgtgcagtca gaaacttagg tttacgtaca gcaaagtatg attttgtctc gattctagac     780
tgcgatatgg caccacaaca attatgggtt cattcttatc ttacagaact attagaagac     840
aatgatattg ttttaattgg acctagaaaa tatgtggata ctcataatat taccgcagaa     900
caattcctta acgatccata tttaatagaa tcactacctg aaaccgctac aaataacaat     960
ccttcgatta catcaaaagg aaatatatcg ttggattgga gattagaaca tttcaaaaaa    1020
accgataatc tacgtctatg tgattctccg tttcgttatt ttagttgcgg taatgttgca    1080
ttttctaaag aatggctaaa taaagtaggt tggttcgatg aagaatttaa tcattggggg    1140
ggcgaagatg tagaatttgg ttacagatta tttgccaaag gctgtttttt cagagtaatt    1200
gacggcggaa tggcatacca tcaagaacca cctggtaaag aaaatgaaac agaccgcgaa    1260
gctggtaaaa gtattacgct taaaattgtg aaagaaaagg taccttacat ctatagaaag    1320
cttttaccaa tagaagattc acatattcat agaatacctt tagtttctat ttatatcccc    1380
gcttataact gtgcaaatta tattcaaaga tgtgtagata gtgctcttaa tcaaactgtt    1440
gtcgatctcg aggtttgtat ttgtaacgat ggttcaacag ataatacctt agaagtgatc    1500
aataagcttt atggtaataa tcctagggta cgcatcatgt ctaaaccaaa tggcggaata    1560
gcctcagcat caaatgcagc cgtttctttt gctaaaggtt attacattgg gcagttagat    1620
tcagatgatt atcttgagcc tgatgcagtt gaactgtgtt taaaagaatt tttaaaagat    1680
```

-continued

```
aaaacgctag cttgtgttta taccactaat agaaacgtca atccggatgg tagcttaatc    1740
gctaatggtt acaattggcc agaattttca cgagaaaaac tcacaacggc tatgattgct    1800
caccatttta gaatgtttac gattagagct tggcatttaa cggatggatt taacgaaaat    1860
attgaaaacg ccgtggatta tgacatgttc cttaaactca gtgaagttgg aaaatttaaa    1920
catcttaata aaatctgcta taaccgcgta ttacatggtg ataacacatc cattaagaaa    1980
ctcggcattc aaaagaaaaa ccatttttgtt gtagtcaatc agtcattaaa tagacaaggc    2040
atcaattatt ataattatga caaatttgat gatttagatg aaagtagaaa gtatatcttc    2100
aataaaaccg ctgaatatca agaagaaatg gatattttaa aagatcttaa actcattcaa    2160
aataaagatg ccaaaatcgc agtcagtatt ttctatccca atacattaaa cggcttagtg    2220
aaaaaactaa acaatattat tgaatataat aaaaatatat tcgttattat tctacatgtt    2280
gataagaatc atcttacacc agacatcaaa aaagaaatat tggctttcta tcataagcac    2340
caagtgaata tttactaaa taatgacatc tcatattaca cgagtaatag actaataaaa    2400
actgaggcac atttaagtaa tattaataaa ttaagtcagt taaatctaaa ttgtgaatac    2460 atcattttg ataatcatga cagcctattc gttaaaaatg acagctatgc ttatatgaaa    2520
aaatatgatg tcggcatgaa tttctcagca ttaacacatg attggatcga aaaatcaat     2580 gcgcatccac catttaaaaa gctgattaaa acctatttta atgacaatga cttaagaagt    2640
atgaatgtga aggggcatc acaaggtatg tttatgaagt atgcgctacc gcatgagctt     2700
ctgacgatta ttaaagaagt catcacatcc tgccaatcaa ttgatagtgt gccagaatat    2760
aacactgagg atatttggtt ccaatttgca cttttaatct tagaaaagaa aaccggccat    2820
gtatttaata aacatcgac cctgacttat atgccttggg aacgaaaatt acaatggaca     2880
aatgaacaaa ttcaaagtgc aaaaaaaggc gaaaatatcc ccgttaacaa gttcattatt    2940
aatagtataa cgctataaaa catttgcatt ttattaaaa                           2979
```

<210> SEQ ID NO 4
<211> LENGTH: 965
<212> TYPE: PRT
<213> ORGANISM: Pasteurella multocida

<400> SEQUENCE: 4

```
Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Asn Ser Val Cys Asp Ser Ser
    50                  55                  60

Leu Asp Ile Ala Thr Gln Leu Leu Ser Asn Val Lys Lys Leu Thr
65                  70                  75                  80

Leu Ser Glu Ser Glu Lys Asn Ser Leu Lys Asn Lys Trp Lys Ser Ile
                85                  90                  95

Thr Gly Lys Lys Ser Glu Asn Ala Glu Ile Arg Lys Val Glu Leu Val
            100                 105                 110

Pro Lys Asp Phe Pro Lys Asp Leu Val Leu Ala Pro Leu Pro Asp His
        115                 120                 125

Val Asn Asp Phe Thr Trp Tyr Lys Asn Arg Lys Lys Ser Leu Gly Ile
    130                 135                 140
```

```
Lys Pro Val Asn Lys Asn Ile Gly Leu Ser Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Ala Asp Asp Gly Ser Lys
            180                 185                 190

Glu Asn Leu Leu Thr Ile Val Gln Lys Tyr Glu Gln Lys Leu Asp Ile
                195                 200                 205

Lys Tyr Val Arg Gln Lys Asp Tyr Gly Tyr Gln Leu Cys Ala Val Arg
        210                 215                 220

Asn Leu Gly Leu Arg Thr Ala Lys Tyr Asp Phe Val Ser Ile Leu Asp
225                 230                 235                 240

Cys Asp Met Ala Pro Gln Gln Leu Trp Val His Ser Tyr Leu Thr Glu
                245                 250                 255

Leu Leu Glu Asp Asn Asp Ile Val Leu Ile Gly Pro Arg Lys Tyr Val
                260                 265                 270

Asp Thr His Asn Ile Thr Ala Glu Gln Phe Leu Asn Asp Pro Tyr Leu
            275                 280                 285

Ile Glu Ser Leu Pro Glu Thr Ala Thr Asn Asn Pro Ser Ile Thr
290                 295                 300

Ser Lys Gly Asn Ile Ser Leu Asp Trp Arg Leu Glu His Phe Lys Lys
305                 310                 315                 320

Thr Asp Asn Leu Arg Leu Cys Asp Ser Pro Phe Arg Tyr Phe Ser Cys
                325                 330                 335

Gly Asn Val Ala Phe Ser Lys Glu Trp Leu Asn Lys Val Gly Trp Phe
                340                 345                 350

Asp Glu Glu Phe Asn His Trp Gly Gly Glu Asp Val Glu Phe Gly Tyr
            355                 360                 365

Arg Leu Phe Ala Lys Gly Cys Phe Phe Arg Val Ile Asp Gly Gly Met
        370                 375                 380

Ala Tyr His Gln Glu Pro Pro Gly Lys Glu Asn Glu Thr Asp Arg Glu
385                 390                 395                 400

Ala Gly Lys Ser Ile Thr Leu Lys Ile Val Lys Glu Lys Val Pro Tyr
                405                 410                 415

Ile Tyr Arg Lys Leu Leu Pro Ile Glu Asp Ser His Ile His Arg Ile
            420                 425                 430

Pro Leu Val Ser Ile Tyr Ile Pro Ala Tyr Asn Cys Ala Asn Tyr Ile
                435                 440                 445

Gln Arg Cys Val Asp Ser Ala Leu Asn Gln Thr Val Val Asp Leu Glu
        450                 455                 460

Val Cys Ile Cys Asn Asp Gly Ser Thr Asp Asn Thr Leu Glu Val Ile
465                 470                 475                 480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Asp Tyr Leu Glu Pro Asp
        515                 520                 525

Ala Val Glu Leu Cys Leu Lys Glu Phe Leu Lys Asp Lys Thr Leu Ala
            530                 535                 540

Cys Val Tyr Thr Thr Asn Arg Asn Val Asn Pro Asp Gly Ser Leu Ile
545                 550                 555                 560
```

-continued

```
Ala Asn Gly Tyr Asn Trp Pro Glu Phe Ser Arg Glu Lys Leu Thr Thr
            565                 570                 575
Ala Met Ile Ala His His Phe Arg Met Phe Thr Ile Arg Ala Trp His
        580                 585                 590
Leu Thr Asp Gly Phe Asn Glu Asn Ile Glu Asn Ala Val Asp Tyr Asp
        595                 600                 605
Met Phe Leu Lys Leu Ser Glu Val Gly Lys Phe Lys His Leu Asn Lys
    610                 615                 620
Ile Cys Tyr Asn Arg Val Leu His Gly Asp Asn Thr Ser Ile Lys Lys
625                 630                 635                 640
Leu Gly Ile Gln Lys Lys Asn His Phe Val Val Asn Gln Ser Leu
                645                 650                 655
Asn Arg Gln Gly Ile Asn Tyr Tyr Asn Tyr Asp Lys Phe Asp Asp Leu
                660                 665                 670
Asp Glu Ser Arg Lys Tyr Ile Phe Asn Lys Thr Ala Glu Tyr Gln Glu
            675                 680                 685
Glu Met Asp Ile Leu Lys Asp Leu Lys Leu Ile Gln Asn Lys Asp Ala
    690                 695                 700
Lys Ile Ala Val Ser Ile Phe Tyr Pro Asn Thr Leu Asn Gly Leu Val
705                 710                 715                 720
Lys Lys Leu Asn Asn Ile Ile Glu Tyr Asn Lys Asn Ile Phe Val Ile
                725                 730                 735
Ile Leu His Val Asp Lys Asn His Leu Thr Pro Asp Ile Lys Lys Glu
            740                 745                 750
Ile Leu Ala Phe Tyr His Lys His Gln Val Asn Ile Leu Leu Asn Asn
        755                 760                 765
Asp Ile Ser Tyr Tyr Thr Ser Asn Arg Leu Ile Lys Thr Glu Ala His
    770                 775                 780
Leu Ser Asn Ile Asn Lys Leu Ser Gln Leu Asn Leu Asn Cys Glu Tyr
785                 790                 795                 800
Ile Ile Phe Asp Asn His Asp Ser Leu Phe Val Lys Asn Asp Ser Tyr
                805                 810                 815
Ala Tyr Met Lys Lys Tyr Asp Val Gly Met Asn Phe Ser Ala Leu Thr
            820                 825                 830
His Asp Trp Ile Glu Lys Ile Asn Ala His Pro Pro Phe Lys Lys Leu
        835                 840                 845
Ile Lys Thr Tyr Phe Asn Asp Asn Asp Leu Arg Ser Met Asn Val Lys
    850                 855                 860
Gly Ala Ser Gln Gly Met Phe Met Lys Tyr Ala Leu Pro His Glu Leu
865                 870                 875                 880
Leu Thr Ile Ile Lys Glu Val Ile Thr Ser Cys Gln Ser Ile Asp Ser
                885                 890                 895
Val Pro Glu Tyr Asn Thr Glu Asp Ile Trp Phe Gln Phe Ala Leu Leu
            900                 905                 910
Ile Leu Glu Lys Lys Thr Gly His Val Phe Asn Lys Thr Ser Thr Leu
        915                 920                 925
Thr Tyr Met Pro Trp Glu Arg Lys Leu Gln Trp Thr Asn Glu Gln Ile
    930                 935                 940
Gln Ser Ala Lys Lys Gly Glu Asn Ile Pro Val Asn Lys Phe Ile Ile
945                 950                 955                 960
Asn Ser Ile Thr Leu
                965
```

<210> SEQ ID NO 5
<211> LENGTH: 1851
<212> TYPE: DNA
<213> ORGANISM: Pasteurella multocida

<400> SEQUENCE: 5

```
atgagcttat ttaaacgtgc tactgagcta tttaagtcag gaaactataa agatgcacta      60
actctatatg aaaatatagc taaaatttat ggttcagaaa gccttgttaa atataatatt     120
gatatatgta aaaaaaatat aacacaatca aaagtaata aaatagaaga gataatatt      180
tctggagaaa acaaattttc agtatcaata aaagatctat ataacgaaat aagcaatagt     240
gaattaggga ttacaaaaga aagactagga gccccccctc tagtcagtat tataatgact     300
tctcataata cagaaaaatt cattgaagcc tcaattaatt cactattatt gcaaacatac     360
aataacttag aagttatcgt tgtagatgat tatagcacag ataaaacatt tcagatcgca     420
tccagaatag caaactctac aagtaaagta aaaacattcc gattaaactc aaatctaggg     480
acatactttg cgaaaaatac aggaattta aagtctaaag gagatattat tttctttcag     540
gatagcgatg atgtatgtca ccatgaaaga atcgaaagat gtgttaatgc attattatcg     600
aataaagata atatagctgt tagatgtgca tattctagaa taaatctaga aacacaaaat     660
ataataaaag ttaatgataa taaatacaaa ttaggattaa taactttagg cgtttataga     720
aaagtattta atgaaattgg ttttttttaac tgcacaacca aagcatcgga tgatgaattt     780
tatcatagaa taattaaata ctatggtaaa aataggataa ataacttatt tctaccactg     840
tattataaca caatgcgtga agattcatta ttttctgata tggttgagtg ggtagatgaa     900
aataatataa agcaaaaaac ctctgatgct agacaaaatt atctccatga attccaaaaa     960
atacacaatg aaaggaaatt aaatgaatta aaagagattt ttagcttcc tagaattcat    1020
gacgccttac ctatatcaaa agaaatgagt aagctcagca accctaaaat tcctgtttat    1080
ataaatatat gctcaatacc ttcaagaata aaacaacttc aatacactat ggagtacta    1140
aaaaaccaat gcgatcattt tcatatttat cttgatggat atccagaagt acctgatttt    1200
ataaaaaaac tagggaataa agcgaccgtt attaattgtc aaaacaaaaa tgagtctatt    1260
agagataatg gaaagtttat tctattagaa aaacttataa aggaaaataa agatggtat    1320
tatataactt gtgatgatga tatccggtat cctgctgact acacaaacac tatgataaaa    1380
aaaattaata aatacaatga taaagcagca attggattac atggtgttat attcccaagt    1440
agagtcaaca gtattttttc atcagacaga attgtctata ttttcaaaa accttagaa     1500
aatgatactg ctgtaaatat attaggaact ggaactgttg cctttagagt atctatttt     1560
aataaattt ctctatctga ttttgagcat cctggcatgg tagatatcta ttttctata     1620
ctatgtaaga aaacaatat actccaagtt tgtatatcac gaccatcgaa ttggctaaca    1680
gaagataaca aaaacactga gaccttattt catgaattcc aaaatagaga tgaaatacaa    1740
agtaaactca ttatttcaaa caacccttgg ggatactcaa gtatatatcc actattaaat    1800
aataatgcta attattctga acttattccg tgtttatctt tttataacga g             1851
```

<210> SEQ ID NO 6
<211> LENGTH: 615
<212> TYPE: PRT
<213> ORGANISM: Pasteurella multocida

<400> SEQUENCE: 6

Met Ser Leu Phe Lys Arg Ala Thr Glu Leu Phe Lys Ser Gly Asn Tyr
1               5                   10                  15

-continued

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Leu Glu Val Ile Val Val Asp
        115                 120                 125

Asp Tyr Ser Thr Asp Lys Thr Phe Gln Ile Ala Ser Arg Ile Ala Asn
    130                 135                 140

Ser Thr Ser Lys Val Lys Thr Phe Arg Leu Asn Ser Asn Leu Gly Thr
145                 150                 155                 160

Tyr Phe Ala Lys Asn Thr Gly Ile Leu Lys Ser Lys Gly Asp Ile Ile
                165                 170                 175

Phe Phe Gln Ser Asp Asp Val Cys His His Glu Arg Ile Glu Arg Cys
            180                 185                 190

Val Asn Ala Leu Leu Ser Asn Lys Asp Asn Ile Ala Val Arg Cys Ala
        195                 200                 205

Tyr Ser Arg Ile Asn Leu Glu Thr Gln Asn Ile Ile Lys Val Asn Asp
    210                 215                 220

Asn Lys Tyr Lys Leu Gly Leu Ile Thr Leu Gly Val Tyr Arg Lys Val
225                 230                 235                 240

Phe Asn Glu Ile Gly Phe Phe Asn Cys Thr Thr Lys Ala Ser Asp Asp
                245                 250                 255

Glu Phe Tyr His Arg Ile Ile Lys Tyr Tyr Gly Lys Asn Arg Ile Asn
            260                 265                 270

Asn Leu Phe Leu Pro Leu Tyr Tyr Asn Thr Met Arg Glu Asp Ser Leu
        275                 280                 285

Phe Ser Asp Met Val Glu Trp Val Asp Glu Asn Ile Lys Gln Lys
    290                 295                 300

Thr Ser Asp Ala Arg Gln Asn Tyr Leu His Glu Phe Gln Lys Ile His
305                 310                 315                 320

Asn Glu Arg Lys Leu Asn Glu Leu Lys Glu Ile Phe Ser Phe Pro Arg
                325                 330                 335

Ile His Asp Ala Leu Pro Ile Ser Lys Glu Met Ser Lys Leu Ser Asn
            340                 345                 350

Pro Lys Ile Pro Val Tyr Ile Asn Ile Cys Ser Ile Pro Ser Arg Ile
        355                 360                 365

Lys Gln Leu Gln Tyr Thr Ile Gly Val Leu Lys Asn Gln Cys Asp His
    370                 375                 380

Phe His Ile Tyr Leu Asp Gly Tyr Pro Glu Val Pro Asp Phe Ile Lys
385                 390                 395                 400

Lys Leu Gly Asn Lys Ala Thr Val Ile Asn Cys Gln Asn Lys Asn Glu
                405                 410                 415

Ser Ile Arg Asp Asn Gly Lys Phe Ile Leu Glu Lys Leu Ile Lys
            420                 425                 430

-continued

```
Glu Asn Lys Asp Gly Tyr Tyr Ile Thr Cys Asp Asp Asp Ile Arg Tyr
        435                 440                 445

Pro Ala Asp Tyr Thr Asn Thr Met Ile Lys Lys Ile Asn Lys Tyr Asn
    450                 455                 460

Asp Lys Ala Ala Ile Gly Leu His Gly Val Ile Phe Pro Ser Arg Val
465                 470                 475                 480

Asn Lys Tyr Phe Ser Ser Asp Arg Ile Val Tyr Asn Phe Gln Lys Pro
                485                 490                 495

Leu Glu Asn Asp Thr Ala Val Asn Ile Leu Gly Thr Gly Thr Val Ala
            500                 505                 510

Phe Arg Val Ser Ile Phe Asn Lys Phe Ser Leu Ser Asp Phe Glu His
        515                 520                 525

Pro Gly Met Val Asp Ile Tyr Phe Ser Ile Leu Cys Lys Lys Asn Asn
    530                 535                 540

Ile Leu Gln Val Cys Ile Ser Arg Pro Ser Asn Trp Leu Thr Glu Asp
545                 550                 555                 560

Asn Lys Asn Thr Glu Thr Leu Phe His Glu Phe Gln Asn Arg Asp Glu
                565                 570                 575

Ile Gln Ser Lys Leu Ile Ile Ser Asn Asn Pro Trp Gly Tyr Ser Ser
            580                 585                 590

Ile Tyr Pro Leu Leu Asn Asn Asn Ala Asn Tyr Ser Glu Leu Ile Pro
        595                 600                 605

Cys Leu Ser Phe Tyr Asn Glu
    610                 615
```

<210> SEQ ID NO 7
<211> LENGTH: 1940
<212> TYPE: DNA
<213> ORGANISM: Pasteurella multocida

<400> SEQUENCE: 7

```
aacaggggat aaggtcagta aatttaggat gatttttgac taatggataa atacttgaat     60
atccccatgg accgttttcc atgatcagct gagtttgttg ctcatcattg tctcgatatt    120
gatgatagag tgtttcgctg tctctattat cttccgttag ccagtttgct ggtcttgaaa    180
tacaaatctg aagaatatta tttttcttac acaagagaga gaaatagata tcagccatgc    240
ctgaatgggt aaagtcagaa agagaaaatt gattaaagag actgactcta aagctaacag    300
ttcctgtacc taatacattg accgctttgt ctttttccag aggtttatag aagctatata    360
ccagtctatc cgccgaaaaa tatttggtca ttctacttgg aaagagaatg ccgtgtaaac    420
caataaccgc tttatcatcg tattcattca gcttcttgat catcgtattg atgtaatcgc    480
ttggatagat aatgtcatca tcacaggtta tataaatatcc atcttgattt ttttcaatca    540
actcttccag taaaatgaat ttgccattat ctctaatgga gttatcttta tctttgcaat    600
gaacaacggt tgctttatta cctaaatttt ttatgaagtc agggatttct acatagccat    660
caagataaat atgaaaatga tcacattgat tttttagtat gccgataata cgtcgtaatt    720
gcgctattct tgagggaata gaacaaatat tgatataaac aggaatctta ggattggaca    780
acttactcat ttcttgtggt actggtaagg catcgtaaat acgagggaat tgaaaaagat    840
ttttgaaatc atgtgaggca gtttcgttat gcatcgcttg aaacagggtt gcataatgtt    900
gtctggtatc agacattttc tgtattatgt tatgattgtc tatccattca accatatcag    960
taaataaaga gttttctctc attgtgttgt agtataacgg caagagtaaa tttttttattt   1020 tttcttttcc ataatatttc gcaattctat gaaaaaactc atcatctgag cctttagtcg   1080
```

-continued

```
tacaattgaa gaaaccaatt tcttgaaata cttttctgtg catacccaag gttataaaac    1140
ctaatctata atccatatta ttgactttaa tgatatgttg tgtttctggt gctagtcttg    1200
agtatgcaca acgaacagca atagtttctt tattagctaa taatatattt acacatcttt    1260
ctattctttc atgatgacat acatcatcac tatcttgaaa gaaataatg tcacctttag     1320 attttaatat gcctgtattt ttcgcaaagt aagttcctag gtttgaattt aatctaaata    1380
ctctgacttt gcttgttgta ttcgctattc tcgaggcaat ttcaaatgta ttatccgagc    1440
tatcatcatc tacaataata atttctatgt ttttatatgt ttgtaacaat aatgaattaa    1500
tagaagcttc gataaattgc gctgtattgt gagatgtcat gataatactg actaatggat    1560
ttacgctgtt ggtttctttg actaacccta aatcacttt agcgacttca ttatataaat     1620
ctgttattga tgttgtttgc ttatctttt ctagctttgc ttctaatgct tgattatagg     1680
tatatatttt ttcaaattct tgcagaacca attggagttg ttttaataaa agtttatttt    1740
cgttttcaag ggatgcggat agcggatgtt tactgtcctg ttttgccaat aaagtttgtt    1800
gagaaataat gtctttgttt aaagttgttt ttagactatc aattttattt tgaaaggtgt    1860
tgagttcatt ttcttttca tgttgggggg gatttttagt catttgtttt tgagtcatct     1920 cttttttct cttcatttca                                                  1940
```

<210> SEQ ID NO 8
<211> LENGTH: 651
<212> TYPE: PRT
<213> ORGANISM: Pasteurella multocida

<400> SEQUENCE: 8

```
Met Lys Arg Lys Lys Glu Met Thr Gln Lys Gln Met Thr Lys Asn Pro
1               5                   10                  15

Pro Gln His Glu Lys Glu Asn Glu Leu Asn Thr Phe Gln Asn Lys Ile
            20                  25                  30

Asp Ser Leu Lys Thr Thr Leu Asn Lys Asp Ile Ile Ser Gln Gln Thr
        35                  40                  45

Leu Leu Ala Lys Gln Asp Ser Lys His Pro Leu Ser Ala Ser Leu Glu
    50                  55                  60

Asn Glu Asn Lys Leu Leu Leu Lys Gln Leu Gln Leu Val Leu Gln Glu
65                  70                  75                  80

Phe Glu Lys Ile Tyr Thr Tyr Asn Gln Ala Leu Glu Ala Lys Leu Glu
                85                  90                  95

Lys Asp Lys Gln Thr Thr Ser Ile Thr Asp Leu Tyr Asn Glu Val Ala
            100                 105                 110

Lys Ser Asp Leu Gly Leu Val Lys Glu Thr Asn Ser Val Asn Pro Leu
        115                 120                 125

Val Ser Ile Ile Met Thr Ser His Asn Thr Ala Gln Phe Ile Glu Ala
    130                 135                 140

Ser Ile Asn Ser Leu Leu Leu Gln Thr Tyr Lys Asn Ile Glu Ile Ile
145                 150                 155                 160

Ile Val Asp Asp Asp Ser Ser Asn Thr Phe Glu Ile Ala Ser Arg
                165                 170                 175

Ile Ala Asn Thr Thr Ser Lys Val Arg Val Phe Arg Leu Asn Ser Asn
            180                 185                 190

Leu Gly Thr Tyr Phe Ala Lys Asn Thr Gly Ile Leu Lys Ser Lys Gly
        195                 200                 205

Asp Ile Ile Phe Phe Gln Asp Ser Asp Asp Val Cys His His Glu Arg
```

-continued

```
            210                 215                 220
Ile Glu Arg Cys Val Asn Ile Leu Leu Ala Asn Lys Glu Thr Ile Ala
225                 230                 235                 240
Val Arg Cys Ala Tyr Ser Arg Leu Ala Pro Glu Thr Gln His Ile Ile
                    245                 250                 255
Lys Val Asn Asn Met Asp Tyr Arg Leu Gly Phe Ile Thr Leu Gly Met
                260                 265                 270
His Arg Lys Val Phe Gln Glu Ile Gly Phe Asn Cys Thr Thr Lys
            275                 280                 285
Gly Ser Asp Asp Glu Phe Phe His Arg Ile Ala Lys Tyr Tyr Gly Lys
290                 295                 300
Glu Lys Ile Lys Asn Leu Leu Leu Pro Leu Tyr Tyr Asn Thr Met Arg
305                 310                 315                 320
Glu Asn Ser Leu Phe Thr Asp Met Val Glu Trp Ile Asp Asn His Asn
                325                 330                 335
Ile Ile Gln Lys Met Ser Asp Thr Arg Gln His Tyr Ala Thr Leu Phe
            340                 345                 350
Gln Ala Met His Asn Glu Thr Ala Ser His Asp Phe Lys Asn Leu Phe
        355                 360                 365
Gln Phe Pro Arg Ile Tyr Asp Ala Leu Pro Val Pro Gln Glu Met Ser
    370                 375                 380
Lys Leu Ser Asn Pro Lys Ile Pro Val Tyr Ile Asn Ile Cys Ser Ile
385                 390                 395                 400
Pro Ser Arg Ile Ala Gln Leu Arg Arg Ile Ile Gly Ile Leu Lys Asn
                405                 410                 415
Gln Cys Asp His Phe His Ile Tyr Leu Asp Gly Tyr Val Glu Ile Pro
                420                 425                 430
Asp Phe Ile Lys Asn Leu Gly Asn Lys Ala Thr Val His Cys Lys
            435                 440                 445
Asp Lys Asp Asn Ser Ile Arg Asp Asn Gly Lys Phe Ile Leu Leu Glu
        450                 455                 460
Glu Leu Ile Glu Lys Asn Gln Asp Gly Tyr Tyr Ile Thr Cys Asp Asp
465                 470                 475                 480
Asp Ile Ile Tyr Pro Ser Asp Tyr Ile Asn Thr Met Ile Lys Lys Leu
                485                 490                 495
Asn Glu Tyr Asp Asp Lys Ala Val Ile Gly Leu His Gly Ile Leu Phe
                500                 505                 510
Pro Ser Arg Met Thr Lys Tyr Phe Ser Ala Asp Arg Leu Val Tyr Ser
            515                 520                 525
Phe Tyr Lys Pro Leu Glu Lys Asp Lys Ala Val Asn Val Leu Gly Thr
    530                 535                 540
Gly Thr Val Ser Phe Arg Val Ser Leu Phe Asn Gln Phe Ser Leu Ser
545                 550                 555                 560
Asp Phe Thr His Ser Gly Met Ala Asp Ile Tyr Phe Ser Leu Leu Cys
                565                 570                 575
Lys Lys Asn Asn Ile Leu Gln Ile Cys Ile Ser Arg Pro Ala Asn Trp
                580                 585                 590
Leu Thr Glu Asp Asn Arg Asp Ser Glu Thr Leu Tyr His Gln Tyr Arg
            595                 600                 605
Asp Asn Asp Glu Gln Gln Thr Gln Leu Ile Met Glu Asn Gly Pro Trp
        610                 615                 620
Gly Tyr Ser Ser Ile Tyr Pro Leu Val Lys Asn His Pro Lys Phe Thr
625                 630                 635                 640
```

```
Asp Leu Ile Pro Cys Leu Pro Phe Tyr Phe Leu
                645                 650

<210> SEQ ID NO 9
<211> LENGTH: 703
<212> TYPE: PRT
<213> ORGANISM: Pasteurella multocida

<400> SEQUENCE: 9

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
```

```
            355                 360                 365
Glu Asp Val Glu Phe Gly Tyr Arg Leu Phe Arg Tyr Gly Ser Phe Phe
370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
                420                 425                 430

Asp Ser His Ile Asn Arg Val Pro Leu Val Ser Ile Tyr Ile Pro Ala
                435                 440                 445

Tyr Asn Cys Ala Asn Tyr Ile Gln Arg Cys Val Asp Ser Ala Leu Asn
450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
                500                 505                 510

Ala Ala Val Ser Phe Ala Lys Gly Tyr Tyr Ile Gly Gln Leu Asp Ser
                515                 520                 525

Asp Asp Tyr Leu Glu Pro Asp Ala Val Glu Leu Cys Leu Lys Glu Phe
530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
                580                 585                 590

Phe Thr Ile Arg Ala Trp His Leu Thr Asp Gly Phe Asn Glu Lys Ile
                595                 600                 605

Glu Asn Ala Val Asp Tyr Asp Met Phe Leu Lys Leu Ser Glu Val Gly
610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
                660                 665                 670

Tyr Asp Glu Phe Asp Asp Leu Asp Glu Ser Arg Lys Tyr Ile Phe Asn
                675                 680                 685

Lys Thr Ala Glu Tyr Gln Glu Glu Ile Asp Ile Leu Lys Asp Ile
690                 695                 700

<210> SEQ ID NO 10
<211> LENGTH: 1953
<212> TYPE: DNA
<213> ORGANISM: Pasteurella multocida

<400> SEQUENCE: 10
atgaatacat tatcacaagc aataaaagca tataacagca atgactatca attagcactc      60
aaattatttg aaaagtcggc ggaaatctat ggacggaaaa ttgttgaatt tcaaattacc     120
aaatgcaaag aaaactctc agcacatcct tctgttaatt cagcacatct ttctgtaaat     180
```

```
aaagaagaaa aagtcaatgt tgcgatagt ccgttagata ttgcaacaca actgttactt    240
tccaacgtaa aaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttcaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa ataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aagggggaag aaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta tcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caa                               1953
```

<210> SEQ ID NO 11
<211> LENGTH: 2112
<212> TYPE: DNA
<213> ORGANISM: Pasteurella multocida

<400> SEQUENCE: 11

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaattagt actttctgac tcggaaaaaa acacgttaaa aaataaatgg    300
aaattgctca ctgagaagaa atctgaaaat gcggaggtaa gagcggtcgc ccttgtacca    360
```

-continued

```
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacaa tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat tttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 12
<211> LENGTH: 2112
<212> TYPE: DNA
<213> ORGANISM: Pasteurella multocida

<400> SEQUENCE: 12

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
```

```
aaattgctca ctgagaagaa atctgaaaat gcggaggtaa gagcggtcgc ccttgtacca      360
aaagattttc ccaaagatct ggttttagcg cctttacctg atcatgttaa tgattttaca      420
tggtacaaaa agcgaaagaa aagacttggc ataaaacctg aacatcaaca tgttggtctt      480
tctattatcg ttacaacatt caatcgacca gcaatttat cgattacatt agcctgttta       540
gtaaaccaaa aaacacatta cccgtttgaa gttatcgtga cagataatgg tagtcaggaa      600
gatctatcac cgatcattcg ccaatatgaa ataaattgg atattcgcta cgtcagacaa       660
aaagataacg gttttcaagc cagtgccgct cggaatatgg gattacgctt agcaaaatat      720
gactttattg gcttactcga ctgtgatatg gcgccaaatc cattatgggt tcattcttat      780
gttgcagagc tattagaaga tgatgattta caatcattg gtccaagaaa atacatcgat       840
acacaacata ttgacccaa agacttctta aataacgcga gtttgcttga atcattacca      900
gaagtgaaaa ccaataatag tgttgccgca aagggggaag gaacagtttc tctggattgg      960
cgcttagaac aattcgaaaa aacagaaaat ctccgcttat ccgattcgcc tttccgtttt     1020
tttgcggcgg gtaatgttgc tttcgctaaa aaatggctaa ataaatccgg tttctttgat     1080
gaggaattta atcactgggg tggagaagat gtggaatttg gatatcgctt attccgttac     1140 ggtagttttct ttaaaactat tgatggcatt atggcctacc atcaagagcc accaggtaaa    1200
gaaaatgaaa ccgatcgtga agcgggaaaa aatattacgc tcgatattat gagagaaaag     1260
gtcccttata tctatagaaa acttttacca atagaagatt cgcatatcaa tagagtacct     1320
ttagtttcaa tttatatccc agcttataac tgtgcaaact atattcaacg ttgcgtagat     1380
agtgcactga atcagactgt tgttgatctc gaggtttgta tttgtaacga tggttcaaca     1440
gataatacct tagaagtgat caataagctt tatggtaata atcctagggt acgcatcatg     1500
tctaaaccaa atggcggaat agcctcagca tcaaatgcag ccgtttcttt tgctaaaggt     1560
tattacattg ggcagttaga ttcagatgat tatcttgagc ctgatgcagt tgaactgtgt     1620
ttaaaagaat ttttaaaaga taaaacgcta gcttgtgttt ataccactaa tagaaacgtc     1680
aatccggatg gtagcttaat cgctaatggt tacaattggc cagaattttc acgagaaaaa     1740
ctcacaacgg ctatgattgc tcaccacttt agaatgttca cgattagagc ttggcattta     1800
actgatggat tcaatgaaaa aattgaaaat gccgtagact atgacatgtt cctcaaactc     1860
agtgaagttg gaaaatttaa acatcttaat aaaatctgct ataaccgtgt attacatggt     1920
gataacacat caattaagaa acttggcatt caaaagaaaa accattttgt tgtagtcaat     1980
cagtcattaa atagacaagg cataaacttat tataattatg acgaatttga tgatttagat     2040
gaaagtagaa agtatatttt caataaaacc gctgaatatc aagaagagat tgatatctta     2100
aaagatattt aa                                                         2112

<210> SEQ ID NO 13
<211> LENGTH: 1614
<212> TYPE: DNA
<213> ORGANISM: Pasteurella multocida

<400> SEQUENCE: 13
atcaatagag taccttttagt ttcaattat atcccag

```
gcagttgaac tgtgtttaaa agaatttta aaagataaaa cgctagcttg tgtttatacc      360
actaatagaa acgtcaatcc ggatggtagc ttaatcgcta atggttacaa ttggccagaa      420
ttttcacgag aaaaactcac aacggctatg attgctcacc actttagaat gttcacgatt      480
agagcttggc atttaactga tggattcaat gaaaaaattg aaaatgccgt agactatgac      540
atgttcctca aactcagtga agttggaaaa tttaaacatc ttaataaaat ctgctataac      600
cgtgtattac atggtgataa cacatcaatt aagaaacttg gcattcaaaa gaaaaaccat      660
tttgttgtag tcaatcagtc attaaataga caaggcataa cttattataa ttatgacgaa      720
tttgatgatt tagatgaaag tagaaagtat attttcaata aaaccgctga atatcaagaa      780
gagattgata tcttaaaaga tattaaaatc atccagaata aagatgccaa aatcgcagtc      840 agtattttt atcccaatac attaaacggc ttagtgaaaa aactaaacaa tattattgaa      900
tataataaaa atatattcgt tattgttcta catgttgata agaatcatct tacaccagat      960
atcaaaaaag aaatactagc cttctatcat aaacatcaag tgaatatttt actaaataat     1020
gatatctcat attacacgag taatagatta ataaaaactg aggcgcattt aagtaatatt     1080
aataaattaa gtcagttaaa tctaaattgt gaatacatca ttttgataa tcatgacagc     1140 ctattcgtta aaaatgacag ctatgcttat atgaaaaaat atgatgtcgg catgaatttc     1200
tcagcattaa cacatgattg gatcgagaaa atcaatgcgc atccaccatt taaaaagctc     1260
attaaaactt attttaatga caatgactta aaaagtatga atgtgaaagg ggcatcacaa     1320
ggtatgttta tgacgtatgc gctagcgcat gagcttctga cgattattaa agaagtcatc     1380
acatcttgcc agtcaattga tagtgtgcca gaatataaca ctgaggatat ttggttccaa     1440
tttgcacttt taatcttaga aaagaaaacc ggccatgtat ttaataaaac atcgaccctg     1500
acttatatgc cttgggaacg aaaattacaa tggacaaatg aacaaattga aagtgcaaaa     1560
agaggagaaa ataccctgt taacaagttc attattaata gtataactct ataa            1614

<210> SEQ ID NO 14
<211> LENGTH: 966
<212> TYPE: DNA
<213> ORGANISM: Pasteurella multocida

<400> SEQUENCE: 14
atcaatagag tacctttagt ttcaatttat atcccagctt ataactgtgc aaactatatt       60
caacgttgcg tagatagtgc actgaatcag actgttgttg atctcgaggt ttgtatttgt      120
aacgatggtt caacagataa taccttagaa gtgatcaata agctttatgg taataatcct      180
agggtacgca tcatgtctaa accaaatggc ggaatagcct cagcatcaaa tgcagccgtt      240
tcttttgcta aaggttatta cattgggcag ttagattcag atgattatct tgagcctgat      300
gcagttgaac tgtgtttaaa agaatttta aaagataaaa cgctagcttg tgtttatacc      360
actaatagaa acgtcaatcc ggatggtagc ttaatcgcta atggttacaa ttggccagaa      420
ttttcacgag aaaaactcac aacggctatg attgctcacc actttagaat gttcacgatt      480
agagcttggc atttaactga tggattcaat gaaaaaattg aaaatgccgt agactatgac      540
atgttcctca aactcagtga agttggaaaa tttaaacatc ttaataaaat ctgctataac      600
cgtgtattac atggtgataa cacatcaatt aagaaacttg gcattcaaaa gaaaaaccat      660
tttgttgtag tcaatcagtc attaaataga caaggcataa cttattataa ttatgacgaa      720
tttgatgatt tagatgaaag tagaaagtat attttcaata aaaccgctga atatcaagaa      780
```

-continued

| | |
|---|---|
| gagattgata tcttaaaaga tattaaaatc atccagaata aagatgccaa aatcgcagtc | 840 |
| agtattttt atcccaatac attaaacggc ttagtgaaaa aactaaacaa tattattgaa | 900 |
| tataataaaa atatattcgt tattgttcta catgttgata agaatcatct tacaccagat | 960 |
| atctaa | 966 |

<210> SEQ ID NO 15
<211> LENGTH: 1821
<212> TYPE: DNA
<213> ORGANISM: Pasteurella multocida

<400> SEQUENCE: 15

| | |
|---|---|
| atgaaacctg aacatcaaca tgttggtctt tctattatcg ttacaacatt caatcgacca | 60 |
| gcaattttat cgattacatt agcctgttta gtaaaccaaa aaacacatta cccgtttgaa | 120 |
| gttatcgtga cagatgatgg tagtcaggaa gatctatcac cgatcattcg ccaatatgaa | 180 |
| aataaattgg atattcgcta cgtcagacaa aaagataacg ttttcaagc cagtgccgct | 240 |
| cggaatatgg gattacgctt agcaaaatat gactttattg cttactcga ctgtgatatg | 300 |
| gcgccaaatc cattatgggt tcattcttat gttgcagagc tattagaaga tgatgattta | 360 |
| acaatcattg gtccaagaaa atacatcgat acacaacata ttgacccaaa agacttctta | 420 |
| aataacgcga gtttgcttga atcattacca gaagtgaaaa ccaataatag tgttgccgca | 480 |
| aaaggggaag gaacagtttc tctggattgg cgcttagaac aattcgaaaa aacagaaaat | 540 |
| ctccgcttat ccgattcgcc tttccgtttt tttgcggcgg gtaatgttgc tttcgctaaa | 600 |
| aaatggctaa ataaatccgg tttctttgat gaggaattta tcactgggg tggagaagat | 660 |
| gtggaatttg gatatcgctt attccgttac ggtagtttct ttaaaactat tgatggcatt | 720 |
| atggcctacc atcaagagcc accaggtaaa gaaaatgaaa ccgatcgtga agcgggaaaa | 780 |
| aatattacgc tcgatattat gagagaaaag gtcccttata tctatagaaa actttaccaa | 840 |
| atagaagatt cgcatatcaa tagagtacct ttagtttcaa tttatatccc agcttataac | 900 |
| tgtgcaaact atattcaacg ttgcgtagat agtgcactga atcagactgt tgttgatctc | 960 |
| gaggtttgta tttgtaacga tggttcaaca gataatacct tagaagtgat caataagctt | 1020 |
| tatggtaata atcctagggt acgcatcatg tctaaaccaa atggcggaat agcctcagca | 1080 |
| tcaaatgcag ccgtttcttt tgctaaaggt tattacattg ggcagttaga ttcagatgat | 1140 |
| tatcttgagc ctgatgcagt tgaactgtgt ttaaaagaat ttttaaaaga taaaacgcta | 1200 |
| gcttgtgttt ataccactaa tagaaacgtc aatccggatg gtagcttaat cgctaatggt | 1260 |
| tacaattggc cagaattttc acgagaaaaa ctcacaacgg ctatgattgc tcaccacttt | 1320 |
| agaatgttca cgattagagc ttggcattta actgatggat tcaatgaaaa aattgaaaat | 1380 |
| gccgtagact atgacatgtt cctcaaactc agtgaagttg aaaatttaa acatcttaat | 1440 |
| aaaatctgct ataccgtgt attacatggt gataacacat caattaagaa acttggcatt | 1500 |
| caaaagaaaa accattttgt tgtagtcaat cagtcattaa atagacaagg cataacttat | 1560 |
| tataattatg acgaatttga tgatttagat gaagtagaa agtatatttt caataaaacc | 1620 |
| gctgaatatc aagaagagat tgatatctta aaagatatta aaatcatcca gaataaagat | 1680 |
| gccaaaatcg cagtcagtat tttttatccc aatacattaa acggcttagt gaaaaaacta | 1740 |
| aacaatatta ttgaatataa taaaaatata ttcgttattg ttctacatgt tgataagaat | 1800 |
| catcttacac cagatatcta a | 1821 |

<210> SEQ ID NO 16
<211> LENGTH: 2112
<212> TYPE: DNA
<213> ORGANISM: Pasteurella multocida

<400> SEQUENCE: 16
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgaagg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 17
<211> LENGTH: 2112
<212> TYPE: DNA
<213> ORGANISM: Pasteurella multocida

<400> SEQUENCE: 17
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagataaagg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcga ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620
ttaaaagaat ttttaaaaga taaaacgcta gcttgtgttt ataccactaa tagaaacgtc 1680
aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 18
<211> LENGTH: 2112
<212> TYPE: DNA
<213> ORGANISM: Pasteurella multocida

<400> SEQUENCE: 18

```
atgaatacat tatcacaagc aataaaagca tataacagca atgactatca attagcactc      60
aaattatttg aaaagtcggc ggaaatctat ggacggaaaa ttgttgaatt tcaaattacc     120
aaatgcaaag aaaaactctc agcacatcct tctgttaatt cagcacatct ttctgtaaat     180
aaagaagaaa aagtcaatgt ttgcgatagt ccgttagata ttgcaacaca actgttactt     240
tccaacgtaa aaaaattagt actttctgac tcggaaaaaa acacgttaaa aaataaatgg     300
aaattgctca ctgagaagaa atctgaaaat gcggaggtaa gagcggtcgc ccttgtacca     360
aaagatttc ccaaagatct ggttttagcg cctttacctg atcatgttaa tgattttaca     420
tggtacaaaa agcgaaagaa aagacttggc ataaaacctg aacatcaaca tgttggtctt     480
tctattatcg ttacaacatt caatcgacca gcaattttat cgattacatt agcctgttta     540
gtaaaccaaa aaacacatta cccgtttgaa gttatcgtga cagatgatgg tagtcaggaa     600
gatctatcac cgatcattcg ccaatatgaa aataaattgg atattcgcta cgtcagacaa     660
aaagataacg gttttcaagc cagtgccgct cggaatatgg gattacgctt agcaaaatat     720
gactttattg gcttactcga ctgtgatatg gcgccaaatc cattatgggt tcattcttat     780
gttgcagagc tattagaaga tgatgattta acaatcattg gtccaagaaa atacatcgat     840
acacaacata ttgacccaaa agacttctta aataacgcga gtttgcttga atcattacca     900
gaagtgaaaa ccaataatag tgttgccgca aaaggggaag gaacagtttc tctggattgg     960
cgcttagaac aattcgaaaa aacagaaaat ctccgcttat ccgattcgcc tttccgtttt    1020
tttgcggcgg gtaatgttgc tttcgctaaa aaatggctaa ataaatccgg tttctttgat    1080
gaggaattta atcactgggg tggagaagat gtggaatttg gatatcgctt attccgttac    1140
ggtagtttct ttaaaactat tgatggcatt atggcctacc atcaagagcc accaggtaaa    1200
gaaaatgaaa ccgatcgtga agcgggaaaa aatattacgc tcgatattat gagagaaaag    1260
gtcccttata tctatagaaa acttttacca atagaagatt cgcatatcaa tagagtacct    1320
ttagtttcaa tttatatccc agcttataac tgtgcaaact atattcaacg ttgcgtagat    1380
agtgcactga atcagactgt tgttgatctc gaggtttgta tttgtaacga aggttcaaca    1440
gataatacct tagaagtgat caataagctt tatggtaata atcctagggt acgcatcatg    1500
tctaaaccaa atggcggaat agcctcagca tcaaatgcag ccgtttcttt tgctaaaggt    1560
tattacattg ggcagttaga ttcagatgat tatcttgagc ctgatgcagt tgaactgtgt    1620
ttaaaagaat ttttaaaaga taaaacgcta gcttgtgttt ataccactaa tagaaacgtc    1680
aatccggatg gtagcttaat cgctaatggt tacaattggc cagaattttc acgagaaaaa    1740
ctcacaacgg ctatgattgc tcaccacttt agaatgttca cgattagagc ttggcattta    1800
actgatggat tcaatgaaaa aattgaaaat gccgtagact atgacatgtt cctcaaactc    1860
agtgaagttg gaaaatttaa acatcttaat aaaatctgct ataaccgtgt attacatggt    1920
gataacacat caattaagaa acttggcatt caaaagaaaa accattttgt tgtagtcaat    1980
cagtcattaa atagacaagg cataacttat tataattatg acgaatttga tgatttagat    2040
gaaagtagaa agtatatttt caataaaacc gctgaatatc aagaagagat tgatatctta    2100
```
aaagatattt aa 2112

<210> SEQ ID NO 19
<211> LENGTH: 2112
<212> TYPE: DNA
<213> ORGANISM: Pasteurella multocida

<400> SEQUENCE: 19

| | | | | | |
|---|---|---|---|---|---|
| atgaatacat | tatcacaagc | aataaaagca | tataacagca | atgactatca | attagcactc | 60 |
| aaattatttg | aaaagtcggc | ggaaatctat | ggacggaaaa | ttgttgaatt | tcaaattacc | 120 |
| aaatgcaaag | aaaaactctc | agcacatcct | tctgttaatt | cagcacatct | ttctgtaaat | 180 |
| aaagaagaaa | aagtcaatgt | ttgcgatagt | ccgttagata | ttgcaacaca | actgttactt | 240 |
| tccaacgtaa | aaaaattagt | actttctgac | tcggaaaaaa | cacgttaaa | aaataaatgg | 300 |
| aaattgctca | ctgagaagaa | atctgaaaat | gcggaggtaa | gagcggtcgc | ccttgtacca | 360 |
| aaagattttc | ccaaagatct | ggttttagcg | cctttacctg | atcatgttaa | tgattttaca | 420 |
| tggtacaaaa | agcgaaagaa | aagacttggc | ataaaacctg | aacatcaaca | tgttggtctt | 480 |
| tctattatcg | ttacaacatt | caatcgacca | gcaattttat | cgattacatt | agcctgttta | 540 |
| gtaaaccaaa | aaacacatta | cccgtttgaa | gttatcgtga | cagatgatgg | tagtcaggaa | 600 |
| gatctatcac | cgatcattcg | ccaatatgaa | aataaattgg | atattcgcta | cgtcagacaa | 660 |
| aaagataacg | gttttcaagc | cagtgccgct | cggaatatgg | gattacgctt | agcaaaatat | 720 |
| gactttattg | gcttactcga | ctgtgatatg | gcgccaaatc | cattatgggt | tcattcttat | 780 |
| gttgcagagc | tattagaaga | tgatgattta | acaatcattg | gtccaagaaa | atacatcgat | 840 |
| acacaacata | ttgacccaaa | agacttctta | aataacgcga | gtttgcttga | atcattacca | 900 |
| gaagtgaaaa | ccaataatag | tgttgccgca | aaagggggaag | gaacagtttc | tctggattgg | 960 |
| cgcttagaac | aattcgaaaa | aacagaaaat | ctccgcttat | ccgattcgcc | tttccgtttt | 1020 |
| tttgcggcgg | gtaatgttgc | tttcgctaaa | aaatggctaa | ataaatccgg | tttctttgat | 1080 |
| gaggaattta | tcactggggg | tggagaagat | gtggaatttg | gatatcgctt | attccgttac | 1140 |
| ggtagttct | ttaaaactat | tgatggcatt | atggcctacc | atcaagagcc | accaggtaaa | 1200 |
| gaaaatgaaa | ccgatcgtga | agcgggaaaa | aatattacgc | tcgatattat | gagagaaaag | 1260 |
| gtccctata | tctatagaaa | acttttacca | atagaagatt | cgcatatcaa | tagagtacct | 1320 |
| ttagtttcaa | tttatatccc | agcttataac | tgtgcaaact | atattcaacg | ttgcgtagat | 1380 |
| agtgcactga | atcagactgt | tgttgatctc | gaggtttgta | tttgtaacaa | aggttcaaca | 1440 |
| gataatacct | tagaagtgat | caataagctt | tatggtaata | atcctagggt | acgcatcatg | 1500 |
| tctaaaccaa | atggcggaat | agcctcagca | tcaaatgcag | ccgtttcttt | tgctaaaggt | 1560 |
| tattacattg | ggcagttaga | ttcagatgat | tatcttgagc | ctgatgcagt | tgaactgtgt | 1620 |
| ttaaaagaat | ttttaaaaga | taaaacgcta | gcttgtgttt | ataccactaa | tagaaacgtc | 1680 |
| aatccggatg | gtagcttaat | cgctaatggt | tacaattggc | cagaattttc | acgagaaaaa | 1740 |
| ctcacaacgg | ctatgattgc | tcaccacttt | agaatgttca | cgattagagc | ttggcattta | 1800 |
| actgatggat | tcaatgaaaa | aattgaaaat | gccgtagact | atgacatgtt | cctcaaactc | 1860 |
| agtgaagttg | gaaaatttaa | acatcttaat | aaaatctgct | ataaccgtgt | attacatggt | 1920 |
| gataacacat | caattaagaa | acttggcatt | caaaagaaaa | accattttgt | tgtagtcaat | 1980 |
| cagtcattaa | atagacaagg | cataacttat | tataattatg | acgaatttga | tgatttagat | 2040 |
| gaaagtagaa | agtatatttt | caataaaacc | gctgaatatc | aagaagagat | tgatatctta | 2100 |

-continued

| | |
|---|---|
| aaagatatttt aa | 2112 |

<210> SEQ ID NO 20
<211> LENGTH: 2271
<212> TYPE: DNA
<213> ORGANISM: Pasteurella multocida

<400> SEQUENCE: 20

| | |
|---|---|
| atgaatacat tatcacaagc aataaaagca tataacagca atgactatca attagcactc | 60 |
| aaattatttg aaaagtcggc ggaaatctat ggacggaaaa ttgttgaatt tcaaattacc | 120 |
| aaatgcaaag aaaaactctc agcacatcct tctgttaatt cagcacatct ttctgtaaat | 180 |
| aaagaagaaa aagtcaatgt ttgcgatagt ccgttagata ttgcaacaca actgttactt | 240 |
| tccaacgtaa aaaaattagt actttctgac tcggaaaaaa acacgttaaa aaataaatgg | 300 |
| aaattgctca ctgagaagaa atctgaaaat gcggaggtaa gagcggtcgc ccttgtacca | 360 |
| aaagattttc ccaaagatct ggttttagcg cctttacctg atcatgttaa tgattttaca | 420 |
| tggtacaaaa agcgaaagaa aagacttggc ataaaacctg aacatcaaca tgttggtctt | 480 |
| tctattatcg ttacaacatt caatcgacca gcaattttat cgattacatt agcctgttta | 540 |
| gtaaaccaaa aaacacatta cccgtttgaa gttatcgtga cagatgatgg tagtcaggaa | 600 |
| gatctatcac cgatcattcg ccaatatgaa ataaaattgg atattcgcta cgtcagacaa | 660 |
| aaagataacg ttttcaagc cagtgccgct cggaatatgg gattacgctt agcaaaatat | 720 |
| gactttattg gcttactcga ctgtgatatg gcgccaaatc cattatgggt tcattcttat | 780 |
| gttgcagagc tattagaaga tgatgattta acaatcattg gtccaagaaa atacatcgat | 840 |
| acacaacata ttgacccaaa agacttctta ataacgcga gtttgcttga atcattacca | 900 |
| gaagtgaaaa ccaataatag tgttgccgca aaaggggaag gaacagtttc tctggattgg | 960 |
| cgcttagaac aattcgaaaa aacagaaaat ctccgcttat ccgattcgcc tttccgtttt | 1020 |
| tttgcggcgg gtaatgttgc tttcgctaaa aaatggctaa ataaatccgg tttctttgat | 1080 |
| gaggaattta tcactggggg tggagaagat gtggaatttg gatatcgctt attccgttac | 1140 |
| ggtagtttct ttaaaactat tgatggcatt atggcctacc atcaagagcc accaggtaaa | 1200 |
| gaaaatgaaa ccgatcgtga agcgggaaaa aatattacgc tcgatattat gagagaaaag | 1260 |
| gtcccttata tctatagaaa acttttacca atagaagatt cgcatatcaa tagagtacct | 1320 |
| ttagtttcaa tttatatccc agcttataac tgtgcaaact atattcaacg ttgcgtagat | 1380 |
| agtgcactga atcagactgt tgttgatctc gaggtttgta tttgtaacga tggttcaaca | 1440 |
| gataatacct tagaagtgat caataagctt tatggtaata atcctagggt acgcatcatg | 1500 |
| tctaaaccaa atggcggaat agcctcagca tcaaatgcag ccgtttcttt tgctaaaggt | 1560 |
| tattacattg ggcagttaga ttcagatgat tatcttgagc ctgatgcagt tgaactgtgt | 1620 |
| ttaaaagaat tttaaaaga taaaacgcta gcttgtgttt ataccactaa tagaaacgtc | 1680 |
| aatccggatg gtagcttaat cgctaatggt tacaattggc cagaattttc acgagaaaaa | 1740 |
| ctcacaacgg ctatgattgc tcaccacttt agaatgttca cgattagagc ttggcattta | 1800 |
| actgatggat tcaatgaaaa aattgaaaat gccgtagact atgacatgtt cctcaaactc | 1860 |
| agtgaagttg gaaaatttaa acatcttaat aaaatctgct ataaccgtgt attacatggt | 1920 |
| gataacacat caattaagaa acttggcatt caaaagaaaa accattttgt tgtagtcaat | 1980 |
| cagtcattaa atagacaagg cataaactta t tataattatg acgaatttga tgatttagat | 2040 |

-continued

```
gaaagtagaa agtatatttt caataaaacc gctgaatatc aagaagagat tgatatctta   2100
aaagatatta aaatcatcca gaataaagat gccaaaatcg cagtcagtat tttttatccc   2160
aatacattaa acggcttagt gaaaaaacta aacaatatta ttgaatataa taaaaatata   2220
ttcgttattg ttctacatgt tgataagaat catcttacac cagatatcta a            2271
```

<210> SEQ ID NO 21
<211> LENGTH: 1704
<212> TYPE: DNA
<213> ORGANISM: Pasteurella multocida

<400> SEQUENCE: 21

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat ctaa                                          1704
```

<210> SEQ ID NO 22
<211> LENGTH: 18
<212> TYPE: PRT
<213> ORGANISM: artificial sequence

```
<220> FEATURE:
<223> OTHER INFORMATION: synthetic peptide based on residues 526-543 of
      pmHAS

<400> SEQUENCE: 22

Leu Asp Ser Asp Asp Tyr Leu Glu Pro Asp Ala Val Glu Leu Cys Leu
1               5                   10                  15

Lys Glu

<210> SEQ ID NO 23
<211> LENGTH: 24
<212> TYPE: DNA
<213> ORGANISM: Artificial sequence
<220> FEATURE:
<223> OTHER INFORMATION: primer Pm10

<400> SEQUENCE: 23
cactgtctaa ctttattgtt agcc                                         24

<210> SEQ ID NO 24
<211> LENGTH: 20
<212> TYPE: DNA
<213> ORGANISM: Artificial Sequence
<220> FEATURE:
<223> OTHER INFORMATION: primer Pm21

<400> SEQUENCE: 24
tttttaacga ataggctgtc                                              20

<210> SEQ ID NO 25
<211> LENGTH: 19
<212> TYPE: PRT
<213> ORGANISM: artificial sequence
<220> FEATURE:
<223> OTHER INFORMATION: synthetic peptide based on residues 526 to 544
      of pmHAS protein

<400> SEQUENCE: 25

Leu Asp Ser Asp Asp Tyr Leu Glu Pro Asp Ala Val Glu Leu Cys Leu
1               5                   10                  15

Lys Glu Phe

<210> SEQ ID NO 26
<211> LENGTH: 2115
<212> TYPE: DNA
<213> ORGANISM: Pasteurella multocida

<400> SEQUENCE: 26
atgaatacat tatcacaagc aataaaagca tataacagca atgactatga attagcactc       60
aaattatttg agaagtctgc tgaaacctac gggcgaaaaa tcgttgaatt ccaaattatc      120
aaatgtaaag aaaaactctc gaccaattct tatgtaagtg aagataaaaa aaacagtgtt      180
tgcgatagct cattagatat cgcaacacag ctcttacttt ccaacgtaaa aaaattaact      240
ctatccgaat cagaaaaaaa cagtttaaaa aataaatgga atctatcac  tgggaaaaaa      300 tcggagaacg cagaaatcag aaaggtggaa ctagtaccca aagattttcc taaagatctt      360
gttcttgctc cattgccaga tcatgttaat gatttacat ggtacaaaaa tcgaaaaaaa      420
agcttaggta taaagcctgt aaataagaat atcggtcttt ctattattat tcctacattt      480
aatcgtagcc gtattttaga tataacgtta gcctgtttgg tcaatcagaa aacaaactac      540
ccatttgaag tcgttgttgc agatgatggt agtaaggaaa acttacttac cattgtgcaa      600
```

```
aaatacgaac aaaaacttga cataaagtat gtaagacaaa aagattatgg atatcaattg    660
tgtgcagtca gaaacttagg tttacgtaca gcaaagtatg attttgtctc gattctagac    720
tgcgatatgg caccacaaca attatgggtt cattcttatc ttacagaact attagaagac    780
aatgatattg ttttaattgg acctagaaaa tatgtggata ctcataatat taccgcagaa    840
caattcctta acgatccata tttaatagaa tcactacctg aaaccgctac aaataacaat    900
ccttcgatta catcaaaagg aaatatatcg ttggattgga gattagaaca tttcaaaaaa    960
accgataatc tacgtctatg tgattctccg tttcgttatt ttagttgcgg taatgttgca   1020
ttttctaaag aatggctaaa taagtaggt tggttcgatg aagaatttaa tcattggggg    1080
ggcgaagatg tagaatttgg ttacagatta tttgccaaag gctgttttt cagagtaatt     1140 gacggcggaa tggcatacca tcaagaacca cctggtaaaa aaatgaaac agaccgcgaa     1200 gctggtaaaa gtattacgct taaaattgtg aagaaaagg taccttacat ctatagaaag     1260
cttttaccaa tagaagattc acatattcat agaatacctt tagtttctat ttatatcccc   1320
gcttataact gtgcaaatta tattcaaaga tgtgtagata gtgctcttaa tcaaactgtt   1380
gtcgatctcg aggtttgtat ttgtaacgat ggttcaacag ataatacctt agaagtgatc   1440
aataagcttt atggtaataa tcctagggta cgcatcatgt ctaaaccaaa tggcggaata   1500
gcctcagcat caaatgcagc cgtttctttt gctaaaggtt attacattgg gcagttagat   1560
tcagatgatt atcttgagcc tgatgcagtt gaactgtgtt taaaagaatt tttaaaagat   1620
aaaacgctag cttgtgttta taccactaat agaaacgtca atccggatgg tagcttaatc   1680
gctaatggtt acaattggcc agaattttca cgagaaaaac tcacaacggc tatgattgct   1740
caccatttta gaatgtttac gattagagct tggcatttaa cggatggatt taacgaaaat   1800
attgaaaacg ccgtggatta tgacatgttc cttaaactca gtgaagttgg aaaatttaaa   1860
catcttaata aaatctgcta taccgcgta ttacatggtg ataacacatc cattaagaaa    1920
ctcggcattc aaaagaaaaa ccatttttgtt gtagtcaatc agtcattaaa tagacaaggc   1980
atcaattatt ataattatga caatttgat gatttagatg aaagtagaaa gtatatcttc    2040
aataaaaccg ctgaatatca agaagaaatg gatattttaa aagatcttaa actcattcaa   2100
aataaagatg cctaa                                                     2115
```

<210> SEQ ID NO 27
<211> LENGTH: 1980
<212> TYPE: DNA
<213> ORGANISM: Pasteurella multocida

<400> SEQUENCE: 27

```
atgctctcag cacatccttc tgttaattca gcacatcttt ctgtaaataa agaagaaaaa     60
gtcaatgttt gcgatagtcc gttagatatt gcaacacaac tgttactttc caacgtaaaa    120
aaattagtac tttctgactc ggaaaaaaac acgttaaaaa ataaatggaa attgctcact    180
gagaagaaat ctgaaaatgc ggaggtaaga gcggtcgccc ttgtaccaaa agattttccc    240
aaagatctgg ttttagcgcc tttacctgat catgttaatg attttacatg gtacaaaaag    300
cgaaagaaaa gacttggcat aaaacctgaa catcaacatg ttggtctttc tattatcgtt    360
acaacattca atcgaccagc aattttatcg attacattag cctgtttagt aaaccaaaaa    420
acacattacc cgtttgaagt tatcgtgaca gatgatggta gtcaggaaga tctatcaccg    480
atcattcgcc aatatgaaaa taattggat attcgctacg tcagacaaaa agataacggt    540
tttcaagcca gtgccgctcg gaatatggga ttacgcttag caaaatatga ctttattggc    600
```

-continued

```
ttactcgact gtgatatggc gccaaatcca ttatgggttc attcttatgt tgcagagcta    660
ttagaagatg atgatttaac aatcattggt ccaagaaaat acatcgatac acaacatatt    720
gacccaaaag acttcttaaa taacgcgagt ttgcttgaat cattaccaga agtgaaaacc    780
aataatagtg ttgccgcaaa aggggaagga acagtttctc tggattggcg cttagaacaa    840
ttcgaaaaaa cagaaaatct ccgcttatcc gattcgcctt tccgtttttt tgcggcgggt    900
aatgttgctt tcgctaaaaa atggctaaat aaatccggtt tctttgatga ggaatttaat    960
cactggggtg gagaagatgt ggaatttgga tatcgcttat tccgttacgg tagtttcttt   1020
aaaactattg atggcattat ggcctaccat caagagccac caggtaaaga aaatgaaacc   1080
gatcgtgaag cgggaaaaaa tattacgctc gatattatga gagaaaaggt cccttatatc   1140
tatagaaaac ttttaccaat agaagattcg catatcaata gagtaccttt agtttcaatt   1200
tatatcccag cttataactg tgcaaactat attcaacgtt gcgtagatag tgcactgaat   1260
cagactgttg ttgatctcga ggtttgtatt tgtaacgatg gttcaacaga taatacctta   1320
gaagtgatca ataagcttta tggtaataat cctagggtac gcatcatgtc taaaccaaat   1380
ggcggaatag cctcagcatc aaatgcagcc gtttcttttg ctaaaggtta ttacattggg   1440
cagttagatt cagatgatta tcttgagcct gatgcagttg aactgtgttt aaaagaattt   1500
ttaaaagata aaacgctagc ttgtgtttat accactaata gaaacgtcaa tccggatggt   1560
agcttaatcg ctaatggtta caattggcca gaattttcac gagaaaaact cacaacggct   1620
atgattgctc accactttag aatgttcacg attagagctt ggcatttaac tgatggattc   1680
aatgaaaaaa ttgaaaatgc cgtagactat gacatgttcc tcaaactcag tgaagttgga   1740
aaatttaaac atcttaataa aatctgctat aaccgtgtat tacatggtga taacacatca   1800
attaagaaac ttggcattca aaagaaaaac cattttgttg tagtcaatca gtcattaaat   1860
agacaaggca taacttatta taattatgac gaatttgatg atttagatga aagtagaaag   1920
tatattttca ataaaaccgc tgaatatcaa gaagagattg atatcttaaa agatatttaa   1980
```

<210> SEQ ID NO 28
<211> LENGTH: 1902
<212> TYPE: DNA
<213> ORGANISM: Pasteurella multocida

<400> SEQUENCE: 28

```
atgttagata ttgcaacaca actgttactt tccaacgtaa aaaaattagt actttctgac     60
tcggaaaaaa acacgttaaa aaataaatgg aaattgctca ctgagaagaa atctgaaaat    120
gcggaggtaa gagcggtcgc ccttgtacca aaagattttc ccaaagatct ggttttagcg    180
cctttacctg atcatgttaa tgattttaca tggtacaaaa agcgaaagaa aagacttggc    240
ataaaacctg aacatcaaca tgttggtctt tctattatcg ttacaacatt caatcgacca    300
gcaattttat cgattacatt agcctgttta gtaaaccaaa aaacacatta cccgtttgaa    360
gttatcgtga cagatgatgg tagtcaggaa gatctatcac cgatcattcg ccaatatgaa    420
aataaattgg atattcgcta cgtcagacaa aaagataacg gttttcaagc cagtgccgct    480
cggaatatgg gattacgctt agcaaaatat gactttattg gcttactcga ctgtgatatg    540
gcgccaaatc cattatgggt tcattcttat gttgcagagc tattagaaga tgatgattta    600
acaatcattg gtccaagaaa atacatcgat acacaacata ttgacccaaa agacttctta    660
aataacgcga gtttgcttga atcattacca gaagtgaaaa ccaataatag tgttgccgca    720
```

```
aaaggggaag gaacagtttc tctggattgg cgcttagaac aattcgaaaa aacagaaaat    780
ctccgcttat ccgattcgcc tttccgtttt tttgcggcgg gtaatgttgc tttcgctaaa    840
aaatggctaa ataaatccgg tttctttgat gaggaattta atcactgggg tggagaagat    900
gtggaatttg gatatcgctt attccgttac ggtagtttct ttaaaactat tgatggcatt    960
atggcctacc atcaagagcc accaggtaaa gaaaatgaaa ccgatcgtga agcgggaaaa   1020
aatattacgc tcgatattat gagagaaaag gtcccttata tctatagaaa acttttacca   1080
atagaagatt cgcatatcaa tagagtacct ttagtttcaa tttatatccc agcttataac   1140
tgtgcaaact atattcaacg ttgcgtagat agtgcactga atcagactgt tgttgatctc   1200
gaggtttgta tttgtaacga tggttcaaca gataatacct tagaagtgat caataagctt   1260
tatggtaata atcctagggt acgcatcatg tctaaaccaa atggcggaat agcctcagca   1320
tcaaatgcag ccgtttcttt tgctaaaggt tattacattg ggcagttaga ttcagatgat   1380
tatcttgagc ctgatgcagt tgaactgtgt ttaaaagaat ttttaaaaga taaaacgcta   1440
gcttgtgttt ataccactaa tagaaacgtc aatccggatg gtagcttaat cgctaatggt   1500
tacaattggc cagaattttc acgagaaaaa ctcacaacgg ctatgattgc tcaccacttt   1560
agaatgttca cgattagagc ttggcattta actgatggat tcaatgaaaa aattgaaaat   1620
gccgtagact atgacatgtt cctcaaactc agtgaagttg gaaaatttaa acatcttaat   1680
aaaatctgct ataaccgtgt attacatggt gataacacat caattaagaa acttggcatt   1740
caaaagaaaa accattttgt tgtagtcaat cagtcattaa atagacaagg cataacttat   1800
tataattatg acgaatttga tgatttagat gaaagtagaa agtatatttt caataaaacc   1860
gctgaatatc aagaagagat tgatatctta aaagatattt aa                      1902

<210> SEQ ID NO 29
<211> LENGTH: 1830
<212> TYPE: DNA
<213> ORGANISM: Pasteurella multocida

<400> SEQUENCE: 29
atgttaaaaa ataaatggaa attgctcact gagaagaaat ctgaaaatgc ggaggtaaga     60
gcggtcgccc ttgtaccaaa agattttccc aaagatctgg ttttagcgcc tttacctgat    120
catgttaatg attttacatg gtacaaaaag cgaaagaaaa gacttggcat aaaacctgaa    180
catcaacatg ttggtctttc tattatcgtt acaacattca atcgaccagc aattttatcg    240
attacattag cctgtttagt aaaccaaaaa acacattacc cgtttgaagt tatccgtgaca    300 gatgatggta gtcaggaaga tctatcaccg atcattcgcc aatatgaaaa taaattggat    360
attcgctact cagacaaaaa agataaccggt tttcaagcca gtgccgctcg gaatatggga    420
ttacgcttag caaaatatga ctttattggc ttactcgact gtgatatggc gccaaatcca    480
ttatgggttc attcttatgt tgcagagcta ttagaagatg atgatttaac aatcattggt    540
ccaagaaaat acatcgatac acaacatatt gacccaaaag acttcttaaa taacgcgagt    600
ttgcttgaat cattaccaga agtgaaaacc aataatagtg ttgccgcaaa aggggaagga    660
acagtttctc tggattggcg cttagaacaa ttcgaaaaaa cagaaaatct ccgcttatcc    720
gattcgcctt ccgtttttt tgcggcgggt aatgttgctt cgctaaaaa atggctaaat     780 aaatccggtt tctttgatga ggaatttaat cactggggtg gagaagatgt ggaatttgga    840
tatcgcttat tccgttacgg tagtttcttt aaaactattg atggcattat ggcctaccat    900
caagagccac caggtaaaga aaatgaaacc gatcgtgaag cgggaaaaaa tattacgctc    960
```

```
gatattatga gagaaaaggt cccttatatc tatagaaaac ttttaccaat agaagattcg    1020
catatcaata gagtaccttt agtttcaatt tatatcccag cttataactg tgcaaactat    1080
attcaacgtt gcgtagatag tgcactgaat cagactgttg ttgatctcga ggtttgtatt    1140
tgtaacgatg gttcaacaga taataccttta gaagtgatca ataagcttta tggtaataat    1200
cctagggtac gcatcatgtc taaaccaaat ggcggaatag cctcagcatc aaatgcagcc    1260
gtttcttttg ctaaaggtta ttacattggg cagttagatt cagatgatta tcttgagcct    1320
gatgcagttg aactgtgttt aaaagaattt ttaaaagata aaacgctagc ttgtgtttat    1380
accactaata gaaacgtcaa tccggatggt agcttaatcg ctaatggtta caattggcca    1440
gaattttcac gagaaaaact cacaacggct atgattgctc cacctttag aatgttcacg     1500 attagagctt ggcatttaac tgatggattc aatgaaaaaa ttgaaaatgc cgtagactat    1560
gacatgttcc tcaaactcag tgaagttgga aaatttaaac atcttaataa aatctgctat    1620
aaccgtgtat tacatggtga taacacatca attaagaaac ttggcattca aaagaaaaac    1680
cattttgttg tagtcaatca gtcattaaat agacaaggca taacttatta taattatgac    1740
gaatttgatg atttagatga aagtagaaag tatattttca ataaaaccgc tgaatatcaa    1800
gaagagattg atatcttaaa agatatttaa                                     1830

<210> SEQ ID NO 30
<211> LENGTH: 1764
<212> TYPE: DNA
<213> ORGANISM: Pasteurella multocida

<400> SEQUENCE: 30
atgcttgtac caaagatttt tcccaaagat ctggttttag cgcctttacc tgatcatgtt      60
aatgatttta catggtacaa aaagcgaaag aaaagacttg cataaaaacc tgaacatcaa     120
catgttggtc tttctattat cgttacaaca ttcaatcgac cagcaatttt atcgattaca     180
ttagcctgtt tagtaaacca aaaaacacat tacccgtttg aagttatcgt gacagatgat     240
ggtagtcagg aagatctatc accgatcatt cgccaatatg aaaataaatt ggatattcgc     300
tacgtcagac aaaaagataa cggttttcaa gccagtgccg ctcggaatat gggattacgc     360
ttagcaaaat atgactttat tggcttactc gactgtgata tggcgccaaa tccattatgg     420
gttcattctt atgttgcaga gctattagaa gatgatgatt taacaatcat tggtccaaga     480
aaatacatcg atacacaaca tattgaccca aaagacttct taaataacgc gagttttgctt    540 gaatcattac cagaagtgaa aaccaataat agtgttgccg caaaggggga aggaacagtt    600
tctctggatt ggcgcttaga acaattcgaa aaaacagaaa atctccgctt atccgattcg    660 ccttttccgtt tttttgcggc gggtaatgtt gctttcgcta aaaatggct aaataaatcc   720 ggttctttg atgaggaatt taatcactgg ggtggagaag atgtgaatt tggatatcgc    780 ttattccgtt acggtagttt cttaaaaact attgatggca ttatggccta ccatcaagag    840
ccaccaggta agaaaatga aaccgatcgt gaagcgggaa aaaatattac gctcgatatt    900
atgagagaaa aggtcccctta tctatagaa aactttac caatagaaga ttcgcatatc     960
aatagagtac ctttagtttc aatttatatc ccagcttata actgtgcaaa ctatattcaa   1020
cgttgcgtag atagtgcact gaatcagact gttgttgatc tcgaggtttg tatttgtaac   1080
gatggttcaa cagataatac cttagaagtg atcaataagc tttatggtaa taatcctagg   1140
gtacgcatca tgtctaaacc aaatggcgga atagcctcag catcaaatgc agccgtttct   1200
```

-continued

```
tttgctaaag gttattacat tgggcagtta gattcagatg attatcttga gcctgatgca    1260
gttgaactgt gtttaaaaga attttttaaaa gataaaacgc tagcttgtgt ttataccact   1320
aatagaaacg tcaatccgga tggtagctta atcgctaatg gttacaattg gccagaattt    1380
tcacgagaaa aactcacaac ggctatgatt gctcaccact ttagaatgtt cacgattaga    1440
gcttggcatt taactgatgg attcaatgaa aaaattgaaa atgccgtaga ctatgacatg    1500
ttcctcaaac tcagtgaagt tggaaaattt aaacatctta ataaaatctg ctataaccgt    1560
gtattacatg gtgataacac atcaattaag aaacttggca ttcaaaagaa aaaccatttt    1620
gttgtagtca atcagtcatt aaatagacaa ggcataactt attataatta tgacgaattt    1680
gatgatttag atgaaagtag aaagtatatt ttcaataaaa ccgctgaata tcaagaagag    1740
attgatatct taaaagatat ttaa                                           1764
```

<210> SEQ ID NO 31
<211> LENGTH: 2007
<212> TYPE: DNA
<213> ORGANISM: Pasteurella multocida

<400> SEQUENCE: 31

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg ttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta ataacgcga gtttgcttga atcattacca    900
gaagtgaaaa ccaataatag tgttgccgca aagggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta tcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa atattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga tcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
```

```
tattacattg ggcagttaga ttcagatgat tatcttgagc ctgatgcagt tgaactgtgt    1620
ttaaaagaat ttttaaaaga taaaacgcta gcttgtgttt ataccactaa tagaaacgtc    1680
aatccggatg gtagcttaat cgctaatggt tacaattggc cagaattttc acgagaaaaa    1740
ctcacaacgg ctatgattgc tcaccacttt agaatgttca cgattagagc ttggcattta    1800
actgatggat tcaatgaaaa aattgaaaat gccgtagact atgacatgtt cctcaaactc    1860
agtgaagttg gaaaatttaa acatcttaat aaaatctgct ataaccgtgt attacatggt    1920
gataacacat caattaagaa acttggcatt caaaagaaaa accattttgt tgtagtcaat    1980
cagtcattaa atagacaagg catataa                                       2007
```

```
<210> SEQ ID NO 32
<211> LENGTH: 2061
<212> TYPE: DNA
<213> ORGANISM: Pasteurella multocida

<400> SEQUENCE: 32
atgaatacat tatcacaagc aataaaagca tataacagca atgactatca attagcactc      60
aaattatttg aaaagtcggc ggaaatctat ggacggaaaa ttgttgaatt tcaaattacc     120
aaatgcaaag aaaaactctc agcacatcct tctgttaatt cagcacatct ttctgtaaat     180
aaagaagaaa aagtcaatgt ttgcgatagt ccgttagata ttgcaacaca actgttactt     240
tccaacgtaa aaaaattagt actttctgac tcggaaaaaa acacgttaaa aaataaatgg     300
aaattgctca ctgagaagaa atctgaaaat gcggaggtaa gagcggtcgc ccttgtacca     360
aaagattttc ccaaagatct ggttttagcg cctttacctg atcatgttaa tgattttaca     420
tggtacaaaa agcgaaagaa aagacttggc ataaaacctg aacatcaaca tgttggtctt     480
tctattatcg ttacaacatt caatcgacca gcaatttat cgattacatt agcctgttta      540
gtaaaccaaa aaacacatta cccgtttgaa gttatcgtga cagatgatgg tagtcaggaa     600
gatctatcac cgatcattcg ccaatatgaa aataaattgg atattcgcta cgtcagacaa     660
aaagataacg ttttcaagc cagtgccgct cggaatatgg gattacgctt agcaaaatat      720
gactttattg gcttactcga ctgtgatatg gcgccaaatc cattatgggt tcattcttat     780
gttgcagagc tattagaaga tgatgattta acaatcattg gtccaagaaa atacatcgat     840
acacaacata ttgacccaaa agacttctta aataacgcga gtttgcttga atcattacca     900
gaagtgaaaa ccaataatag tgttgccgca aaagggaag gaacagtttc tctggattgg      960
cgcttagaac aattcgaaaa aacagaaaat ctccgcttat ccgattcgcc tttccgtttt    1020
tttgcggcgg gtaatgttgc tttcgctaaa aaatggctaa ataaatccgg tttctttgat    1080
gaggaattta atcactgggg tggagaagat gtggaatttg atatcgctt attccgttac     1140 ggtagtttct ttaaaactat tgatggcatt atggcctacc atcaagagcc accaggtaaa    1200
gaaaatgaaa ccgatcgtga agcgggaaaa atattacgc tcgatattat gagagaaaag    1260
gtcccttata tctatagaaa acttttacca atagaagatt cgcatatcaa tagagtacct    1320
ttagtttcaa tttatatccc agcttataac tgtgcaaact atattcaacg ttgcgtagat    1380
agtgcactga atcagactgt tgttgatctc gaggtttgta tttgtaacga tggttcaaca    1440 gataataccct tagaagtgat caataagctt tatggtaata atcctagggt acgcatcatg    1500
tctaaaccaa atggcggaat agcctcagca tcaaatgcag ccgtttcttt tgctaaaggt    1560
tattacattg ggcagttaga ttcagatgat tatcttgagc ctgatgcagt tgaactgtgt    1620
```

```
ttaaaagaat ttttaaaaga taaaacgcta gcttgtgttt ataccactaa tagaaacgtc    1680
aatccggatg gtagcttaat cgctaatggt tacaattggc cagaattttc acgagaaaaa    1740
ctcacaacgg ctatgattgc tcaccacttt agaatgttca cgattagagc ttggcattta    1800
actgatggat tcaatgaaaa aattgaaaat gccgtagact atgacatgtt cctcaaactc    1860
agtgaagttg gaaaatttaa acatcttaat aaaatctgct ataaccgtgt attacatggt    1920
gataacacat caattaagaa acttggcatt caaaagaaaa accattttgt tgtagtcaat    1980
cagtcattaa atagacaagg cataacttat tataattatg acgaatttga tgatttagat    2040
gaaagtagaa agtatattta a                                              2061
```

<210> SEQ ID NO 33
<211> LENGTH: 2112
<212> TYPE: DNA
<213> ORGANISM: Pasteurella multocida

<400> SEQUENCE: 33

```
atgaatacat tatcacaagc aataaaagca tataacagca atgactatca attagcactc      60
aaattatttg aaaagtcggc ggaaatctat ggacggaaaa ttgttgaatt tcaaattacc     120
aaatgcaaag aaaaactctc agcacatcct tctgttaatt cagcacatct ttctgtaaat     180
aaagaagaaa aagtcaatgt ttgcgatagt ccgttagata ttgcaacaca actgttactt     240
tccaacgtaa aaaattagt actttctgac tcggaaaaaa acacgttaaa aaataaatgg     300
aaattgctca ctgagaagaa atctgaaaat gcggaggtaa gagcggtcgc ccttgtacca     360
aaagattttc ccaaagatct ggttttagcg cctttacctg atcatgttaa tgattttaca     420
tggtacaaaa agcgaagaa aagacttggc ataaaacctg aacatcaaca tgttggtctt     480
tctattatcg ttacaacatt caatcgacca gcaatttat cgattacatt agcctgttta     540
gtaaaccaaa aaacacatta cccgtttgaa gttatcgtga cagatgatgg tagtcaggaa     600
gatctatcac cgatcattcg ccaatatgaa aataaattgg atattcgcta cgtcagacaa     660
aaagataacg ttttcaagc cagtgccgct cggaatatgg gattacgctt agcaaaatat     720
gactttattg gcttactcga atgtgatatg cgccaaatc cattatgggt tcattcttat     780
gttgcagagc tattagaaga tgatgattta acaatcattg gtccaagaaa atacatcgat     840
acacaacata ttgacccaaa agacttctta aataacgcga gtttgcttga atcattacca     900
gaagtgaaaa ccaataatag tgttgccgca aaggggaag gaacagtttc tctggattgg     960
cgcttagaac aattcgaaaa aacagaaaat ctccgcttat ccgattcgcc tttccgtttt    1020
tttgcggcgg gtaatgttgc tttcgctaaa aaatggctaa ataaatccgg tttctttgat    1080
gaggaattta atcactgggg tggagaagat gtggaatttg gatatcgctt attccgttac    1140
ggtagtttct ttaaaactat tgatggcatt atggcctacc atcaagagcc accaggtaaa    1200
gaaaatgaaa ccgatcgtga agcgggaaaa atattcgc tcgatattat gagagaaaag    1260 gtccccttata tctatagaaa acttttacca atagaagatt cgcatatcaa tagagtacct    1320
ttagtttcaa tttatatccc agcttataac tgtgcaaact atattcaacg ttgcgtagat    1380
agtgcactga atcagactgt tgttgatctc gaggtttgta tttgtaacga tggttcaaca    1440
gataatacct tagaagtgat caataagctt tatggtaata atcctagggt acgcatcatg    1500
tctaaaccaa atggcggaat agcctcagca tcaaatgcag ccgtttcttt tgctaaaggt    1560
tattacattg ggcagttaga ttcagatgat tatcttgagc ctgatgcagt tgaactgtgt    1620
ttaaaagaat ttttaaaaga taaaacgcta gcttgtgttt ataccactaa tagaaacgtc    1680
```

-continued aatccggatg gtagcttaat cgctaatggt tacaattggc cagaattttc acgagaaaaa 1740
ctcacaacgg ctatgattgc tcaccacttt agaatgttca cgattagagc ttggcattta 1800
actgatggat tcaatgaaaa aattgaaaat gccgtagact atgacatgtt cctcaaactc 1860
agtgaagttg gaaaatttaa acatcttaat aaaatctgct ataaccgtgt attacatggt 1920
gataacacat caattaagaa acttggcatt caaaagaaaa accattttgt tgtagtcaat 1980
cagtcattaa atagacaagg cataacttat tataattatg acgaatttga tgatttagat 2040
gaaagtagaa agtatatttt caataaaacc gctgaatatc aagaagagat tgatatctta 2100
aaagatattt aa 2112

<210> SEQ ID NO 34
<211> LENGTH: 2112
<212> TYPE: DNA
<213> ORGANISM: Pasteurella multocida

<400> SEQUENCE: 34
atgaatacat tatcacaagc aataaaagca tataacagca atgactatca attagcactc 60
aaattatttg aaaagtcggc ggaaatctat ggacggaaaa ttgttgaatt tcaaattacc 120
aaatgcaaag aaaaactctc agcacatcct tctgttaatt cagcacatct ttctgtaaat 180
aaagaagaaa aagtcaatgt ttgcgatagt ccgttagata ttgcaacaca actgttactt 240
tccaacgtaa aaaaattagt actttctgac tcggaaaaaa acacgttaaa aaataaatgg 300
aaattgctca ctgagaagaa atctgaaaat gcggaggtaa gagcggtcgc ccttgtacca 360
aaagattttc ccaaagatct ggttttagcg cctttacctg atcatgttaa tgattttaca 420
tggtacaaaa agcgaaagaa aagacttggc ataaaacctg aacatcaaca tgttggtctt 480
tctattatcg ttacaacatt caatcgacca gcaattttat cgattacatt agcctgttta 540
gtaaaccaaa aaacacatta cccgtttgaa gttatcgtga cagatgatgg tagtcaggaa 600
gatctatcac cgatcattcg ccaatatgaa aataaattgg atattcgcta cgtcagacaa 660
aaagataacg gttttcaagc cagtgccgct cggaatatgg gattacgctt agcaaaatat 720
gactttattg gcttactcaa ctgtgatatg gcgccaaatc cattatgggt tcattcttat 780
gttgcagagc tattagaaga tgatgattta acaatcattg gtccaagaaa atacatcgat 840
acacaacata ttgacccaaa agacttctta aataacgcga gtttgcttga atcattacca 900
gaagtgaaaa ccaataatag tgttgccgca aaaggggaag gaacagtttc tctggattgg 960
cgcttagaac aattcgaaaa aacagaaaat ctccgcttat ccgattcgcc tttccgtttt 1020
tttgcggcgg gtaatgttgc tttcgctaaa aaatggctaa ataaatccgg tttctttgat 1080
gaggaattta atcactgggg tggagaagat gtggaatttg gatatcgctt attccgttac 1140
ggtagtttct ttaaaactat tgatggcatt atggcctacc atcaagagcc accaggtaaa 1200
gaaaatgaaa ccgatcgtga agcgggaaaa aatattacgc tcgatattat gagagaaaag 1260
gtcccttata tctatagaaa acttttacca atagaagatt cgcatatcaa tagagtacct 1320
ttagtttcaa tttatatccc agcttataac tgtgcaaact atattcaacg ttgcgtagat 1380
agtgcactga atcagactgt tgttgatctc gaggtttgta tttgtaacga tggttcaaca 1440
gataatacct tagaagtgat caataagctt tatggtaata atcctagggt acgcatcatg 1500
tctaaaccaa atggcggaat agcctcagca tcaaatgcag ccgtttcttt tgctaaaggt 1560
tattacattg ggcagttaga ttcagatgat tatcttgagc ctgatgcagt tgaactgtgt 1620

-continued

| | |
|---|---|
| ttaaaagaat ttttaaaaga taaaacgcta gcttgtgttt ataccactaa tagaaacgtc | 1680 |
| aatccggatg gtagcttaat cgctaatggt tacaattggc cagaattttc acgagaaaaa | 1740 |
| ctcacaacgg ctatgattgc tcaccacttt agaatgttca cgattagagc ttggcattta | 1800 |
| actgatggat tcaatgaaaa aattgaaaat gccgtagact atgacatgtt cctcaaactc | 1860 |
| agtgaagttg gaaatttaa acatcttaat aaaatctgct ataaccgtgt attacatggt | 1920 |
| gataacacat caattaagaa acttggcatt caaaagaaaa accattttgt tgtagtcaat | 1980 |
| cagtcattaa atagacaagg cataacttat tataattatg acgaatttga tgatttagat | 2040 |
| gaaagtagaa agtatatttt caataaaacc gctgaatatc aagaagagat tgatatctta | 2100 |
| aaagatattt aa | 2112 |

<210> SEQ ID NO 35
<211> LENGTH: 2112
<212> TYPE: DNA
<213> ORGANISM: Pasteurella multocida

<400> SEQUENCE:

-continued

```
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 36
<211> LENGTH: 2112
<212> TYPE: DNA
<213> ORGANISM: Pasteurella multocida

<400> SEQUENCE: 36

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgaaatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
```

```
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112

<210> SEQ ID NO 37
<211> LENGTH: 2112
<212> TYPE: DNA
<213> ORGANISM: Pasteurella multocida

<400> SEQUENCE: 37
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaatttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg ttttcaagc cagtgccgct cggaatatgg gattacgctt agcaaaatat    720
gactttattg gcttactcga ctgtaatatg gcgccaaatc cattatgggt tcattcttat    780
gttgcagagc tattgaagaa tgatgattta caatcattg gtccaagaaa atacatcgat    840
acacaacata ttgacccaaa agacttctta ataacgcga gtttgcttga atcattacca    900
gaagtgaaaa ccaataatag tgttgccgca aaagggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260 gtccccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
```

-continued

```
tattacattg ggcagttaga ttcagatgat tatcttgagc ctgatgcagt tgaactgtgt    1620
ttaaaagaat ttttaaaaga taaaacgcta gcttgtgttt ataccactaa tagaaacgtc    1680
aatccggatg gtagcttaat cgctaatggt tacaattggc cagaattttc acgagaaaaa    1740
ctcacaacgg ctatgattgc tcaccacttt agaatgttca cgattagagc ttggcattta    1800
actgatggat tcaatgaaaa aattgaaaat gccgtagact atgacatgtt cctcaaactc    1860
agtgaagttg gaaaatttaa acatcttaat aaaatctgct ataaccgtgt attacatggt    1920
gataacacat caattaagaa acttggcatt caaaagaaaa accattttgt tgtagtcaat    1980
cagtcattaa atagacaagg cataacttat tataattatg acgaatttga tgatttagat    2040
gaaagtagaa agtatatttt caataaaacc gctgaatatc aagaagagat tgatatctta    2100
aaagatattt aa                                                        2112
```

<210> SEQ ID NO 38
<211> LENGTH: 2112
<212> TYPE: DNA
<213> ORGANISM: Pasteurella multocida

<400> SEQUENCE: 38

```

-continued

```
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 39
<211> LENGTH: 2112
<212> TYPE: DNA
<213> ORGANISM: Pasteurella multocida

<400> SEQUENCE: 39

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
```

```
tctaaaccaa atggcggaat agcctcagca tcaaatgcag ccgtttcttt tgctaaaggt    1560
tattacattg ggcagttaaa ttcagatgat tatcttgagc ctgatgcagt tgaactgtgt    1620
ttaaaagaat ttttaaaaga taaaacgcta gcttgtgttt ataccactaa tagaaacgtc    1680
aatccggatg gtagcttaat cgctaatggt tacaattggc cagaattttc acgagaaaaa    1740
ctcacaacgg ctatgattgc tcaccacttt agaatgttca cgattagagc ttggcatttα    1800 actgatggat tcaatgaaaa aattgaaaat gccgtagact atgacatgtt cctcaaactc    1860
agtgaagttg gaaaatttaa acatcttaat aaaatctgct ataaccgtgt attacatggt    1920
gataacacat caattaagaa acttggcatt caaaagaaaa accattttgt tgtagtcaat    1980
cagtcattaa atagacaagg cataacttat tataattatg acgaatttga tgatttagat    2040
gaaagtagaa agtatatttt caataaaacc gctgaatatc aagaagagat tgatatctta    2100
aaagatattt aa                                                        2112
```

<210> SEQ ID NO 40  
<211> LENGTH: 2112  
<212> TYPE: DNA  
<213> ORGANISM: Pasteurella multocida

<400> SEQUENCE: 40

```
atgaatacat tatcacaagc aataaaagca tataacagca at

-continued

```
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga atcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 41
<211> LENGTH: 2112
<212> TYPE: DNA
<213> ORGANISM: Pasteurella multocida

<400> SEQUENCE: 41

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagatttcc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
```

-continued

```
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaaa atcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                        2112
```

<210> SEQ ID NO 42
<211> LENGTH: 2112
<212> TYPE: DNA
<213> ORGANISM: Pasteurella multocida

<400> SEQUENCE: 42

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaagat gtggaatttg gatatcgctt attccgttac   1140
ggtagtttct ttaaaactat tgatggcatt atggcctacc atcaagagcc accaggtaaa   1200
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
```

```
agtgcactga atcagactgt tgttgatctc gaggtttgta tttgtaacga tggttcaaca    1440
gataatacct tagaagtgat caataagctt tatggtaata atcctagggt acgcatcatg    1500
tctaaaccaa atggcggaat agcctcagca tcaaatgcag ccgtttcttt tgctaaaggt    1560
tattacattg ggcagttaga ttcagaagat tatcttgagc ctgatgcagt tgaactgtgt    1620
ttaaaagaat ttttaaaaga taaaacgcta gcttgtgttt ataccactaa tagaaacgtc    1680
aatccggatg gtagcttaat cgctaatggt tacaattggc cagaatttc acgagaaaaa    1740 ctcacaacgg ctatgattgc tcaccacttt agaatgttca cgattagagc ttggcattta    1800
actgatggat tcaatgaaaa aattgaaaat gccgtagact atgacatgtt cctcaaactc    1860
agtgaagttg aaaatttaa acatcttaat aaaatctgct ataaccgtgt attacatggt    1920
gataacacat caattaagaa acttggcatt caaaagaaaa accattttgt tgtagtcaat    1980
cagtcattaa atagacaagg cataacttat tataattatg acgaatttga tgatttagat    2040
gaaagtagaa agtatatttt caataaaacc gctgaatatc aagaagagat tgatatctta    2100
aaagatattt aa                                                       2112

<210> SEQ ID NO 43
<211> LENGTH: 2112
<212> TYPE: DNA
<213> ORGANISM: Pasteurella multocida

<400> SEQUENCE: 43
atgaatacat tatcacaagc aataaaagca tataacagca atgactatca attagcactc      60
aaattatttg aaaagtcggc ggaaatctat ggacggaaaa ttgttgaatt tcaaattacc     120
aaatgcaaag aaaaactctc agcacatcct tctgttaatt cagcacatct ttctgtaaat     180
aaagaagaaa aagtcaatgt ttgcgatagt ccgttagata ttgcaacaca actgttactt     240
tccaacgtaa aaaaattagt actttctgac tcggaaaaaa acacgttaaa aaataaatgg     300
aaattgctca ctgagaagaa atctgaaaat gcggaggtaa gagcggtcgc ccttgtacca     360
aaagattttc ccaaagatct ggtttagcg cctttacctg atcatgttaa tgattttaca     420
tggtacaaaa agcgaaagaa aagacttggc ataaaacctg aacatcaaca tgttggtctt     480
tctattatcg ttacaacatt caatcgacca gcaattttat cgattacatt agcctgttta     540
gtaaaccaaa aaacacatta cccgtttgaa gttatcgtga cagatgatgg tagtcaggaa     600
gatctatcac cgatcattcg ccaatatgaa aataaattgg atattcgcta cgtcagacaa     660
aaagataacg gttttcaagc cagtgccgct cggaatatgg gattacgctt agcaaaatat     720
gactttattg gcttactcga ctgtgatatg gcgccaaatc cattatgggt tcattcttat     780
gttgcagagc tattagaaga tgatgattta caatcattg gtccaagaaa atacatcgat     840
acacaacata ttgacccaaa agacttctta aataacgcga gtttgcttga atcattacca     900
gaagtgaaaa ccaataatag tgttgccgca aaagggaag gaacagtttc tctggattgg     960
cgcttagaac aattcgaaaa aacagaaaat ctccgcttat ccgattcgcc tttccgtttt    1020
tttgcggcgg gtaatgttgc tttcgctaaa aaatggctaa ataaatccgg tttctttgat    1080
gaggaattta tcactgggg tggagaagat gtggaatttg gatatcgctt attccgttac    1140
ggtagtttct ttaaaactat tgatggcatt atggcctacc atcaagagcc accaggtaaa    1200
gaaaatgaaa ccgatcgtga agcgggaaaa atattacgc tcgatattat gagagaaaag    1260
gtcccttata tctatagaaa actttttacca atagaagatt cgcatatcaa tagagtacct    1320
ttagtttcaa tttatatccc agcttataac tgtgcaaact atattcaacg ttgcgtagat    1380
```

```
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcaaatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                      2112

<210> SEQ ID NO 44
<211> LENGTH: 2112
<212> TYPE: DNA
<213> ORGANISM: Pasteurella multocida

<400> SEQUENCE: 44
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg ccttttacctg atcatgttaa tgattttaca    420
tggtacaaaa agcgaaagaa aagacttggc ataaaacctg aacatcaaca tgttggtctt    480
tctattatcg ttcaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta caatcattg gtccaagaaa atacatcgat    840
acacaacata ttgacccaaa agacttctta ataacgcga gtttgcttga atcattacca    900
gaagtgaaaa ccaataatag tgttgccgca aaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta tcactggggg tgagaagat gtggaattg gatatcgctt attccgttac   1140
ggtagtttct ttaaaactat tgatggcatt atggcctacc atcaagagcc accaggtaaa   1200
gaaaatgaaa ccgatcgtga agcgggaaaa atattacgc tcgatattat gagagaaaag   1260 gtccccttata tctatagaaa acttttacca atagaagatt cgcatatcaa tagagtacct   1320
```

```
ttagtttcaa tttatatccc agcttataac tgtgcaaact atattcaacg ttg

```
ttagtttcaa tttatatccc agcttataac tgtgcaaact atattcaacg ttgcgtagat      1380
agtgcactga atcagactgt tgttgatctc gaggtttgta tttgtaacga tggttcaaca      1440
gataatacct tagaagtgat caataagctt tatggtaata atcctagggt acgcatcatg      1500
tctaaaccaa atggcggaat agcctcagca tcaaatgcag ccgtttcttt tgctaaaggt      1560
tattacattg ggcagttaga ttcagatgat tatcttgagc ctgatgcagt tgaactgtgt      1620
ttaaaagaat ttttaaaaga taaaacgcta gcttgtgttt ataccactaa tagaaacgtc      1680
aatccggatg gtagcttaat cgctaatggt tacaattggc cagaattttc acgagaaaaa      1740
ctcacaacgg ctatgattgc tcaccacttt agaatgttca cgattagagc ttggcattta      1800
actgatggat tcaatgaaaa aattgaaaat gccgtagact atgacatgtt cctcaaactc      1860
agtgaagttg gaaaatttaa acatcttaat aaaatctgct ataaccgtgt attacatggt      1920
gataacacat caattaagaa acttggcatt caaaagaaaa accattttgt tgtagtcaat      1980
cagtcattaa atagacaagg cataaactat tataattatg acgaatttga tgatttagat      2040
gaaagtagaa agtatatttt caataaaacc gctgaatatc aagaagagat tgatatctta      2100
aaagatattt aa                                                         2112

<210> SEQ ID NO 46
<211> LENGTH: 2112
<212> TYPE: DNA
<213> ORGANISM: Pasteurella multocida

<400> SEQUENCE:

-continued

| | |
|---|---|
| gtcccttata tctatagaaa acttttacca atagaagatt cgcatatcaa tagagtacct | 1320 |
| ttagtttcaa tttatatccc agcttataac tgtgcaaact atattcaacg ttgcgtagat | 1380 |
| agtgcactga atcagactgt tgttgatctc gaggtttgta tttgtaacga tggttcaaca | 1440 |
| gataatacct tagaagtgat caataagctt tatggtaata atcctagggt acgcatcatg | 1500 |
| tctaaaccaa atggcggaat agcctcagca tcaaatgcag ccgtttcttt tgctaaaggt | 1560 |
| tattacattg ggcagttaga ttcagatgat tatcttgagc ctgatgcagt tgaactgtgt | 1620 |
| ttaaaagaat ttttaaaaga taaaacgcta gcttgtgttt ataccactaa tagaaacgtc | 1680 |
| aatccggatg gtagccttaat cgctaatggt tacaattggc cagaattttc acgagaaaaa | 1740 |
| ctcacaacgg ctatgattgc tcaccacttt agaatgttca cgattagagc ttggcattta | 1800 |
| actgatggat tcaatgaaaa aattgaaaat gccgtagact atgacatgtt cctcaaactc | 1860 |
| agtgaagttg aaaatttaa acatcttaat aaaatctgct ataaccgtgt attacatggt | 1920 |
| gataacacat caattaagaa acttggcatt caaaagaaaa accattttgt tgtagtcaat | 1980 |
| cagtcattaa atagacaagg cataacttat tataattatg acgaatttga tgatttagat | 2040 |
| gaaagtagaa agtatatttt caataaaaacc gctgaatatc aagaagagat tgatatctta | 2100 |
| aaagatattt aa | 2112 |

<210> SEQ ID NO 47
<211> LENGTH: 2112
<212> TYPE: DNA
<213> ORGANISM: Pasteurella multocida

<400> SEQUENCE: 47

| | |
|---|---|
| atgaatacat tatcacaagc aataaaagca tataacagca atgactatca attagcactc | 60 |
| aaattatttg aaaagtcggc ggaaatctat ggacggaaaa ttgttgaatt tcaaattacc | 120 |
| aaatgcaaag aaaaactctc agcacatcct tctgttaatt cagcacatct ttctgtaaat | 180 |
| aaagaagaaa aagtcaatgt ttgcgatagt ccgttagata ttgcaacaca actgttactt | 240 |
| tccaacgtaa aaaaattagt actttctgac tcggaaaaaa acacgttaaa aaataaatgg | 300 |
| aaattgctca ctgagaagaa atctgaaaat gcggaggtaa gagcggtcgc ccttgtacca | 360 |
| aaagattttc ccaaagatct ggttttagcg ccttttacctg atcatgttaa tgattttaca | 420 |
| tggtacaaaa agcgaaagaa aagacttggc ataaaacctg aacatcaaca tgttggtctt | 480 |
| tctattatcg ttacaacatt caatcgacca gcaattttat cgattacatt agcctgttta | 540 |
| gtaaaccaaa aaacacatta cccgtttgaa gttatcgtga cagatgatgg tagtcaggaa | 600 |
| gatctatcac cgatcattcg ccaatatgaa aataaattgg atattcgcta cgtcagacaa | 660 |
| aaagataacg ttttcaagc cagtgccgct cggaatatgg gattacgctt agcaaaatat | 720 |
| gactttattg gcttactcga ctgtgatatg cgccaaatc cattatgggt tcattcttat | 780 |
| gttgcagagc tattagaaga tgatgattta acaatcattg gtccaagaaa atacatcgat | 840 |
| acacaacata ttgacccaaa agacttctta aataacgcga gtttgcttga atcattacca | 900 |
| gaagtgaaaa ccaataatag tgttgccgca aaggggaag gaacagtttc tctggattgg | 960 |
| cgcttagaac aattcgaaaa aacagaaaat ctccgcttat ccgattcgcc tttccgtttt | 1020 |
| tttgcggcgg gtaatgttgc tttcgctaaa aatggctaa ataaatccgg tttcttttgat | 1080 |
| gaggaattta tcactgggg tggacacgat gtggaattg gatatcgctt attccgttac | 1140 |
| ggtagtttct ttaaaactat tgatggcatt atggcctacc atcaagagcc accaggtaaa | 1200 |
| gaaaatgaaa ccgatcgtga agcgggaaaa aatattacgc tcgatattat gagagaaaag | 1260 |

```
gtcccttata tctatagaaa acttttacca atagaagatt cgcatatcaa tagagtacct    1320
ttagtttcaa tttatatccc agcttataac tgtgcaaact atattcaacg ttgcgtagat    1380
agtgcactga atcagactgt tgttgatctc gaggtttgta tttgtaacga tggttcaaca    1440
gataatacct tagaagtgat caataagctt tatggtaata atcctagggt acgcatcatg    1500
tctaaaccaa atggcggaat agcctcagca tcaaatgcag ccgtttcttt tgctaaaggt    1560
tattacattg ggcagttaga ttcagatgat tatcttgagc ctgatgcagt tgaactgtgt    1620
ttaaaagaat ttttaaaaga taaaacgcta gcttgtgttt ataccactaa tagaaacgtc    1680
aatccggatg gtagcttaat cgctaatggt tacaattggc cagaattttc acgagaaaaa    1740
ctcacaacgg ctatgattgc tcaccacttt agaatgttca cgattagagc ttggcattta    1800
actgatggat tcaatgaaaa aattgaaaat gccgtagact atgacatgtt cctcaaactc    1860
agtgaagttg gaaatttaaa acatcttaat aaaatctgct ataaccgtgt attacatggt    1920
gataacacat caattaagaa acttggcatt caaaagaaaa accattttgt tgtagtcaat    1980
cagtcattaa atagacaagg cataacttat tataattatg acgaatttga tgatttagat    2040
gaaagtagaa agtatatttt caataaaacc gctgaatatc aagaagagat tgatatctta    2100
aaagatattt aa                                                        2112

<210> SEQ ID NO 48
<211> LENGTH: 2112
<212> TYPE: DNA
<213> ORGANISM: Pasteurella multocida

<400> SEQUENCE: 48
atgaatacat tatcacaagc aataaaagca tataacag

```
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112

<210> SEQ ID NO 49
<211> LENGTH: 2112
<212> TYPE: DNA
<213> ORGANISM: Pasteurella multocida

<400> SEQUENCE: 49
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaatttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg ttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta caatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaaaat gtggaatttg gatatcgctt attccgttac   1140
ggtagtttct ttaaaactat tgatggcatt atggcctacc atcaagagcc accaggtaaa   1200
```

-continued

```
gaaaatgaaa ccgatcgtga agcgggaaaa aatattacgc tcgatattat gagagaaaag   1260
gtcccttata tctatagaaa acttttacca atagaagatt cgcatatcaa tagagtacct   1320
ttagtttcaa tttatatccc agcttataac tgtgcaaact atattcaacg ttgcgtagat   1380
agtgcactga atcagactgt tgttgatctc gaggtttgta tttgtaacga tggttcaaca   1440
gataatacct tagaagtgat caataagctt tatggtaata atcctagggt acgcatcatg   1500
tctaaaccaa atggcggaat agcctcagca tcaaatgcag ccgtttcttt tgctaaaggt   1560
tattacattg ggcagttaga ttcagatgat tatcttgagc ctgatgcagt tgaactgtgt   1620
ttaaaagaat ttttaaaaga taaaacgcta gcttgtgttt ataccactaa tagaaacgtc   1680
aatccggatg gtagcttaat cgctaatggt tacaattggc cagaattttc acgagaaaaa   1740
ctcacaacgg ctatgattgc tcaccacttt agaatgttca cgattagagc ttggcattta   1800
actgatggat tcaatgaaaa aattgaaaat gccgtagact atgacatgtt cctcaaactc   1860
agtgaagttg gaaaatttaa acatcttaat aaaatctgct ataaccgtgt attacatggt   1920
gataacacat caattaagaa acttggcatt caaaagaaaa accattttgt tgtagtcaat   1980
cagtcattaa atagacaagg cataacttat tataattatg acgaatttga tgatttagat   2040
gaaagtagaa agtatatttt caataaaacc gctgaatatc aagaagagat tgatatctta   2100
aaagatattt aa                                                       2112
```

<210> SEQ ID NO 50
<211> LENGTH: 2112
<212> TYPE: DNA
<213> ORGANISM: Pasteurella multocida

<400> SEQUENCE: 50

```
atgaatacat tatcacaagc aataaaagca tataacagca atgactatca attagcactc     60
aaattatttg aaaagtcggc ggaaatctat ggacggaaaa ttgttgaatt tcaaattacc    120
aaatgcaaag aaaaactctc agcacatcct tctgttaatt cagcacatct ttctgtaaat    180
aaagaagaaa aagtcaatgt ttgcgatagt ccgttagata ttgcaacaca actgttactt    240
tccaacgtaa aaaaattagt actttctgac tcggaaaaaa acacgttaaa aaataaatgg    300
aaattgctca ctgagaagaa atctgaaaat gcggaggtaa gagcggtcgc ccttgtacca    360
aaagattttc ccaaagatct ggttttagcg cctttacctg atcatgttaa tgattttaca    420
tggtacaaaa agcgaaagaa aagacttggc ataaaacctg aacatcaaca tgttggtctt    480
tctattatcg ttacaacatt caatcgacca gcaattttat cgattacatt agcctgttta    540
gtaaaccaaa aaacacatta cccgtttgaa gttatcgtga cagatgatgg tagtcaggaa    600
gatctatcac cgatcattcg ccaatatgaa aataaattgg atattcgcta cgtcagacaa    660
aaagataacg gttttcaagc cagtgccgct cggaatatgg gattacgctt agcaaaatat    720
gactttattg gcttactcga ctgtgatatg gcgccaaatc cattatgggt tcattcttat    780
gttgcagagc tattagaaga tgatgattta acaatcattg gtccaagaaa atacatcgat    840
acacaacata ttgacccaaa agacttctta aataacgcga gtttgcttga atcattacca    900
gaagtgaaaa ccaataatag tgttgccgca aaaggggaag gaacagtttc tctggattgg    960
cgcttagaac aattcgaaaa aacagaaaat ctccgcttat ccgattcgcc tttccgtttt   1020
tttgcggcgg gtaatgttgc tttcgctaaa aaatggctaa ataaatccgg tttctttgat   1080
gaggaattta atcactgggg tggagaaaaa gtggaatttg gatatcgctt attccgttac   1140
```

-continued

```
ggtagtttct ttaaaactat tgatggcatt atggcctacc atcaagagcc accaggtaaa      1200
gaaaatgaaa ccgatcgtga agcgggaaaa aatattacgc tcgatattat gagagaaaag      1260
gtcccttata tctatagaaa acttttacca atagaagatt cgcatatcaa tagagtacct      1320
ttagtttcaa tttatatccc agcttataac tgtgcaaact atattcaacg ttgcgtagat      1380
agtgcactga atcagactgt tgttgatctc gaggtttgta tttgtaacga tggttcaaca      1440
gataatacct tagaagtgat caataagctt tatggtaata atcctagggt acgcatcatg      1500
tctaaaccaa atggcggaat agcctcagca tcaaatgcag ccgtttcttt tgctaaaggt      1560
tattacattg ggcagttaga ttcagatgat tatcttgagc ctgatgcagt tgaactgtgt      1620
ttaaaagaat ttttaaaaga taaaacgcta gcttgtgttt ataccactaa tagaaacgtc      1680
aatccggatg gtagcttaat cgctaatggt tacaattggc cagaattttc acgagaaaaa      1740
ctcacaacgg ctatgattgc tcaccacttt agaatgttca cgattagagc ttggcattta      1800
actgatggat tcaatgaaaa aattgaaaat gccgtagact atgacatgtt cctcaaactc      1860
agtgaagttg aaaatttaa acatcttaat aaaatctgct ataaccgtgt attacatggt      1920
gataacacat caattaagaa acttggcatt caaaagaaaa accattttgt tgtagtcaat      1980
cagtcattaa atagacaagg cataaacttat tataattatg acgaatttga tgatttagat      2040
gaaagtagaa agtatatttt caataaaacc gctgaatatc aagaagagat tgatatctta      2100
aaagatattt aa                                                          2112
```

<210> SEQ ID NO 51
<211> LENGTH: 2136
<212> TYPE: DNA
<213> ORGANISM: Pasteurella multocida

<400> SEQUENCE: 51

```
atgaacacat tatcacaagc aataaaagca tataacagca atgactatca attagcactc       60
aaattatttg aaaagtcggc ggaaatctat ggacggaaaa ttgttgaatt tcaaattacc      120
aaatgccaag aaaaactctc agcacatcct tctgttaatt cagcacatct ttctgtaaat      180
aaagaagaaa aagtcaatgt ttgcgatagt ccgttagata ttgcaacaca actgttactt      240
tccaacgtaa aaaaattagt actttctgac tcggaaaaaa acacgttaaa aaataaatgg      300
aaattgctca ctgagaagaa atctgaaaat gcggaggtaa gagcggtcgc ccttgtacca      360
aaagattttc ccaaagatct ggttttagcg cctttacctg atcatgttaa tgatttttaca      420 tggtacaaaa agcgaaagaa aagacttggc ataaaacctg aacatcaaca tgttggtctt      480
tctattatcg ttacaacatt caatcgacca gcaattttat cgattacatt agcctgtttta      540 gtaaaccaaa aaacacatta cccgtttgaa gttatcgtga cagatgatgg tagtcaggaa      600
gatctatcac cgatcattcg ccaatatgaa aataaattgg atattcgcta cgtcagacaa      660
aaagataacg ttttcaagc cagtgccgct cggaatatgg gattacgctt agcaaaatat      720
gactttattg gcttactcga ctgtgatatg gcgccaaatc cattatgggt tcattcttat      780
gttgcagagc tattagaaga tgatgattta acaatcattg gtccaagaaa atacatcgat      840
acacaacata ttgacccaaa agacttctta aataacgcga gtttgcttga atcattacca      900
gaagtgaaaa ccaataatag tgttgccgca aaggggaaag aacagttttc tctggattgg      960
cgcttagaac aattcgaaaa aacagaaaat ctccgcttat ccgattcgcc tttccgtttt     1020
tttgcggcgg gtaatgttgc tttcgctaaa aaatggctaa ataaatccgg tttctttgat     1080
gaggaattta atcactgggg tggagaagat gtggaatttg gatatcgctt attccgttac     1140
```

```
ggtagtttct ttaaaactat tgatggcatt atggcctacc atcaagagcc accaggtaaa    1200
gaaaatgaaa ccgatcgtga agcgggaaaa aatattacgc tcgatattat gagagaaaag    1260
gtcccttata tctatagaaa acttttacca atagaagatt cgcatattca tagaatacct    1320
ttagtttcta tttatatccc cgcttataac tgtgcaaatt atattcaaag atgtgtagat    1380
agtgctctta atcaaactgt tgtcgatctc gaggtttgta tttgtaacga tggttcaaca    1440
gataatacct tagaagtgat caataagctt tatggtaata atcctagggt acgcatcatg    1500
tctaaaccaa atggcggaat agcctcagca tcaaatgcag ccgtttcttt tgctaaaggt    1560
tattacattg ggcagttaga ttcagatgat tatcttgagc ctgatgcagt tgaactgtgt    1620
ttaaaagaat ttttaaaaga taaaacgcta gcttgtgttt ataccactaa tagaaacgtc    1680
aatccggatg gtagcttaat cgctaatggt tacaattggc cagaattttc acgagaaaaa    1740
ctcacaacgg ctatgattgc tcaccatttt agaatgttta cgattagagc ttggcattta    1800
acggatggat ttaacgaaaa tattgaaaac gccgtggatt atgacatgtt ccttaaactc    1860
agtgaagttg gaaaatttaa acatcttaat aaaatctgct ataaccgcgt attacatggt    1920
gataacacat ccattaagaa actcggcatt caaaagaaaa accattttgt tgtagtcaat    1980
cagtcattaa atagacaagg catcaattat tataattatg acaaatttga tgatttagat    2040
gaaagtagaa agtatatctt caataaaacc gctgaatatc aagaagaaat ggatattta    2100 aaagatctta aactcattca gaataaagat gcctaa                              2136
```

<210> SEQ ID NO 52
<211> LENGTH: 2091
<212> TYPE: DNA
<213> ORGANISM: Pasteurella multocida

<400> SEQUENCE: 52

```
atgaatacat tatcacaagc aataaaagca tataacagca atgactatga attagcactc      60
aaattatttg agaagtctgc tgaaacctac gggcgaaaaa tcgttgaatt ccaaattatc     120
aaatgtaaag aaaaactctc gaccaattct tatgtaagtg aagataaaaa aaacagtgtt     180
tgcgatagct cattagatat cgcaacacag ctcttacttt ccaacgtaaa aaaattaact     240
ctatccgaat cagaaaaaaa cagtttaaaa aataaatgga atctatcac tgggaaaaaa     300 tcggagaacg cagaaatcag aaaggtggaa ctagtaccca agattttcc taaagatctt     360 gttcttgctc cattgccaga tcatgttaat gattttacat ggtacaaaaa tcgaaaaaaa     420
agcttaggta taaagcctgt aaataagaat atcggtcttt ctattattat tcctacattt     480
aatcgtagcc gtattttaga tataacgtta gcctgtttgg tcaatcagaa acaaactac     540 ccatttgaag tcgttgttgc agatgatggt agtaaggaaa acttacttac cattgtgcaa     600
aaatacgaac aaaaacttga cataaagtat gtaagacaaa aagattatgg atatcaattg     660
tgtgcagtca gaaacttagg tttacgtaca gcaaagtatg attttgtctc gattctagac     720
tgcgatatgg caccacaaca attatgggtt cattcttatc ttacagaact attagaagac     780
aatgatattg tttaattgg acctagaaaa tatgtggata ctcataatat taccgcagaa     840
caattcctta cgatccata tttaatgaaa tcactacctg aaaccgctac aaataacaat     900
ccttcgatta catcaaaagg aaatatatcg ttggattgga gattagaaca tttcaaaaaa     960
accgataatc tacgtctatg tgattccaccg tttcgttatt ttagttgcgg taatgttgca    1020
ttttctaaag aatggctaaa taaagtaggt tggttcgatg aagaatttaa tcattgggg    1080
```

-continued

```
ggcgaagatg tagaatttgg ttacagatta tttgccaaag gctgttttt cagagtaatt    1140 gacggcggaa tggcatacca tcaagaacca cctggtaaag aaaatgaaac agaccgcgaa    1200
gctggtaaaa gtattacgct taaaattgtg aaagaaaagg taccttacat ctatagaaaa    1260
cttttaccaa tagaagattc gcatatcaat agagtacctt tagtttcaat ttatatccca    1320
gcttataact gtgcaaacta tattcaacgt tgcgtagata gtgcactgaa tcagactgtt    1380
gttgatctcg aggtttgtat ttgtaacgat ggttcaacag ataataccct agaagtgatc    1440
aataagcttt atggtaataa tcctagggta cgcatcatgt ctaaaccaaa tggcggaata    1500
gcctcagcat caaatgcagc cgtttctttt gctaaaggtt attcattgg gcagttagat    1560 tcagatgatt atcttgagcc tgatgcagtt gaactgtgtt taaaagaatt tttaaaagat    1620
aaaacgctag cttgtgttta taccactaat agaaacgtca atccggatgg tagcttaatc    1680
gctaatggtt acaattggcc agaattttca cgagaaaaac tcacaacggc tatgattgct    1740
caccacttta aatgttcac gattagagct tggcatttaa ctgatggatt caatgaaaaa    1800
attgaaaatg ccgtagacta tgacatgttc ctcaaactca gtgaagttgg aaaatttaaa    1860
catcttaata aaatctgcta taaccgtgta ttacatggtg ataacacatc aattaagaaa    1920
cttggcattc aaaagaaaaa ccattttgtt gtagtcaatc agtcattaaa tagacaaggc    1980
ataacttatt ataattatga cgaatttgat gatttagatg aaagtagaaa gtatattttc    2040
aataaaaccg ctgaatatca agaagagatt gatatcttaa aagatattta a            2091
```

<210> SEQ ID NO 53
<211> LENGTH: 29
<212> TYPE: DNA
<213> ORGANISM: artificial sequence
<220> FEATURE:
<223> OTHER INFORMATION: primer P1

<400> SEQUENCE: 53

```
atgaacacat tatcacaagc aataaaagc                                        29
```

<210> SEQ ID NO 54
<211> LENGTH: 27
<212> TYPE: DNA
<213> ORGANISM: artificial sequence
<220> FEATURE:
<223> OTHER INFORMATION: primer P2
<220> FEATURE:
<221> NAME/KEY: misc_feature
<222> LOCATION: (23)..(23)
<223> OTHER INFORMATION: Y = C/T

<400> SEQUENCE: 54

```
gcgaatcttc tattggtaaa agyttc                                          27
```

<210> SEQ ID NO 55
<211> LENGTH: 26
<212> TYPE: DNA
<213> ORGANISM: artificial sequence
<220> FEATURE:
<223> OTHER INFORMATION: primer P3

<400> SEQUENCE: 55

```
cttttaccaa tagaagattc gcatat                                          26
```

<210> SEQ ID NO 56
<211> LENGTH: 33
<212> TYPE: DNA
<213> ORGANISM: artificial sequence

```
<220> FEATURE:
<223> OTHER INFORMATION: primer P4

<400> SEQUENCE: 56
gaagacgtct taggcatctt tattctgaat gag                          33

<210> SEQ ID NO 57
<211> LENGTH: 43
<212> TYPE: DNA
<213> ORGANISM: artificial sequence
<220> FEATURE:
<223> OTHER INFORMATION: primer P5

<400> SEQUENCE: 57
gggaattctg cagttaaata tcttttaaga tatcaatctc ttc               43

<210> SEQ ID NO 58
<211> LENGTH: 33
<212> TYPE: DNA
<213> ORGANISM: artificial sequence
<220> FEATURE:
<223> OTHER INFORMATION: sense primer
<220> FEATURE:
<221> NAME/KEY: misc_feature
<222> LOCATION: (9)..(9)
<223> OTHER INFORMATION: inosine
<220> FEATURE:
<221> NAME/KEY: misc_feature
<222> LOCATION: (12)..(12)
<223> OTHER INFORMATION: inosine
<220> FEATURE:
<221> NAME/KEY: misc_feature
<222> LOCATION: (18)..(18)
<223> OTHER INFORMATION: inosine
<220> FEATURE:
<221> NAME/KEY: misc_feature
<222> LOCATION: (24)..(24)
<223> OTHER INFORMATION: inosine
<220> FEATURE:
<221> NAME/KEY: misc_feature
<222> LOCATION: (27)..(27)
<223> OTHER INFORMATION: inosine

<400> SEQUENCE: 58
garttybtnm rngarggnaa rgcnytntay gay                          33

<210> SEQ ID NO 59
<211> LENGTH: 39
<212> TYPE: DNA
<213> ORGANISM: artificial sequence
<220> FEATURE:
<223> OTHER INFORMATION: antisense primer
<220> FEATURE:
<221> NAME/KEY: misc_feature
<222> LOCATION: (7)..(7)
<223> OTHER INFORMATION: inosine
<220> FEATURE:
<221> NAME/KEY: misc_feature
<222> LOCATION: (10)..(10)
<223> OTHER INFORMATION: inosine
<220> FEATURE:
<221> NAME/KEY: misc_feature
<222> LOCATION: (16)..(16)
<223> OTHER INFORMATION: inosine
<220> FEATURE:
<221> NAME/KEY: misc_feature
<222> LOCATION: (22)..(22)
<223> OTHER INFORMATION: inosine
<220> FEATURE:
<221> NAME/KEY: misc_feature
<222> LOCATION: (25)..(25)
<223> OTHER INFORMATION: A, G, C or T
```

<400> SEQUENCE: 59
rcartanccn ccrtanccra answnggrtt rttrtartg                                   39

<210> SEQ ID NO 60
<211> LENGTH: 30
<212> TYPE: DNA
<213> ORGANISM: artificial sequence
<220> FEATURE:
<223> OTHER INFORMATION: 2nd antisense primer

<400> SEQUENCE: 60
tatatttaca gcagtatcat tttctaaagg                                              30

<210> SEQ ID NO 61
<211> LENGTH: 501
<212> TYPE: PRT
<213> ORGANISM: Pasteurella multocida

<400> SEQUENCE: 61

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Glu Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
```

-continued

```
    290                 295                 300

Gln Lys Thr Ser Asp Ala Arg Gln Asn Tyr Leu His Glu Phe Gln Lys
305                 310                 315                 320

Ile His Asn Glu Arg Lys Phe Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Thr Phe Arg Lys
            500
```

<210> SEQ ID NO 62
<211> LENGTH: 1510
<212> TYPE: DNA
<213> ORGANISM: Pasteurella multocida

<400> SEQUENCE: 62

```
aatgagctta tttaaacgtg ctactgagct atttaagtca ggaaactata aagatgcact      60
aactctatat gaaaatatag ctaaaattta tggttcagaa agccttgtta aatataaatat    120 tgatatatgt aaaaaaaata taacacaatc aaaaagtaat aaaatagaag aagataatat    180
ttctggagaa aacgaatttt cagtatcaat aaaagatcta tataacgaaa taagcaatag    240
tgaattaggg attacaaaag aaagactagg agccccccct ctagtcagta ttataatgac    300
ttctcataat acagaaaaat tcattgaagc ctcaattaat tcactattat tgcaaacata    360
caataactta gaagttatcg ttgtagatga ttatagcaca gataaaacat ttcagatcgc    420
atccagaata gcaaactcta caagtaaagt aaaaacattc cgattaaact caaatctagg    480
gacatacttt gcgaaaaata caggaatttt aaagtctaaa ggagatatta ttttctttca    540
ggatagcgat gatgtatgtc accatgaaag aatcgaaaga tgtgttaatg cattattatc    600
gaataaagat aatatagctg ttagatgtgc atattctaga ataaatctag aaacacaaaa    660
tataataaaa gttaatgata ataaatacaa attaggatta ataactttag gcgtttatag    720
aaaagtattt aatgaaattg gtttttttaa ctgcacaacc aaagcatcgg atgatgaatt    780
ttatcataga ataattaaat actatggtaa aaataggata aataacttat ttctaccact    840
gtattataac acaatgcgtg aagattcatt attttctgat atggttgagt gggtagatga    900
```

-continued

```
aaataatata aagcaaaaaa cctctgatgc tagacaaaat tatctccatg aattccaaaa    960
aatacacaat gaaaggaaat ttaatgaatt aaaagagatt tttagctttc ctagaattca   1020
tgacgcctta cctatatcaa agaaatgag taagctcagc aaccctaaaa ttcctgttta   1080
tataaatata tgctcaatac cttcaagaat aaaacaactt caatacacta ttggagtact   1140
aaaaaaccaa tgcgatcatt ttcatattta tcttgatgga tatccagaag tacctgatt   1200
tataaaaaaa ctagggaata aagcgaccgt tattaattgt caaacaaaaa atgagtctat   1260
tagagataat ggaaagttta ttctattaga aaaacttata aaggaaaata aagatggata   1320
ttatataact tgtgatgatg atatccggta tcctgctgac tacataaaca ctatgataaa   1380
aaaaattaat aaatacaatg ataaagcagc aattggatta catggtgtta tattcccaag   1440
tagagtcaac aagtattttt catcagacag aattgtctat aattttcaaa aaacctttag   1500
aaaatgatac                                                          1510
```

<210> SEQ ID NO 63
<211> LENGTH: 238
<212> TYPE: PRT
<213> ORGANISM: Escherichia coli

<400> SEQUENCE: 63

```
Met Ile Val Ala Asn Met Ser Ser Tyr Pro Pro Arg Lys Lys Glu Leu
1               5                   10                  15

Val His Ser Ile Gln Ser Leu His Ala Gln Val Asp Lys Ile Asn Leu
            20                  25                  30

Cys Leu Asn Glu Phe Glu Glu Ile Pro Glu Glu Leu Asp Gly Phe Ser
        35                  40                  45

Lys Leu Asn Pro Val Ile Pro Asp Lys Asp Tyr Lys Asp Val Gly Lys
    50                  55                  60

Phe Ile Phe Pro Cys Ala Lys Asn Asp Met Ile Val Leu Thr Asp Asp
65                  70                  75                  80

Asp Ile Ile Tyr Pro Pro Asp Tyr Val Glu Lys Met Leu Asn Phe Tyr
                85                  90                  95

Asn Ser Phe Ala Ile Phe Asn Cys Ile Val Gly Ile His Gly Cys Ile
            100                 105                 110

Tyr Ile Asp Ala Phe Asp Gly Asp Gln Ser Lys Arg Lys Val Phe Ser
        115                 120                 125

Phe Thr Gln Gly Leu Leu Arg Pro Arg Val Val Asn Gln Leu Gly Thr
    130                 135                 140

Gly Thr Val Phe Leu Lys Ala Asp Gln Leu Pro Ser Leu Lys Tyr Met
145                 150                 155                 160

Asp Gly Ser Gln Arg Phe Val Asp Val Arg Phe Ser Arg Tyr Met Leu
                165                 170                 175

Glu Asn Glu Ile Gly Met Ile Cys Val Pro Arg Glu Lys Asn Trp Leu
            180                 185                 190

Arg Glu Val Ser Ser Gly Ser Met Glu Gly Leu Trp Asn Thr Phe Thr
        195                 200                 205

Lys Lys Trp Pro Leu Asp Ile Ile Lys Glu Thr Gln Ala Ile Ala Gly
    210                 215                 220

Tyr Ser Lys Leu Asn Leu Glu Leu Val Tyr Asn Val Glu Gly
225                 230                 235
```

<210> SEQ ID NO 64
<211> LENGTH: 520
<212> TYPE: PRT

<213> ORGANISM: Escherichia coli

<400> SEQUENCE: 64

```
Met Asn Ala Glu Tyr Ile Asn Leu Val Glu Arg Lys Lys Lys Leu Gly
1               5                   10                  15

Thr Asn Ile Gly Ala Leu Asp Phe Leu Leu Ser Ile His Lys Glu Lys
            20                  25                  30

Val Asp Leu Gln His Lys Asn Ser Pro Leu Lys Gly Asn Asp Asn Leu
        35                  40                  45

Ile His Lys Arg Ile Asn Glu Tyr Asp Asn Val Leu Glu Leu Ser Lys
    50                  55                  60

Asn Val Ser Ala Gln Asn Ser Gly Asn Glu Phe Ser Tyr Leu Leu Gly
65                  70                  75                  80

Tyr Ala Asp Ser Leu Arg Lys Val Gly Met Leu Asp Thr Tyr Ile Lys
                85                  90                  95

Ile Val Cys Tyr Leu Thr Ile Gln Ser Arg Tyr Phe Lys Asn Gly Glu
            100                 105                 110

Arg Val Lys Leu Phe Glu His Ile Ser Asn Ala Leu Arg Tyr Ser Arg
        115                 120                 125

Ser Asp Phe Leu Ile Asn Leu Ile Phe Glu Arg Tyr Ile Glu Tyr Ile
    130                 135                 140

Asn His Leu Lys Leu Ser Pro Lys Gln Lys Asp Phe Tyr Phe Cys Thr
145                 150                 155                 160

Lys Phe Ser Lys Phe His Asp Tyr Thr Lys Asn Gly Tyr Lys Tyr Leu
                165                 170                 175

Ala Phe Asp Asn Gln Ala Asp Ala Gly Tyr Gly Leu Thr Leu Leu Leu
            180                 185                 190

Asn Ala Asn Asp Asp Met Gln Asp Ser Tyr Asn Leu Leu Pro Glu Gln
        195                 200                 205

Glu Leu Phe Ile Cys Asn Ala Val Ile Asp Asn Met Asn Ile Tyr Arg
    210                 215                 220

Ser Gln Phe Asn Lys Cys Leu Arg Lys Tyr Asp Leu Ser Glu Ile Thr
225                 230                 235                 240

Asp Ile Tyr Pro Asn Lys Ile Ile Leu Gln Gly Ile Lys Phe Asp Lys
                245                 250                 255

Lys Lys Asn Val Tyr Gly Lys Asp Leu Val Ser Ile Ile Met Ser Val
            260                 265                 270

Phe Asn Ser Glu Asp Thr Ile Ala Tyr Ser Leu His Ser Leu Leu Asn
        275                 280                 285

Gln Thr Tyr Glu Asn Ile Glu Ile Leu Val Cys Asp Asp Cys Ser Ser
    290                 295                 300

Asp Lys Ser Leu Glu Ile Ile Lys Ser Ile Ala Tyr Ser Ser Ser Arg
305                 310                 315                 320

Val Lys Val Tyr Ser Ser Arg Lys Asn Gln Gly Pro Tyr Asn Ile Arg
                325                 330                 335

Asn Glu Leu Ile Lys Lys Ala His Gly Asn Phe Ile Thr Phe Gln Asp
            340                 345                 350

Ala Asp Asp Leu Ser His Pro Glu Arg Ile Gln Arg Gln Val Glu Val
        355                 360                 365

Leu Arg Asn Asn Lys Ala Val Ile Cys Met Ala Asn Trp Ile Arg Val
    370                 375                 380

Ala Ser Asn Gly Lys Ile Gln Phe Phe Tyr Asp Asp Lys Ala Thr Arg
385                 390                 395                 400
```

```
Met Ser Val Ser Ser Met Ile Lys Lys Asp Ile Phe Ala Thr Val
                405                 410                 415

Gly Gly Tyr Arg Gln Ser Leu Ile Gly Ala Asp Thr Glu Phe Tyr Glu
            420                 425                 430

Thr Val Ile Met Arg Tyr Gly Arg Glu Ser Ile Val Arg Leu Leu Gln
                435                 440                 445

Pro Leu Ile Leu Gly Leu Trp Gly Asp Ser Gly Leu Thr Arg Asn Lys
    450                 455                 460

Gly Thr Glu Ala Leu Pro Asp Gly Tyr Ile Ser Gln Ser Arg Arg Glu
465                 470                 475                 480

Tyr Ser Asp Ile Ala Ala Arg Gln Arg Val Leu Gly Lys Ser Ile Val
                485                 490                 495

Ser Asp Lys Asp Val Arg Gly Leu Leu Ser Arg Tyr Gly Leu Phe Lys
                500                 505                 510

Asp Val Ser Gly Ile Ile Glu Gln
            515                 520

<210> SEQ ID NO 65
<211> LENGTH: 746
<212> TYPE: PRT
<213> ORGANISM: Mus musculus

<400> SEQUENCE: 65

Met Gln Ala Lys Lys Arg Tyr Phe Ile Leu Leu Ser Ala Gly Ser Cys
1               5                   10                  15

Leu Ala Leu Leu Phe Tyr Phe Gly Gly Val Gln Phe Arg Ala Ser Arg
            20                  25                  30

Ser His Ser Arg Arg Glu Glu His Ser Gly Arg Asn Gly Leu His Gln
        35                  40                  45

Pro Ser Pro Asp His Phe Trp Pro Arg Phe Pro Asp Ala Leu Arg Pro
    50                  55                  60

Phe Phe Pro Trp Asp Gln Leu Glu Asn Glu Asp Ser Ser Val His Ile
65                  70                  75                  80

Ser Pro Arg Gln Lys Arg Asp Ala Asn Ser Ser Ile Tyr Lys Gly Lys
                85                  90                  95

Lys Cys Arg Met Glu Ser Cys Phe Asp Phe Thr Leu Cys Lys Lys Asn
            100                 105                 110

Gly Phe Lys Val Tyr Val Tyr Pro Gln Gln Lys Gly Glu Lys Ile Ala
        115                 120                 125

Glu Ser Tyr Gln Asn Ile Leu Ala Ala Ile Glu Gly Ser Arg Phe Tyr
    130                 135                 140

Thr Ser Asp Pro Ser Gln Ala Cys Leu Phe Val Leu Ser Leu Asp Thr
145                 150                 155                 160

Leu Asp Arg Asp Gln Leu Ser Pro Gln Tyr Val His Asn Leu Arg Ser
                165                 170                 175

Lys Val Gln Ser Leu His Leu Trp Asn Asn Gly Arg Asn His Leu Ile
            180                 185                 190

Phe Asn Leu Tyr Ser Gly Thr Trp Pro Asp Tyr Thr Glu Asp Val Gly
        195                 200                 205

Phe Asp Ile Gly Gln Ala Met Leu Ala Lys Ala Ser Ile Ser Thr Glu
    210                 215                 220

Asn Phe Arg Pro Asn Phe Asp Val Ser Ile Pro Leu Phe Ser Lys Asp
225                 230                 235                 240

His Pro Arg Thr Gly Gly Glu Arg Gly Phe Leu Lys Phe Asn Thr Ile
                245                 250                 255
```

-continued

```
Pro Pro Leu Arg Lys Tyr Met Leu Val Phe Lys Gly Lys Arg Tyr Leu
            260                 265                 270

Thr Gly Ile Gly Ser Asp Thr Arg Asn Ala Leu Tyr His Val His Asn
        275                 280                 285

Gly Glu Asp Val Leu Leu Thr Thr Cys Lys His Gly Lys Asp Trp
    290                 295                 300

Gln Lys His Lys Asp Ser Arg Cys Asp Arg Asp Asn Thr Glu Tyr Glu
305                 310                 315                 320

Lys Tyr Asp Tyr Arg Glu Met Leu His Asn Ala Thr Phe Cys Leu Val
                325                 330                 335

Pro Arg Gly Arg Arg Leu Gly Ser Phe Arg Phe Leu Glu Ala Leu Gln
            340                 345                 350

Ala Ala Cys Val Pro Val Met Leu Ser Asn Gly Trp Glu Leu Pro Phe
        355                 360                 365

Ser Glu Val Ile Asn Trp Asn Gln Ala Ala Val Ile Gly Asp Glu Arg
    370                 375                 380

Leu Leu Leu Gln Ile Pro Ser Thr Ile Arg Ser Ile His Gln Asp Lys
385                 390                 395                 400

Ile Leu Ala Leu Arg Gln Gln Thr Gln Phe Leu Trp Glu Ala Tyr Phe
                405                 410                 415

Ser Ser Val Glu Lys Ile Val Leu Thr Thr Leu Glu Ile Ile Gln Asp
            420                 425                 430

Arg Ile Phe Lys His Ile Ser Arg Asn Ser Leu Ile Trp Asn Lys His
        435                 440                 445

Pro Gly Gly Leu Phe Val Leu Pro Gln Tyr Ser Ser Tyr Leu Gly Asp
    450                 455                 460

Phe Pro Tyr Tyr Tyr Ala Asn Leu Gly Leu Lys Pro Pro Ser Lys Phe
465                 470                 475                 480

Thr Ala Val Ile His Ala Val Thr Pro Leu Val Ser Gln Ser Gln Pro
                485                 490                 495

Val Leu Lys Leu Leu Val Ala Ala Lys Ser Gln Tyr Cys Ala Gln
            500                 505                 510

Ile Ile Val Leu Trp Asn Cys Asp Lys Pro Leu Pro Ala Lys His Arg
        515                 520                 525

Trp Pro Ala Thr Ala Val Pro Val Ile Val Ile Glu Gly Glu Ser Lys
    530                 535                 540

Val Met Ser Ser Arg Phe Leu Pro Tyr Asp Asn Ile Ile Thr Asp Ala
545                 550                 555                 560

Val Leu Ser Leu Asp Glu Asp Thr Val Leu Ser Thr Thr Glu Val Asp
                565                 570                 575

Phe Ala Phe Thr Val Trp Gln Ser Phe Pro Glu Arg Ile Val Gly Tyr
            580                 585                 590

Pro Ala Arg Ser His Phe Trp Asp Asn Ser Lys Glu Arg Trp Gly Tyr
        595                 600                 605

Thr Ser Lys Trp Thr Asn Asp Tyr Ser Met Val Leu Thr Gly Ala Ala
    610                 615                 620

Ile Tyr His Lys Tyr Tyr His Tyr Leu Tyr Ser His Tyr Leu Pro Ala
625                 630                 635                 640

Ser Leu Lys Asn Met Val Asp Gln Leu Ala Asn Cys Glu Asp Ile Leu
                645                 650                 655

Met Asn Phe Leu Val Ser Ala Val Thr Lys Leu Pro Pro Ile Lys Val
            660                 665                 670
```

```
Thr Gln Lys Lys Gln Tyr Lys Glu Thr Met Met Gly Gln Thr Ser Arg
            675                 680                 685

Ala Ser Arg Trp Ala Asp Pro Asp His Phe Ala Gln Arg Gln Ser Cys
        690                 695                 700

Met Asn Thr Phe Ala Ser Trp Phe Gly Tyr Met Pro Leu Ile His Ser
705                 710                 715                 720

Gln Met Arg Leu Asp Pro Val Leu Phe Lys Asp Gln Val Ser Ile Leu
                725                 730                 735

Arg Lys Lys Tyr Arg Asp Ile Glu Arg Leu
            740                 745

<210> SEQ ID NO 66
<211> LENGTH: 718
<212> TYPE: PRT
<213> ORGANISM: Mus musculus

<400> SEQUENCE: 66

Met Cys Ala Ser Val Lys Ser Asn Ile Arg Gly Pro Ala Leu Ile Pro
1               5                   10                  15

Arg Met Lys Thr Lys His Arg Ile Tyr Tyr Val Thr Leu Phe Ser Ile
            20                  25                  30

Val Leu Leu Gly Leu Ile Ala Thr Gly Met Phe Gln Phe Trp Pro His
        35                  40                  45

Ser Ile Glu Ser Ser Asp Gly Gly Val Glu Lys Arg Ser Ile Arg
    50                  55                  60

Glu Val Pro Val Val Arg Leu Pro Thr Asp Ser Pro Ile Pro Glu Arg
65                  70                  75                  80

Gly Asp Leu Ser Cys Arg Met His Thr Cys Phe Asp Val Tyr Arg Cys
                85                  90                  95

Gly Phe Asn Pro Lys Asn Lys Ile Lys Val Tyr Ile Tyr Pro Leu Lys
            100                 105                 110

Lys Tyr Val Asp Asp Ala Gly Val Pro Val Ser Ser Ala Ile Ser Arg
        115                 120                 125

Glu Tyr Asn Glu Leu Leu Thr Ala Ile Ser Asp Ser Asp Tyr Tyr Thr
    130                 135                 140

Asp Asp Ile Asn Arg Ala Cys Leu Phe Val Pro Ser Ile Asp Val Leu
145                 150                 155                 160

Asn Gln Asn Pro Leu Arg Ile Lys Glu Thr Ala Gln Ala Leu Ala Gln
                165                 170                 175

Leu Ser Arg Trp Asp Arg Gly Thr Asn His Leu Leu Phe Asn Met Leu
            180                 185                 190

Pro Gly Ala Pro Pro Asp Tyr Asn Thr Ala Leu Asp Val Pro Arg Asp
        195                 200                 205

Arg Ala Leu Leu Ala Gly Gly Phe Ser Thr Trp Thr Tyr Arg Gln
    210                 215                 220

Gly Tyr Asp Val Ser Ile Pro Val Phe Ser Pro Leu Ser Ala Glu Met
225                 230                 235                 240

Ala Leu Pro Glu Lys Ala Pro Gly Pro Arg Arg Tyr Phe Leu Leu Ser
                245                 250                 255

Ser Gln Met Ala Ile His Pro Glu Tyr Arg Glu Glu Leu Glu Ala Leu
            260                 265                 270

Gln Ala Lys His Gln Glu Ser Val Leu Val Leu Asp Lys Cys Thr Asn
        275                 280                 285

Leu Ser Glu Gly Val Leu Ser Val Arg Lys Arg Cys His Gln His Gln
    290                 295                 300
```

-continued

```
Val Phe Asp Tyr Pro Gln Val Leu Gln Glu Ala Thr Phe Cys Thr Val
305                 310                 315                 320

Leu Arg Arg Ala Arg Leu Gly Gln Ala Val Leu Ser Asp Val Leu Gln
            325                 330                 335

Ala Gly Cys Val Pro Val Ile Ala Asp Ser Tyr Ile Leu Pro Phe
        340                 345                 350

Ser Glu Val Leu Asp Trp Lys Lys Ala Ser Val Val Pro Glu Glu
    355                 360                 365

Lys Met Ser Asp Val Tyr Ser Ile Leu Gln Asn Ile Pro Gln Arg Gln
370                 375                 380

Ile Glu Glu Met Gln Arg Gln Ala Arg Trp Phe Trp Glu Ala Tyr Phe
385                 390                 395                 400

Gln Ser Ile Lys Ala Ile Ala Leu Ala Thr Leu Gln Ile Ile Asn Asp
                405                 410                 415

Arg Ile Tyr Pro Tyr Ala Ala Ile Ser Tyr Glu Glu Trp Asn Asp Pro
            420                 425                 430

Pro Ala Val Lys Trp Ala Ser Val Ser Asn Pro Leu Phe Leu Pro Leu
            435                 440                 445

Ile Pro Pro Gln Ser Gln Gly Phe Thr Ala Ile Val Leu Thr Tyr Asp
    450                 455                 460

Arg Val Glu Ser Leu Phe Arg Val Ile Thr Glu Val Ser Lys Val Pro
465                 470                 475                 480

Ser Leu Ser Lys Leu Leu Val Val Trp Asn Asn Gln Asn Lys Asn Pro
                485                 490                 495

Pro Glu Glu Ser Leu Trp Pro Lys Ile Arg Val Pro Leu Lys Val Val
            500                 505                 510

Arg Thr Ala Glu Asn Lys Leu Ser Asn Arg Phe Phe Pro Tyr Asp Glu
            515                 520                 525

Ile Glu Thr Glu Ala Val Leu Ala Ile Asp Asp Ile Ile Met Leu
530                 535                 540

Thr Ser Asp Glu Leu Gln Phe Gly Tyr Glu Val Trp Arg Glu Phe Pro
545                 550                 555                 560

Asp Arg Leu Val Gly Tyr Pro Gly Arg Leu His Leu Trp Asp His Glu
            565                 570                 575

Met Asn Lys Trp Lys Tyr Glu Ser Glu Trp Thr Asn Glu Val Ser Met
            580                 585                 590

Val Leu Thr Gly Ala Ala Phe Tyr His Lys Tyr Phe Asn Tyr Leu Tyr
            595                 600                 605

Thr Tyr Lys Met Pro Gly Asp Ile Lys Asn Trp Val Asp Ala His Met
        610                 615                 620

Asn Cys Glu Asp Ile Ala Met Asn Phe Leu Val Ala Asn Val Thr Gly
625                 630                 635                 640

Lys Ala Val Ile Lys Val Thr Pro Arg Lys Phe Lys Cys Pro Glu
            645                 650                 655

Cys Thr Ala Ile Asp Gly Leu Ser Leu Asp Gln Thr His Met Val Glu
            660                 665                 670

Arg Ser Glu Cys Ile Asn Lys Phe Ala Ser Val Phe Gly Thr Met Pro
    675                 680                 685

Leu Lys Val Val Glu His Arg Ala Asp Pro Val Leu Tyr Lys Asp Asp
        690                 695                 700

Phe Pro Glu Lys Leu Lys Ser Phe Pro Asn Ile Gly Ser Leu
705                 710                 715
```

```
<210> SEQ ID NO 67
<211> LENGTH: 76
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: ANY AMINO ACID
<220> FEATURE:
<221> NAME/KEY: MISC_FEATURE
<222> LOCATION: (6)..(6)
<223> OTHER INFORMATION: Leu or Ile
<220> FEATURE:
<221> NAME/KEY: MISC_FEATURE
<222> LOCATION: (8)..(11)
<223> OTHER INFORMATION: any amino acid
<220> FEATURE:
<221> NAME/KEY: MISC_FEATURE
<222> LOCATION: (14)..(14)
<223> OTHER INFORMATION: any amino acid
<220> FEATURE:
<221> NAME/KEY: MISC_FEATURE
<222> LOCATION: (15)..(15)
<223> OTHER INFORMATION: Ser or Thr
<220> FEATURE:
<221> NAME/KEY: MISC_FEATURE
<222> LOCATION: (16)..(16)
<223> OTHER INFORMATION: Ser or Thr
<220> FEATURE:
<221> NAME/KEY: MISC_FEATURE
<222> LOCATION: (18)..(18)
<223> OTHER INFORMATION: Lys or Asn
<220> FEATURE:
<221> NAME/KEY: MISC_FEATURE
<222> LOCATION: (19)..(19)
<223> OTHER INFORMATION: Thr or Ser
<220> FEATURE:
<221> NAME/KEY: MISC_FEATURE
<222> LOCATION: (20)..(25)
<223> OTHER INFORMATION: any amino acid
<220> FEATURE:
<221> NAME/KEY: MISC_FEATURE
<222> LOCATION: (28)..(28)
<223> OTHER INFORMATION: any amino acid
<220> FEATURE:
<221> NAME/KEY: MISC_FEATURE
<222> LOCATION: (29)..(31)
<223> OTHER INFORMATION: Ser or Thr
<220> FEATURE:
<221> NAME/KEY: MISC_FEATURE
<222> LOCATION: (32)..(32)
<223> OTHER INFORMATION: Lys or Arg
<220> FEATURE:
<221> NAME/KEY: MISC_FEATURE
<222> LOCATION: (34)..(34)
<223> OTHER INFORMATION: Lys or Arg
<220> FEATURE:
<221> NAME/KEY: MISC_FEATURE
<222> LOCATION: (35)..(40)
<223> OTHER INFORMATION: any amino acid
<220> FEATURE:
<221> NAME/KEY: MISC_FEATURE
<222> LOCATION: (42)..(42)
<223> OTHER INFORMATION: any amino acid
<220> FEATURE:
<221> NAME/KEY: MISC_FEATURE
<222> LOCATION: (44)..(44)
<223> OTHER INFORMATION: any amino acid
<220> FEATURE:
<221> NAME/KEY: MISC_FEATURE
<222> LOCATION: (46)..(61)
<223> OTHER INFORMATION: any amino acid
<220> FEATURE:
<221> NAME/KEY: MISC_FEATURE
<222> LOCATION: (65)..(65)
<223> OTHER INFORMATION: any amino acid
```

```
<220> FEATURE:
<221> NAME/KEY: MISC_FEATURE
<222> LOCATION: (68)..(68)
<223> OTHER INFORMATION: any amino acid
<220> FEATURE:
<221> NAME/KEY: MISC_FEATURE
<222> LOCATION: (69)..(69)
<223> OTHER INFORMATION: Cys or Ser
<220> FEATURE:
<221> NAME/KEY: MISC_FEATURE
<222> LOCATION: (71)..(71)
<223> OTHER INFORMATION: His or Pro
<220> FEATURE:
<221> NAME/KEY: MISC_FEATURE
<222> LOCATION: (75)..(75)
<223> OTHER INFORMATION: any amino acid

<400> SEQUENCE: 67

Gln Thr Tyr Xaa Asn Xaa Glu Xaa Xaa Xaa Xaa Asp Asp Xaa Xaa Xaa
1               5                   10                  15

Asp Xaa Xaa Xaa Xaa Xaa Xaa Xaa Xaa Ile Ala Xaa Xaa Xaa Xaa Xaa
            20                  25                  30

Val Xaa Xaa Xaa Xaa Xaa Xaa Xaa Asn Xaa Gly Xaa Tyr Xaa Xaa Xaa
        35                  40                  45

Xaa Xaa Xaa Xaa Xaa Xaa Xaa Xaa Xaa Xaa Xaa Xaa Phe Gln Asp
    50                  55                  60

Xaa Asp Asp Xaa Xaa His Xaa Glu Arg Ile Xaa Arg
65                  70                  75

<210> SEQ ID NO 68
<211> LENGTH: 102
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Lys or Arg
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (8)..(19)
<223> OTHER INFORMATION: each position may be any amino acid
<220> FEATURE:
<221> NAME/KEY: MISC_FEATURE
<222> LOCATION: (20)..(24)
<223> OTHER INFORMATION: may be missing from sequence; each position may
      be any amino acid
<220> FEATURE:
<221> NAME/KEY: MISC_FEATURE
<222> LOCATION: (20)..(24)
<223> OTHER INFORMATION: all or part of sequence comprising residues
      20-24 may be missing; each position may be any amino acid
<220> FEATURE:
<221> NAME/KEY: MISC_FEATURE
<222> LOCATION: (29)..(29)
<223> OTHER INFORMATION: Arg or Ile
<220> FEATURE:
<221> NAME/KEY: MISC_FEATURE
<222> LOCATION: (32)..(32)
<223> OTHER INFORMATION: amy amino acid
<220> FEATURE:
<221> NAME/KEY: MISC_FEATURE
<222> LOCATION: (35)..(37)
<223> OTHER INFORMATION: any amino acid
<220> FEATURE:
<221> NAME/KEY: MISC_FEATURE
<222> LOCATION: (39)..(84)
<223> OTHER INFORMATION: each position may be any amino acid
```

```
<220> FEATURE:
<221> NAME/KEY: MISC_FEATURE
<222> LOCATION: (85)..(94)
<223> OTHER INFORMATION: all or part of sequence comprising residues
      85-94 may be missing; each position may be any amino acid
<220> FEATURE:
<221> NAME/KEY: MISC_FEATURE
<222> LOCATION: (96)..(96)
<223> OTHER INFORMATION: any amino acid

<400> SEQUENCE: 68

Xaa Asp Xaa Gly Lys Phe Ile Xaa Xaa Xaa Xaa Xaa Xaa Xaa Xaa
1               5                   10                  15

Xaa Xaa Xaa Xaa Xaa Xaa Xaa Xaa Asp Asp Ile Xaa Tyr Pro Xaa
                20                  25                  30

Asp Tyr Xaa Xaa Xaa Met Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Val Asn Xaa
                85                  90                  95

Leu Gly Thr Gly Thr Val
            100

<210> SEQ ID NO 69
<211> LENGTH: 1854
<212> TYPE: DNA
<213> ORGANISM: Pasteurella multocida

<400> SEQUENCE: 69 atgagcttat

-continued

```
aaaaaccaat gcgatcattt tcatatttat cttgatggat atccagaagt acctgatttt   1200
ataaaaaaac tagggaataa agcgaccgtt attaattgtc aaaacaaaaa tgagtctatt   1260
agagataatg gaaagtttat tctattagaa aaacttataa aggaaaataa agatggatat   1320
tatataactt gtgatgatga tatccggtat cctgctgact acataaacac tatgataaaa   1380
aaaattaata aatacaatga taaagcagca attggattac atggtgttat attcccaagt   1440
agagtcaaca agtatttttc atcagacaga attgtctata attttcaaaa acctttagaa   1500
aatgatactg ctgtaaatat attaggaact ggaactgttg cctttagagt atctattttt   1560
aataaatttt ctctatctga ttttgagcat cctggcatgg tagatatcta tttttctata   1620
ctatgtaaga aaaacaatat actccaagtt tgtatatcac gaccatcgaa ttggctaaca   1680
gaagataaca aaaacactga gaccttattt catgaattcc aaaatagaga tgaaatacaa   1740
agtaaactca ttatttcaaa caacccttgg ggatactcaa gtatatatcc attattaaat   1800
aataatgcta attattctga acttattccg tgtttatctt tttataacga gtaa         1854
```

```

<210> SEQ ID NO 70
<211> LENGTH: 617
<212> TYPE: PRT
<213> ORGANISM: Pasteurella multocida

<400> SEQUENCE: 70

Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255
```

```
Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
            275                 280                 285

Ser Leu Phe Ser Asp Met Val Glu Trp Val Asp Glu Asn Asn Ile Lys
            290                 295                 300

Gln Lys Thr Ser Asp Ala Arg Gln Asn Tyr Leu His Glu Phe Gln Lys
305                 310                 315                 320

Ile His Asn Glu Arg Lys Leu Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
            355                 360                 365

Arg Ile Lys Gln Leu Gln Tyr Thr Ile Gly Val Leu Lys Asn Gln Cys
            370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Glu Lys Leu
            420                 425                 430

Ile Lys Glu Asn Lys Asp Gly Tyr Tyr Ile Thr Cys Asp Asp Ile
            435                 440                 445

Arg Tyr Pro Ala Asp Tyr Ile Asn Thr Met Ile Lys Lys Ile Asn Lys
            450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Pro Leu Glu Asn Asp Thr Ala Val Asn Ile Leu Gly Thr Gly Thr
            500                 505                 510

Val Ala Phe Arg Val Ser Ile Phe Asn Lys Phe Ser Leu Ser Asp Phe
            515                 520                 525

Glu His Pro Gly Met Val Asp Ile Tyr Phe Ser Ile Leu Cys Lys Lys
            530                 535                 540

Asn Asn Ile Leu Gln Val Cys Ile Ser Arg Pro Ser Asn Trp Leu Thr
545                 550                 555                 560

Glu Asp Asn Lys Asn Thr Glu Thr Leu Phe His Glu Phe Gln Asn Arg
                565                 570                 575

Asp Glu Ile Gln Ser Lys Leu Ile Ile Ser Asn Asn Pro Trp Gly Tyr
            580                 585                 590

Ser Ser Ile Tyr Pro Leu Leu Asn Asn Asn Ala Asn Tyr Ser Glu Leu
            595                 600                 605

Ile Pro Cys Leu Ser Phe Tyr Asn Glu
    610                 615

<210> SEQ ID NO 71
<211> LENGTH: 2112
<212> TYPE: DNA
<213> ORGANISM: Pasteurella multocida

<400> SEQUENCE: 71
atgaatacat tatcacaagc aataaaagca tataacagca atgactatca attagcactc    60
```

```
aaattatttg aaaagtcggc ggaaatctat ggacggaaaa ttgttgaatt tcaaattacc      120
aaatgcaaag aaaaactctc agcacatcct tctgttaatt cagcacatct ttctgtaaat      180
aaagaagaaa aagtcaatgt ttgcgatagt ccgttagata ttgcaacaca actgttactt      240
tccaacgtaa aaaattagt actttctgac tcggaaaaaa acacgttaaa aaataaatgg       300
aaattgctca ctgagaagaa atctgaaaat gcggaggtaa gagcggtcgc ccttgtacca      360
aaagattttc ccaaagatct ggttttagcg cctttacctg atcatgttaa tgattttaca      420
tggtacaaaa agcgaaagaa aagacttggc ataaaacctg aacatcaaca tgttggtctt      480
tctattatcg ttacaacatt caatcgacca gcaatttat cgattacatt agcctgttta       540
gtaaaccaaa aaacacatta cccgtttgaa gttatcgtga cagatgatgg tagtcaggaa      600
gatctatcac cgatcattcg ccaatatgaa ataaaattgg atattcgcta cgtcagacaa      660
aaagataacg ttttcaagc cagtgccgct cggaatatgg gattacgctt agcaaaatat       720
gactttattg gcttactcga ctgtgatatg gcgccaaatc cattatgggt tcattcttat      780
gttgcagagc tattagaaga tgatgattta acaatcattg gtccaagaaa atacatcgat      840
acacaacata ttgacccaaa agacttctta ataacgcga gtttgcttga atcattacca      900
gaagtgaaaa ccaataatag tgttgccgca aagggggaag aacagttttc tctggattgg      960
cgcttagaac aattcgaaaa aacagaaaat ctccgcttat ccgattcgcc tttccgtttt     1020
tttgcggcgg gtaatgttgc tttcgctaaa aaatggctaa ataaatccgg tttctttgat     1080
gaggaattta atcactgggg tggagaagat gtggaatttg atatcgctt attccgttac      1140 ggtagtttct ttaaaactat tgatggcatt atggcctacc atcaagagcc accaggtaaa     1200
gaaaatgaaa ccgatcgtga agcgggaaaa aatattacgc tcgatattat gagagaaaag     1260
gtcccttata tctatagaaa acttttacca atagaagatt cgcatatcaa tagagtacct     1320
ttagtttcaa tttatatccc agcttataac tgtgcaaact atattcaacg ttgcgtagat     1380
agtgcactga atcagactgt tgttgatctc gaggtttgta tttgtaacga tggttcaaca     1440
gataatacct tagaagtgat caataagctt tatggtaata atcctagggt acgcatcatg     1500
tctaaaccaa atggcggaat agcctcagca tcaaatgcag ccgtttcttt tgctaaaggt     1560
tattacattg ggcagttaga ttcagatgat tatcttgagc ctgatgcagt tgaactgtgt     1620
ttaaaagaat ttttaaaaga taaaacgcta gcttgtgttt ataccactaa tagaaacgtc     1680
aatccggatg gtagcttaat cgctaatggt tacaattggc cagaattttc acgagaaaaa     1740
ctcacaacgg ctatgattgc tcaccacttt agaatgttca cgattagagc ttggcattta     1800
actgatggat tcaatgaaaa aattgaaaat gccgtagact atgacatgtt cctcaaactc     1860
agtgaagttg gaaaatttaa acatcttaat aaaatctgct ataaccgtgt attacatggt     1920
gataacacat caattaagaa acttggcatt caaaagaaaa accatttgt tgtagtcaat      1980 cagtcattaa atagacaagg cataaacttat tataattatg acgaatttga tgatttagat     2040
gaaagtagaa agtatatttt caataaaacc gctgaatatc aagaagagat tgatatctta     2100
aaagatattt aa                                                        2112
```